US011992523B2

(12) United States Patent
Nabel et al.

(10) Patent No.: US 11,992,523 B2
(45) Date of Patent: May 28, 2024

(54) METHOD FOR PRODUCING CHIKUNGUNYA VIRUS (CHIKV) VIRUS-LIKE PARTICLES COMPRISING THE C, E2, AND E1 STRUCTURAL PROTEINS

(71) Applicant: The United States of America, as represented by the Secretary, Department of Health and Human Services (the Government), Bethesda, MD (US)

(72) Inventors: Gary J. Nabel, Chestnut Hill, MA (US); Wataru Akahata, Kensington, MD (US); Srinivas Rao, Columbia, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 6 days.

(21) Appl. No.: 17/850,706

(22) Filed: Jun. 27, 2022

(65) Prior Publication Data

US 2023/0025038 A1    Jan. 26, 2023

Related U.S. Application Data

(60) Continuation of application No. 16/520,113, filed on Jul. 23, 2019, now Pat. No. 11,369,674, which is a division of application No. 15/145,483, filed on May 3, 2016, now Pat. No. 10,369,208, which is a division of application No. 13/131,287, filed as application No. PCT/US2009/006294 on Nov. 24, 2009, now Pat. No. 9,353,353.

(60) Provisional application No. 61/201,118, filed on Dec. 5, 2008, provisional application No. 61/118,206, filed on Nov. 26, 2008.

(51) Int. Cl.
  *A61K 39/12*    (2006.01)
  *C12N 7/00*    (2006.01)
  *C12N 7/04*    (2006.01)
  *A61K 39/00*    (2006.01)

(52) U.S. Cl.
  CPC ............... *A61K 39/12* (2013.01); *C12N 7/00* (2013.01); *C12N 7/045* (2013.01); *A61K 2039/5258* (2013.01); *A61K 2039/55566* (2013.01); *C12N 2740/16043* (2013.01); *C12N 2770/36123* (2013.01); *C12N 2770/36134* (2013.01); *Y02A 50/30* (2018.01)

(58) Field of Classification Search
  CPC ............ A61K 39/12; A61K 2039/5258; C12N 2770/36123
  See application file for complete search history.

(56) References Cited

U.S. PATENT DOCUMENTS

| 7,947,822 B2 | 5/2011 | Nabel et al. |
| 9,353,353 B2 | 5/2016 | Nabel et al. |
| 10,369,208 B2 | 8/2019 | Nabel et al. |
| 2006/0216702 A1 | 9/2006 | Compans et al. |

FOREIGN PATENT DOCUMENTS

| EP | 1736538 | 12/2006 | |
| WO | WO 2008/026225 | 3/2008 | |
| WO | WO 2008/030220 | 3/2008 | |
| WO | WO-2008030220 A2 * | 3/2008 | ............. A61K 39/00 |

OTHER PUBLICATIONS

Akahata et al., "A VLP vaccine for epidemic Chikungunya virus protects nonhuman primates infection," *Nature Medicine* 16: 334-339, 2010.
Akahata et al. "A Specific Domain of the Chikungunya Virus E2 Protein Regulates Particle Formation in Human Cells: Implications for Alphavirus Vaccine Design," *Journal of Virology* 86.16: 8879-8883, Aug. 2012.
Chang et al., "Safety and Tolerability of Chikungunya Virus-Like Particle Vaccine in Healthy Adults: A Phase 1 Dose-Escalation Trial," *Lancet* 384: 2046-2052, Dec. 2014.
Gould et al., "Understanding the alphaviruses: Recent research on important emerging pathogens and progress towards their control," *Antivir Res.* 87: 111-124, 2010.
Huang et al. "Generation of Synthetic Severe Acute Respiratory Syndrome Coronavirus Pseudoparticles: Implications for Assembly and Vaccine Production," *Journal of Virolog*78.22: 12557-12565, Nov. 2004.
Intention to Grant for European Patent Application No. 098294 77.0, dated Jan. 23, 2019, 5 pages.
International Search Report for International Patent Application No. PCT/US09/06294, dated Oct. 19, 2010.
Kim, Medical Molecular Virology, pp. 89-91, Science press, published on Feb. 2001 (evidence 1 cited in Official Action of related Chinese Patent Application No. 200980155476.X, dated Sep. 28, 2014, English translation of text from p. 90), 1 page.
Muthumani et al., "Immunogenicity of novel consensus-based DNA vaccines against Chikungunya virus," *Vaccine* 26: 5128-5134, Apr. 2008.
Notice of Allowance for U.S. Appl. No. 15/145,483, dated Mar. 19, 2018, 12 pages.
Notice of Reexamination with English Translation for China Patent Application No. 200980155476.X, dated Aug. 4, 2016, 15 pages.
Official Action for Australian Patent Application No. 2009320287, dated Dec. 11, 2014, 3 pages.
Official Action (with English translation) for Chinese Patent Application No. 200980155476.X, dated May 14, 201, 20 pages.
Official Action (with English translation) for Chinese Patent Application No. 200980155476.X, dated Sep. 28, 2014, 20 pages.

(Continued)

*Primary Examiner* — Jeffrey S Parkin

(74) *Attorney, Agent, or Firm* — Klarquist Sparkman, LLP

(57) ABSTRACT

The invention features compositions and methods for the prevention or treatment of one or more strains of Chikungunya virus, as well as other alphavirus-mediated diseases.

4 Claims, 118 Drawing Sheets

Specification includes a Sequence Listing.

(56) References Cited

OTHER PUBLICATIONS

Official Action for European Patent Application No. 09829477.0, dated Jun. 4, 2012, 6 pages.
Official Action for European Patent Application No. 09829477.0, dated Mar. 9, 2015, 4 pages.
Official Action for European Patent Application No. 098294 77 .0, dated Jul. 22, 2016, 5 pages.
Official Action for European Patent Application No. 098294 77 .0, dated Sep. 28, 2017, 5 pages.
Official Action for Malaysia Patent Application No. PI2011002376, dated May 15, 2015, 2 pages.
Official Action for Malaysia Patent Application No. PI 2011002376, dated Mar. 31, 2016, 2 pages.
Official Action for Philippines Patent Application No. 1-2011-501012, dated Jul. 25, 2014, 2 pages.
Official Action for Philippines Patent Application No. 1-2011-501012, dated Oct. 10, 2014, 2 pages.
Official Action for Philippines Patent Application No. 1-2011-501012, dated Jan. 22, 2015, 2 pages.
Official Action for Philippines Patent Application No. 1/2011/501012, dated Apr. 14, 2015, 2 pages.
Official Action with English Translation for Vietnam Patent Application No. 1-2011-01662, dated Jun. 29, 2015, 2 pages.
Official Action (Restriction Requirement) for U.S. Appl. No. 13/131,287, dated Jun. 4, 2013, 7 pages.
Official Action for U.S. Appl. No. 131,287, dated Nov. 4, 2013.
Official Action for U.S. Appl. No. 13/131,287, dated May 8, 2014, 6 pages.
Official Action for U.S. Appl. No. 13/131,287, dated May 7, 2015, 13 pages.
Official Action for U.S. Appl. No. 13/131,287, dated Nov. 6, 2015, 12 pages.
Official Action (Restriction Requirement) for U.S. Appl. No. 15/145,483, dated Sep. 25, 2017, 7 pages,.
Official Action for U.S. Appl. No. 15/145,483, dated Apr. 24, 2018, 13 pages.
Official Action for U.S. Appl. No. 15/145,483, dated Nov. 19, 2018, 10 pages.
Official Action for European Patent Application No. 09829477.0, dated Aug. 6, 2018, 3 pages.
Pulmanausahakul et al., "Chikungunya in Southeast Asia: understanding the emergence and finding solutions," *International J. Infect. Dis.* 15: e671-e676, 2011.
Suhrbier et al., "Arthritogenic aphaviruses—an overview," *Nature* 8: 420-429, Jul. 2012.
Tan, Therapeutic Immunology, Science press, pp. 459-461, Mar. 2007 (evidence 3 cited in Official Action of Chinese Patent Application No. 200980155476.X dated Sep. 28, 2014, English translation of lines 4-5 and 18-22 of p. 460), 1 page.
Thiboutot et al., "Chikungunya: A potentially emerging epidemic?" *PLoS Neglected Tropical Diseases* 4.4: e623, Apr. 2010 (8 pages).
Wang et al., "Chimeric alphavirus vaccine candidates for chikungunya," *Vaccine* 26: 5030-5039, Aug. 2008.
Wang et al., "Chimeric sindbis/eastern equine encephalitis vaccine candidates are highly attenuated and immunogenic in mice," *Vaccine* 25: 7573-7581, Aug. 15, 2007.
Weaver et al., "Chikungunya virus and prospects for a vaccine," *Expert Rev Vaccines* 11.9: 1087-1101, 2012.
Weider, Science press, published on Jun. 2008, p. 234 (evidence 2 cited in Official Action of Chinese Patent Application No. 200980155476.X dated Sep. 28, 2014, English translation of text from p. 234), 1 page.

\* cited by examiner

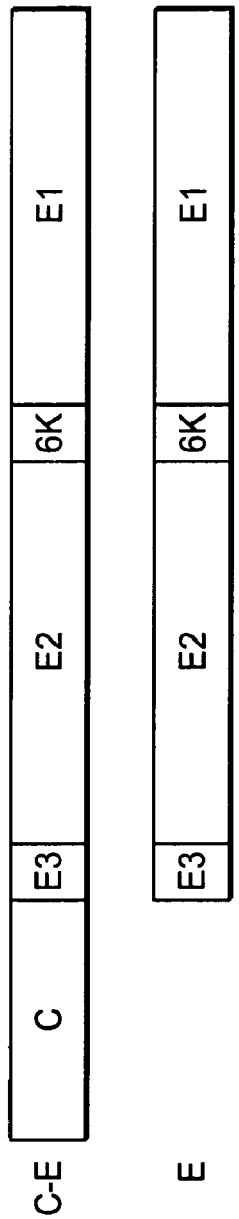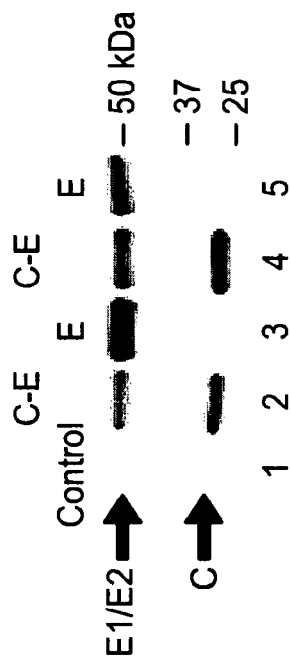
FIG. 2A

CHIKV VLP            Sindbis virus core
membrane
glycoproteins

SEQ ID NO: 1
Insert C-E3-E2-6K-E1 (strain 37997)

atggagttcatccgacgcaaacttctataacagaaggtaccaaccccgacccctgggcccacgccctacaattcaagtaattagacctaga
ccacgtccacagagaggcaggctgggcaactctgcccagctgatctccgcagtcaacaaattgaccatgccgcgcggtacctcaacagaagcctc
gcagaaatcggaaaaacaagaagcaagacaaggcagaagaagcaggcgccgcaaaagcaccaaaagaagcaaccaccacaa
aagaagccggctcaaaagaagaagaagaaccaggccgtaggagagaatgtgcatgagagtgcatgaaaattgaagattgcatcttcgaagtcaagcat
gaaggcaaagttgatgggctacgcatgccatgcctgtggtgggggataaagtaatgaaaccagcacatgtgaaggaactatcgacaatgccgatctg
gctaaactggccttaagcgtcgtctaaatacgatcttgaatgtgcacagataccggtgcacatgaaggtctgatgcctcgaagttaccccacga
gaaaccgagggtactataactgcatcacggagcgagcagtattcaggaggccgttcactatccgacggtgcagccaaggtgcaggcaagccggg
agacagcggcagaccgatcttcgacaacaaaggacgggttggtcgcatcgtcctagggaggggcaacgaaggtgccgcacggccctct
ccgtggtgacgtggaacaaagacatgtcacaaaattacccctgctgagggagccgaagagtgcctgcctccgcgctcttgtgcctgttg
gcaaacactacattccctgctctcagccgcctgactaaaagactgcacacctgaactgctctcccaccgccaaagacgcagtaaggacaatttaatgtc
cgtgatgagaccggatactaccagctgactactgctcattgtcactgctgaagggcattcgtgccacagcctatcgcattggagcgcatcagaaat
tataaagccacaagaccatatctagctcattgtcctgactgcgagagccggagatcaatgtaaagcatgcgggatcagtgcacgagcgcattgattggaaagactttcagcaccgcgatcaccggaccatggacac
gaagcaacggacggaacgctgaaaatccagttcgtctcttttgcagatcggagagcgcggagagcgcgcgatttgcttgaaggactcatcagcacgcgcgatcaccggaccatggacac
atggatagccataacgcccgatcgccgaaagagaagacgctgacagtggaaattacggagattacgacacagcagcaaagcacgcagaggcgccacgtgggccacggttcc
tttattctgcccgatgccacctgtgataggttaggagagataggtgcatatgccccagatactcctgaccgcacgctgatgacgcacgctgcaacgtgaagatca
cagttaatggcagacggtgcgcgtacaagtcaactgcggtggtgcaaatacaagaattgcaatacaacaagagagactgacaacacaagacaaagtgatcaataactgca
aaattgatcagtgactgctgcagttcactaatcacaagaattgcaatacaactccccttttagtccccgcaacgctgaactcgggggaccgta
aagaaagatcaacatccattccattccttgcaaatgacttgactgcagtgctgcaagtgccaagaaagcaagaaacctacagtaacttacggaaaaaacc
aagtcaccatgctgctgtatcctgaccatcgcgacactctttgtcttaccgtaacatgggaccagagaaccaaattaccacgagagttgggtgacac
acaagaagaaggttaccttgaccgtgcctactgaggctcactgggagtcaacaacatacaagtacgccgagatgtct
acgaacggtactgctcatggtcacccacatgagatatactttgtactccactactgagctgtaccccactatgactgtagtcattgcctgcctcgtt
cgtcttcgtgatggtgtgggcacagcagtggaatgtgtgtgccacgcgcagatgcattaccacatatgaattaacaccaggagccac
tgttcccttcctgctcagccctgctatgcctgctatgcctcagaacgtcgtcagaacgaccaaggcgccacatattacgaggctgcggtgcggcatatctatgtggaacagcag

FIG. 7A (continued)

ccctgttctgttgcaggctcttatccgctggccgccttgatcgtcctgtgcaactcttgccatgctgctgtaagaccctggcttttt
agccgtaatgagcatcgtggtgcccacactgtgagcgcgtgacgcaagtaacacgtcgaacacggtgggagtaccgtataagactcttg
tcaacagaccgggttacagccccatgtgtgttggagatggagctacaatcagtcacttgaaccaacactgtcacttgactacatcacgtgcg
agtacaaaactgtcatcccctcccgtacgtgaagtgctgttggtacagagagtgcaaggagacaagagagctaccagactacagctgcaaggt
ctttactggagtctaccccatttatgtgggggcggcgcctactgctttgcgacgccgaaaatacgcaattgagcgaggcacatgtagagaaatctg
aatcttgcaaaacagagtttgcatcgctacagagcccacaccgtcggcgaagctccgcgtcctttaccaaggaaacaacatt
accgtagctgcctaacggtgaccatgccgtcacagtaaaggacgcgtcacagagcgccaagtttgtcgtgggcccaatgtcctccgctggacacctttg
acaacaaatcgtggtgtacaaaggcgacgctcacaacatggactactaccaccttgccgcgaggaagacaggacaggcaattggtgacattcaa
agtcgtacaccggaaagaagacgtttatgctgaaggaagacgagagagcatcagttggtactacagagagccagcagcaggcaccgcgttcggttgccagattgcgacaaccg
gcaccatctgcttcaagtattgcgctgtgggaacatacaattccatcgacataccggatgcggcctttactaggtttgtcgatgcaccctctgtaacg
gtaagagctgtaaattgcgctgtggggaacatacaattccatcgacataccggatgcggcctttactaggtttgtcgatgcaccctctgtaacg
gacatgtcatgcgaagtaccagctgaccagcctgactttggggcgtgccatcatcaaatacacagctagcaagaaggtaaatgt
gcagtacattcgatgacgatgccgttaccattcgagaagccgacgtagaagccgagcgtagagaggggaactccagctgcaaatatcctctcaacagc
cctggcaagccgagtttcgctgcaagtgtcctccacacaagtacactgcgcagccgcatgcaaagagaccacatagtcaatt
accagaccatcacacaccctttgggtcttccaggatatatcacaacgccaatgtcttgggtgcagaagattacggaggaggagtaggattaatt
gttgctgcttgccttaatttttaattgtggtgctatgcgtgtcgtttagcaggcactaa

FIG. 7B

SEQ ID NO: 2
CMV/R 37997 C-E3-E2-6K-E1 tcgcgcgtttcgtgatgacgacgtgtgaaaacctctgacacatgcagctcccggagacgtcacagcttgtctgtaagcggatgccgggagcaga
caagcccgtcagggcgcgtcagggggtgttggcgggtgtcggggctaactatgcggcatcagagcagattgtactgagagtgcacca
tatgcggtgtgaaataccgcacagatgcgtaaggagaaaataccgcatcagattgcattgcatgtcgattctcatcatatatg
tacatttatattggctcatgtccaacattaccgccatgttgacattgattattgactagttattaatagtaatcaattacggggtcattagttcatagcc
atatatatggagttccgcgttacataacttacggtaaatggcccgcctggctgaccgcccaacgacccccgcccattgacgtcaataatgacgtat FIG. 7B (continued)

gttccatagtaacgccaataggcaattcattgacgtcaatgggtggagtatttacgtaaactgcccactggcagtacatcaagtgtatcat
atgccaagtacgccccctattgacgtcaatgacgtaaatggcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctcaccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgtttgac
ctccatagaagacaccgggaccagccagccgatcagtcgctcgactcctccatcgctccttcacgcgccgccgccacctgaggccgcccatccacgc
cggttgagtcgcgttctgccgcctcccgcctgtggtgcctcctgaactgcgtccgccgtctaggtaagtttaaagctcaagtgtagaccgggcctt
tgtccggcgtccttggagctctcacgcgcctagaactcagccggctctgacccttgctcaactcagtaacgttaacgttggtggagggcagt
gtagtctgagcagtactcgttgctgccgcgccaccagacataatagtgacagactaaacagactgttccttcatggtcttttctgcagtc
acgtctgtcgacacgtgtgatcagatatcgcggccgtcactagagtcatccgacgagtcaggaagttcataacagaaggtaccaac
cccagaccctggcccacgccacgcctacaattcaagtaatttagaccctcaacagaagcctgaacacgtccacagagggcaggcaactcgcccagctgatctc
cgcagtcaacaaattgaccatgccaagacccaaagaacgaccaaaagaagcaaaacaaccaccaaagaagccggtcaaagaggaggaaccaggcgtaggga
ggcgccgcaaagaccgaccaaaagaacaaaagaaccacacaaagaaagccggtcaaagaagatgatggctacgcatgcctggtgggggataaag
gagaatgtgcatgaaaaattgaaaattgattgcatcttcgaagtcgatctcgaacaatgcgatctggctaaactggccttaagcggtcgtctaaatacgatcttgaatgtgc
taatgaaaccagcacatgtgaaggaacatatcgacaatgccgatctggctaaactggccttaagcggtcgtctaaatacgatcttgaatgtgc
acagataccggtgcacatgaagtctgatgcctcgaagtttaccacgagcaagcgaggggactactaaactggcatcacggagcagtgcagt
attcaggaggccggttcactatcccgacggtcaggcaagcaggaagtgccccgcacgacctctccgtggtgacgtggaacaacatcgtcacaaaattaccctg
gccatcgtcctaggagggccaacgaagagtggcccgcacgacctctccgtggtgacgtggaacaacatcgtcacaaaattaccctg
agggagccgaagagttggagcctgccctcccgctcttgttgccttgagaacgtgatgcttgaggacaacgtgatgagcaacgtgatgagccgatacaccatcagctactaaaagcatcgctact
ctacgaaaaggaaccggaaaagcaccttgccatgttgaggacaacgtgatgagcaacgtgatgagccgatacaccagctactaaaagcatcgctact
tgctctcccaccgccaaagacgcagtactaaggacacatttaatgtctataaagcaccacaaagaccatatctagtcattgtcctgactgcggag
aagggcattcgtgccacagccctatgccattggagcgcaagctgacccagtgccatatagcataccgccatagcgacttcttctcgccgatccgcaagcgcgaagccgagccgagccgattgctt
gggataaagacagatgacaccgtgcacagatcagccacgattgaccaagctgcgtatatgatatagccatacgccgaagccgagccgagccgattgctt
gtaaggacttcagcaccggcgcagaaagatcagccacacatgcacaccccgttccatcatgaaccacctgtgataggtaggagaggttccactctgacca
tacggacagcagaagatcagcaatcagccacacatgcacaccccgttccatcatgaaccacctgtgataggtaggagaggttccactctgacca
caacatgtaaagataagagttacctgcagcacgtgcagagccactgtcagagccactgtcactgctgaggagataagagtgcatatgcccccagatactcc FIG. 7B (continued)

tgaccgcacgctgatgacgcagcagtctggcaacgtgaagatcacagtaatgggcagacggtgcgtacaagtgcaactgcggtggctca
aacgagggactgacaaccacagacaaagtgatcaataactgatcatgccatgctgcagtcagtcactaatcacaagaattggcaat
acaactccctttagtccgcgcaacgctgaactcggggaccgtaaaggaaagatccacatccattccatgcaaacgtgacttgcaga
gtgccaaaagcaagaaaccctacagtaacttacgagaaaaaaccaagtcaccatgctgtgtatcctgaccatccgacactcttgtcttaccgta
acatgggacaggaaccaaattaccacgagagagtgggtgacacaagaaggaggttaccttgaccgtgcctactgagggtctgaggtca
cttggggcaacaacgaaccatacaagtactggccgcagatgtctacgaacggtactgctcatgtcactcaccacatgagataatcttgactattat
gagctgtacccactactgactgtagtcattgtgcgttgcctgtcgttcgtctgtgcttctgtcgatgtgggcacagcagtgggaatgtgtgtgcgcac
ggcgcagatgcattacaccatatgaattaacacaggagcactgttccctcctgctcagcctgtatgctgcgtcagaacgaccaaggcgg
ccacatattacgaggctgcggcatatctatgaacgaacagcagccctgttctgttgcaggctcttatcccgctgccgccttgatcgtcctgt
gcaactgtctgaaactcttgccatgctgcttaagacctgtgtaagagaccgtataagagactcttgtcaacagaccggttacagccccatggtgttggagatggagctaca
gtaacagtgatcccgaacacggtgggagtaccgtataagagactcttgtcaacagaccggttacagccccatggtgttggagatggagctaca
atcagtcacctggaaccaacactgctcacttgactacagctgcgagtacacaagtgtcatccctccgtacgtgaagtgctgtggtacag
cagagtgcaagagcaagagctaccagagactacagctgcaaggtctttactgagtctaccatttatgtggggggcgcctactgcttttgcga
cgccgaaaatacgcaattgagcgaggcacatgtagagaaatctgaatctgcaaaacagagttgcatcggcctaacggtgaccatgcgtaacgtgaccagtaagga
tcgggtcggcgaagctccggccgtccttaccaagaaaacaacattaccgtagctgcctacgcaaggtgaccatgcgtaacgtgaccagtaagga
cgccaagtttgtcgtgggccaatgtcctccgcctgacaattggtgactacagcaattcaaagtgtaaaggcgactgtacaacatgaactac
ccaccttttggcgcaggaagaccaggacaatttggtgactaccaaagtgctaccatctcaggcaccatctggctaaattgctgaaggaacgtttatgccaactcagttggta
ctacagaggccagcagcacgtacatgtgccagattgccagaaaaccgtaagagctgtaagtgctgtgggaacataccaattccatcgacat
acagcacacgcaccgttcggttgccgatgtgccagattgccagaaaaccgtaagagctgtaagtgctgtgggaacataccaattccatcgacat
accggatgcggcttactagggtttgtcgatgcacctgtcctgtaacgacatgtcatgtcatgcgaagtaccagccgcttaccattcgagaagccgacgta
gcgtcgccatcatcaaatatacacaggctagcaagaaagtaaatgtcagtacattcgatgaccaacgcgccagtttgcgtgcaagtgctccacacaagtaca
gaagtagagggaactcccagctgccaccctccaaagaccacatagtcaattacccagccatcacacaccagcccttgggtcaggatatccaaacg
ctgcgcagccgcatgcgaagatttcggtgcagaagattacgggagaggagtaggattaattgttgctgctgccttaatttaattggtgctgtgtatgcgtgcgtgcgtgtcgttgtcgttagcagac
gcaatgctcttggtgtgcagaagattacgggagaggagtaggattaattgttgctgctgccttaatttaattggtgctgtgtatgcgtgcgtgcgtgtcgttgtcgttagcagac
actaatgaggatcagatctgtctgtccttctagttgccagccatcgttgtttgccctccccgtgccttccttgacctgaagtgccactccc
actgtccttcctttccttcctaaataatgaggaattgcatcgattgtgagtagtagtcattgctcattctattctgagtagtaggtcattctattctgagtggcaggcaaggg FIG. 7B (continued)

ggaggattgggaagacaatagcaggcatgctggggatgcggtgggctctatgggtaccaggtgctgaagaattgaccggttcctctggg
ccagaagaagcaggcacatcccctctgtgacacacctgtccacctggttcttagttcagccactcataggacactcatagct
caggaggctccgccttcaatccaccgctaaagtacttggagcggtctccctcatcagcccaccaaaccaaactagcctccaag
agtgggaagaagaattaaagcaagataggctattaagtgcagaggagagaaatgcctcaacatgtgaggaagtaatgagagaaatcata
gaattttaaggccatgattaaggccatcatgcgcttaatcttccgcttcctcgctactgactcgctgcctcggtcgctcggcgagcggt
atcagctcactcaaaggcgtaatacggttatccacagaatcaggggataacgcaggaaaagaacatgtgagcaaaaggccagcaaaag
gccaggaaccgtaaaaaggccgcgttgctggcgttttttccataggctccgcccccctgacgagcatcacaaaaatgacgctcaagtcagag
gtggcgaaacccgacagactataaagatacccaggcgtttccccctggaagctccctcgtgcgctctcctgttcgaccctgccgcttaccgga
tacctgtccgcctttctccttcggaagcgtggcgctttctcatagctcacgctgtaggtatctcagttcgtgtaggtcgttcgctccaagctggc
tgtgtgcacgaaccccccgttcagccgacccgctgcgccttatccggtaactatcgtcttgagtcaacccggtaagacacgacttatcgccact
ggcagcagccactggtaacaggattagcagagcgaggtatgtaggcggtgctacagagttcttgaagtggtggcctaactacggctacacta
gaagaacagtatttggtatctgcgctctgctgaagccagttaccttcggaaaaagagttggtagctcttgatccgccaaaacaaaccaccgctgg
tagcggtggtttttttgtttgcaagcagcagattacgcgcagaaaaaaggatctcaagaagatcatcttgatctttctacgggtctgacgctcagt
ggaacgaaaactcacgttaagggattttggtcatgagattatcaaaatgaagttttaaattaaaaatgaagttttaaatcaat
ctaagtatatgagtaaacttggtctgacagttaccaatgcttaatcagtgaggcacctatctcagcgatctgtctatttcgttcatccatagttgc
ctgactcgggggggggggcctgagtgctgaggtgctgaggcgtctgcctcgtgaagaagtggtgctgactactaccaggcccatcatccagccaga
aagtgaggagccacggttgatgagagagctttgttgaggtggaccagttgtaggtgcttgaacttgtctttgccacgaacggtcgcgttgtcggg
aagatgcgtgatcgatcttcaactcagcaaaagttcgatttattcaacaagccgcgtccgtcaagtcagcgtaatgctgccagtgttac
aaccaattaaccaattctgattagaagagaagaactcatcgagcatcaatgaaactgcaattattcatatcagattatcaataccatattttgaaaaa
gccgtttctgtaatgaagaagagaaactcaccgaggcagttccataggatgcaagatcgtatcgtctgcgattccgactcgtccaacatc
aatacaacctattaattcccctcgtcaaaaataaggttatcaagtgagaaatcaccatgagtgacgactgaatcggtgagaatgccaaaag
cttatgcatttctttccagacttgttcaacaggccagcattacgctgtccagctccatcaaaatcactcgcatcaaccaaccgttattcattcgtgatcgc
ctgagcgagacgaaatacgcgatcgctgttaaaggacaattacaaacaggaatcgaatcaaccgcgcaggaacactgccagcgcat
caacaatatttcacctgaatcaggatattcttaataccctggaatgctgtttccggatcgcagtttagtcgaccatcatcatcgtaacatcattggcaacatcaggagt
acggataaaatgcttgatgtcggaagaggcataaaattccgtcagccagtttagtcgaccatcatcatcgtaacatcattggcaacgctaccttt
gccatgtttcagaaacaactctggcgcatcgggcttcccatacaatcgatagattgtcgcacctgattgcccgacattatcgcgagccattata FIG. 7B (continued)

cccatataatcagcatccatgttggaattaatcgcggcctcgagcaagacgtttccgttgaatatggctcataacaccccttgtattactgtttat
gtaagcagacagttttattgttcatgatgatatattttatctgtgcaatgtaacatcagagatttgagacacaacgtggctttcccccccccatt
attgaagcatttatcaggttattgtctcatgagcggatacatatttgaatgtattagaaaataaacaaatagggggttccgcgcacatttccccg
aaagtgccacctgacgtcaagaaaccattattatcatgacattaacctataaaaatagcgtatcacgaggccctttcgtc

FIG. 8B

SEQ ID NO: 3
Insert C-E3-E2-6K-E1 (strain OPY-1)

atggagttcatccaaccaaacttttacaatagaggtaccagcctgacctcgcgccctactatccaagtcatcaggcccagac
cgcgccctcagaggcaagctgggcaacttgccagctgatctcagcagttaataactgacaatgcgcggtaccacacagaagccac
gcaggaatcggaagaataagaagcaaaagcaaaacaacagcgccacaaaacaacaaatcaaaagaagcagccacctaaaaa
gaaaccggctcaaaagaaaaagaagaagccggtcgtgcctggtgggggacaaagtaatgaaaccagcacacgtaaagggaccatcgataacgcggacctg
aaggtaagtaacagttacgcgtgctggtggggacaaagtaatgaaaccagcacacgtaaagggaccatcgataacgcggacctg
gccaaactggccttttaagcggtcatcaagtatgaccttgaatgcgcgcagataccggtgcacatgaagtccgacgcttcgaagttcaccatg
agaaaccggagggtactacaactggcacacgagcagtacagtactcaggaggccggttcaccatcctacaggtgctgcaaacca
ggggacagcggcagaccgatcttcgacaacaagggacggtggtggcagtacacgcgtgtggtggccatagtcttaggaggagtctaatgaaggagccgtacagccctc
tcggtgggtgacctggaataagacattgtcactaaaatcaccccgaggggggccgaagatcttgagtcttgccatccagttatgtcctgttgg
caaacaccagttccctgtccagcccctgcacgctgctacaagcatccttaacatgttccccacgcagcgacgcagcaaggacaacttcaatgt
cgtcatgagacctggtactatcagctgctacaagacaatctactactagttagctactgtccgactgtggagaaggcactcgtgcatagtccgtagcactagaacgcatcagaa
atgaagcgacagacgggacgctgaaaatcaggtctccttgcaaatcgaataaagacgatgacagccacgattgaccaagctcgtt
atatggacaaccacatgccagcagacagaggggacagcagaagcagcagcggctatttgtaagaacatcagcagcccgtgacgattactgaacaatgggac
acttcatcctggccgatgtccaaaagggaaaatctgacgtgggattcactgacagtaggaagattagtcactcatgtacgcaccattca
ccacgaccctcctgataggtcggaagatagaggtaccacatgccccccagacacacccctgatcgcacattaatgtcacaacagtccgcaacgtaaagatc
gccgcaactaccgagagagataagaggtaccacatgccccccagacacacccctgatcgcacattaatgtcacaacagtccgcaacgtaaagatc
acagtcaatgccgagacggtgcgtgccagagcggtgcgtacaagtgaattgcgtggcgtacaagtgaattgcgtgtattgcgttaattgcgttaattgcgttaattgcgttaattgcgttaattggtcaaatgaaggactaacaactacagacaagtgatataactgca
agttgatcaatgtcatgccgggtcaccaatcacaaaagtgcagtataactccctgttccgctaatgctgaacttgggaccgaa
aaggaaaaattcacatccgtttccgctggcaaatgtaacatgcaggtgctaaagcaaggtaaccccacgtgacgtacgggaaaaacc
aagtcatcatgtctactgtatcctgaccaccaacactcgtcctaccggaatatgggagaagaacaaatcaagaagagtggtgatgc
ataagaaggaagtcgtgctaaccgtgccactgaggtcacgtgggcaacaacgagccgtataagtattattggccagttatct
acaaacgtacagccccatggcagcgggatgtcatgtgcacgacgcagatgcatcaccgtgactgcactgtagtagtgtcagtggccacg
ttcatactcctgtcgatgtgggttgggtatggcagcgggatgtcatgtgcacgacgcagatgcatcaccgtgactgaactgtagtagtgtcagtggccacg

FIG. 8B (continued)

acgtcccttcctgcttagcctaatatgtgcatcagaacagctaaagcggccacataccaagagaggctgcgatataccttgtggaacgagcag
caacctttgttttggctacaagcccttattccgctggcagccctgattgttctatgcaactgtctgagactcttaccatgctgctgtaaaacgttggctt
ttagccgtaatgagcgtcggtgccacactgttgagcgcgtacgaacagtaacactgtcagtcactttggagccaacactgccttgattacatcacgtgcg
agtcaatagaccggctacagccccatgtatggagatggaactactgtcagtcacttggagccaacactatccttgattacatcacgtgcg
agtacaaaacgtcatccgtccgtacgtaagtgctgctgcgctacgtgaagtgcaaggacagagagacaaaaaacctacctgactacagctaaggtc
ttcaccggcgtctaccattatgtggggcggcgcctactgtctctgcgacgtgaaaacacgcagttgagcgaagcacgtggagaagtcc
gaatcatgcaaaacagaatttgcatcagcatacagggctcatacacgggtcataagcgtcctaagctccgcgtcctttaccaaggaaataacatc
actgtaactgcctatgcaaacggcgaccatgccgtcacagttaaggacgccaaattcattgtggggcaaatgtcttcagcctggacaccttcg
acaacaaaattgtggtgtacaaaggtgacgtctataacaatgaactaaagagacgtctatgctaataacacaacgactaccgctctgaagagacacacaaccgt
agtcgcacacctgagagtaagacgtaaagacgtctatgctaataacaatgaactactgcagagacccggctgtggtgactgtacagtgccatactctcag
gcaccatctggcttaagtattggctaaaagaacatgccccatctccatcgacatacggaagcggcctgccatttattaaatatgcgacgcgccctcttaa
aagagcggtgaactgcgccgtaggaacatgccaccattcctcagacttgggggcgtgccattattaaatatgcgacgcgccaagaaaggcaagt
cggacatgtcgtgccagcctgatgactaaccgctcactattggggaagcgtgagatagaagttgcagcgaagaagttctcagctgcaaatctttctgacggcc
gtgcggtgcattcgatccgaattccgctacaagtctgttctacacaagtacactgtcagccgagtgcagcgccgatgtcatgggtcatgggtgcagaagatcacggaggtgtgggactgttg
ttagcagccgcgaattccgctacaagtctgttctacacaagtacactgtcagccgagtgcagcgccgatgtcatgggtcatgggtgcagaagatcacggaggtgtgggactgttg
ccggcgtcacataccacctcgggtccaggacatccgcggtccaggacatccgcggctatgtcgtgcgttcagcaggcac
ttgctgttgccgcactgattctaatcgtgtcgtcgttcgttcagcaggcac

FIG. 8C

SEQ ID NO: 4
CMV/R C-E3-E2-6K-E1 strain OPY-1 tcgcgcgtttcggtcggtgatgacggtgaaaacctctgacacat

FIG. 8C (continued)

gttccatagtaacgccaataggggacttccattgactgcgtcaatggtgtggagtatttacgtggtaaactgcccacttggcagtacatcaagtgtatcat
atgccaagtacgcccctattgacgtcaatgacgtaaatgcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctccaccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgtttgac
ctccatagaagacaccgggaccgatcagccgatcctccatcttcccatcctctcccttcacgcgccgccctaccgaggccgcatccacgc
cggttgagtcgcgttctgccgcctccccgcctgtggtgcctccctgaactgctgcgtccgcgtcctaggtaagtttaaagctcagtcgagaccgggcctt
tgtccggcgctcctttggagcctactagactcagcgctctccacgcttgcctgacctctgtctcaactctagttaacggtggagggcagt
gtagtctgagcagtactgttgctgccgcgcgcaccagacataatagctgacagactacaacagactgttctttccatggtctttctgcagtc
accgtcgtcgacacgtgtgatcagatatcgcgggccgtcctagaacaccaggcccaagtcatcaggccaagtcatcagccccaacttttacaataggaggtaccagcc
tcgaccctggactccgcgccctactatccaagtcatcaggcccagatcatcaggcccagaagccacgcaggaatcggctgggcaactgcccagctgatctcag
cagttaataaactgacaatgcgctaccacaacaaagaagaccacgcaggaatcggctcaaaagaaaaagaagccgggcgcagagaga
cgccacaaaacaaacaaatcaaaagaagcagccacctaaaaagaaaaacggctcaaaagaaaaagaagccgggcgcagagaga
ggatgtgcatgaaatgcgaaaatgattgtatttcgaagtcaagcacaggttacgcgtgctgcgtgtggggacaaagta
atgaaaccagcacacgtaaaggggacaaatcgataacgcggaacctggccaaactggcctttaagcggtcatctaagtatgacctgaatgcgc
gcagataccccgtgcacatgaagtcgacgcttcgaagttcaccatgagaaaccagggacgcaccagagcggcagcaccaccgagcagtaca
gtactcaggaggccggttcaccatccctacaggtgctgccaaaccagggacgcagaccgatcttgacaacaaggagcgcgtgggt
ggccatagtcttaggaggagctaatgaaggagccccagttatgtgcctgttgcaaccaccaggtcccccagccccttgcacgcctgctg
agggggcgaagagttggagttcttgccatccagttcttgagggacaacgtcatgagaccttgaggacaactgtctataaagccacaagcatcttaacat
ctacgaaaaggaaccggaggaaacccctacgcatgcttgaggacaagcatgtctataaagccacaagcatcttcccgactgtga
gttctcccaccgccagcgaccgcagcaccaaggacaaacttcaatgtctataaagccacaagcaccatcacgatatactcaagtctcactgtga
gaaggcactcgtgccatagtccgtagcactgagacttcatcgatgaaatgaaagcgaacacacggggacgctgaaaatcaggtctccttgcaa
atcggaataaagacgatgacagccacgattgaccaagctgccgttatgtgacaacacatggacactccatctggccctgtccatgtcaaagggaaactctgacggtgg
atttgaagaacatcagcacccgtgactagttactgaacatggaacactccatctggccctgtccatgtcaaagggaaactctgacggtgg
attcactgacagtaggagatagttactcatgtacgcaccccctctgataggtcggaaaattccattcccgaccgc
agcacggtaagagctaccttgcacgtacggttcagcagcgtcagagcaccgccaactaccgaggagtagagtgaggttacatagaggttacatgcccccagacacc FIG. 8C (continued)

cctgatcgcacattaatgtcacaacagtccggcaacgtaaagatcacagtcaatggccagacggtgcggtacaagtgtaattgcggtggctca
aatgaaggactaacaactacagacaaagtgattaataactgcaaggttgatcaagtgcgcggtcaccaatcacaaaaagtggcagt
ataactcccctcgtcccgcgtaatgctgaacttggggaccgaaaaagaaaaattcacatccgtttccgctgcaaatgtaacatgcagggt
gcctaaagcaaggaaccaccgtgactacggacgaaaaaaccaagtcatcatgctactgatcctgaccaccaactctgtcctaccgg
aatatgggagaagaaccaaactatcaagaagagtgggtgatgcataagaagaagtcgtgctaaccgtccgactgaaggctgaggtc
acgtggggcaacaacgagcgtataagtattggccgcagttatctacaaacggtacagccacccgcatgagataattctgtattat
atgagctgtacccactactgactgtagtagttgtgtcagtggccacgttcatactcctgtcgatggtgggtatggcagcggggatgtcatgtgtgc
acgacgcagatgcatcacacgtatgaactgacacaggagctgagcagcagcaacctttgttttgctacaagccctattccgctgcagcctgattgtct
ggccacatacccaagaggctgcgatatacctgtggaacgagcagcagcaacgttggttttttagccgtaatgagcgtcggtgccacactgtgagccgctgaaca
atgcaactgtctgagactcttaccatgctgctgtaaacgttggttttttagccgtaatgagcgtcggtgccacactgtgagccgctgaaca
cgtaacagtgatccgaacacgtgggagtaccgtataagacctgctaatagacctgtcaatagaccgtcatcccgctccgaagtctccactgcttctgcga
gtcagtcactttggagccaacactatgctgattacatcacgtgcgagtacaaaccgtcatcccgtccgaagtctgcgtaagtgctgcggtacag
cagagtgcaaggacaaaaaaccacctgactacagtcgtaaggtcttcaccggctctaccatttatgtggggcgctactgctttctgcga
cgctgaaaacacgcagttgagcgaagcacacgtggagcaagaagtccgaatcatgcaaaacagaattgcatcagcatacagggctcatacccgc
atctgcatcagctaagctccggtccgtccttaccaagaaaataacatcactgtaactgcctatgcaaacgccgaccatgcgtcacagttaaggac
gccaaattcattgtgggccaatgtcttcagcctgcacaatttgcgatatccaaagtgcacactgagagtaaagacgtctatgctaatacacaactggtact
gccctttgccgcaggaagaccaggacaatttgcgatatccaaagtgcacactgagagtaaagacgtctatgctaatacacaactggtact
gcagagaccggtgctggtacacgtggtacgtgccaaatagcaacaaaaccggtaagagcggtaactgcgccgtaggaaacatgccatctccatcgacata
gcacacagcacatttgctgccaccccgaaggaacacacatagccacacctcggtcaggacatctccgctacgcga
ccggaagcgcgccttcactaggtgcgtgacgcgccccctcttttaacgacgcaagacaagcaagtgcgtcatcagcagccgtcactattcgggaagctgagatag
gcgtcgccattaaatatcagccagcaagaaagcaagtgcgtcatcagcagccgtcactattcgggaagctgagatag
aagttgaaggaattctcagtcgcaaatctctttctcagacggcctttagccagccgaatccgctttagccagccgaattccgaaaatccgcgaattccgctgttcacaagtacactgtg
cagccgagtgcaccccgaaggacacatagccacacctcggtcaggacatctccgctacgcga
tgtcatgggtgcagaatcacggaggtggggactgttggtttgttgtctgccgactgattctaatcgtggtgtctatgcgtgtcgtttcagcaggca
ctaatgaggatccagatctgtctgtcagttgccagcatcgtttgccctctccccgtgccttcttgaccctgaagtgccactccaa
ctgccttttcctaataaaatgaggaaattgcatcgcattgtcgagtagttcattctcgtgagtagttcattcttggggtgggttgggtcaggacagcaagggg

FIG. 8C (continued)

```
gaggattgggaagacaatagcaggcatgctggggatgcggtgggctctatgggtaccagtggtgctgaagaattgacccggttcctcctggc
cagaagaaagcaggcacatcccctctctgtgacacacccctgtccacgtccagtgttcttagttccagcccactataggacactcatagctc
aggagggctccgccttcaatccaccgctaaagtacttggagcggtctctccctccatcagccaccaaaccaaactagcctccaaga
gtgggaagaaattaaagcaagataggctattaagtgcagagggagagaaaatgcctccaacatgtgaggaagtaatgagagaaatcatag
aatttaaggccatgattttaaggccatcatgcggccttaatcttccgcttcctcgctcactgactcgctgcctggtcgttcggctgcggagcggta
tcagctcactcaaaggcgtaatacggttatccacagaatcaggggatacgcaggaagaacatgtgagcaaaggccagcaaaaggc
caggaaccgtaaaaaggccgcgttgctggcgtttttccataggctccgccccccctgacgagcatcacaaaaatcgacgctcaagtcagaggt
ggcgaaacccgacagactataaagatacaccaggcgtttccccctggaagctccctcgtgcgctctcctgttccgaccctgccgcttaccggata
cctgtccgcctttctcccttcggggaagcgtggcgcttttctcatagctcacgctgtaggtatctcagttcggtgtaggtcgttcgtcaagctggcgctg
tgtgcacgaaccccccgttcagccccgaccgctgcgccttatccggtaactatcgtcttgagtccaacccggtaagacacgacttatcgccactg
gcagcagccactggtaacaggattagcagagcgaggtatgtaggcggtgctacagagttcttgaagtggtggcctaactacggctacactag
aagaacagtatttggtatctgcgctctgctgaagccagttaccttcggaaaaagagttggtagctcttgatcgccaaaacaaccacgctggt
agcggtggttttttttgtttgcaagcagcagattacgcgcagaaaaaagatctcaagaagatcctttgatctttctacgggctgacgctcagt
ggaacgaaactcacgttaaggattggtctgacagttaacatgctacaagttaatcagtgaggcacctatctcagcgatctgtctatttcgttcatccatagttgc
ctgactcggggggggggccccctgcgtgaagaaggttgctgactaccatgcccatcatccaggccaga
aagtgaagggccacggttgatgagagctttgttgaggtggaccagttgttaggtcgttgaactttgacgttgcttgccacgaacgtcgcgttgtcgg
aagatgcgtgatcgatccttcaactcagcaaaagttcgattttattcagcatcaaaatgaaactcaatttattcatcaggattatccatatttgaaaaa
accaattaaccaattctgattagaagaaaactcatgagcatcagcagggcttccatatccgaggcagcagttccataggatcgcaagatcctgtatccggtcttgcagattccgactcgtccaacatc
gccgttctgaatgaaggagaaactcaccgaggcagcagttccataggttatcaagtgaagaaataaccatgagtgacgactaacatccgtgagaatggcaaaag
aatacaaccctattaatttcccctgtcaaaaataagttcaacaggccaccagccattacgctcgtcatcaaaatcactcgcatcaacaaaccgttcattcattcgttgccgc
cttatgcatttcttcagactgttcaacaggcgctgttaaaggacaatcaaacaggaatcaacggcgcaggaacactgccagcat
ctgagcgagacgaaatacgatcgctgttaaactcttctaatacctgaatgctgtttccgggatgcagttggttgagtaaccatgcatcatcaggagt
caacaatatttcacctgaatcaggatattttcaataaatcctgttagtctgaaccatttaaaatcttgttgatgttcgtcgagcagttagtctgaccatctcatctaacatcattggcaacgctaccttt
acggataaaatgcttgatgtcggaagaggcataaatccgtcaggcagttagtgcataaattccgtgattagtttgtcgaccatctcatctaacatcattggcaacgctaccttt
gccatgtttcagaacaactctggcgcatcgggcttcccatacaacaatcgatagattgtcgcacctgatttgcgaccgattatgcgaccgattatcgcgagccatttata
```

FIG. 8C (continued)

cccatataatcagcatccatgttggaatttaatcgcggcctcgagcaagacgtttcccgttgaatatggctcataacaccccttgtattactgtttat
gtaagcagacagtttattgttcatgatgatatattttatcttgtcaatgtaacatcagagatttgagacacaacgtggctttcccccccccatt
attgaagcatttatcagggttattgtctcatgagcggatacatatttgaatgtattagaaaaataaacaaataggggttccgcgcacatttcccg
aaaagtgccacctgacgtctaagaaaccattattatcatgacattaacctataaaaataggcgtatcacgaggccctttcgtc

SEQ ID NO: 5 tcgccgtttcgtgatgacggtgaaaacctgacacatgcagctcccggagacggtcacagcttgtctgtaagcggatgccggga
gcagacaagcccgtcaggcgcgtcagccgcgggttggcggtgttggcggtgcgggtcgggggtggcttaactatgcggcatcagagcagattgtactg
agagtgcaccatatgcggtgtgaataccgcacagatgcgtaaggagagaaaaataccgcatcagattgcctattggcctatcgttg
tatccatatcataatgtacattattggctcatgtccaacattaccgccatgttgacattgattattgactagttattaatagtaatcaatta
cgggtcattagttcatagccatatagtgttccgcatataactttaccgttaacataactttacgttaaatgccctggctgaccgcccaacgaccca
cgcccattgacgtcaataatgacgtatgttcccatagtaacgccaataggaatttccattgacgtcaatgggtggagtattacgtaaa
ctgcccacttggcagtacatcaagtgtatcatatgccaagtacgcccctattgacgtcaatgacggtaaatggcccgcctggcattatg
cccagtacatgaccttatgggactttcctactggcagtacatctacgtattagtcatcgtattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatcagcctcc
atcggctctgcatctctccttcacgcgtccgccgccgtctaggtaagttaaagctcaggtcgagaccggatccggcctcgcgctccgcc
tgtggtgcctcctgaactgcgtccgccgcgttctaggtaagttaacgctgcctgccgtcaactctagttaacagactgttccttctgcagtgact
acgttagactgccgccgcccaccaccatgagactactagctcgagaagcagcgctctccatgggtctcgccgatgcctcgtccgtcg
acacgtgatcaatgaattacatactacgcagagacgttctacggccgcctatgcgtcctcgccgatgccaagccgcaggccgaggatcaaatgcaacaacttattgctgcgtcaat
tccaccaccgtatactatcaccaccgcgaacacctgacaacaagcgaaggaaacgtcaatcaaacaacaaagagaaaacag
acgctgctataaggcagaatgcaccggaaactgcgaaaacaaagagaaaacagaaccagccaacagccaagctaagaaacggaaaaccggg
caagagaaagaaatgcatgaagaatagagaaatgattgcatattcgaggtcaaggctcaaggcaaggtcactggtacgcctgcct
ggtaggagataaagttgatgaaacagccaccgtgaaagagagtcatagataaccctgaaggtccaagctagctttaagaaatcgagc
aagtatgaccttgagtgtgcagtacaatcctgtccacataagtcaagtcaggagatatttacccacgagaaaccagaaggaaggacactaca
actggcaccatgcgtgcagtacaatacctgaacggtcgaagatttaccatcccgacaagtgctgggaagccaaggacaggactaggcctg
atcttgaccaacaaggtcgcgtagtggcgtagtggccattgtctgtggggaggaagccaaggaagtggagtgcgaggacggctctacgcgttgtcacctgg
aacaaagacatggttacgcctgcaccatgcgccctgctgctgtatgaaaagacgcagaggtgaggacccctgaggtctgaggacaacgtc
actttcgattgcagcctgacctgcatcaccccagaaggacccctgctgctgtatgaaaagacgcagaggtgcacccgaggatgctgaggacaacgtc
gataaccccggatactacgatcctgctgctgcaacgcattgtgacgccgcagcagtcgccccgcagcggcgtcccaggggctaactgagga FIG. 9B (continued)

```
ctacgaggcttataaactcactaagcctacatagcctatgtctgactgcggaacggacagtttgctacagcccgatagctatga
gagagtcaggccgagccatccgaccggaatgctcaagatacagatctctgcaaatagccctgcaggtgacggagctcatgcgt
ggacgaaatcagatacatgaaaggcacgacggtggaggaacacagaggaactcactggagtgttcaccaccggagagtgtac
ggtccatggcaccatgggcatttcatcgtagctacatgccccgaaggtgactcctgacagtggcgtcgttgacaaacataaggtca
ggcacgcttgcaggatagcataacaagcatcgtgtccgtattggcagaagcactttacggtacggccacatcatggagtagaatt
gccatgcaccacgtacgccatgagaacatcagtcactaccgaagaaatagaaatgcacgtggccatgacgtgcccgacaacactt
tctatccaagaccgagaaaataagtgaagataacgccaaaggaaaagtcattgctcacaactgcacgtgtgggtcaaggagagcggt
gtcacaaagacaaaagaattgacaactgcagtgccacaccatggtgaccgccccacgataagtgcagtttaact
ctcctatgtccctaggcaggtcaggcaacatcccgggcaaagaaggaaagaatcacactgcagttcatcgagcaactctacgtcagagttccgttg
gcgccttaccgaacaccatccgtgagactgtgagactgtggcacactgacgactaaggttcagcacgagatgccgcacgaaatctctcat
tcggagagaaaccagaaaccacacagaaatggatatcagaaagttgcaacgtacactccccgtaccgagagaggtgagtac
acatgggcaatcacgccccctgtgagactgtgagactgtggcacactgacgactaaggttcagcacgagatgccgcacgaaatctctcat
attactatggattgtaccctgccacgacggttgcagtgtgcgtggggtctagcgtgtgatcttgctgctcgtgtcccgctcctgcct
gtgccgtcagccgaggaaataagtgctgaccccgtacgcgttgacgcaggagccgtgttgccgtcacttgagcttagcttgtgcg
cccccagagccaaggcgaaggccgaaacgtttgcggagacagcggcatatctatggacgagaaccagacgacggtgttctgatgcaattcgca
atcccgtagcatgcttatgatagtgacatatgcctgccgcccactgatgctgtcgtgaaccgcggtcggattccgtacagagccatgagacagacc
ggaatgggggcgaccagcgtatgagcaaggcgtataggagtctccactagcctagagcctcgcccctgagagccgctccgagtaacaa
agggtctctccattaacgctccatatggaggtagtctccactagcctagagcctcgcccctgagagcctccgagtagtcactgcgagtacaa
aacggtgctgcgtcgcctaaggtcacctgtgcggcatgcggagtgtgcacaccagcaaaaaagcggacttcaatgtaaagctac
acgggcgctaccccttttgtgggcgtggtgcctactgctttgcaattcgaaaaacactcagctgagcgaagcttatgttgagcggagc
gaggtgtgcaaacgatcacgcagcggcgctaccagacggagagagcaccattgaaggctaaaatcagagtgacctacggtccacg
aacggacgcggtgaggcgtttgaacgggttgtcaacgagcagagcaccgagagctaccagcgagagtaacgatgcgataggtccacccgc
gtggagcccctttgacccaaagatcgtcgtctacaagacgagttcagcgagtaaacgatgtgtacgcaatactgcactgaagctgctcgcccatcgccgc
agattggggacttacagacgagcaggaaccoccgtaagggcctgagtgcgaggtgccattgaatattgctaaaagaaaaaaggggacgcattgaaccacaaggctccttt
acggtcacgttccatatccagacgagcagccgcgtccggtttaagtattgctaaaagaaaaaaggggacgcattgaaccacaaggctcctt
cggctgcatcatcaagacgaaccccgtaaggcgtaaccggtcacggtcacacgagagtaccagtgctcgcagtgctctagacattccgacgc
ttacacgcatagtcgacgaccacatgctaaacggtcacggtaaccggtcacggcgacttgcacgcactcatcggactttgagcactt
tggtggtggaagtacaagaccgacaagtggggacgtgccgtccactcagaatccagtcccgttatgcagacgagtctgt
```

FIG. 9B (continued)

ccgtgacgatggacggccgagtacgttgcattctccaccgtcctcagcctcaccgtccttgtactgaaagtgtgcagtagcaaaacc
acttgcacagcaaagtgcgtccgccgaaggaccacgtcgtcccttttcctgccaacacaacaatgttgttccgactttccagt
actgcagtgtcttggctcaccaccactatgggcgaagctactgtgtgattgctattgggatcaccatattcttaatagttacttgcatagct
ttagtaggcaactaggcggccgctctagaccaggccctgatccagatctgctgcttctagttgccagccatcgtgtttgccctc
cccgtgccttcctgaccctggaagtgccactccactgtcttcctaataaaatgagaaattgcatcgcattgtctgagtaggtgt
cattctattctggggggtggggtggggcaggacagcaagggagagattgggaagacaatagcaggcatgctggggatgcgtgg
gctctatgggtaccagtgtcgaagaattgacccgttcctcctgggccagaaagaagcaggcacatcccctctgtgaccacac
ctgtccacgccccctggtcttagttccagccccactcatagacactcaggaagctccgcccttcaatccaccgctaaagt
actggagcggtctccctcctcatcagcccccaaactagcccaaaactagcctccaagagtgggaagaaattaaagcaagatagctat
taagtgcagaggagagaaaatgcctccaacatgtgaggaagtaatgagagaaaatcatagaatttaaggccatgattaaggccatc
atggcctaatcttccgcttcctcgctcactgactgctgcgctcgtgctgagcggtatcagctcactcaaaggcggt
aatacggttatccacagaatcagggagataacgcaggaaagaacatgtgagcaaaaggccagcaaaaggccaggaaccgtaaaaag
gccgcggttgctgcgttttccataggctccgccccctgaagctccgctgctctcgttccgaccctgccgcttaccggataccgtcc
gcctttctcccttcggaagcgtggcgctttctcatagctcacgctgtaggtatctcagttcggtgtaggtcgttcgctccaagctgggct
gtgtgcacgaacccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaactac
ggctacactagaagaacagtattggtatctgcgctctgctgaagccagttaccttcggaaaaaagagttggtagctcttgatccggcaaa
caaaccaccgctggtagcggtggtttttttgttgcaagcagcagattacgcgcagaaaaaaaggatctcaagaagatcctttgatctttt
ctacggggtctgacgctcagtggaacgaaaactcacgttaaggattttgtcatgagattatcaaaatgaagttttaaatcaatctaaagt
atatatgagtaaacttggtctgacagttaccaatgcttaatcagtgaggcacctatctc
agcgatcgtctatttcgttcatccatagttgcctgactcggggggggggggcgctgagttctgcctcgtgaagaagtgtgctgactc
ataccaggcctgaatcgccccatcatccagccagaaagtgaggcacggttgatgagagctttgttgtagggaccagttggtg
atttgaactttgctttgccacggacgtgtcgttgtcggaagatgcgttgatcgtgatcttcaactcagcaaaagttcgattattcaa
caaagccgccgtcccgtcaagtcagcagtctcgccagtgttacaaccaattaaccaattctgattagaaaaactcatcgagcatca
aatgaaactgcaattattcatacagatttcatatacccatattttgaaaaagcgttctgtaaggagaaaactcaccgaggcag
ttccataggatggcaagatcctggtctgcgattccgactcgtccaacatcaaatacaacctattaatttccctcgtcaaaataag
gttatcaagtgagaaatcaccatgagtgacgactgaatccgtgagaatggcaaaagcttatgcatttctttccagacttgttcaacaggc FIG. 9B (continued)

cagccattacgctcgtcatcaaaatcactcgcatcaaacgttattcattcgtgattgcgcctgagcgagacgaaatacgcgatcg
ctgttaaaaggacaattacaaacaggaatcgaatgcaacggcgcaggaacactgccagcgcatcaacaatatttcacctgaatcag
gatatcttctaatacctggaatgctgtttcccgsggatcgcagtggtgagtaaccatgcatcatcaggagtacggataaaatgcttgat
ggtcggaagaggcataaaatccgtcagccagttagtctgaccatctcatctgtaacatcattggcaacgctaccttgccatgttcagaa
acaactctggcgcatcgggcttcccataacaatcgatagattgtcgcacctgattgcccgacattatcgcgagcccattatactgaa
atcagcatccatgttgaattaatcgccgtcgagaagacgttcccgttgaatatgctcataacaccctgtattactgttatgta
agcagacagtttattgtcatgatatatttatcttgtgcaatgtaacatcagagatttgagacacaacgtggctttcccccccccc
cattattgaagcattatcaggtattgtctcatgagcggatacatattgaatgattagaaaaataaacaaatagggttccgcgcaca
tttccccgaaaagtgccacctgacgtctaagaaaccattattatcatgacattaaacctataaaaatggcgtatcacgaggccctttcgtc FIG. 10B (continued)

SEQ ID NO: 6 tcgccgttcggtgatgacgtgaaaactctgacacatgcagctcccggagacgtcacagcttgtctgtaagcggatgccggagcagacaagcccgtcagccgcgtcagccggttggccggtgtcggggttggccggtgtggcttaactatgcggcatcagagcagattgtactgagagtgcaccatgcggttgaaatccgtcacagatgcgtaaggagtgagaaaataccgcatcagattggccattgcccattgcatacgttgtatccatatcataatatgttacattatattggctcatgtccaacattacgcccatgttgacattgattattgactagttattaatagtaatcaattacggggtcattagttcatagcccatatatggagttccgcgttacataacttacgtaaatggcccgcctggctgaccgcccaacgacccccgcccattgacgtcaataatgacgtatgttcccatagtaacgccaataggactttccattgacgtcaatgggtggagtatttacggtaaactgcccacttggcagtacatcaagtgtatcatatgccaagtacgccccctattgacgtcaatgacggtaaatggcccgcctggcattatgcccagtacatgaccttatgggactttcctacttggcagtacatctacgtattagtcatcgctattaccatggtgatgcggttttggcagtacatcaatgggcgtggatagcggtttgactcacggggatttccaagtctccaccccattgacgtcaataatgggactttccaaaatgtcgtaacaactccgccccattgacgcaaatgggcggtaggcgtgtacggtgggaggtctatataagcagagctcgtttagtgaaccgtcagatcgcctggagacgccatccacgctgttttgacctccatagaagacaccgggaccgatccagcctccgcggccgcgatctcctcggcctctccacgcgggaaggctcttccacgaactgctcaactcagttgcctgaccctgcttcaacataactagactgcagaagttgccccttcgaaccgtcagatatgcggcttcgagagcagacactactcagcctgccggcacgtcgttgctgccgcgccagacataatgctggccgccaccatgtttccatgccaccatcagctaccctacccaacctaacactgcgtgatcagataatcgcggcctctcgaggaccagatgagccgcgtccagctggccaggtggctgcaggttgccggctgcaggtgctggacttgcccgccgcaaggtggacctcgccatgctatcgcggcctcgaactagaaaacaaaccaagaaggaaagcgccaaagaagagcaagttgaccagaaggtcccaaaccctcgaggaagacgtgctcgcgaaccagatgacggcgcggcaatcggcgcgtcttaaccggcaggtcctccagctggccaccaaccaggagaggtgaagcagatccagcctcaagatgagcacgtgtcccgtcagcgcctcggcttgaccggcaatcgcaagagagagaggagagtgagatccgtaaagcgtgccgacagagcaccttcccgtgtaccatgacgtgcatatcggcgtcgtcggctatcagttccagagtcgccgagttcatgatgtcatgggggaccagaggttaagcagccaacgcacgtgaatttgtactatttattggggggactgaaccagagcagcaaccaacgacaactcaccgacaaactcaggagttggcaacaggttgtcggtatcgtcctcgaggaggaccatccctgatgcggcacgtctctctgctgctccgtgatagtttcgataagaagccaagaagctgaagagagatcgcctacagccaatacctttgattgctccaaaccgtcctgccagattgttgttgccattactgctgaaccaaagaaggccatgactatgctgaaggactgaaagaccctgaaggactgaacctgaaatgacccgaa FIG. 10B (continued)

ctactggaccgtctcattgcctgtcaccactgccgcccgaaaaagaggcgtgtcctgccgtgccgttacgaca
cacaaattctgccgccacgcagctgcctgcctcccgtataggcgtactgccgattgtgacggaactgctcgcatagc
tatcgacgaggtggtaagtagcggtagtgaccacgtcctgcggtcgttctcaatcggagtgaccgctaaaggcggtgc
gcggggtgaaacctctcgcgatacctgggaaggacgcgtaagtttacgccgccgacaacacgcgtcggctgtgctgccaccactg
caaagtgacgtgctgcaggccatcgccactacattcgccactgccccagtggggccagagtcactgttgcggcacactgg
acggtaccccggcatcaatgccaccacgtttgaacatcaagtaacggaaagttcacaagagaacgcagcaaggccaccacctg
tccgatcgaccaagaaaatgcaccagttctccaccaccccgaagaagtccgctctatctcgttgatgtgtatgatgtctgccgact
tctgtagagatcagcaccgtggtgacatgcaacagaaagacagtgcacagtgaggtgccaccccagacgttacgtgcgaggagccgtcctaacggcgc
aggtgcaagaaccgtgccaaagagaaccgtcacccttcaccagcgtcccagcgttacgtgcgaggagccgtcctaacggcgc
cagcatcaccaggcaagccgcactcagatgtgcccactgcagtgtgccgagcgtcaagagagtgaaagcgaggattcattccgt
tcccgccagagactgcgactgcagagtgcagagtgagcatcgccccactgccatcgattacctatgaggaaagcgatgtctgctgccgcac
tgcgaaatacccgtgctctgctaactacacggaaccttggtttccatagcaacgccacatctgaatgatccaggtaagtacctgcgcc
gcatcccggtcacgcccaaggattgaactttctggtgccacacaagcgcaccgctgcactttcgtcacttctgtcattctcaggtacgcatctgg
agacgccgacgccgtacccctgggaacttctgttgccacacaagcgcgagtacgcgtggcgtttgtaggagttgcatgt
ggcctgctggccgtgccatgcatgttcgccagcaacaagggtgcggtactctctgctcgccaacacgttcaaccgaacc
caccaccattgaccgcactgactgcagcattgtctgcatccgggctcgccgcggatcaacctacctggacatcattgcctacttgt
ggaccaacagcaaagtggccttcgggctgcaatgcgcggccccgtggcctgcatgctcatcttgctgtatgtacagagctgcaaggcgtacgaacac
attgtctgcaattcttttaggggtaagggtggctcggtctggtctgctcatcctgctatgtacagagctgcaaggcgtacgaacac
accgtggtgtccaatggatccaagagccccgtcgtacgagaggtgtatgaatggagtccctgctcgtcgagcgcccatgggg
gcagtgaactttaccgtcatctcaccaactacggcctgtgaatactggaactgtgcaggagtccctgctcgagcgcccatgggg
ctgctgcacgtcagtgtccccctgttgtggggtgcggctcactgcttctgttccactgaaaacacgcagttcagcgctgtgcgtccgaccgt
cacacgaacgtgtaccccctgttgtggggtgcggctcactgcttctgttccactgaaaacacgcagttcagcgctgtgccgtgatgtg
tctgagttctgtcgctcagagacggcgcccgaggcgtcacgttcgagagggtaccagcagcgggtaccgacctcaagatcgtggctgcgccaata
gtgaagtggtgacggtccacgttacggtcacgtaccgagggtaacatcagcgactcactccggatcgcctcttacgggtccgttcg
acaaagctgactactcccgtttgaccgcaaagtacgtccgtatcggcaagagggtcataattaacgactgcctcttacggggctggcg
accaggcacactcgaagacattcagacgtacggcttcaaccaactatgtcaaaccaatgatctgtacggacatcgaatgaagtactg
cagccgactaatgcaccgcacgtggcttacacgtatacgaccctctggcttcaccccgattgtgagtttgggttgcagacgctccgaaacactca
gtgtcacagcaccacggttgtaagatcagtcagtacccgctctaaccgcgctaccccgattgtggagttgcagttgtgcgtcccatgtccatcaac
attccgacgcagcaccgcacctaatgaccacggtcacccgaaactaaagaccgaaaccttcggcctgaaatgcgtgtgcgacgtttgcgagttgcgagtacgggt FIG. 10B (continued)

```
ggactacggggcgccgccacgatcacctacgaggccacgaggctggaagtgcggatccattccctgaccaccaggatccct
ctgagaacatcagtggttgaagtagttgccggcgctaataccgtcaaaaacgaccttctctcaccacgcccgaggttacactcgaggt
agagatctgttcggcaatagtgaagtgcgccagtgcgccagtgcactccaccgaaggaacacgtagtgcagccaggcctcgccatggca
gcgacactggagctgagctacatccggggcccgcaatgcgctggccgtgaaggattgtaggaacctagtggtcctgttcctcatctt
ggccgtcacctactgcgtggtgaagaagtgccgctcaaagaaatccgatagtcaagagcgataatcagagccctggatccag
atctgctgtgccttctagttgccagccatctgtgttgccctccccgtgcctcottgaccctggaaggtgccactccactgtccttc
ctaataaaatgaggaaaattgcatcgcattgctgtctgagtaggtgtcattcttctgggggtgggtgggcaggacagcaaggggggag
gattgggaagacaatagcaggcatgctgggatgcggtggctctatgggtaccccagtgctgaagaattgaccccggtcctcctgg
gccagaaagaagcaggcacatccccttctctgtgacacaccctgttcacgcccctgttcttagtcagcccactcatagggacactc
atagctcaggagggctcgccttcaatccaccccgtaaagtacttggagcgtgtctctccctcatcagcccaccaaccaaacct
agcctccaagagtgggaagaaaattaaagcaagataggccattaagtgcagaggagaaaaatgcctccaacatgtgaggaagtaat
gagagaaatcatagagatttaaggccatgattaaggccatcaagggtaataacttccgcttcctcgtcactgactcgctgcgctcggtc
gtccggctgcggcgagcggtatcagtcactcaaaggccgtaaatacagcaggattaacgcaggaagaagaacat
gtgagcaaaaggccagcaaaagccgtaaaaggccgcgttgctggcgtttttccataggctccgccccctgacgagc
atcacaaaaatcgacgctcaagtcagaggtggcgaaacccgacagactataaagatcaccaggcgttcccccctggaagctccctcg
tgcgctctcctgttccgaccctgccgcttaccggatacctgtccgcttctcctgggaagcgtggcgctttctcatagctcacgctgt
aggtatctcagttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcagagcgaggtat
gtaggcggtgctacagagttcttgaagtggtggcctaactacggctacactagaagaacagtattggatccgctctgctgaagcca
gttaccttcggaaaaagagttggtagctcttgatccggcaaacaaaccaccgctggtagcggtggtttttttgttgcaagcagcagatta
cgcgcagaaaaaaaggatcaaaaggatcttcacctagatccttttaaattaaaatgaagttttaaatcaatctaaagtaatatgagtaaacttg
gtctgacagttaccaatgcttaatcagtgaggcacctatctcagcgatctgtctatttcgttcatccatagttgcctgactcgggggg
gggcgctgaggtctgcctgcaactgaggaaggttgctgactaccagcacctcatcaccgcccatcatccagcagaaaagtgaggag
ccacggttgatgagagctttgttgtaggtggaccagttggtgatttattcaacaaaagccgccgtccgtcaagtcagcgtaatgctgccagttaca
cgtgatctgatccttcaactcagcaaaagttcgatttattcaacaaactcatcatcaggatatcatcattactcttttgaaa
accaattaccaattctgattagtgaaggagaaaactcatcgagcagttcataggatgcaagatcggtaccgctgcaagtaccatttcgaa
aagccgtttctgtaatgaaggagaaaactcaccgaggcagttcaaggatgcaagatccttcatatggcagaatccttccttccgttcttcgtcgactcgtc
caacatcaactaacctattaattccctcgtcaaaaataaggttatcaagtgagaaatcaccatgagtgacgactgaatccggtgaga
```

FIG. 10B (continued)

atggcaaaagcttatgcattctttccagactgttcaacaggccagccattacgctcgtcatcaaaatcactcgtcatcaaccaaaccgtta
ttcattcgtgattgcgcctgagcgagcgagcgatcgctgttaaaaggacaattacaaacaggaatcgaatgcaaccggcga
ggaacactgccagcgccatcaacaatatttcacctgaatcaggatattcttctaatacctggaatgctgtttcccgggatcgcagtggt
gagtaaccatgccatcatcaggagtacggataaaatgcttgatgtgcggaagaggcataaattccgtcagccagtttagtcgaccatctc
atctgtaacatcattggcaacgctaccttgccatgtttcagaaacaactctggcgtcagggcttccatacaatcgatagattgtcgca
cctgattgcccgacattatcggagccgagccccattalaccccatataaatcagcatccatgttggaattaatcgcgggcctcgagcaagacgttt
cccgttgaatatgctcataacacccctgattactgtttatgtaagcagacagttattgttcatgatatttatcttgtgcaatgta
acatcagagatttgagacacaacgtgcctttcccccccccattattgaagcattatcaggttattgtctcatgagcggatacatatt
tgaatgtattagaaaaaaataaaacaaatagggtcccgcgcacattcccgaaaagtgccacctgacgtcaagaaaaccattattcatg
acattaacctataaaaaataggcgtatcacgaggcccttcgtc

FIG. 11A

CMV/R Getah virus VLP
8166 bp

- CMV/R Backbone
- ApaLI (178)
- CMV IE Enhancer/Promoter
- NcoI (697)
- HTLV-1 R Region/Splicing Donor
- CMV IE Splicing Acceptor
- NcoI (1317)
- PstI (1334)
- NcoI (1428)
- NcoI (1459)
- HindIII (1737)
- HindIII (1836)
- ApaLI (1890)
- ApaLI (2230)
- XmaI (2297)
- AvaI (2297)
- SmaI (2299)
- AvaI (2316)
- ApaLI (2344)
- ApaLI (3120)
- ApaLI (3172)
- Structure
- NcoI (3401)
- NcoI (4018)
- NcoI (4645)
- BamHI (5142)
- Tbgh
- ApaLI (6170)
- AvaI (6746)
- HindIII (7308)
- Kan
- XmaI (7554)
- AvaI (7554)
- SmaI (7556)
- ClaI (7737)
- AvaI (7828)

FIG. 11B

SEQ ID NO: 7 tcgcgcgtttcgttcggtgatgacggtgaaaaccctcgacacatgcagctcccggagacggtcacagcttgtctgtaagcggatgccggga
gcagacaagcccgtcagggcgtcagcggtgttggcggtgtcgggctgcttaactatgcggctgctgcatcagagcagattgtactg
agagtgcaccatatgccggtgtgaaataccgcacagatgcgtaaggagaaaatacccatcagattgctattgccattgccatttgcatacgttg
tatccatatcattatatgtacattatattggctcatgccaacattacgccatgttgacattgattattgactagttattaatagtaatcaatta
cggggtcattagttcatagcccatatatggagttccgcgttacataacttacggtaaatggcccgcctggctgaccgcccaacgaccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaaatgggcggtaggcgtgtacggtgggaggtctatataagcaga
gctcgtttagtgaaccgtcagatcgcctggagacgccatccacgctgttttgacctccatagaagacaccgggaccgatcagcctcc
atcggctctgcatctctcctcacgcgtcctgcgccgccacctacctgagttaaagctcaggtcgagacgccatccacgccgttgagtcgttctgcgctccgccgc
tgtgtgcctcctgaactgcgtccgccgtctaggtaagttaaagctcaggccttgccgaggcagtgggctctgagcct
acctagactcagccggctctccacgcttgcctgacctgcttgctcaactctagttaacggtgaggcagtagtctgagcagtact
cgttgctgccgcgcgcaccagacataagctgacagacagactgtccttccatggtcttcagtcttcgcagtcaccgtcg
acacgtgatcacaccatgaattacattccaactcaaaaccatttacggacgcgttgccgaccacgccccggctacggtccatgcg
ggtgccgatgcagccgccccaccatggtccctgaccgctgcagctgcgaaactcctgagctgcaaactccgatcgtccaacagatgccaacagatgcagctaatcag
tgcagtttctgcccgctgacgaccaagcaagacagcaaaatggcaagccgaagaaaaatccggcaaaaagccgaaaaaagcgaagctaagaa
aacgaacagcaagcaaaagaagaacgaagaacaagagaatgctccaagacgaatccgtcaaggaagaagaaccaggaaaaag
ggaacgggtcatgtgtcatgaagatgagagaacagcttcagtccgatgatagattgcatcttcgaggtcgaggtcgaggatacgcctagtcgg
gataaagtgatgaagcggccacacgtcaaaggtgatcgacaaggcgaagcttacctacaagaaatcgagcaagtat
gacctggagtgccccagatacccagtgcacatgaagtcagatgcttcaaagtacaccatgaaaaccagaagggcactacaattgg
catcacggtgcagtgcagtacagcggtgcaggtgcaggttcacaatcccgacagcgcaggtaaaccagagacagcgcgcgatct
tcgaacaaaggacacgtgttcacacgtggtcgcgtacacccagaaggaaggaaggcccaacgaagagagagagagcccaggactgcctatccgtcgtgaccctgac
caaagacaatgtcacagccccgtgtgcaccccagaaggaacagagaatgtccccgcctttgatgatgtccaacgttacattc
ccatgctcagagcccgctgcgaccctgaggccacgatgaccgtgttcctatgaaaaacaagcagaacactgagagatgttagaggacaacgtggaccgc
ccgggctactacgtcgacctgctcgagccacgatgacgtgaacaaatagcacgccaccgtcgacgtgcagtgtgacgtgcacacttcaacgtc FIG. 11B (continued)

tacaaggccacgaaaccgtatctagcgtattgcgcgactgccggagacgggcgggcagttcgttgttacagcccggtggctatagaaaaatta
gggatgaggcttccgatggcatgatgataaaatcagtcgcagcgcaaattggcatcaacaaagggaggaacacgaacacgaacaacaaa
atcagtacatcgccggtcatgcatgaaagacatgaaagagcaaaccggactcttacaagtcatactccggtgtgtgcgctattcgaggca
cgatgggccacttcatcgtggcctactgccctccaggggacgaactaaaagtccagttccagttcaagatgcagaatcgcacaccaggcct
gcaaagtcagtacaaacacgcactggccccagtacgccccagtagcgaggaagagagatcgacatgcataccccaccggatatccagacataacgttgctgtcg
acaaagtaccagcgtgactaccggcaccgacggaggaagagatcgacatgcataccccaccggatatccagacataacgttgctgtcg
cagcagtcagtaatgtaaagatcacagcaggagagaaaaaccatcagatacaactgcacgtgtgtagtgcaacgtgggcaccac
cagtagccgacaagactatcaattgtcaaaatagcacagtgccacgctggactaaccacgataagtggcagtaccacctcctcg
tttgtccctagagccgacagttgtctgcaaagagagaggtgcacgtacctttccctcgaccaactccacgctgttgacgtaccggagtcta
cgtgcaccagttgtcacatacgccgtatgaggagtgcgcttgtgggccccagtcagtgaaactgcacccagatcatccacgctgttgacgtaccggagtcta
ggagcagatccgcgccgtatgaggagtgcgcttgtgggccccagtcagtgaaactgcacccagatcatccacgctgttgacgtaccggagtcta
gatgggaaacacccaccgtcgtgcgttgtggggccccatcgccgtctcagccggtctgcagtcgtgtcgttcccggtaccactaggagtactatgct
tattactatgggctataccagcagccaccatcgccgtctcagccggtctgcagtcgtgtcgttcccggtaccactaggagtactatgct
atgttcgccactgcacgccaaagtcctgacccatacgcccctgacccctgagcgtgtccttcccgtaccactaggagtactatgct
gcgcaccacgaccgcatgcgggcgtcatttgccgggaatctatggcgtatcatggatgagaatcaaacccgtttgctgagcttgca
acgccgtcgcgccaatcatactttgtatgctgcctgaagaaccctgcttctgcgaaacgcttctttttagtgctgtgtgagcctg
ggaactccgtcgtaaaatcttacgaacacaaccgcaaacgatccgaatgtggtggattccgtaaggcttccatttgagaggaacg
gctttccccgatgacccctacagtcgaagtacttggaaccagtcctactcgcgctaaacttagagtacataactgaatacaagaa
cagtcgtgccatcacctttatcaagtgctgcgggacatcagaatgcagatccatgggcgccccgactatcaatgccagtctacac
aggagtgtaccatttatgggcgcgcatactgcttctgcgacactgagaacaccagctgagtgaagcatacgttgatagatcg
gacgtatgcaagcagaccatgccgccgctactaaaggccgcatactgccggcaaggggaaaagccaccatcgcgaatagactacgggaacct
caatcagacaacaacggcgttcgtcaacggagcgagcgtcggagcagcagttcacccactgccccactgcc
tggacgcctttcgacaacaagatcgtcgtctacaagaacgacgtctacaaccaggacttcccaccctacgggtcaggacaaccaggg
aggtttggagacatccagagcaggacggtagagagcaggcaagggtatgccaaccgctgtcaagttcaagacttcgtcggt
actgttcacgtgcttacacacacagaccccctctgcttaagtactgcaaaactggatgcttggcccaagtggcggtccactcatcgcattcactcggcggatc
ggatgcgtaatcaagaccatttatgggcgttgatgatgccacctgccgtcacaaacctggagtgccaagtggccgtgcactcatcggacacgc
gttacgcggtgattgatgccaccctgccgtcacaaacctggagtgccaagtggccgtgcactcatcgcttggcggatc
gcgactctgactttcaaaactgacaaaccgaaaatgctgtccattcattcgaacgtagccacatacgagcagaggcagcgctgtgga FIG. 11B (continued)

```
catcaaaacagatgcaagataacctgcattctctacagcatcagcatcccggcattcaagtatctgtgtcagtgccaaaacga
catgcatggcagcgtgagccgccgaagcgccacatcgtccttatgggcgagccataacaaccaagttttcctgacatgtctgg
cacggcaatgacatgcgccgctaatcagaccaggccctgagtagccgggtagccgggctaacactcgccgcagtggcagtactactatactggtgacgt
gtgtgactatgccgcgctaatcagaccaggccctgatccagatcgtctgccttcagttgccagccatctgtgttgcccctccc
cgtgccttccttgacccgtggggtgggtggcaggacagcaaggggggaggattggaagacaatagcaggcatgctgggatgcggggct
ctattctggggggtggggtggggcaggacagcaaggggggaggattggaagacaatagcaggcatgctgggatgcggggct
ctatgggtaccaggtgctgaagaattgaccggttcctcctggccagaagaagcaggcacatccccttctctgtgacacccctgt
ccacgccctgtgttcttagttcagccctcatcagccccactcatagccaccaaaccaagccaaccaagccacatcccaaccgctaaagtactt
ggagcggtctctccctcctcatcagcccaacatgcctccaacatgtgaggaagtaatgagagaaatcatagaattaagccatgatttaagccatcatgg
tgcagagggagagaaaatgcctccaacatgtgaggaagtaatgagagaaatcatagaattaagccatgatttaagccatcatgg
ccttaatctccgcttcctgcctcactgactcgctgctgctgtcgttcgggtcgggcgagcggtatcagctcactcaaggcgtaata
cggtatccacagaatcaggaggataacgcaggaaagaacatgtgagcaaaaggccagcaacaaggccaggaaccgtaaaaggcc
gcgttgctgcgtttccataggctccgccccctgaagctccctcgtgcgctcctgttccgaccctgccgcttaccggatacctgtccgcc
ggactataaagatacaggcgtttcccctgaaggctgcgccctgtcgctgttaggctgtccgacagttccaggactgacctgcgcc
ttctcccttcggaagcgtggcgctttctcatactgcacgtgtaggtatctcagttcgtgtaggtcgttcgctccaagctgggctgtgt
gcacgaacccccgttcagccgaccggctgcgccttatccggtaactatcgtcttgagtccaacccggtaagacacgacttatcgcca
ctggcagcagccactggtaacaggattagcagcagagagcgaggtatgtaggcggtgctacagagtcttgaagtgtggcctaactacggct
acactagaagaacagatttggtatctgcgctctgctgaagccagttaccttcggaaaaaaagagttggtagctcttgatccggcaaacaaa
ccaccgctggtagcggtggtttttttgttgcaagcagcagattaccgcgcagaaaaaaaggatctcaagaagatcctttgatcttttctacg
gggtctgacgctcagtggaacgaaaactcacgttaaggggattttggtcatgagattatcaaaaaggatcttcacctagatcctttaaatta
aaaatgaagttttaaatcaatctaaagtatatatgagtaaacttggtctgacagttaccaatgcttaatcagtgaggcacctatctcagcgat
ctgtctatttcgttcatccatagttgcctgactcgggggggggcgctgagggtcgctgagctcgctgaagaagccttgttgttaggtgaccagttgtgctgactcatacca
ggcctgaatcgccccatcatccagccagaaagtgaggagccacgttgatcgatccttcaactcagcaaaagtctgatttatcaacaaagc
actttgctttgcactgccccatcatccagccagaaagtgaggagccacgttgatcgatccttcaactcagcaaaagtctgatttatcaacaaagc
cgccgtcccgtcaagtcagccgtaatgtctgccagttgtacaaccaattaccaattctgattagaaaaactcatcgagcatcaaatgaa
actgcaattatttcatcaggattatcaatacatatttttgaaaaagccgtttctgtaatgaaggagaaaactcaccgaggcagttccata
ggatgcaagatcctggtatcggtctgcgattccgactcgtcaacatcaataacaactattttccctgtcaaaaataaggttatca
agtgagaaatcaccatgagtgacgactgaatccggtgaatgtggcaaaaagcttatgcatttctttccagacttgttcaacaggccagcc
```

FIG. 11B (continued)

attacgctcgtcatcatcaaaatcactcgtcatcaaccaaaccgttattcattcgtgattgcgcctgagcgagacgaaatacgcgatcgctgta
aaaggacaattacaaacaggaatcgaatgcaaccggcgcaggaacactgccagcgcatcaacaatatttcacctgaatcaggatatt
cttctaatacctggaatgctgttttcccgggatcgcagtggtgagtaaccatgcatcatcaggagtacggataaaatgcttgaatggtcg
gaagaggcataaattccgtcagccagttagtctgaccatctcatcgtaacatcatcatgtcaacgctaccttgccatgtttcagaaacaac
tctggccgcatcggccttccatacaatcgatagatgtcgcacctgatgcccgacattatcgcgagccgacttataccatataatcag
catccatgttggaatttaatcgcggcctcgaacagcgtttcccgttgaatatgcctcataacaccccttgtattactgtttatgtaagcag
acagttttattgttcatgatgatatatttttatctgtcaatgtaacatcagagatttgagacacaacgtggctttcccccccccccattatt
gaagcatttatcaggttattgtctcatgagcggatacatattgaatgtatttagaaaaataaacaaataggsgttccgcgcacattcc
cgaaaagtgccacctgacgtctaagaaacaccattattatcatgacattaacctataaaaataggcgtatcacgaggccctttcgtc

FIG. 12A

Plasmid map: CMV/R Venezuelan equine encephalitis virus VLP, 8186 bp

Features:
- CMV/R Backbone
- ApaLI (178)
- CMV IE Enhancer/Promoter
- NcoI (697)
- HTLV-1 R Region/Splicing Donor
- CMV IE Splicing Acceptor
- NcoI (1317)
- PstI (1334)
- XmaI (2323)
- AvaI (2323)
- SmaI (2325)
- NcoI (2712)
- XmaI (2887)
- AvaI (2887)
- SmaI (2889)
- ApaLI (3037)
- PstI (3075)
- structure
- XmaI (3642)
- AvaI (3642)
- SmaI (3644)
- PstI (4306)
- PstI (4482)
- BamHI (5162)
- Tbgh
- ApaLI (6190)
- AvaI (6766)
- HindIII (7328)
- Kan.
- XmaI (7574)
- AvaI (7574)
- SmaI (7576)
- ClaI (7757)
- AvaI (7848)

FIG. 12B

SEQ ID NO: 8 tcgcgcgttcggttgatgacggtgaaaacctctgacacatgcagctcccggagacggtcacagcttgtctgtaagcggatgccgga
gcagacaagcccgtcaggcgcgtcagccgtgtggcgggtgttggcgggtgttgccgggctggcttaactatgccggcatcagagcagattgtactg
agagtgccaccatatgccggtgtgaaatacccgcacagatgcgtaaggagagaaaataccgcatcagattgccatggccatgcatacgttg
tatccatatcatatatgtacattattattattggctcatgtccaacatattaccgccatgttgacattgattattgactagtattaatagtaatcaatta
cgggtcattagttcatagcccatatatggagttccgcgttacataacttacggtaaatggcccgcctggctgaccgcccaacgaccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatggacgttcctactggcagtacatctacgtattagtcatcgctattaccatggtgatgcggttttggcagtaca
tcaatgggcgtggatagcggttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgatccagctcc
atcggctcgcatctctccttcacgcgccccgccccctacctgaggtaagcttgtagttaaagctctcaactctagttaacggtagcagtact
tgtgtgcctcctgaaccgctgcgtccgcgtctaggtaagtttaaagctctcaactctgcttgctgacctgttgacagagctaatagtcagtact
acctagactcagcccgcctttgcctgaccctgctggcgtccgcggccttgtgtgtgcccggttgcctgagcagtcagtcgagcagtact
cgttgctgccgccgcgccgccaccagacataagccgctctgacagactactgccgttcctttccccatggtctttctgcagtcagcgtctg
acacgtgatcagatatcggcgccaaccagaaccgcccgccaccatgttcccgttcaaccaatgtatccgatcagcaatgtatccgatgcagcacctgcccaatgtatccgatcgtaacccgtcg
cggccccgcgcaggcccctggttcccggggacgcgcgttcccagaaccgaccctttctggcgatgcaggtgcaggaattaaccccgctcgatgctaacctga
cgttcaagcaaccgccggacgccggcacctgagggcgcccctgagggcgccctgagggcgccaacccgcccaatccgaaggcacagagtgga
ggaggccaagggaagaagaagaaccaggagaagaagaagcaagacagaaaccaaggcaagaacggaagagggaggcccgcctaatccgaaggcacagagtgga
aacaagaagaagcccaacaaggaaggcaagaacgccaaaccagaacagcgcatggtcatgaaatgagaatcgacaagagacattccaattaatctg
gaaggggaagattaacggctacgcttcgttgtcggagttattcaggccgatgcacgtggaaggcaagatgccaagatcgacaacgacgt
tctgccgcacttaagacgaagaaagccatccaaatatgatcttgagtatgcagatcgcagtgccagaacatgcgggccgatcattcaagt
acaccatgagaagccaaggctattacagaccatctggagtcatcagctgcgcagtcaatcaatatgaaaatgggcgttcacggtgccaaaaggag
ttgggcaaggagacagccccaagggcgaagaacagggacgggtcgtattcgataatcaggacgggtcgtctggaatgtctggaggtgtgaatgaaggat
ctaggaccagccctttcagtcgtcatgtgaacgagaaggagtaactgtgaagtatccggagaactgtgagcaatgtcactagt
gaccactgtgcctgctcgcgccaatgtgacgttccaatgccgaaccaccaattgctacgacgacagagaaaaccagcgagcaacttggcca FIG. 12 B (continued)

tgctcagcgttaacgttgacaaccccggctacgatgagctgctggaagcagctgttaagtgcccggaagaaaaggagatctaccg
aggagctgtttaaggagtataagctaacgcgcccttacacggcgccctgatgcatcagatgtgccgttgggagctgccatagtccaatagca
attgaggcagtgaagagcgacgggcacgacgggcacggctatgttagacttcagacttcctcgcagtatgcctggattcctctgcaacttaaa
gggaaggactatgcggtatgatatgcacgggaccattgaagagatacccactacactacaagtcactccacatctcgcccgtcac
attgtggatgggcatggttatttctgcttgctagtgtgcccggcaggggactccatcatccatggaattaagaaaggttcagtcacacact
cctgctcagtgccgtatgaagtgaacattaatcctgtagggcagagaactctacactcatccaccagaacacggagcagagcaagcgtg
ccaagtctacgcgcgatgcacgatgcacagaacagaggagcttatgtcgagtcacctcccggctcagaagtggacagcagtttgattcc
ttgagcggcagttcagtcaccgtgcacctcgtcgctgactagcgcctgtgaatgcaagtgcgggcggcacaaagatctccgaa
accatcaacaaggcaaaaacagttcagccagtcagtgcacaaagaaggagcagcatatcgactgcagaatgcaagtgggta
taattctgacaaactgcccaaagcagcgggagccacctaaaaggaaaaactacacgtccgttcttgctgcgacggcaaatgcac
cgtgcctcagcacggaacctatgataacctcggtcgatcagtgtcactgaaactgcacctaagaatcccacatatcgaccact
cgccaacttgctgatgagcctcattacacgcacgagctcatatctgaaccagctgttaccgtcactgaaaagggtgga
gtttgatgtggaaaaccatcgcgccgaaaagttttgggcacagaaaatcacagcaccccggaaatccacatggctgccacatgaggtgat
aacctcatttattaccacagataccctagtccaccatcctggttgtccaccacatcctggttccgttgcagcgtccacctg
gctgttttgcaaatccagagtttcgtgcctaactccttaccggctaacacctaacgccaggatgccgagggatgcctgcgctttgctgc
gcccgcactgcccgggccgagaccactggagtcttggatcacctatggaacaataaccaacagatgttctgattcaattgctgat
ccctctgccgccttgattgtagtgactgctcgcctgctcaagtcgctgtgttgtagtcgtataacacatagtcaacagcaggccgcca
cggccgcctacgagcgagccaccgatcagccgagccgagccaagctgaactcgtataaccacatggcgtgttcacctgccactaacaggaatgg
ctccctatcagcataacaccaaagatcaagctgcggatctcaggaatctgcgacactgagaatactccaccttgagtactgcacctgccactaacaggatgtttac
attcaccagccatcaaatgtgccgatctcaggaatcttgcgacactcagatctgcgacactgagaatactccaccttgagtactgcacctgccactaacaggggtttac
cgttcatgtggaggtgcatattgctttcagcacacaagcgcacacagcctcagtgccaggcgttcctcaactacagggcctaaatcgacgactgcctt
gcggatcatgctgaagcatacaaagcgcacaagcgcacacagcctcagtgccaggcgttcctcaactacagtgggaacactctattgtgacc
accgtatgtgatgcaagtcagtatgcggagatgcggagatcgtatccctgagtatgggcagggaacaaaccaggagaccttgaac
agaaaaatcggcagtgtcaagctcagatctgtatgccaataccaacctagtgctgcagagaccccaaagcaggagcccaaagcggagacataca
atccagaacagtcaagctcgggtttgagcaatgaagaaagatataagctccgtcattgaaatacccgtcattgaaattaccgcccctttcgatgcgaaatatataca
actcaggcaccaatcgggtttgagcaatgaagaaagatataagctccgtcattgaaattaccgcccctttcgatgcgaaatatataca
aaccccattcgcgccgaaaattgctgtaggtcaattccatagcctttgacattccgacgccttgttcaccaggtgtcagaaaca FIG. 12 B (continued)

ccgcacttcagcggccggcgaatgcactcttaacgagtgcgtgtattcatccgactttggcgggatcgccacggtcaagtattcggccag
caagtcaggcaagtcgcgagtcgcgagtccatgtgccatcaggactgctaccctaaaagaagcagcagtcgagctaaccgagcaaggtcg
gcgaccatcattctcgaccgcaaatatccaccggagttcagctccaaatgcacatcatatgtcacgtgcaaaggtgattgtcac
ccccgaaagaccacattgtgacacacccccagtcacgcgggtgtcaaaaaccgcgtggacgtggtta
acatccctgctgggaggatcggccgtaattattataattggcttagtgctgccatcatgtgccatcatgttgtgccctcccccgtgccttcttga
ataatgatcagaccaggcccctgatcagatcgctgcgtgccttcagtgccagccatcgcatttgtgagtagtgtcatctattctgggggtt
ccctggaagtgccactcccactgtccttcctaataaatgaggaaattgcatcgcatttgtgagtagtgtcatctattctgggggt
ggggtggggcaggacagcaagggggagattggccagaacaatagcagccatgcgtgggatgcggtgggctcatgggtaccag
gtgctgaagaattgaccgggttcctctgggccagaagaagcaggcacatcccttctgtgaccacacccgtccacgccctggtt
cttagttccagccccactcatagacactcatagctcaggagggctccgcctcaatccaccgctaaagtacttggagcggtctctc
cctccctcatcagcccactcatagcccaacactagcctccaagatgggaagaaattaaagcaagatagctattaagtgcagaggaga
gaaaatgcctcaacatgtgaggaagtaatgagagaaatcatagaaatttaaggccatgattaaggccatcatggccttaatcttccgct
tcctcgctcactgactcgctgcgctcggctcgtcgttcggcgctgcgagcgtatcagctcactcaaagcgtaatacggttatccacaga
atcagggatacgcaggaaaacatgtgagcaaaaggccagcaaaaggccaggaaccgtaaaaaggccgcgttgctgcgtt
ttccataggctccgcccccctgacgagcatcacaaaaatcgacgctcaagtcagaggtggcgaaacccgacaggactataaagatac
caggcgtttccccctggaagctccctcgtgcgctctcctgttccgaccctgccgcttaccggatacctgtccgcctttctccctcgggaa
gcgtggcgctttctcatagctccacgctgtaggtatctcagttcggtgtaggtcgttcgctccaagctgggctgtgtgcacgaaccccccg
ttcagcccgaccgctgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaagaaca
gtatttggtatctgcgctctgctgaagccagttaccttcggaaaaagagttggtagctcttgatccggcaaacaaaccaccgctggtagc
ggtggtttttttgtttgcaagcagcagattacgcgcagaaaaaaaggatctcaagaagatcctttgatctttctacgggtctgacgctca
gtggaacgaaaactcacgttaagggattttggtcatgacagttaccaatgcttaatcagtgaggcacctatctcagcgatctgtctatttcgttca
atcaagtaagtatatatatgagtaaacttggtctgacagttaccaatgcttaatcagtgaggcacctatctcagcgatctgtctatttcgttca
tccatagttgcctgactccccgtcgtgtagataactacgatacgggagggcttaccatctggccccagtgctgcaatgataccgcgagaccc
acgctcaccggctccagatttatcagcaataaaccagccagccggaagggccgagcgcagaagtggtcctgcaactttatccgcctcca
tccagtctattaattgttgccgggaagctagagtaagtagttcgccagttaatagtttgcgcaacgttgttgccattgctacaggcatcgtgg
tgtcacgctcgtcgtttggtatggcttcattcagctccggttcccaacgatcaaggcgagttacatgatcccccatgttgtgcaaaaaagcggt
tagctccttcggtcctccgatcgttgtcagaagtaagttggccgcagtgttatcactcatggttatggcagcactgcataattctcttactgtca
tgccatccgtaagatgcttttctgtgactggtgagtactcaaccaagtcattctgagaatagtgtatgcggcgaccgagttgctcttgcca
cggaacgtctgtcgggagggcttaccatctggccccagtgctgcaatgataccgcgagacccacgctcaccggctccagatttatcagcaataaaccagccagccggaagggccgagcgcagaagtggtcctgcaactttatccgcctccatccagtctattaattgttgccgggaagctagagtaagtagttcgccagttaatagtttgcgcaacgttgttgccattgctacaggcatcgtgg
agtcagcgtaatgctctgccagtgttacaaccaattaaccaattctgattagaaaactcgattagaaaaactcatcgagcatcaaatgaaactgcaatttatca

FIG. 12 B (continued)

tatcaggattatcaataccatattttgaaaaagccgttctgtaatgaaggagaaaactcaccgaggcagttccataggatggcaagatc
ctggtatcgtctgcgattccgattccgactcgtccaacatcaatacaacctattaattcccctcgtcaaaataagttatcaagtgagaaatcac
catgagtgacgactgaatccggtgagaatggcaaaagcttatgcattctttccagacttgttcaacaggccagccattacgctcgtcatc
aaaatcactcgcatcaaccaaaccgttattcatcgtgattgcgcctgagcgagacgaaatacgcgatcgctgttaaaaggacaattaca
aacaggaatcgaatgcaacggcgcagtaacactgccagcgcatcaacaatatttcacctgaatcaggatattcttctaatacctgga
atgctgtttccgggggatcgcagtggtgagtaaccatgcatcatcaggagtacggataaaatgcttgatggtcggaagaggcataaat
tccgtcagccagtttagtctgaccatctcatcgtaacatcattgcaacgctaccttgccatgtttcagaaacaactctggcgcatcgggg
cttccatacaatcgatagattgtcgcacctgattgcccgacattatcgcgagcccattatacaccccttatactgttatgtaagcagacagttattgttcat
taatcgcggcctcgagcaagacgtttcccgttgaatatgctcataacacccctgtattactgttattgtaagcagacagttattgttcat
gatgatatattttatcttgtcaatgtaacatcagagatttgagaacacaacgtggctttccccccccattattgaagcattatcagg
gttattgtctcatgagcggatacatatttgaatgtatttagaaaaataaacaaatagggttccgcgcacattcccgaaaagtgccacct
gacgtctaagaaaccattattatcatgacattaacctataaaaataggcgtatcacgaggcccttcgtc

FIG. 13B

SEQ ID NO: 9 tcgcgcgttcggttgatgacggtgaaaacctctgacacatgcagtcccggagacggtgtctgtaagcggatgccggagcagacaagccgtcaggccgtcagcgggtgttggcgggtgtcggagtcggagcttaactatgcggcatcagcagattgtactgagagtgcaccatatgccgtgtgaaataccgcacagatgctgaaggagaaaataccatcagatggctattggctattggccattgcatacgttgtatccatatcataatgtacattatattggctcatgtccaacattaccgccatgttgactgttgacattgattatgattattaataagtaatcaattacgggtcattagttcatagcccatatatggagttccgcgttacataacttacggtaaatggcccgcctggctgaccgcccaacgacccccgcccattgacgtcaataatgacgtatgttcccatagtaacgccaataggcactttccattgacgtcaatgggtggagtatttacggtaaactgcccacttggcagtacatcaagtgtatcatatgccaagtacgcccctattgacgtcaatgacggtaaatggcccgcctggcattatgcccagtacatgaccttatggacttccacactggcagtacatctacgtattagtcatcgctattaccatggtgatgcggttttggcagtacatcaatgggcgtggatagcggtttgactcacgggatttccaagtctccaccccattgacgtcaatgggagtttgttttggcaccaaaatcaacggactttccaaaatgtcgtaacaactccgccccattgacgcaaatgggcggtaggcgtgtacggtgggaggtctatataagcagagctcgtttagtgaaccgtcagatcgcctggagacgccatccacgctgttttgacctccatagaagacaccgggaccgatccagcctccatcgctgcctctctcctccacggcgcgtgcgcccgtctagtaagtaattaaagctcgctatcgccggccagccgcttgtggtgcctctctcgaacgcctgtgctccctaggtgttcctgaccctgccttgccgccggcagttgttagtctgagcagtacttagtgtccgccgccgccacccagacataatagctgacagactaacactgagtcgtcttttctgcagtcacgtcgtcgcacgtgatcagatatcgcggccgccaccaccagttacctacacaatcgatgccttaccgagatccaaacccctaaggccgctgtaagcccgttcgccccccgctcgactttaccctcaaatcgaagatcttaggagtcgatgaagcaacgatcacctaatccgccgccagttccacccgccagccgaaaagaagaagtgtcctaagccaaaaacttactcagcctaaaagaagaacattccgatcatgctgaacggcaaaccaagcccaaacagcgaaacgacaacgtatgtgtaagtttggagtcggacaagacatttccgatcatgctgaacggccaagtgatcatgctgaaggctgccttggtgtgcaagcttgagggaagctcgatgaaccactccacgttgaaggagaaaattgataatgagcaatttagcggcgttgaaaattgaagaaggctagcatgtacgactgaggtacgactgacgttcccagaacatgaaatcagacgacgacgtcaaatcagcgggaaaaaggcgacgaggaagcgacaacaggaagaccgatcctgaaccaagacagaggcagagtgtgaatgttgagatttctaggagttgcaaatgaggcacgcgtacggcgcttcagtgtcacttggaaccaggaaggggtgaccattagggatagctattgtcttaggagtgaaccgtgttcactgaagcgctatgtcgtcttcgaatgtccaatgtccatgcgacaaaccaccctgtgctccccgaaggttctgaaccgtcacactacgaatcgtcgacaaaggggtcgacaaaccaccctgtgctatcactgacgccagaacactgacgtctcgaaggagaacgaatccaaaattacgacacgtctgaaacgtcttga FIG. 13B (continued)

aatgtccatcacgcccggcccaaacgaagcattacgatgacttcacactgaccagtccctacctgggttctgcccgtattgcagacac
tcaacgccgtgtttcagcccaatataaaattgagaacgtgtgggacgaatctgatgatggatcgattagaatccaggtctggcacaattc
ggctacaatcaggcaggcactgcggatgtcaccaaattccgttacatgtcttcgaccacgaccatgacatcaaggaagacagtatgg
agaaaatagctcatcagcacatctggaccctgccgtcgtcttggccacaaaggtactcctgttagtcaatgtcctccaggtgacagtg
taaccgtcagtatcacgagcggagcatctgagaattcatgcaccgtggagaaaaagatcaggaggaagttgtcgtagagaggagt
acttgttccaccgtccatggaaagctggtaaagtgcacgttacgatcacttgaaggagacgtgccggtacataaccatgcac
aggccaggcccacacgcgtataagtcctatctggaggaagcgtcaggcgaagtgcattaaccaccttctggcaagaacgtcacc
tacgaatgtaagtgtggcgactacagcacagtatcgtgagcacgcgaacgaagatgaacggctgcactaaagcaaaacagtgcatt
gcctacaagagcgaccaaaacgaaatgggtcttcaactcgccggatcttattaggccacacagaccactcagtgcaaggtaaattgcaca
ttccattccgcttgacaccgacagtctgcccgttccgttagctcacacgcctacagtgcacgaagtgttcaaaggcatcacctccacc
tgactgcaatgcgaccaacattgctgacaacgagaaaattgggcgtgcagcagcaacagcagaatgattacaggtctacat
ccaggaattttctgtggcgagaaggctggagtacgtatgggtaaccatgaaccagtcagatctggcccagggtcggcac
caggcgaccacatggagccgcatgagatcatcagatcatcactattatcatcgcaaagcaagaagagactgcctgacgccatacgcgctgcacc
ctcttgctatcctgtaggcactgcatcatcagacggttgcattcgtgcattccctggcacagttgctgaaacattggagaaacttgaaccatcgt
gaacgcaaacgtaccacacagctttctctgggcacagttgtgcattcctggcacagctgcgcttgttattctgttccgctgctttcatgctgcatgcctttt
ggttaacaaccaaccgtttctctgggcacagttgtgcattcctggcacagctgcgcttgttattctgttccgctgctttcatgctgcatgcctttt
tattggttcaggcgtcgcctgcctggggaagtagagacgccttcgaacatgcgaccactgcgaccactgccaaatgtccgggatccgtaaaggc
gttggtcgaacgcgcaggttacgcgccacttaacctgccacctttcaccacaagttaaatgctgcgggtccctcgagtgcaaggcatcctcaaaggcgggattac
tgacctgcaaattccacacagtcattccttcaccacaagttaaatgctgcgggtccctcgagtgcaagtgcaaggcatcctcaaaggcgggattac
acatgccgcgtttgccgtgtgtaccctttcatgtgggaggaggcgcacaatgctttctgtgacagtgagaacacacaactgagtgagggc
gtacgtcgagttcgctcagactgcactatgatcacgctcgcagtgtccactaaagttcacacagtcgtctgaaagtcgcctgctatag
tatacggcaacaccaccggcactcctggacctgtcatgccgcaggttcatcggccaggtccacggaacctgaaggtcatagcagggc
cgatatcagccgctttttccacctttgaccataaggtcgtcatcagaaaggggcttgtttaactactacgacttcccgtcagtatggagctatg
aaaccaggacgcgttcgccgatattcaagctactgcctgctagacatagcccgctacagaacatcaggacgcgtcgtgaagccttc
tgtcaagaacaacactgccccacacactccaagcagtatcaggtatgaaatgtgaagaacaacactcaggacgcgtcgtgaagccttc
agcaccattggatgtaaaattgaagtgagcctcgcgagcctcgagcgctcaactgcttacggcacatgccacatcctatctgattgacatccctgat
gcagcttttgagatcatcagaatcaccaaacaatttagaagttagaagtcgcacagtagctgcacagtagcagactgcattattctgcagacttgtgttct FIG. 13B (continued)

ctaacattacagtacaaagtgacaggaaggaggacattgtccagtcagttcactccactccacgacagctgtttgaaggaagcgaccacac
atgtgactgccgtaggcagcataacactacattagcacatcgagcccacaagcaaattatagtttcgctatgcggcaagagtcca
cctgcaatgctgaatgtaaaccaccggccgaccacataattgaccgagaaccacataaagtcgaccaagaattccaggcggcagttccaa
aacatcttggaactgctgcttgcactgttggaggagcatcatcctcattgttgtagactaagttggtctgcagtctcatgcttata
aacacacgtagatgatccagaccaggccctggatccagatctgctgccttctagttgccagccatctgttgttgcccctccccgtgc
cttcctgaccctggaaggtgccactcccactgtcctttcctaataaaatgacatcgcattgtctgagtagtgtcattcattct
ggggggtgggtgggcaggacagcaagggggaggattgggaagaacaatagcaggcatgctgggatgcggtgggctcatgg
gtacccaggtgctgaagaattgacccgtcctcctgggccagaagaagcaggcacatcccttctcgtgacacaccctgtccacg
cccctggttcttagttccagccccactcatagaccactcatagcctcaggagtcccgccttcaatccaccgctaaagtacttggag
cggtctctccctccctcatcagccccaccaaaccaaccaaactagcctccaagagtgggaagaaataaagcaagataggctattaagtgca
gagggagagaaaatgcctccaacatgtgaaggaagtaatgagagaaatcatagaatttaaggcatcagctcactcaaagtcggtatacggtt
atcttccgcttcctcgctcactgactgctgcgtcgttccgctatcgcgggagctgatcacagctcactcaaagtcggtaatacggtt
atccacagaatcagggatagggatcacgcaggaagaacatgtgagcaacatggccagcaaaaggccagcaaaggccgtaaaaaggccgcgt
gctggcgtttttccataggctccgcccccctgacgagcatcacaaaaatcgacgctcaagtcagaggtggcgaaacccgacaggact
ataaagatccaggcgtttccccctggaagctccctcgtgcgctctcctgttccgacccctgccgcttaccggatacctgtccgcctttctc
cctcggaagcgtggcgctttctcatagctccaagctgtaggtatctcagttcggtgtaggtcgttcgctccaagctgggctggtgtgcac
gaaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacact
agaagaacagtagttggtatctgcgctctgctgaagccagttaccttcggaaaaagagttggtagctcttgatccggcaaacaaaccac
cgctggtagcggtggtttttttgttgcaagcagcagattacgcgcagaaaaaagatctcaagaagatcctttgatcttttctacgggt
ctgacgctcagtgaacgaaaactcacgttaaggggatttgtcatgagagattatcaaaaaggatcttcacctagatccttttaaattaaaaa
tgaagttttaaatcaatctaaagtatatatgagtaaacttggtctgacagttaccaatgcttaatcagtgaggcacctatctcagcgatctgt
ctatttcgttcatccatagttgcctgactccccgtcgtgtagataactacgatacgggagggcttaccatctggccccagtgctgcaatgataccgcgagacccacgctcaccggctccagatttatcagcataaccagccagccggaagggccgagcgcagaagtggtcctgcaactttatccgcctccatccagtctattaatttgttgccgggaagctagagtaagtagttcgccagttaatagtttgcgcaacgttgttgccattgctacaggcatcgtggtgtcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtctaagaaaccattattatcatgacattaacctataaaaataggcgtatcacgaggccctttcgtc FIG. 13B (continued)

cgtcccgtcaagtcagcgtaatgtctgccagtgttacaaccaattctgattaaccaattctgattagaaaaactcatcgagcatcaaatgaaactg
caattattcatatcaggattatcaatacccatatttgaaaaagccgtttctgtaatgaaggagaaaactcaccgaggcagttccataggat
ggcaagatcctggtatcggtctgcgattccgactcgtccaacatcaatacaacctattaattccctcgtcaaaaataaggttatcaagtg
agaaatcaccatgagtgacgactgaatcggtgagaatgccaaaagcttatgcaaaagttcaacaggccagccattac
gctcgtcatcaaaatcactcgcatcaaccaaaccgttattcattcgtgattgcgctgagcgcatcaacaatatttcacctgaatcaggatattcttct
gacaattacaaacaggaatgcgaatgcaaccggcgcaggaacactgcaggtaaccatgcatcatcaggagtacggataaaatgcttgatgtcggaag
aatacctgaatgctgttttcccgggatgcagtggtgagtaacatctgaacatcattggcaaacgctaccttgccatgttcagaaacaactctg
aggcataaattccgtcagcagttagtctgaccatctcatctgtaacatcatgcccgacattatgcgagccatttataccatataatcagcatc
gcgcatcggcttcccatacaatcgatagattgtcgcacctgattgccgaagcgttcccgttgaatatgtctcataacacccttgtattactgtttagtaagcagaca
catgttgaatttaatcgcctcgagcaagacgtttcccgttgaatatgtctcataacacccttgtattactgtttagtaagcagaca
gtttattgttcatgatgatgatatttatctgcaatgtaacatcagagatttgagacaacaacgtggcttccccccccattattgaa
gcattatcaggttattgtctcatgagcggatacatattgaatgtattagaaaaataacaaatagggttccgcgcacatttcccga
aaagtgccacctgacgtcaagaaaccattatcatgacattaacctataaaaataggcgtatacgaggcccttcgtc

FIG. 14B

SEQ ID NO: 10 tcgccgcgttcggttgatgacggtgaaaactctgacacatgcagtcccggagacggtcacagcttgtcgtaagcggatgccggga
gcagacaagcccgtcagggccgtcagcggtgttggccggtgtcgggcttaactatgcggcatcagagcagattgtactg
agagtgcaccatatgcggtgaaatacccgtaaggagaaaataccgcatcagattggctattggccattggcatacgtg
tatccatatcatatatgtacattatttgctcatgtccaacattaccgccatgttgacattgattattgactagttaatagtaatcaatta
cggggtcattagttcatagcccatatatggagttccgcgttacataactacgtaaatggccccgcctggctgaccgcccaacgaccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgcaaatgggcggtaggcgtgtacggtggga
gctcgtttagtgaaccgtcagatcgcctggagacgccatccacgctgttttgacctccatagaagacaccgggaccgatcagcctcc
atcggctcgcatctctcctccttgaactcggctcgcgccgcgtctagtaggttaaagctcaggtcgagaaccggtgagtcgccgctccctggagcct
tgtggttgcctctgaactcgaccggctctccacgctcttgcctgaccctgtctcaactcagtaacgtgaggcagtagtcgagcagtact
acctagactcagccgcgcggcgcaccagacataatagctgcacagtggtccttttctcagctggtcttcagtcacgtcgtcg
cgttgctgccggcgcgccaccagacataatagctgccgccaccatgttccatcagctcgcctatcgcctatggcgccgattaaccgatggctta
acacgtgatcagatatcgcggccgccaccatgttccatcagctccatcacagtggcttgcaccactgcagttcaaatttgaggaccctgagacgttccatcgct
ccgggatcctaatccgctagggccaggtggcgggcccttaggccaccacttgcagtcaaatgaggaccctgcgccaagcgtcaaccgatggctta
aacctgacttgaacaacgagcaccaccctaacctccaggaccgcccgccaagccgcaagaaagcctgccagcctaagcctgc
gcagaaaaagaagcgaccaccaccctgccaagaaacaaaacgtaaactaaaccagccaaaccgacgaataccagcctgtatgaa
gctagagtcagataaaacgttccaatcatgttgaacgacaggttagcgtgtcgtgggtcgacgagtgtcaacccgc
tgcacgtagaaggcagaatagacaatgaccgccgcatcaagctcgaagaaggccagcatatgacccttgagtggtatg
tgccacaatgcatgaaatcagataccccccagtagacagataaccctcggctcttttataactggccaccatggagctgtacagtatg
agaacaataaaggttcaccgtcacggacagcaacgaaggctcaaacggctgaagaccatgacccgagcgcagtcatg
gcaattgtcctgggttgagtcagatcaggacgctctatcagtggtgacatcagaaccccaaaagggtacaagtgacatagtcgtc
acaccaagagagggtcagagtcagatcacagccatgtcgtctgctgcactgtcgtcgtgccaaatataccagttccagtgatcaaccacgct
gccatgctgttgataactcacctatgcaggccacagaatcagcagcagcctgctcgatg FIG. 14B (continued)

ccgctgtgaaatgtaatgtaggagaaccaggagaagagattggacactcattcacccagtataagctggcacgcccgtatattgctgatt
gccctaaactgtgggcatagtcgtgcgaagacccctatagctagtcagaagaagtcaggatgcgcacgcaggagtcatccgcatc
cagacatcagctagtcgtcgaagacggatggagttgattggcctacatgagttcatgaacggcaaaacgcagaaatcaataaa
gatcgacaaacctgcatgtgccgcacctcagccccctgttcctgtcgtccgcgtattacatcctggctcaatgccaccaggggg
acacggttacagttgggttcacgacggcgggcctaaccgcatacgtgcacagtgccatcaaggtagaattcaggccagtggtagaga
gaaatccgtcaccaccctgaactggagttgaataccatgcaaaccgtacaccacaagcgtgcagaccaaggacactgcgttgag
atgcatcaaccggctagttgccgaccactctccttagcatccacagtgccaaggtgaaaattacgtacgagcgg-gcgcccaag
tgaaatactactgcaagtgccagaccgcagagaggaactaccagccgactatacaaccacctgcacgcacgatgcaaacaatgca
gggcttacctgattgacaacaaaaaatgggtgtacaactctggaagactgcctcgaggagaggcgacactttaaaggaaaacttca
tgtgccctttgtccctgttaagccaccgaccttgcgacgaccaggtcacttggaagttgatgcaaatccaactcgacaatgattgagcgaccaac
cctgtacccggaccaccgaccttcgacagtcacgtgcgaagaaggttggagtatacctggaagaaaccatccaccaaaagagtatgggctcaagagtcagg
aactgtcaattcacagtccacatggatgccgcacgaagtggtagtctattactaacacagataccattaaccacacaattatcggttatgcacct
gtgtggctatcatcatggtctcttgtgtcacatccgtggccaatcttgcaggactgccaatctttgcataaccccgtaaactagcccg
aacgctcaagtccaatactcctggcgttacttgctgcattaagccgacgagggcagatgacacctgcaagtgtcgaagtctgaattaccgtgg
aacaacaatcaaaaacttttctggatgcagacgcttatccacttgcagcgcttattgtatgcatgccgcatgctgccgctgcttattttgctgt
gggccggctttttacttgctgtccgcggcggcctgggcgccctgagctacgaacacacagcagtgatgccgaacaaggtgggatccg
tacaaagcttagtcgaacgcccagttatgcaccgttcacctacagatacagctgttaataccagatattccatcaactaacctg
gagtacatcacctgcaagtataagacaagtcatttccagtagtgaaaagtgcgtggtgccactcagatgctgcctcctaattgtacctccaaacccatcct
gactatcagtgtcaggttacaggtgttacagatgtttacccattcatgtggggaggagagctactgcttctgcgacactgaaaaacaccagatgagc
gagggtatgagagagcgctcgaagagcgtctgagatgctctattgaccacgcacgcacaaagcttataaagatacacacaggcactgttcaggcaatggtga
acataacttatgggagcgtcagctggagatctgcagatcttcagatgtttacgtcaatggtgaaactcccgcgaaaataggagatgccaaactcatc
ataggtccactgtcatccgctggtccccattcgcgataaacaagtgttgttcatgggcatgaagtgtataattacgactttcctgagtacg
gcaccggcaaagcaggctgttttggagcgtcccatcacgcacaccagcagcgatcgtacgcaaacaccaactgaagctac
aacgacgaccagttcggtatcgtgcacacacctttcacccagccgcccctccggcttcgaacgatgtcgagaaaggagcaaagggcacc
gttaacgacgtagccccgttgcttgctgattgccctgagcgctcgtgaagccgtcagaaaaattgtcagtgggaagcatccctatatctat
agataccgatgccactggcggctttaccagaatatctgaaacaccgaatgcaaatgcaaatgcaaaattacggagtgtacttatgcctc FIG. 14B (continued)

FIG. 14B (continued)

gcagttccataggatggcaagatcctgtatcgtcgcgattccgactcgtcgcaatcaatacaacctattaattcccctgtcaaaa
ataagttatcaagtgagaaatcaccatgagtgacgactgaatccgtgagaatggcaaaagcttatgcattcttccagacttgttcaa
caggccagccattacgctcgtcatcaaaatcactcgcatcaaccaaaccgttattcattcgtgattgcgcctgagcgagacgaaatacg
cgatcgctgttaaaaggacaattacaaacaggaatgcaaccggcgcaggaacactgccagcgccatcaacaatatttcacctg
aatcaggatatcttctaatacctggaatgctgttttcccgggatcgcagtggtgagtaaccatgcatcatcaggagtacggataaaatg
cttgatggtcggaagaggcataaattccgtcagccagttagtctgaccatctcatcgtaacatcattggcaacgctaccttgccatgtt
cagaaacaactctggcgtcatcggcgcttccatacaatcgatagattgtcgcacctgattgcccgacattatcgcgagcccattatacc
atataaatcagcatccatgttggaattaatcgcggcctcgagcaagacgttccgttgaatatggctcataaacacccccttgtattactgtt
tatgtaagcagacagttttattgttcatgatgatatattttatctgtgcaatgtaacatcagagatttgagacacaacgtggcttccccc
cccccccattattgaagcatttatcaggttattgtctcatgagcggatacatatttgaatgtatttagaaaaataaacaaataggggttccgc
gcacatttcccgaaagtgccacctgacgtcctaagaaaccattattatcatgacattaacctataaaaataggcgtatcacgaggcctt
tcgtc

FIG. 15B

SEQ ID NO: 11 tcgcggcgttcggttgatgacggtgaaaacctctgacacatgcagctcccggagacgtcacagcttgtctgtaagcggatgccgga
gcagacaagcccgtcaggcggcgtcagcggtgttggcggtgtggcggtgcttaactatgccggcatcagagcagattgtacig
agagtgcaccatatgccggtgtgaaatatccgcacagatgcgtaaggagagaaaatatccgcatcagattggctattggccattgcatacgttg
tatccatatcatatatgtacattatatatgctcatgtccatatctccaacattatactaccgccatgttgacattgattattgactagttattaatagtaatcaatta
cggggtcattgtcatagtccatatatggagttccgcgttacataacttacggtaaatatggcccgcctggctgaccgccgcaacgaccc
cgcccattgacgtcaatatgacgtatgttccatagtaacgccaatagggactttccattgacgtcaatgggagtattacgtaaa
ctgcccacttggcagtacatcaagtgtatcatatgccaagtacgccccctattgacgtcaatgacggtaaatggcccgcctggcattatg
cccagtacatgaccttatggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaaatgggcggtaggcgtgtacggtgggaggtctatataagcaga
gctcgtttagtgaaccgtcagatcgcctggagacgccatccacgctgttcgacctccacgctgtttgacctccacgctgatccagctcc
atcggctcgcatctctcctcacgcgccctggctccacgctcgccgcccgtctagttaacgccgttgactgccttgtccggctccgtcgctccccttggagcct
tgtgtgcctcgaactcgcatctctcacgcgtccgccccgtctagttaagtttaaagctccgtcaactctagttaacgttgaaggcagtgtagtctgagcagtact
acctagactcagccgcccggctccacgctttgcctgactccgccgggctgactaacacagactgttcctttccatggtctttctgcagtcaccgtctcg
cgttgctgccgcgcgcgccaccagacataatagctgacagactaatagaggatcttaacatgctcggccgccgccctttccgcgccgccactgcc
acacgtgatcagatatcgcggccgccaccatgaatcggccgcaacatgaataggagcctgcccgatgcctgccaactcagcaactgaccaca
atgtggaggcccgggaagaggaggcccactagcggcaactagaccctcaaccccacgtccacgccccgccagaagaagcaggcgc
gccgtcagtgcctagtcattggacaggcaactagaccaaaaaccgcaggagaagagaagaaagcaggacgaagaaaccgaaagag
ccaagcaaccaccgaagccgaagtaagttgaggccgacagattgttcgacgtcaaggaccatgtcatcaaagctcaaattaccaagtcgtcagc
acagccgcacttaagttgaggccgacagattgttcgacgtcaaggaccatgtcatcaaagctcaaattaccaagtcgtcagc
atacgacatggaggtcgcacagttgccagtcaatgaaccatgcaaccaactgtcatcacacagagttgatttaaagctccatcaaagctcaaattaccaagtcgtcagc
ggcaccacgagccggttgcttcgggttgcgtgatagtgaggtagattaccatccctcgggagtaggcagaggagacagcggtgtcgat
catggataactccggtcgggttgtcgcgatagtcctcgggtggcgctgatgaaggaacacgaactgccctttcggtcgtcacctggaata
gtaagggaagacaattaagacgacccgagggaccccatgcgaaaccatctaccccgaaccttcaagagggagtgtccgcagcccctgtcacggcaatgtgttcgtcga
aatgtgagctccatgcgaccgccaccgccgcgcccacatgcagccctacccgaaccttccagacccctgcgtgtgaaccgcagacatcctgaagagagaacgtgaacc FIG. 15 B (continued)

atgaggcctacgataccctgctcaatgccatattggtgcggatcgtctgcagaagcaaaagaagcgtcattgacgacttacctg
accagccctactgtggacatgctgctcgtactgctcgtcaccatactgtaccgtgcttcagccctgttaagatcgagcaggtctgggacgaagc
ggacgataacaccatacgcatacagacttccgccccagtttggatacgacacaaagcggagcagcaaagcgcaaacaagtaccgctaca
tgtcgcttaagcagcagatcacaccgttaagagaaggccctccaaatgcctcctccaggggacgtaacagcgtaacagcagattagcacctcaggaccgtgtagaaggcttagcta
caaaggatacttctcctcgcaaaatgcctccaggggacgtaacagcgtaacagcggtagcaaagtgagtagcaactcagcaacgtcatgtaca
ctggccccgaagataaaccaaaattcgtgggacgggaaaaatatgatctacctcccgttcacggtaaaaaaattccttgcacagtgta
cgaccgtcgaaaagaaacaactcaggctacatcactgcggagaccgcacgcttatacatcctacctggaagaatcatca
gggaaagttacgcaaaagccgcatctggaagaacattacgtatgagtgcggcgactacaaagaccgaaccgttcgacc
cgcaccgaaatactggttgcaccgccatcaagcagtgcgtcgcctataagagcgaccaaacgaagtggggcttcaactcaccggac
ttgatcagacatgacgaccacacaggcccaaggaaattgcattgccttcaagttgatcccgagtaccgtcatggcccctgttgcccac
gcgccgaatgtaataacatgggtaaaaccaacatcaagcctccaattagatacagagaccactgtcaccaccaggagactaggggc
aaacccggaaccaaactactgaggtctgggaaagacgtcagaaaacttcaccgtcgaccgagatggcctggaatacatatggc
gaaatcatgagccagtgaggtctatgccaccaggagtcagcaccaggagaccctcaccgatggccacacgaaatagtacagcattact
accatcgccatcctgtatacaccatcttagcccgtcgcatcagccgtggcgatgatgattgcgtaactgttgcagttgttgtatgtcctg
taaagcgccgtgagtgcctgacgccatacgcccctggcccaaacgcctaatccaactcgctggcactcttgtgctgcgttagg
tcggccaatgctgaaacgttcaccgagacatgagttacttgtgctgaacagtgccgtccttctgggtaacgtgtgcataccttgg
ccgctttcatcgttctaatgcctgtctgctcctgcctgcctttttagtggttgccggcgcctacctggcgaaggtagacgcctacga
acatgcgaccactgttccaatgtgccacagatacctgttaaagggcacttgttgaaagtgcactgcctgagatcgccccgctcaattggagatca
ctgtcatgtcctcgaggttgccttccaccaagagtacattacctgcaagttcaccactgtgaggggtctaccccttatgtgggagga
ctgcggggctccttcctggaatgtgcgaagtgagcagtgtgagaacagcagagtagtgaggctacgctcgaaattgcgtcgttgcagagatgcgcag
gccaatgtttttgcgacagtgagaacagcagagtagtgaggctacgctcgaattgtcagcagattgcgtcgctgaccagcgcag
gcgattaaggtgcacactgccgcgatgaaagactgaaagttaggactggtgttgtacggaacactaccagttcctagatgtgacctggaacgg
agtcaccaggaacgtcaaagactcagcgataagtcatagctggaccaattcagcatcgttacgccattcgatcataaggtcgttatccat
cgccggcctggtgtacaactatgactccggaatatggacgatgaaccaggagcgttggagacattcaagctacctcttgactag
caaggatctcatcgccagcacagacattagcctcaagcctccgccaagaacgtgcatgtccgtacacgcaggcctcatcagg
atttgagatgtggaaaaaactcaggccgcccactcaggaaaccgcaccttcgggtgtagattgcagtaaatccgtccgagcg
gtggactgttcatacgggaacattccatttctattgacatcccgaacgctccttatcaggacacactcaggatcagatgcaccactgctcaacag FIG. 15B (continued)

tcaaatgtgaagtcagtgagtgcacttattcagcagacttcgccgggatggccaccctgcagtatgtatccgaccgcgaagtcaatgc
cccgtacactcgagcacagcaacctccaagagtcgacagtgtcctgagaaaggagcggtgacagtacagtcacttagca
ccgcgagtccacaggcgaacttatcgtatcgtgtgggaagaagcaacatgcaatgcagaatgcaatgtaaaccaccagctgaccatat
cgtgagcacccccgcacaaaaatgaccaagaattcaagccgccatctcaaaaacatcatgagttggctgtttgcccttcggcg
cctcgtcgctattaattataggacttatgattttgcttgcagcagatgatgcgacagcgaagatgatctagaccaggccctggatcc
agatctgctgcctttcagttgccagccatctgttttgcccctccccgtgccttcctgaccctggaaggtgccactccactgtcctt
tcctaataaaattgaggaaattgcatcgcattgtctgagtaggtgtcattctattctgggggtgggtgggggcaggacagcaagggg
aggattgggaagacaaatagcaggcatgcgttgtggggatgcggtggtggctatcaccagtgtcgaagaattgacccggttcctcct
gggccagaaaagaaagaagcaggagggctccgcctttcaatccaccccgctaaagtacttggagtcgtctcccttctccactcataggaca
ctcatagctcaggagggctccgcctttcaatccaccccgctaaagtacttggagcggtctctcctcccctcatcagccccaccaaaccaaa
cctagcctccaagagtggggaagaaattaagcaagatagcgctattaagtgcaggaggagagaaaatgcctccaacatgtgaggaagt
aatgagagaaatcatagatggccatcatgatttaaggcctaatcttccgctctcgctcactgactcgtctgctcgg
tcgttcgggctgggcgagcggtatcagtcactcaaaagggtatcccacagaatcagggtataacgcaggaaagaaca
tgtgagcaaaaggccagcaaaaggccaggaaccgtaaaaaggcgttgctgcgttttccataggctccgccccctgacgag
catcacaaaaatcgacgctcaagtcagaggtggcgaaacccgacaggactataaagataccaggcgttcccctggaagctccctc
gtgcgctcctcctgttccgaccctgccgcttaccggatacctgtccgcctttctcccttcgggaagcgtggcgctttctcatagctcacgct
gtaggtatctcagttcggtgtaggtcgttcgctccaagctgggctgtgcacgaaccccccgttcagcccgaccgctgcgccttatcc
ggtaactatcgtcttgagtccaacccggtaagacacgacttatcgccactggcagcagccactggtaacaggattagcagagcgaggt
atgtaggcggtgctacagagtcttgaagtggtggcctaactacggctacactagaagaacagtatttggtatctgcgctctgctgaagc
cagttaccttcggaaaaagagttggtagctcttgatccggcaaacaaaccaccgctggtagcggtggttttttgtttgcaagcagcagat
tacggcagaaaaaaaggatctcaagaagatccttttgatcttttctacggggtctgacgctcagtggaacgaaaactcacgttaaggga
tttggtcatgagattatcaaaaaggatcttcacctagatccttttaaattaaaatgaagttttaaatcaatctaaagtatatatgagtaaactt
ggtctgacagttaccaatgcttaatcagtgaggcacctatctcagcgatctgtctatttcgttcatccatagttgcctgactccccgtcgtg
tagataactacgatacgggagggcttaccatctggccccagtgctgcaatgataccgcgagacccacgctcaccggctccagatttatc
ggggcgctgaggtcgtgcctcgtgaagaaggtgttgctgactcatacccaagcctcatcaccaggcctcatccagcctcgggggggga
gggcgctgaggtcgtgcctcgtgaagaaggtgttgctgactcatacccaagcctcatcaccaggcctcatccagcctcgggggggga FIG. 15B (continued)

gccacgyttgatgagagctttgttgttggaccagttggtgatttgaactttgcttgccacggaacggtctgcgttgtcgggaagat
gcgtgatctgatccttcaactcagcagcaaaagttcgatttattcaacaaagccgcgtccgtcaagtcagctctgccagtgttac
aaccaattaaccaattctgattagaaaaactcatcgagcatcaaatgaaactgcaattattcatatcagattatcaataccatattttgaa
aaagccgttctgtaatgaaggagaaaactcaccgaggcagttccataggatggcaagatcctgtatcggtctgcgattcgactcgt
ccaacatcaatacaacctattaattccctctgtcaaaaataaggttatcaagtgagaaaatcaccatgagtgacgactgaatccggtgag
aatggcaaaagctatgtcattcttccagactgttcaacaggccagccattacgctcgtcatcaaaaatcactcgcatcaaccaaaccgtt
attcattcgtgattgcgcctgagcgagcgagacgaaatacgcgatcgtgttaaaaaggacaattacaaacaggaatcgaatgcaaccggcgc
aggaacactgccagcgcatcaacaatatttcacctgaatcaggatatttcttcaataccctggaatgctgttccggggatcgcagtgg
tgagtaaccatgcatcatcaggagtacggataaaatgcttgatggtcggaagaaggcataaaattccgtcagccagtttagtctgaccatct
catctgtaacatcattgcaacgctaccttgccatgttcagaaaacaactctggcgcatcgggcttcccatacaatcgatagattgtcgc
acctgattgccgacattatggctctataacaccccctgtattactgtttatgtaactgtttcatgatgataataattttatcttgtcaatgta
tcccgttgaatatgcgtcataaaacaggaatttgagacacaacgtggcgttccccccccattattgaagcattatcaggttatgtctcatgagcggatacatatt
tgaatgtatttagaaaaaataaacaaataggggtttccgcgcacattcccgaaaagtgccacctgacgtctaagaaaccattattcatg
acattaacctataaaaataggcgtatcacgaggccctttcgtc

FIG. 16B

SEQ ID NO: 12 tcgccggttcgttcggtgatgacggtgaaaacctgacacatgcagtcccggagacggtcacagcttgtctgtaagcggatgccggagcagacaaagcccgtcaggccgcgtcaggcggtgttggcggtgtcggtgtcggcttaactatgcggcatcagagcagattgactgagagtgcaccatatgcggtgaaatacccgacagatgcgtaagagagaaatacgcatcagattggctattggccattgcatacgttgtatccatatcataatatgtacattatattggctcatgtccaacattaccgcatgtgacattgattattgactagttataatagtaatcaattacggggtcattagttcatagcccatatatggagttccgcgttacataactacggtaaatgccgcctggctgtgaccgcccaacgacccccgccattgactgactcaataatgacgtatgttcccatagtaacgccaatagggactttccattgacgtcaatgggtggagtattacggtaaactgcccacttggcagtacatcaagtgtatcatatgccaagtacgccccctattgacgtcaatgacggtaaatggcccgcctggcattatgcccagtacatgaccttatggcagtacttcctacttggcagtacatctacgtattagtcatcgctattaccatggtgatgcggttttggcagtacatcaaatgggcgtggatagcggtttgactcacggggattcaagtctccaccccattgacgtcaatgggagtttgttttggcaccaaaatcaacgggactttccaaaatgtcgtaacaactccgccccattgacgcaaatgggcggtaggcgtgtacggtgggaggtctatataagcagagctcgtttagtgaaccgtcagatcgcctggagacgccatccacgctgttttgacctccatagaagacaccgggaccgatccagcctcatgggctccatctcccttcacgcgtccgccccctactgagttaaagctctagttaaagctcagtcgagaccgcggccttgtcgccggctctccccttggagcctgtggtgctgcctcctgaactgcgtccgccgtctaggtaaggttaaagctgctcaactcactagttgcttgtcaagactactaggggaagaggatccaaaccaaagctagagccggctttaacggttctcttctgacgtggcgtcacacgggctccctccgcctgaactgctaacagcggaagacagaaatcaaaccgccaccatgaaataatgcgccagtacatgatctggtgctgcacgtgagagagttctccctcctttctaacgctgacctcggtcccatcagcgccaaaaaagcagccggccaggaattcatcatgacgtttacggcccagactccaaaccctacgttctcccatcggcaaactggcaataacgccaaccggctgcactgcggcctcctgggaataggccccgtttgtggaccacccctacaagctctgttagagctggtagcgtgagtcatgtccccggccaaatcatgctccacgcgcccagggtcatccaactagtggtgtgcagaggatttcgccccgcgttagatgacactggactggcccctgcggcccaactagtggcatgctgcctacccaatcagcggtaatcaacgcgtcgagacgtgtgatcagataccggggacgccaccagaacagcaatcaaacgcaagaatcaacgcagatgccagaacggaaggcggagtcaaggtcgcacttggggcagcagctcttagggtaccccgaacaaagaagaaagacaacaagcaaaagacaagaaaagagaacagcaatcaagcagatgcgtaaatgccctgacaatgagacagaaccccaagaatgggatttacggcccagactccaaaccccaaggcctcaaacaaaggaagaacgactctgccagcggaatcagttgcccgaaaaagagaaaagattgcatgaagatttacttcgaaggcagaagggcctccaaaacaaaggagaagaaggaccccaaatatgcctgggggtcaatccccgcaagcggaaaaatgcccacgttcagtcagtgccacagagtcagtagttcactataccgacagaagtcatgaaacgccaccaacgaatggtccaaaacccaaagaggcccaaaaaacctgcgaagaagcgtttcgtaaaagtgaagtcgagtctctgtccccggggaggatgctccagggccgatcgaacgcagattgctaccgacagaaagtcttcactgggaaaacgcctccgaaacgccgcaacctactaccggggccccccactgggagtaggtcccgggaaccaaacaccccaaaaccccaaggcctcaaaggtccaagacgagtttgagacgagtcggcccccaaccaggtcccgcacaggcgctatcctcgtcgcggaggtccaaccaggccaaccgatcaggcaggggccccgagagtggtccccgctattactgcctgccgtgtgtgcaggtcctccaacaacctgtaggcaccacctaggcacggcaacttctgcgtaccgggcaagagtatggtagtctttctgaaacacagcactgaagatcgccgtttcaagcctacttcgttgagtcacgttgagagagttgaacgcaaaacgcaaggccgtcgcaggccgctattaaagctacctggccgcccaaactgcctgtgtaatgatcacccatcaatcactagaacaagcgtgttagcaagctgttgagagcaatatctccgcctcgcgagaggcaagagccggatcgccgcgccctcagccattcggaacatcaccagtgcccaaggcctgcgggccgcatgccctcgatattgtcatctagacgggatgttcatactgaagcccaaaaccgaatacatagttgaggactaggtgttgactgatattgagactcaactgggactaggggcttggttgagacagattactagcctgacgatgaagcgagctagaccatcatcgggcggggccccctatggctcacagcagcaaagggtcctgccagggcattagatcaccgctggtgcccgctagacacacatctgaagttcacgcaccagctgaagaagcggaaccgtcgcttgctgccaccggcttaacgcggcttgagcggccatgcctgcttgcgtgaaaaccgcggaaggcgttggtaccaacaagggaaaaccgcgaatcaattcaggatgcagctacggcgtcaagccctaacggcaaagagagcatgcaaggcgtgaggcccgaggcagaggagtctggcgaatcgcaacaacaaaggtcgtcatggagacattcactatcccgcaaggagagcacaggctggccagagatcgcccccacaatgccgcagaaatgtcccccgtctctagctcagagcaggatccgaagacgtcaatgctcctagagagaggggtctgtctctcgtcttgagcagaatcatctatcgccgcgcccgacatccctcagctcggtagagactcgacaaaatggtatgcagtctgcaggaaaagagattgtccgcgcagagtctgtcgggagactctcgaaagcttagagacgccggactcccccccagccggactggaggagggcatgatctgatgcgggagatgcgtactagttggagtggtactaactcgacagatcgcccccagaacaccagccccgacaagctagaccatgctttgctagtaccgacttgctgcgaggaaaaacctaagcgctcagtcgagctcgtaaagatttacgcgtcggaaggcccaacgagcagctgcttggggccgcaccaccccgggacctggtccgcgctggccacggatggtagttcggcggggtgcgtacttgacactctctgacggaaagtccaggcagtgtgctctcgcgtgaagcttgaaaccgtggcggcaaggcgctctggactcaggccacagagacacaggaggaccagttgggcttgcggcagatcaggggacctcctcccgagtcctggagaacgccgcaagcgcgatatgcccccggttgcttcagcttgcctatgctaatgcccggcccaaccatacgaacgccaagcactactagttgaagaaagtcaaggtgtgttatcgaaccgagagcggaagacatgccctggcacgcccagcgccactattaaatgcagcccaaggccccagtggggttcccagccgatcgccgcgaagatagacaatcaaaactccatgcgctagcagcctgaaatgtggccgttcagccgccgccccccctctctgtctactcccctgaccatctcagcaatctccaccaacctgtttccacaccgcttccattacgggtgcagagaggtcagcgggcatcatcgtcgttccctggggaacaggcatcggcaccactggctgcctcggccgatcagaattggttccagcagggtcctgcccaaatgatgggagtaaccaggcctctcaggaggacttcaattaccaaatggatcaagactagacgacctgcttgtgacccacttcatccaaagtcagacccagccacctgcgcgaagcctgcggcgtacatcgaagccccgcctttgaggagtccaacagaaagaatatcatgcccggtcaactcagcccgatacttgtcatactcggcaagattgggcggctcacaccgtgcattagcctgagtggcttcccgttctgctggtggagtcagtaggaacaccagggaaggaaagagggtgcattgacattcttgtactgtgcctgaaagccccaagcgcatggaatagactctctgatttcggcgggaacatgttggtcacgctcaaggctggacagtaccttcggtgaccatgtgggaagaccatagatgatcaagcaacgactgcactgtatcgacagccccgcagtagatcgctctcggagcatcggcggaaggagaggaaatagaggagccacaggagctgattctggcaactatgatctcgacctagttgttcagctggaggctgatggatgagtgtctgtagtgtaaggttgactcatcgcctgttcgttgagccaagctgctcgcacgcgtgacgctagctttcagcgtacgagctgctagctacttcgcatcattggaaaaggtgactaatggagatgaatcatcatgtcatagccggaatctagagacaaatgcccggaatatccttctgtgtgctggtgctggccgtgcgtgtgactgtgtcgtagaagaagccatgcttactagagccgaatcctatacaagcagaatgcatagcggaacttcgacagcaggagttacccatcaattcgtacacctctagcttctcatgccaatcacctcagactctgcgcccacttgcacccatcaaaagccgagcccgaactctcatgcactgcgccttccgctgtggcagcacagcttcgcacgggaatcgcctgagcgctgcgccacctcacaatgacgactgactgcactggcccagactgctagctctatatacgccacgctatgccatacgctccatttcgcagccgtcacaagcagtcatggtccaggtcccgcgtgcgtttatgaaccctaagctgtgactggcctgcggaagcaacactatcagcaggaccagctctaggttaatcgcagagagcctgcaatcgaaaagcacacacgaaaacggcaacgccgcacccgagctgcgacgcctgcgccatcgagcgccgccatctcgggtagggagaatatggtcagagcgacatctgcggtgagagcgacaggtcgcgagcagagcctaactgccgccaccgcttgcaaagcatcctcacggccgcaaggcgtgactggcttacccgacttcaccagacagtggaagaccgatagaagagagagccgaggccaatagaccgaggcaggccgctagatagcctatcagcttgccgatatctctgagcttagcgctaaggaggtgcacaatgtaggggctgagtacaaagaaatactctctgcctgggaagatcaaagaggaggaatagcaggtccccgttatgcggaaacagcgcttcggccatccgccgaccagcaccccacaccctcagcacaccagcagccccagcaagcccaccctggacccctgagccggtcgatgcggcagtggtctcagagatcagcagagcttgccgtgcggagtcgagcagtactctgacctccccgctgtacttctcgcctgctcagacgtgtgcgtatgcctaggctgggcgccgagaggcccagcaggtcaggtgggatctcgggtgtgtagtttctccccactacaaccttcccaccctcggtccacagcgtagagccccaaatgaccgttgagctccgagcgttcagcctggggcgccaggacgaggtcaaggtctcgaagccaagtgcatagcaacagctttgcccaggtatactgtggagccccctgctgtctggctctcgacatcctagagcaaacctccccaaaggccctccaaggggttgcgaagggaacgcgatagagctcaggatgagaccaaggaggccacctgggcccccagggcatagacaacatagcgacctcccgggcgtctgtggccgaggctgccctgcgaggtcgggcgaagacgaggccagaccaagtgtctacagcgcatgagcaagcctaccaccatcccaccactaactgctgtcaggccgaaggcatcagtctggccatcagcgacgagcgcatcggcctcagcgctcaatgacaaacacaaggcctagcaagttccgatttcggaagaggttctgctcagcaaaactgcagtcaggtggtgcaggcacagctacatcagacacagcaatcagtagcatgcccttcgcgtcattcaagagtctgcatgacatgcgcaccggtatctaatggcgaggccgccctcgggggaggtgacaggctcgaggcatcaggccgagggcttctccatggcagtagctgcagcagaggtcacaaacaccctcgtcggcatgcagcttagactctaagggggacctcgctgcccagggaaatctgcttacatcgaccgccgcaatcaatcaggtactgtgcgccccgtcctagagcaagccccaacaagactctgtccgagcaacccgaagaaggaagacaagctggaaggggcgaacgcagaaccggcccgctcccatcgccccgagagaggatcagcaggacgagcgctgtcagcaacaggcccagccgaaggcccagccctgcagaccaatagcccccgctgtcaggagccaaggttaaccagatagcagctccccaacttgagcctggtgatcaatccaatgagacgcaaaggggtgcagcgccagagggaccctctttcagaagccaaccagtctggttctgtcagtgtcgctcgcgttcgtccagctctagcccgggcggcaagaggtgcgctgcgccagccccaagctagttcatccggcggccacagatcatcatccaccgacttgcatctccagaactacgagcaatcgactgcaactggtgcgcagcttgtgagcgcgtcgcgacagtgacggatttcgctcctgggctttacaggctcggagctaccgacgcccaggctggacgaagcagacgtacgcagcaccgggtcactatagcttctaacgaaaggaatatcgactccgatgggcagctcgagcagaccacgcagacgtggccaccggaatagcaggccccgcggtgagcacaagcccgtacctcaccgatggtcagaggccgccttgccactggcgccggggtagagacgtcctcacaagaaagcgaagggcttcctacgccctggtgacctgcgtgcctggcaacccaagcaaggagaggcgccatttagcacaaaagccgccaccgcaaccacaccaccggagcctgcagccgagctctccgcgcgccagaaatcgtcgcgccgtctgagcactctggaaccttccaagcgggcacagcacaatagcaaagcaaatgtatgagtaggcaatatgatctgcgcagcagacagtagggagtccactaggaaatacacgaagatgtagggatagaagaagcagcaaaaggccacagtccagcgcgccgatgcgcgcagcaagaaagccaaccaccgccaggcaacggcacagcccgaacggcggccacagcaaccctagcgctgctacatgaagatgcaaagctctctccagcaaagacccgacaagcaaagacgcacagcggccaccccagcaactgcaagcatcccagctgagcccggagcgcctagtacgcctcgcagaaggcaagaggaggaagagagaacacgcgaagacaatggacagcatagtccggaaactgagcccccgcagccgaaggtgacaaaccctgggcccgaggcttgcagcgaggcagaaacgaccagggcaagccgacagtgggtaaggacctgctgccacgagagttcagaagccgagcccaatcccggagaacaatgagaaaagccacacaaagaacaaatggaagacagaatgagggagcaacgtgtccaagatcatcagttgggagagcgacaagcaaacaagctcatgaaagcgaatcgaagaggggcctgtcaattacgagattcgatctcagcagaaacgccagagcatgacgcaacgcgagaagggctccgaccaaggaccacagagccagcgcgcagccgccatgctgaagaacccgcctgccactagcctgaccagcttcgacaatcgctcctttcccgtcgtgtaccggcccgggccagacctgtcgctctgtgcatactcagactgcggggacctgaatgggagatcagaacagttgttctcgtggaccttggtcaccaggatctgcaacagatacgcgccagcgaccgagcgagggcaagcccagctctacgaaggggcctggggacctcagcttccggcgatgaagccccactgactcccccagggccacgtgctccacagcctgcgagtaaccgtcagaattcgaactcttcctgtccacccggggccgtcgccgcgccgcccctcgcgactgcgggctcggcccgccgtgctgtatgcggccaactgagcgtctcagcaccaccaccgtctcaaccggcagcaatgcggtgacttcgcacagaaacagagcaaaccaccacagaaccaaacggaaaccgtcaccaactgccagcgtcttcaccccttgaccccacgacagccacctcaacgtgccaagactgcctgggccagtcaggagggcgaatttgaggatcagaccagctcccacaagggtctggaccaagccgcccagcaccgctcgcaaattaatcccaggaaagccgggtcagcaagctggaggcacaccaagagaaagatttcgagtcgaagtcagaagtaggaagtagagtagcgaaagccgccggaccaatgcagatcggcagccaggactctaccccgcacaccaatcgggccatgtgcacattaaccgacagactaccagcttctatagcgggccacagcacccaacgggagctcacaatatgggcaaaggccaaagggacatagaagagtcagcccttacaatcgcacaatagcgaagaatccctactccgggggcagaagccagccagcagccaactcccttaaagcttccggcacaccccgtttcatctccgcttccagtacagccctccaggcatcaccaagggccacctaccctgctttctcccccaccagaacctgcttaagaagagccatccacgctggggagctgaagaggacgtcatccagccaagcgacctgcgctgaccctgaagtccatcagaaaaaacagaatggaggccacgcagcagcctgatagtatggcaaaagagcagccacagtcagggcctaatcatgctcccacacccgaaaaccgaacccgtcctgaaccctgcgcgcatactcgtccggacccccaaagaagtccctgggccttgctgggcggcgcaaagtcgccgtcccggcccaatcatgactttccgtggctctcagggaagggcgtgaacagcgacatgggctttcaaaccatgtgcaagactgctcacgaagaaaagacaaaccaggcgaaggcgtatatcgagaagccgcacgatccgccggcgtcgagccagcatccatcggagcaacagggcttcaacggcgccatggatgtctgcaaaatgcgactggtgccctggactgggtagcagaatgcggacgggttctggccactgcgctccaccagcaacgcgggcccgcgtcccccctacaactaggtcaagtcgagctcaagggctgagtacaaagaatatactctctgcctgggaagatcaaagaggaggaatagcaggtccccgttatgcggaaacagcgcttcggccatccgccgaccagcaccccacaccctcagcacaccagcagccccagcaagcccaccctggacccctgagccggtcgatgcggcagtggtctcagagatcagcagagcttgccgtgcggagtcgagcagtactctgacctccccgctgtacttctcgcctgctcagacgtgtgcgtatgcctaggctgggcgccgagaggcccagcaggtcaggtgggatctcgggtgtgtagtttctccccactacaaccttcccaccctcggtccacagcgtagagccccaaatgaccgttgagctccgagcgttcagcctggggcgccaggacgaggtcaaggtctcgaagccaagtgcatagcaacagctttgcccaggtatactgtggagccccctgctgtctggctctcgacatcctagagcaaacctccccaaaggccctccaaggggttgcgaagggaacgcgatagagctcaggatgagaccaaggaggccacctgggcccccagggcatagacaacatagcgacctcccgggcgtctgtggccgaggctgccctgcgaggtcgggcgaagacgaggccagaccaagtgtctacagcgcatgagcaagcctaccaccatcccaccactaactgctgtcaggccgaaggcatcagtctggccatcagcgacgagcgcatcggcctcagcgctcaatgacaaacacaaggcctagcaagttccgatttcggaagaggttctgctcagcaaaactgcagtcaggtggtgcaggcacagctacatcagacacagcaatcagtagcatgcccttcgcgtcattcaagagtctgcatgacatgcgcaccggtatctaatggcgaggccgccctcgggggaggtgacaggctcgaggcatcaggccgagggcttctccatggcagtagctgcagcagaggtcacaaacaccctcgtcggcatgcagcttagactctaagggggacctcgctgcccagggaaatctgcttacatcgaccgccgcaatcaatcaggtactgtgcgccccgtcctagagcaagccccaacaagactctgtccgagcaacccgaagaaggaagacaagctggaaggggcgaacgcagaaccggcccgctcccatcgccccgagagaggatcagcaggacgagcgctgtcagcaacaggcccagccgaaggcccagccctgcagaccaatagcccccgctgtcaggagccaaggttaaccagatagcagctccccaacttgagcctggtgatcaatccaatgagacgcaaaggggtgcagcgccagagggaccctctttcagaagccaaccagtctggttctgtcagtgtcgctcgcgttcgtccagctctagcccgggcggcaagaggtgcgctgcgccagccccaagctagttcatccggcggccacagatcatcatccaccgacttgcatctccag FIG. 16B (continued)

aggataacgtggataggccaggtaccggtactacgaccttcaggcagccagccttgacgtgccgaaacggaacaagacacggccagcgt
gtcgcaacacttcaacgtgtataaggctacacatcgcgtactgcgactgcggagccagcaggcactcgtgtcatagcccc
gtagcaattgaagcggtcagttccgaagctaccgacgggatgctgaagattcagttctcggcacaaattggcatagataagagtgaca
atcatgactacacgaagataaggtacgacagggcacgccattgagaatgccgtccgtcatctttgaaggtagccacctccggag
actgttcgtccatgccacaatggacattcatactggcaaagtgcccaccggggtgaattcctgcaggtctgatccaggacaccaga
aacgcggtccgtcctgcctgcagaatacaatatcatcatgaccgtcaaccgtgggtagaagaaattacaattagaccacacatggaaa
agagatccctgcaccacttatcaacagacgggagaccgtgaggaaatcgacatgccagatacgccggaca
ggacgttgctatcacagcaatctggcaatgtaaagatcacagtcggagagaaagaaggtgaaatacaactgcacctgtggaaccggaa
acgttggcactactaattcggacatgacgatcaacacgtgtctaatagagcagtgccagtcagtgacggaccataagaaatggca
gttcaactcaccttcgtcccgagagccgagcggacgaaccggctagaaaaggcaaagtccatatccattccgttgacaacatcacatgc
agagttccaatggcgcgcgcaaaccgtcatccacggctgcaccagcgacactgcacccttcaccccagatcatccacgctctttt
cctaccgcacactggtgaggctgaggaccggcagtcacgagaagtggtgacagccgcgtggaacgtgaccatacccgtaccagtgga
cgggatggagtaccactgggaaacaacgaccagtgaggcttgctcaactcacgtgaaggaaacgcacggctgccg
catcagatcgtacagtactatggctttaccgcccgctacagtatccgcggtcgtcggatgagcttactgcgttgtgtatcgatct
tcgcgtcgtgctacatgcgtcgtcgcgccgggtgggcccgacgtaagtgctgaccctatgctttaacaccaggagtgcagttccgtgacgctg
gggatactctgctgcgccccgggcgctgcgccagcagtgtgcagagactatggctacttgtggaccaaaaccaagcgttgttc
tggttggagtttgccgcccctgttgccgccctgtgctcatcctcatcatcacgtgcctcagaaacgtcgtgttgctgtaagagccttcttttag
tgctactgagcctcggcaaccgccagagctacgaacattgacagtgccgaaacgtaatgccgaacggtgggttcccgtataaggctcacat
tgaaaggccaggatatagcccctcacttgcagatgcaggttgttgaaaccagcctcgaaccaaccctaattgaataccataacctg
tgagtacaagacggtcgtccgtcccgtccgtgccgtacgttgaagtgctgcgcgctcagagtgtccactaaaggaagaagcctgactactaaccaatg
caaggttacacaggcgttcaggcgtgtaccgtcatgtgggagagggcatatttgcctcgactcagaaagacacgcaactcagcaggcgtac
gtcgatcgatcggacgtatgcaggcatgatcaccttgctacaaagcccatacagcatcgtgaaggcgtactcagttcatatccggcgct
acggcaacgtaaaccagactgtgatgtttacgtgaacgggaaccatgcgtcacgatagggtactcagttcatattcggccgct
gtcatcggcctgaccccgtccgacacaagatagtcgtgtacaaagacgaagtgttcaatcagacgactccggctacgatctggg
caaccagggccttcggcactggcctgcgacaacatcaaagtgaagtaacgtacgccaactcaggcactgaagctggcacgc
ccttcaccggccatggcctgtcatgcagtagagacacttcaggttcaaatattgctaaaggaaaagcgacagccctaaata
cgaaggctcctttgctgccaatcaaaacgaaacctgtcaggcctgcatgaactgccgctgaacatccctgtctccatgaatttg FIG. 16B (continued)

```
cctgacagcgcctttacccgcttcgaggtcgccattgtcgaggcgccgaccatcattgacctgactgcacagtggctactgtacgcactcctcggattc
ggcggcgtcttgacactgactgctacaagacagcaggaccaacaaggtgacctgctctgtacactcgcactctaacgtagctactctacaggag
gccacagcaaaagtgaagacagcaggtaagtgaccttacacttctccacggccaagcgcatcaccttcttttggtgtcgctatgcag
tgctaggggccacctgttcagcgtcgtgtgagcccgtgagcccctatagtcccatatgcggctagccacagtaacgtaagtagtgttccca
gacatgtcgggcaccgcactatcatggtgcagataatctagaccaggccctggatccagatctgtgcctctagttgccagccatctgttttgc
ggtcacttgcattggctccgcagataatctagaccaggccctggatccagatctgtgcctctagttgccagccatctgttttgc
ccctcccccgtgccttccttgacccttggaagtgccactccacactgtccttcctaataaaatgaggaaatgatcgcattgtctgagta
ggtgtcattcattcggggtgggggtgggcaggacagcaggaagggaaagaagaaagcaggcacatccccttctgtgac
ggtgggctcatgggtaccccagttgctgaagaattgaccgggttcctccctgggccagaaagaagcaggcacatccccttctgtgac
acacccgtccacgcccctgttcttagttccagcccactagctcaggagctccgccttcaatccaccgc
taaagtacttgagcggtctctctccctcctcatcagcccacaaactagcctccaagagtggaagaaagcaagata
ggctattaagtgcagaggagagaaaatgcctccaaacatgtgaggaagtaatgagagaaatcatagaatttaaggccatgattaagg
ccatcatggccttaatcttccgcttcctgctcactgactgctgctccgtcgccgagcgtatcagctgctcactcaaag
gcggtaatacggttatcacagaatcaggggataacgcaggaaagaacatgtgagcaggaaacatgagcgccagagcccagagcgta
aaaagcccgcgttgctgcgtttttccatagcgtcccccctgacgagcatcacaaaaatcgacgctcaagtcagaggtggcgaa
acccgacagggactataaagatacaggcgtttcccccctgaagctcccctcgtgcgctcctgttccgaccctgcgcttaccggatac
ctgtccgcctttctcccttcgggaagcgtggcgctttctcatagctccgctgtatctcagttcggtgtaggtcgttcgctccaagct
gggctgtgtgcacgaaccccccgttcagccgcctgtcgccttatccggtaactatcgtcttgagtccaaccggtaagcacgac
ttatcgccactggcagcagccactggtaacaggattagcagcgaggtatgcaggcaggtgcaggtactacagagttcttgaagtgtgccta
actacggctacactagaagaacagtattggtatctgcgctcttgaagccagtactcccggaaaagtctgacttgcttgatccg
gcaaacaaccaccgctggtagcggtggtttttttttgttgcaagcagcagattacgcgcagaaaaaaaaggatctcaagaagatcctttg
atcttttctacggggtctgacgctcagtggaacgaaaactcacgttaaggatttggtcatgagattatcaaaaggatcttcacctagat
cctttaaattaaaaatgaagttttaaatcaatcaaagtatatatgagtaaacttggtctgacagttaccaatgcttaatcagtgaggcacct
atctcagcgatctgtctatttcgttcatccatagttgcctgactccgggggggcgtgaggtcgctcgttgtagtggtgct
gactcataccaggcctgaatcatccagcgcccatcatccagccagaaagtgaggagccacggttgatgagagctttgttgttggtgaccagt
tggtgatttgaacttttgcttgccacggacgtctgcgttcggaagatgtgatctgatcctcaactcagcaaagttcgattta
ttcaacaaagcccgtccgtccgaagtaagcctgcaagttacaaccaatttatggtacaaccaattaccaattctgattagaaaaactcatcgag
```

FIG. 16B (continued)

catcaaatgaaactgcaattattcatatcaggattatcaataccatattttgaaaaagccgtttcgttctgtaatgaaggagaaaactcaccgag
gcagttccataggatggcaagatccttggtatcggtctgcgattccgactcgtccaacatcaataacaacctattaatttccctcgtcaaaa
ataaggttatcaagtgagaaatcaccatgagtgacgactgaatccgttgagaaatggcaaaagcttatgcattcttccagactgttcaa
caggccagccattacgctcgtcatcaaaaatcactcgcatcaaccaaaccgttattcattcgtgattgcgcctgagcgagacgaaatacg
cgatcgctgttaaaaggacaattacaaacaggaatgcaaaccggcgcaggaacactgccagcgcatcaacaatatttcacctg
aatcaggatattcttctaatacctggaatgctgttttcccggggatcgcagtggtgagtaaccatgcatcatcaggagtacggataaaatg
cttgatggtcggaagaggcataaattccgtcagccagttagtctgaccatcatctgtaacatcattggcaacgctaccttgccatgttt
cagaaacaactctggcgcatcgggcttcccatacaatcgatagattgtcgcacctgattgccgacattatcgagccccattatacc
atataatcagcatccatgttggaattaatcggcctcgagcaagacgtttccgttgaatatggctcataacaccccttgtattactgtt
tatgtaagcagacagtttattgttcatgcatttatcttgtcatgataatatttttatgtctctcatgagcggatacatatttgaatgtatttagaaaaataaacaaataggggttccgc
gcacatttcccgaaaagtgccacctgacgtctaagaaaaccattaacctataaaaataggcgtatcacgaggccctt
tcgtc

FIG. 17B

SEQ ID NO: 13 tcgcgcgtttcgttgatgacggtgaaaacctgacacatgcagctcccggagacggtcacagcttgtcgtaagcggatgccggagcagacaagcccgtcaggccgcgtcagcggtgttggcggtgttgcgtgttcggacatgtgaactatgcggttaactatgccatcagagcagattgtactgagagtgcaccatatgcggtgtgaaatccgcacagatgcgtaaggagaaaataccgcatcagattgcctattgccattgcatacgttgtatccatatcataatatgtacattatatggctcatgtccaacatattaccgccatgttgacatattgactgttattataatagtaataatcaacgggtgtcattagttcatagcccatatatggagttccgcgttacatacttacggtaaatggcccgcctggctgaccgcccaacgacccccgcccattgacgtcaataatgacgtatgttcccatagtaacgccaatagggactttccattgacgtcaatgggtggagtatttacggtaaactgcccacttggcagtacatcaagtgtatcatatgccaagtacgccccctattgacgtcaatgacggtaaatggcccgcctggcattatgcccagtacatgaccttatgggactttcctacttggcagtacatctacgtattagtcatcgctattaccatggtcgatgtggcagtacatcaatgggcgtggatagcggtttgactcacggggatttccaagtctccaccccattgacgtcaatgggagtttgttttggcaccaaaatcaacgggactttccaaaatgtcgtaacaactccgccccattgacgcaaatgggcggtaggcgtgtacggtgggaggtctatataagcagagctcgtttagtgaaccgtcagatcgcctggagacgccatccacgctgttttgacctccatagaagacaccggaccgatccagcctccggcatctgttaaccgtcctcttcacgcgtctcagatgcctgtctgcgccgcccatccacctgaggcccatcacgccgtttgactgaggcccttttgtccggcctcgtcgcctccgcccctgttgtgtcctcgaactgctgtgcgccgcccaccagacataaagctggcgcgcctactgtctttgcctgacactaacagactgttcctttccatggtctttctgcagtcactgccgcgtcgtcgcgggacactagcggcatcaagctgcggggtagactgcggtgtcgcatttggcgggcatcaggcaccggcatcggactaacactacttcaccatgtcaacacgcgtcgatcagataaccagacaagtaacagcccgtaccgcggtcaggtagctggaccttccgctggcgcgcctactgccctctccgaggacagatgccaactgccgcagcagcaccaagagaagggcctgcccatcgcctatgaccacagcggcagcagatggcaacgccctactgccctcgcgaaccagatgagtgcgtccagttgcaggtgtcaggtagctggactgccggcgctgccgacttgccaagctggcaagtccgaaccgccgttggcccaagctgacccgcctgggccaagacgtgtcagaagaacaagccgctccagtaacttccacgggaaaactttccaacggaagaacaactaggaaaaacccaaagagaaaagaaggaagaacaaggaggaaccgggaagaaggaggttaagatctcctaaagtcccaaacagcagcaaggaaggcggtggcgaaaaagtcaagaagactaggaaaaaagtaagagaacgcgggagagaagaactaaagaggttaagatctcgtattgcctgattcaagccgcgatcgcgtattcaagcccgcacacgtgaagggagcccacttcccccgtaccacgaaggtgtactcagagttctgctaatatccgctacgtgttgcgattgccgtatcagccgagctggaccgtgaaggctaagatcgaccaccctgaactgcagacatggccagattccaggtcgcgagacctcgaaggcagcagcgacctgcgtaccggaagagcatgcggaccaagcaagcggctgacaccagaccgtcagccgctcgcctggttacccaatgcctccgagacatggacctgtgaccactcggccatcaccgacaactcgggaaactcggaaaggttcttgttgtcctataatcgacgcagccaagccggggtcgacagtcccagggccatgtggaccagtggcaggccgcctcaccgacaactccggtttcagccttccagcatcggccagaactggcccaccgcaacaagatggaaacgaagccgagtttcgaatgtcaggttctaggccgccgcatcaccggcagcgtttgcctgatacgtcacacctttcgaccaacaagaagaactcaaaaactcaaaagccggtcgtagggatcaagtgatcctggcggaggcatcaaaaatacaacgagaccaaccccctcctcccgtctctggcggtcaaaggtggtctaggcctcgaaggctcaaaaatgtcctggtggtaaccctgcttcaagccattccaccacctattcgaccaccggaatcctgtatggtccaccatagggatagttcggagatcgtcaccatctgaaaggcgcatcagagtcaccccctgatagtaggttcttcgagaattttctaatttcggcctactgagccgccactgcggaggcaattcaaacaaccagatgctgatttgctcca FIG. 17B (continued)

aaccgtcctgccaggactgctgcattactgctgaagaaggccatgaccatgctgaaggacaatctgaacgaccgaactact
gggacctactcattgctgtcaccactgtggctcctgtggctccgccccggagaagaagggctgtctacgtcgtcgccgcctttacgacacaca
gatcctcgccgccacgcagtcgctcccccatacagaggcgtactgcccgattgtgacggaacagcgtgtatctcgccgatagccat
cgacgagtgtgagcagtggcagcgaccagctcctccgcatgcggcggttggttgtctcaatcgggagtgaccgctaaggggtggtggcgg
cgggtgaaacctctctgcgatacctgggaaggagcgggaaggttcacgccgcagacaacgcgactcgtggtgcgcacgactgc
aaagtgcgactgtgctgcaggccactgtcggccactacatcctgccaactgcccagtgggcagagccgcagagccatcgcaactgg
atggcaccggcatcaatgcaccacgtttcgaacacaccaagtaacggagaagttcaccagagaacgcagcaagggccaccatctg
tccgacatgaccaagaaatgcaccagatttccactaccacaaaaaagtccgccctctacctcgttgatgtgtatgacgctctgccgatt
ctgtagagattagcaccgtcgtaacatgcagcgtcgacagcccagtgcacagtgaggtgccacctggtaccacagtgaaattcgacaaga
aatgcaagagcgctgactcgcaactccactttcaccagcgactccagtgtgagagcagtccagtccaagcctgcca
gtatcaacccagggccaagcaacctcagagatcggccaatgtgccccactcggccaatgtgaggaagtgaaagcaaggatcccgttccgtc
ccgccggaaaccgcaactgcaagagtgagtgtagccaaccttggttccatagcaacgccacatccgatcacctctacgagggaaagcgatgtcctgctagccggtac
cgcaaaataccccgtgctgctaaccacacggaaccttgggttccatagcaacgccacatccgatcacccaaatggatccaggcaagtactgcgc
ggcatccggtcagcccaaggatcgatcgagcgaacatggggaaacaacgcgccgatgcactttggtcatccgtcaggtacgcatcc
gggcagcgtgatgcggtaccccttggctacttctgttgcatgttcgtgcgcatcttggcgcatgttcgtgcgcatcgttgtaggagtgcat
gcggcctgctgctatcgcagcgtgcatgtttgcgtgcgcactgtgtgcatacccaagcagcaggggctgcgcggaccaacctactttgacatcattgcctact
cccaccaccattgaccgctgactgactgcagcactgtgtgcataccaagcagggggctcgcgcggcctgtgccgttgtgcgttgtaggcgtcaacactgttggagttgcat
tgtgaccaacagcagaaagtgctttttaggtgtaagagggttgtcagcctgtgtcatcctttgcgtatgtaagagctgcaagagctacgaa
agattgctgcaagcttcttttggtgtaagagggttgtcagctgtacgaagcagtgataaaccgaatggtatgatcattgaagctgacc
cacaccgctgtggtccaatgatccaagagacccccgctcggctacgaaggcaaggctcagaatattggacctgccggaagtcgagccgccatgtg
atctcagtgaattcaccgctcatcaccaactacgctggtcatgctcaggaatattgcaaagctgtctccgacgtgcactgcgatgtg
ggctgctgcacgtcggtcgtcctgccctgacctctacgctgcatgcgtttactgccaaagctgctctccgactgcactgcgatgtg
cacacaaagtgtacccctgttgtgggcgccagacgtcagagcgtccaggactgcccgaaatacacaagtcagcgctgagtctgtgaccgtt
tttctgagtctgcgtggccaggactcagaggcagtttacgggacggccgaagccgttcagcggacagttacaagcaccgctacgcagatcactcaggtgggtagtcggtagtcctgtgacgctt
ggtgaagtggtgacggcagtccacgttacgtggacgggtaacatcagtccgaagcacgagacgggtaacatcagtgcacccaagatcgtggctggaccaat
aacaaccgactactcccattcgagacattcaagtcaaccaactatgtcaaccaactatgtaactcaggcgaagagagtctataactatgacgtgcctcctacggggctgc
cgaccaggcacacattcgagacattcaagtcaaccaactatgtcaaccaactatgtcaaccaactatgtaactcaggcgaagagagtctataactatgacgatcgtatgggacatcggaattgaagtac FIG. 17B (continued)

tgcagccgactaacgaccagtaacatgtggttacacgtatacgacctcggttactgcttgctgcaggacgctccgaaaccactc
agtgtcacagcaccgacaccgacggttgaagatcagtgccaatcgcgtcctgtcctggcctcggcctgattgtggcgttggtgccgtcccatgtccatcaa
catccggacgcggaagttaccgccacgtcgaaattaaaggatccgaaaccatcggccctgaaatgctgtgtggacagctgagtgactacgggt
ggactacggggcgccgccacgatcactacgaggccacgaggaaagtgcggattcattcctgacaccagagtccc
cctgagaacatcggttgcttgaagtggttgctggcgccaataaccgtcaaaaacgaccttctcctcaccacgcccgagggttcactcgag
gtagagatcgttcggcaatagtgaagtgcgctggtgagtgcactcaccgaaggaacatgtggtcgcaaccaggcctcgccatggc
agcgaccctgaggctacatctcggggccccgcaatgcgctgggccgccaatgtgtaggacctagtgctcgttcctgttcctgtcctgttcctatcctg
ccgtcatctactcgtgtgaagaagtgccgctccaaaagaatccggatagtcaagctaatcgagaccagccctgcgatccagatc
tgctgctgctcctctagttgccagccatctgtttgccctcccccgtgcctctttgacccctgaaggtgccactccactgtccctcta
ataaaatgaggaaattgcatcgcattgctgagtaggtgtcattctattctggggttgtggcaggacagcaaggggaggat
tgggaagacaatagacagcagggatgcggtgggctctatggtgtaccagctgctgaagaattgaccccggttcctcctgggcc
agaagaagcaggcacacatcccctctgtgacacacccgtccaccagctcttagttccagcccccactcataggacactcata
gctcaggagggctccgcccttcaatccaccccgctaaagtacttggacgctctcccctcatcagcccaccaaaaccaaacctag
cctccaagagtggggaagaaattaaagcaagatgggcctattaagtgcagaggcagagagaaaaatgcctccaacatgtgaggaagtaataga
gagaaatcatagaccttaaggcatgatttaaggccatacagcccttaatcttccgcttcctcgctcactgactgctgctgcgtcgtt
cggctccggcgagcggcgtatcagctcactcaaaggccgtaatacagagttatcccacagaatcaggggataacgcaggaaagaacatgtg
agcaaaggccagcaaaaggccaggaaccgtaaaaaggccgcgttgctggcgtttttccataggctccgcccccctgacgagcatc
acaaaaatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgctgtag
gtatctcagttcggtgtaggtcgttcgctccaagctgggctgtgtgcacgaaccccccgttcagcccgaccgctgcgccttatccggta
actatcgtcttgagtccaacccggtaagacacgacttatcgccactggcagcagccactggtaacaggattagcagagcgaggtatgt
aggcggtgctacagagttcttgaagtggtggcctaactacggctacactagaagaacagtatttggtatctgcgctctgctgaagccagt
taccttcggaaaaagagttggtagctcttgatccggcaaacaaaccaccgctggtagcggtggttttttgttgcaagcagcagattacg
cgcagaaaaaaggatctcaagaagatccttgatcttttctacggggtctgacgctcagtggaacgaaaactcacgttaagggattttg
gtcatgagattatcaaaaaggatcttcacctagatccttttaaattaaaaatgaagttttaaatcaatctaaagtatatatgagtaaactttggtc
tgacagttaccaatgcttaatcagtgaggcacctatccagccctatccagtgcacctatctcagcgatctgtctattcagccccatcagtgctcctgactcgggggggggtc
cgctgaggtctgcctcgtgaagaaggtgttgctgactcataccaggcctgaatcgccccatcagtgcaatcgccccatcagccagccatcagcaagaaagtgaggagcca FIG. 17B (continued)

cggttgatgagagctttgttgtagtggaccagttggtgattgaactttgctttgccacggaacggtcgcgttgtcggaagatgcgt
gatcgatccttcaactcaagttcgattattcaacaaagccgcgtcccgtcaagtcagctcagcgtaatgtctgccagtgttacaacc
aattaaccaattctgattagaaaaactcatcgagcatcaaatgaaaactgcaattattcatatcaggattatcaataccatattttgaaaaag
ccgtttctgaatgaaggagaaaactcaccgaggcagttcccataggatggcaagatcctgtatcggtctcgcgattccgactcgtccaa
catcaatacaaacctattaattccccctcgtcaaaaataaggttatcaagtgagaaatcaccatgagtgacgactgaatccggtgagaatg
gcaaaagcttatgcattcttccagactgttcaacaggcccattacgctcgtcatcaaaatcactcgcatcaaccaaaccgttattc
attcgtgattgcgcctgagcgagacgaaatacgcgatcgtgttaaaaggacaattacaaacaggaatcgaatgcaaccgcgcgcagg
aacactgccagcgcatcaacatcaggagtatcaggatattcttctaatacctggaatgctgttttccggggatcgcagtggtga
gtaaccatgcatcattggcaacgctaccttttgccatgtttcagaagaggcataaattccgtcagccagttagtctgaccatctcat
ctgtaacatcattggcaacgctaccttttgccatgtttcagaaacaactctgccatcggcttccatacaatcgatagattgtcgcacc
tgattgcccgacattatcgcgagccgagcccattataccatataaatcagccatgttgaattaatcgggcctgagcaagacgttcc
cgttgaatatggctcataacaccccctgttattactgtttatgtaagcagacagttattgttcatgatgatatattttatcttgtcaatgtaac
atcagagatttgagacacaaacgtggctttccccccccccattattgaagcattatcaggttattgtctcatgagcggatacatattg
aatgtattgagaaaataaacaaatagggttccgcacatttcccgaaaagtgccacctgacgtctaagaaaccattattatcatgac
attaacctataaaaaataggcgtatcacgaggccctttcgtc

FIG. 18B
SEQ ID NO: 14 tcgcgcgttcgttgatgacggtgaaaacctgacacatgcagctcccggagacggtcacagcttgtctgtaagcggatgccgga
gcagacaagcccgtcaggcgcgtcaggcgcgtcagcgggtgttggcgggtgttgcgggtgttcggcttaactatgcggcatcagagcagattgtactg
agagtgcaccatatgcggtgtgaaataccgcacagatgcgtaaggagaaaataccgcatcagattgctattgccattgccatacgttg
tatccatatcataatatgtacattatattggtcatgtccaacattaccgccatgttgacatttgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacgtaaa
ctgcccacttggcagtacatcaagtgtatcatatgccaagtacgcccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acggggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctgcatctctccttcacgcgtcgtcgccacggccctagtaagcctcagttaaagcctcgctgttcctgaaactaacagagatctaacag
tgtgtgcctcctgaactgcgtcgcgtctgctctccacgcttgcctgaccgcgtcggccctgaggcagtagtcgagcagtact
cgttgctgccggcgcggccgccaccagcagcagcataagctgacgacataacagcgttcctttccatggctcttctgagtcatccgtgcg
acacgtgatcagatatcgcggccatgaattacataccaaaccagacttttacggacgccgttgggcgccctcgccggttcc
gtccatggcaggtgccgatgcagccgaccgcactactatggttaccaccatgtgcaagcaccgcccacagcaagtgcaggt
aactgatcagcgcagtctgctcactaaccaccaaacagataagcaccaaaggcaacaagcagaaaacagcagaaaacc
aaaggaaaaacagaaaaacagagaaagaaaatagcgcgaaaagccgacgcnnaagaaaggccgcagaaagcagaaaaccaaggctaagaag
aagaaaccaggagagaaagaagaatgcatgaagatcatgaagatgactgcatattcgaggtcaaactggacggcaaggttaccgg
ctatgcctagtcgagataagtcgatgaagccggctcacgttaaaggcacaattgataaccgcagaccttgcgaagttgacttaca
agaaatccagtaagtatgacctcgaatgcgccagatccgagtgcacatgaagtccgacgctccaagtacacacacgtgaaaagcccg
aagtcattacaaattggcaccatggagcagtcagtacagcgnngaaggttaccatcccacacaggcgccccggcaaaccaggagat
agccggtaaggcctattttgacaacaaaggcgagtngtggccatcgtgttaggcggtgttaggcggggccaacgaaggtgccgccactgcctgtct
gtggttgacgtggacaaaagagcgagtgtcactccggtaacgccagaaggaaccagaagtgtctgccgcgatgatgtatcct
gccaacaccttccatgtcctgctcactcctccctgctgctacgaaaaacagccagaaggaacagaacactgcggatgctggaag FIG. 18B (continued)

acaacgtgaatagacctggtactatgagttactgaagcgtccatgacatgcagaaacagatcacgccaccgccgcagtgtaatag
agcacttcaatgtataaggctactagacgtactagconaactgcgctgactgcgggacggtacttctgctatagcccggttgcta
tcgagaagatccgagatgcagggcgtctgatggcatgtcaagatccaagtctccgcccaaataggtctggacaaggcaggtaccacg
cccacgaagatgcgatatatggctggtcatgatgttcaggaatctaagagagaattccttgaggtgtatacgtccgcagcgtgctcta
tacatggacgatggacacttcatcgtcgcacactgtgccaccaggcgactacctcaaggnttcgttcgaggacgcaaattcacacgt
gaaggcatgtaaggtccaatacaagcacgacccattgccggtggttagagagaagtttggttagaccacacttggcgtagagctg
ccatgcaccctcatacagctgacaaacgtcccaccgacgagaggattgacatacaccgccagatataccggatcgcaccctg
ctatcacagacgcgggcaaacgtcaaaataacagcaggccggactatcagttacctgccgctgacaacgtagg
cactaccagtactgacaagaccatcaacacatgcaagatagaccaatgccatgtgccgttaccagccatgacaaatggnaattacct
ctccattgttccaggctgatcagacagccaggaggcaaagtgcatgttccattccctttgactaacgtcacctgccgagtgccgt
tggcacgagcgccggatgcacctatgctgagaatgggttgacaagttctctgagcgcatcatcccagtgacggaagaaggggattgagtac
ttagagccgtaccgcaccgtacgagaagaatgggttgacaagttctctgagcgcatcatcccagtgacggaagaaggggattgagtac
cagtgggtaacaaccgcccggtccgctggcgcaactgacgactgaaggtaaacccatgctgccacatgaaatcattca
gtactattatgactatacccgccgccactattgccgccagtatccgggcgagtctgatgccctcctaactctagcggccacatgct
catgctggccaccgcgaggagaaagtgcctaacaccgtacgcttgacgactatggcctacactgtgggacgagagagcggtgtaccgttgacattggggctgcttn
nntgcgcaccgaggcgaacgcagcagcatcatttgctgaactatggcctactgtgggacgagagcgcggtgtaccgttgacattggggctgcttn
nnnnnnnnnnnnnnngccttgcttcgttgctgtgccatgctggccacagccacagccaattccgaacgtgg1gggttcccgtataaggctcacattgaaagga
gccgtggagccctcgccaaagctgtgagctgatgcttgaagtggtgaanncaagcttgaaccacacttaacctggaacctggaagtctcacattactgcgaatac
abnnntctcgcccatgactctgcagttgaagtgtggaanncaagcttgaaccacacttaacctggatactaccatgcgaatac
aagacggtggtccttcgccattatcaaatgttgcggaacatcagaatgtcatctaaagagcagcagactaccaatgcaaggtgta
cacgggtgtataccctttcatgtggagctacttgttctgcgactccgagaacacgcagcttagcgcagcctatgcgacaggt
cagacgtttgcaaacatgatcatgcctctacaaggcacacggcctctcaaaagcacaatcaggatcagctacggcaccat
caaaccacaccgaggcctcgtcaatgagaacacaccggtcaaagtgggcgaagcaagttcatctttggaccgatctcaaaacagc
ttggtcaccgttcgacaataaaattgtcgtgtaaaagatgatgctacaaccaggacttccacctacgaccatcagccagccgggna
gattcggagacatccagagacgacagacaggagacaggacaggagagcaaagactttgtgctaatacggccctaaaactcaagaccatcaccgggg
tgtgcatgtgccatacacgcgacacaccatccgcgattaagtattggctgaaggagagaaagatcttcattgaatacaaaggccctttg
gctgcaagataaaagaccaatcacgcacgagagcgtatgcagcagcagcatcagagcagcacaactctcagaagcgcatagcagcagcacagcagcagcatcagagcagcacaactctcagaagcgcatagcagcagcacagcagcagcatcagagcagcagtcagtggcagttggcagttggcagtggcagttggcagtggcagttggcagttggcagttggcagttggcagttggcagtattcaggctgcattca FIG. 18B (continued)

cacgagtgtagatgcccgctgtaacagacctgagctgctcaggtagctgtctgtacacactcctccgatttcggannngttgccac
attgtcttacaagacgccaagatgccaagtgcgccgttcactcacattccaacgtcgaacgttgcaagcgtgcaagaggcgacggtgatgtc
aaggaggatgccaagtgcacagtgcactttctnnnnngtccgcctcccccggcattcaaagtgtccgtctgtgacgcaaaaacaacgt
gcacggcggcgtgcgagcctgcgaaagaccacatcgtccccttatgggcgcagccataacaaccaggtctttccggacatgtcagga
actgcgatgacgtggtacagagaggatggcagtggttaggtggctggcctggcagcgcatctgttgtgtctggtcttggtaacctgca
taacaatgctgcgtcggtaatctagaccaggccctggatccagatcgtgtgtccttcagtgccagccatctgttgtttgcccctcccccgt
gccttccttgaccctggaagtgccactcccacgtcctcttccataaaatgaggaaattgcatcgcattgtcgtagtggtgtcattctat
tctgggggtgggtggggtcaggacagcaggggtccctcctgtggccagaaagaagcaggacaataggcacatggcatggggctctat
gggtaccagttgctgaagaattgacccggttcctcctgggccagaaagaagcaggcacatcccttctcgtgacacaccctgtcca
cgccccctggttcttagttccagtcccactcataggacactcaggaggctccgcccttcaatccaccgctaaagtacttgg
agccggtctctccctcctcatcagcccccaaaccagcctccaagtgccaagtgggaagaaaattaaagccaagataggccattaagtg
cagaggagaagaaaatgcctccaacatgtgtgaggaagtaatcatagaagaatcatgaatccatgattaaggccatcatggcc
ttaatcttccgccttcctcgctcactgactgctgcgtgccggtcttgcggctgcgcgtatcagctcactcaaggccgtaaatacg
gttatccacagaatcagggatccgataacgccaggaaaagaacatgtgagcagcaaaaatcgacgctcaagtcagagttggcgaaaccgacagg
gttgctgcgttttcccataggctccgcccccccgaccagagttcctgccctcgttccgaccctgccgcttaccgatacctgtccgccttt
actataaagataccaggcgttccccctggaagctccactcacgctctagggtatctcagttcgtgttagtgtcgttcgctccaagctggcgtgtgc
ctccttccggaagcgtggccgctttctcatagctccacgctcttgagtatccgtaactatcgtcttgagtccaaccagagacacgacttatccgccactg
acgaaccccgttcagtccgaccgttagctcgcgtcagtagcgagttatgcgagccgagttcttgaagtggtctgctcttgatccggcaacaaacc
gcagcagccactggtaacagatttgtatctgcctctgtcaagcagcagattcacgcagcagtaccttcggaaaaaagagttggtgctgctcttgatcggcaacaaacc
actagaagaacagtattggtatctgcctctgtcaagcagcagattacgcgcagcagttacctttcggaaaaaagagttggtagctgctcttgatccggcaacaaacc
acgctggtagcgctcaagtcggtggttttttgtttgcaagcagcagattggtcatgacagcagttaaggatttggtcatgacagttataccacttataccatcaagaaggccagtcgc
ggtctgacgctcagtggaacgaaaactcacgttaaggatattggtcatgacagttaccacttataccactctctagagaaggatcttcacctagatcctttaaattaa
aaatgaagttttaaatcaatcaaagtatatatagtaaacttggtctgacagttaatcagcttaatcagtttaaatcgacttgaaggatcccctcgtgaagaaggtgtcctatcatcaggtac
tgtctatttcgttcatccatagttgcctgactcccagtagtgaggctcgaggtctgcctcgtgaaggttgtgacctgtacctcatcgagaaggatctcaaggatcagtcatccag
gcctgaatcgccccatcagccccatcatccagccagaaagtgaggagccacgttgttgatgagcttgttggacccagttgtgaccagttggtcatccag
ctttgctttgccacgctcgtgcgttgtcggaaagatgcgtgatcttccaactcaatacaattgtcgatactcgatattattcaacaaagcc
gccgtcccgtcaagtcagtcagcagcaatgctctgccagttgccaagtgttacaaccaattaaccaatccgattcgattgaaaactcgattagaaatgaaa FIG. 18B (continued)

ctgcaattattcatatcaggattatcaatatccatattttgaaaaagccgtttctgtaatgaaggagaaaactcaccgaggcagttccatag
gatggcaagatcctggtatcggtctgcgattccgactcgtccaacatcaatacaacctattaatttccctcgtcaaaataagttatcaa
gtgagaaatcaccatgagtgacgactgaatccggtgagaactggtgagaatgcaaaagcttatgcattcttccagactgttcaacaggccagccat
tacgctcgtcatcaaaatcactcgcatcaaccaaccgttattcattcgtgattgcgcctgagcgagacgaaatacgcgatcgctgttaa
aaggacaattacaaaacaggaatcgaatgcaacggcgccaggaacactgccagcgccatcaacaatatttcacctgaatcaggatattc
ttctaatacctggaatgctgttttcccgggatcgcagtggtgagtgagcatcaggagtacggataaaatgcttgatggtcgg
aagaggcataaattccgtcagccagtttagtctgaccatctcatcgtaacatcattgcaacgctaccttgccatgtttcagaaacaact
ctggcgcatcggcttccataacaatcgatagattgtgcacctgattgccgacattatcgcgagcccattatatccatataatcagc
atccatgttggaatttaatcgcggcctcgagcaagacgttcccgttgaatatggctcataacacccctgtattactgttatgtaagcaga
cagtttattgttcatgatgatatattttatctgtcaatgaacatcagagatttgagacacaaataaacaaataggggttccgcgcacattg
aagcattatcagggttattgctcatgagcggatacatattgaatgtattagaaaaataaacaaataggggttccgcgcacattcccc
gaaaagtgccacctgacgtctaagaaaccattattatcatgacattaacctataaaaataggcgtatcacgaggccctttcgtc

SEQ ID NO: 15 tcgcgcgttcggttgatgacggtgaaaaccctgacacatgcagtcccggagacggtcacagcttgtcgtaagcggatgccggagcagacaagcccgcgtcagggcgtcagcggtgttggcggtgtcggggctgcttaactatgcggcatcagagcagattgtactgagagtgcaccatatgcgtgtgaaataccgcacagatgcgtaagagagaaaataccgcatcagattggctattggccattggcatacgttgtatccatatcataatatgtacattattggctcatgtccaacattaccgccatgttgacattgattattgactagttattaatagtaatcaattacggggtcattagttcatagcccatatatggagtccgcgttacataacttacggtaaatggcccgcctggctgaccgcccaacgaccccgcccattgacgtcaataatgacgtatgttcccatagtaacgccaatagggactttccattgacgtcaatgggtggagtatttacggtaaactgcccacttggcagtacatcaagtgtatcatatgccaagtacgccccctattgacgtcaatgacggtaaatggcccgcctggcattatgcccagtacatgaccttatgggactttcctacttggcagtacatctacgtattagtcatcgctattaccatggtgatgcggttttggcagtacatcaatgggcgtggatagcggtttgactcacggggatttccaagtctccaccccattgacgtcaatgggagtttgttttggcaccaaaatcaacgggactttccaaaatgtcgtaacaactccgccccattgacgcaaatgggcggtaggcgtgtacggtgggaggtctatataagcagagctcgtttagtgaaccgtcagatcgcctggagacgccatccacgctgttttgacctccatagaagacaccgggaccgatccagcctccatcgctgcctgtctgagcctcctgaactgcgtccgccgtctagttaagcttgctgacccgtgctgtcaactctagttaacgcttgctgaggggcagtgtagtctgagcagtactcgttgctgccgcgcgcgccaccagacataatagctgacagactaacagactgttccttccatggctgcttcatgcagcccctggactcaaaccccaaactgacgctacatccagccgtatcaccgtgtaccaccatgaagacagcgaagaggccgaacgccggaccgttgaaaattaagaacaagaacaagaccaagaaaaaccacgccggaaccgccgaaaggaaaaatgaaaagagaccaaggaagcaagaagaagcaggaagacagaaaaattaagaacaaggaaaagcaagaaggatgtgcatgaagattgaaaatgactgcatcttcgaagtcagacactaacggggatgcatgcagtaggtgatgataagaaaccagcacacgtgaaaggaactattgacaacgcagaccagcggtccgttcaaagatcatccaaaatatgatctagtagtgccacagatatccagtgcacatgaaatcggacgcctcaaagttcacccatgaaaagcctatatccatcaactggctattcaactgcagatcatcacgagcagcagtacgtatcggagggaggttcacgatcctacaggcgcaggaacagcctgggacgggacactactgtagtctgtggccaatctttgacaacaaggccgtcgtggctattgttcctaggcgggcaaacgaaggaacaggaacagagacactctgtagtcttggcaaatacaactttccaaccttggaataagacatgtcacaaaaatcacaccagaggtcagttgaatggagccttgccctccctgttgcctgtttggtggaggaccacactgtctacgaaagaaaacggaagaaacctgagaaatgctggaggaccacctgacgttcatgtgccttactccatcagttcagagaaacggaagaaacctgagaaatgctggaggaccacctgacgttcatgtgccttactccatcagttgcctgctc FIG. 19B (continued)

```
acaacgtcgtcaaaaacgtaatgcaagagaaaactteaatgtctacaaagtcactaggccgtacttagcccactgtcctgactgcgggg
agggacactcatgcatgccaagcagcccaatgcatagaaacgatcattagaacgatgaggcaacagatggtaccttgaaaatccagtatctgca
aatcggaataaaagacagacgacagccacgattggacgaagctacggtatatggatagccatacacctgtgatgcagacegatcg
ggttgtttgtcagaacgtcagcaccgtcaccatcacgggaacagtagaaggatcacgtgcatgcaccgttccgccagcaccgtgtccgaaaggagagacgct
gacggtaggattgtagacagtagaaggatcaaagaactacctgcagtatacgtccatacacagcggcaactgctgaggaaatagaagt
agttcactccggcccgcagcatggccaagcatggcaaagaaactaccttgcagtatacgtccatacacagcggcaactgctgaggaaatagaagt
gcatatgccgccagatacccctgactacacgctgatgacacagcaagcggaaacgttaagatcacagttgacgggccagaccgtac
gatacaagtgcaaatgcaggctccaatgaaatgcaatacaaccgctgaccccgcggaactccgaacaaggagatagaaaaggtaagatcc
agcggttacaaaccacaagaaatgcaatacaaatccgctgaccccgcggaactccgaacaaggagatagaaaaggtaagatcc
atatcccattccactggtgaacacaacctgcaggtaccgccagcaaaagcaagaaatccgactgtcacatacggtaaaacagagtcactctg
ctgttacatccagaccaccaaccactccttcgtaccgcctaccgccatggaaggatccgcattggaaggatccgcattaccatgaagaggtgataacaaacaaga
aggaaataagtatcacagtaccagcagaaggcttagagagattacgttaegtggagttacgttggggtaatatgacccataacaatacccacaattgctgtactgctgctt
aatggtactgcgcacgggcaccaacagtaccaccacaggcaccacatagcggagagacgcaggtgcatcacgccatatgagctgactcag
ctatcgtaataacatcttttgtaggtctatcattaggtctatcattaggtgtgccagggactgtgccaggactgtcagctgcaaatagcagctgcgaaagctactacgaagctgcaacatacctcgg
gagctaccatccattcctcctaggtgtcgccaggggaccaggttacagtccttcatctgcaggacctggacaggtggtgccagggaccaggtacagccctatggcgcctatgtcttagaaatggagctacagtcggtcactctgaaccagc
aatgcaacaccattatttgttacagcttccaatcaccacgtcccgtacgtaaaatgctgtggtacagctcgccaagaccagcaaccagtgccgcaacaggtg
caaaacattgactttttagccgtcatgagccatcggtgccgccaggccatcggtgccgcgccactgtgaccgcgtacgagcgacgagcaacagtgatcccgaacacggtg
ggagtaccgtgttaagactcttgttagcagaccaggtccagcccctatggcttagaaatggagctacagtcggtcactctgaaccagc
attatcctggattacattacgtgtgattagtaataaacaatcaccacgtcccgtacgtaaaatgctgtggtacagctcgaatgtaaggccaag
aacctgccaggattataactgccaaagtattcacaaggcgtctacccattatgtgggaggaggagcatacgctcctgtgaccgcagagaacac
acagctaccgaggcacacgttgagaaatcagaaatcagaatgagtttgcatcagccacagagcccacagagcttcagtatca
gctaaactacgtgtctttaccaaggcaataatacaccgtctgcatacgccatggtgatcatgcgccaatggtgaagacgcgaag
ttgtcatcgtccactatcgtccgcctggtcctgtcaattgataatagatcgtggttgcaaaggcgaagtctacaatggactatccacc
ttcggcgcaggagggaggccaggaccagttcggtgacatccaggagccgcaccgccagacgcaaggagcgtcatgcgaatacgcagttaa
tactgcaaagaccagcggcaggagcaatacacgtgccttactcccaggccacctccggctttaagtactggctcaaggaaaagggg
catcattgcagcatactgccaccagtgctgtcagatagcaacaaaccgtaagagcagtcagtggcagtgtcagttgggcaacataccagt
ctccattgacatccagatgcacatgcgcagcttcaccaggcagcttcaccaggcagcttcaccaggcgcctcctccatcacagacatgtcctgcgaagtagcttcgtgtaccat
```

FIG. 19B (continued)

tcatctgatttggagtgccgcagtcagtcataaagtacacagctagtaaaaaggaaaaatgcccgtgcactctgtaacaaatgcggtcac
tatccgcgaacctaacgtagatgtcaaggaacagcacaattgcaaattgccttctcgaccgccactagctagtgcggaattcaaggtgc
agatcgtccacactgtgtacactgtcagcgacgtgccatcctcctaaagccatatagtcaatatccgtcacctcaccactag
gagtcaggacattcaacgacagcagctatgtcttggtccagaagattacaggaggagtggactcgtggttgctatagctgctttgatct
taattatagttctctgctatcattagcagacactaagcggccgtctagaccaggcctggatccagatcgctgtgccttctagttgcc
agccatctgttgtttgccctccccgtgcctcttgaccctgaaggtgccactccactgtcctttcctaataaaatgaggaaatgca
tcgcattgtctgagtagtgtcattctatctgggggggtggggggcaggacagcaagggggaggattgggaagacaatagcagg
catgctgggatgctgtgggtctatgggtaccagtgctgaagaattgaccccgttcctctctggggccagaagaaagcaggcacat
cccttctctgtgacaccctgtccacgccctgttcttagttccagctcatagacacacatcaggctcaggagggctccgcct
tcaatcccaccgctaaagtactttggagcgtctctcctcctcatcagcctccaacaaaccagcctccaagagtgggaagaa
attaaagcaagatagcctattaagtgcagaggagagaaaatgctccaacatgtgaggaagtaatgagagaaatcataggaatttaa
ggccatgattaaggccatcatgggccttaatcttccgcttcctcactgactcgtcgtcgttcggctgcgcgagcggta
tcagctcactcaaagcggtaatacggttatccacagaatcaggggatacgcaggggcgtttccatagcctcccgcgccccctggaagctcctcaggagccagcaaaa
ggccaggaaccgtaaaaaggccgcgttgctgcgttcataggctcgccccccctggaagctccctcgtgcgctcctcgttccgaccctg
tcagaggtggcgaaacccgacaggactataaagataccaggcgtttccccctggaagctccctcgtgcgctcctcagttcggtgaggt
ccgttaccggatacctgtccgcctttctcccttcgggaagcgtggcgctttctcatagctcacgctgtaggtatctcagttcggtgtaggt
cgttcgctccaagctgggctgtgtgcacgaacccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttctt
gaagtgtggcctaactacggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaggatctc
aagaagatcctttgatcttttctacggggtctgacgctcagtggaacgaaaactcacgttaaggggattttggtcatgagattatcaaaaag
gatcttcacctagatccttttaaattaaaatgaagttttaaatcaatctaaagtatatatgagtaaacttggtctgacagttaccaatgcttaa
tcagtgaggcacctatctcagcgatctgtctatttcgttcatccatagttgcctgactccccgtcgtgtagataactacgatacgggagggg
aagaagttgttgccatgttgtgcaaaaaagcggttagctccttcggtcctccgatcgttgtcagaagtaagttggccgcagtgttatcactcatggt
gtaggtggaccagttggtgatttgaacttgaactttgccgcccccaccgaagctcctcctttgatgagagctttgtt
gtaggtggaccagttggtgatttgaacttgaacttgtctttgccacgaacggtcgcgttgtcgggaagatgcgtgatctgatcttcaactcag FIG. 19B (continued)

caaaagttcgattattcaacaaagccgcgtccgtcaagtcagcgtaatgctctgccagttacaaccaattctgattag
aaaaactcatcgagcatcaaatgaaactgcaattattcatatcagattatcaattcatatttgaaaaagccgttctgtaatgaagga
gaaaactcaccgaggcagttccataggatggcaagatcctgcgattccgactcgtccaacatcaatacaacctattaat
ttcccctcgtcaaaaataaggttatcaagtgagaaatcaccatgagtgacgactgaatccggtgagaatgcaaaagcttatgcattctt
tccagacttgttcaacaggccagccagtcacttacgctcgtcatcaaaatcactcgcatcaaccaaacgttattcattcgtgattgcgcctgagc
gagacgaaatacgcgatcgctgttaaaaggccaattacaacaggaatcgaatgcaaccggcgcaggaacactgccagcgcatcaa
caatattttcacctgaatcaggatattcttaaatacctggaatgctgttttcccgggatcgcagtggtgagtaaccatgcatcatcagga
gtacggataaaaatgcttgatggtcggaagaggcataaattccgtcagccagtttagtctgaccatctcatctgtaacatcattggcaacgc
taccttgccatgtttcagaaaacactctggcgcatcggccttccccatacaatcgatagattgtcgacctgattgccgacattatcgcg
agcccatttatacccatataaatcagcatccatcatgttggaatttaatcgcggcctcgagcaagacgttcccgttgaatatggctcataacac
ccctgtattactgttatgtaagacagagtttattgtcatgatgatatttttattcttgtcaatgtaacatcagagatttgagacacaac
gtggctttcccccccccccattattgaagcattatcaggtttattgtctcatgagcgggatacatattgaatgtattagaaaaataaaca
aataggggttccgcgcacatttccccgaaaagtgccacctgacgtctaagaaaccattattcatgacattaacctataaaaatggcg
tatcacgaggccctttcgtc

SEQ ID NO: 16 tcgcggcgtttcggtgatgacggtgaaaacctctgacacatgcagctcccggagacggtcacagctgtctgtaagcggatgccgga
gcagacaagcccgtcagggcggtcagcggtgttggcgggtcggggctggcttaactatgcggcatcagagcagattgtactg
agagtgcaccatatgcggtgaaaataccgcacagatgcgtaaggagaaaataccgcatcagattgcctattgcattgcatacgttg
tatccatatcataatatgcacattatattggctcatgtccaacattaccgccatgttgacattgattattgactagttattaatagtaataatta
cgggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctcctccgcatcaagcctctagagtaagtttaaagcttaactctagttgctgaccctgttgtcaactctagttgcgcctc
tgttgccctcctccgaactcagccggctccgaccctccgacctgttgcctcacctagtcgagatcgagacctcaggtcagttgtgagcct
acctagactcagccggctcctccaccagagacataatagctgacagactccttgcctgaccgtgttcctttcatggtctttctgagcagtact
cgttgctgccgcgcgccccagacacgcctcgcgccaccatgagagacactggagacatgcacggcctggagaccgaatgccg
acacgtgatcagatatgcgccggcaacacgctgcctactagcagaccagcccgacaaatgcccagaaagaaaccaaaaccgcc
ccacgccttgcccctgagccggcagaagcagccccctcagcgtggaaaagaagcagccccctaaacgaagcaggagaaccagcc
cgagaaaccaaagaagcagaaggagcaggaagcccgaagcaaaagaaggcccctaaacgaagtaagtcaggagaagaacgcatgc
atgaagattgagcatgattgcattccgagggttaagcacaagcagatcttgcacgcctgtcgtacaagaaatccagtaagtacgatcggaatgaa
gccagcacacgttccgggtgatagacaatgcttgcggaagaaaccgagtcattaccaactggcactacgtggtgcgtcc
caaataccccgtggctatgaagtcagatgtcttgaagtacaaccatgagaaaccgagtgtcattacaactggcactacgtggtgcgtcc
agtacacgggaggaagattcacggtgcccacagagtgtccaccaggagtgtaagcctgcgcgacaggtgcgtgccacatctttgacaacaagggcc
ggttgtcgcaatagtgctgggagggcactgtgagtgtggagggagccaaacagtccagcagcagaccgccctttccgttgtgacatgtgtgtctttgacaatatatctttccatgttccaaccg
gattacacctgaaggcacgtgctcatgaaaggggtctatgaaaaggggcctgagccgacgctgagcgctgaggatgtgaggagaacgtaaattcagaattcagaaggatattacgac

FIG. 20B (continued)

ctgctgcacgctgccgtgctgtactgtagaaacagttcaagtcgaagagaagcactgcaaatcatttaatgctgtataagttgacccgtcca
tatgtgcttactgcgcagactgcgtagactgccgtgcgtalggtcattcttgccacagcccatgatcgaaatattcaggcgatcaacagatgg
cacgctaaaaattcagttgcttcccaaattggcctgaccaaaacgacacgcacgatcacacacaaagattagatatgctgaaggacac
gacattgcagagagctgccagatcaacccttaagtacacagtagcagtgagtgcacggtaaccggcacacatggacacttatcctgg
ccaaatgtccacctggcgaacgaatcagtgtctcattgttgattgtcgaccgcatcatgaattgagctagctctgcaccacttatcaattgactacgccga
cagaggttaatagggcgagaaagattcacgtgccgccgacattcggatagaacatctcttccaacaatcaggaaatgttaagataacgt
aaccctgaagaaatgatatgcacatgccgccggacattccggatagaacatctcttccaacaatcaggaaatgttaagataacgt
gaatggacgaaccgtcaggtacagctcttcttgcgtacagctggtccccaagccgtcgggacaaaaccagagacaagaccattaatagctgtacc
gttgacaaagtgcaggcttacgtcagagctagagcacagtcaatggcaattcaattcaccttgtcccagtcggatgcaagcagagcgcaa
gggcaaagtgcatatccctttcattgcaccctatccagagccacagtcaatggcaattcaattcaccttgtccctgagccctgttagagccgtaaacgc
aagcacacttcattgcaccctatccacccacattgctaagttacagaacactgagcgagcgggtcttgacggacagtggatca
ccgcccagacgacgaggtaacgatccggtaccgtgtggaggagtgggcaacatataacctgactgcatcctacgacaacattgtcgtg
cactgacgactgaaggcaaagcacatggatggcctcatgaaattattgaataactacggctgcatcctacgacaacattgtcgtg
gtcattcgtctcagtcgtgtggtgctctgtcattcgccgctcgtcgtctacatgcggtggtagcacgaaccaaaatgtctgacaccatatg
cactcacgcccggagagctgtttcctgttaccattggggtgctgtgttgccaccgaaagcacatgcagccagttcgcagaaggtatg
gcctatctgtggggataacaatcagtcagtcgatgttctgatgtcggaggctgaccgacattggccctccttaccgctacatgctgcccgat
cactgctttcctgctcgcaaggggtctttttagtcgcaatgagctcatgttgcgctgaaggttacagtccttgacctgagatgcagatgagattattcc
gaaccaagtggattcccgctaaggatcccatgttgcgctgaaggttacagtccttgacctgagtgcgtgaggtgctgataagagaccagc
cttgagccaacactcaaactggagtatatcacttgccattacaaacaaaagttccatcaccatacgtaaagtgctgcggcacggcaga
atgccgccaacactcaaactggagtatatcacttgccattacaaacaaaagttgtgtgatcctttatgtggggaggtcatactgtttgtgatt
cggagaacacacagagagagaagctgagaagaaattaagcagagctactgtgaaccagacacgaccgacacgcagtgcctaccgtgccacac
cgcatcccttagacacagaagcaaaaatttgggcccagtcgtcaacgcctgagctgaaccagagatgggcagcatttggggacattcagagccggatagtcgagaccattg
attgccggaacaaaaattattttgggcccagtcgtcaacgcctgggaagatttggggacattcagagccggatagtcgagaccattg
atcaggactttccacgtatggtccggcagccggcagccggcagccgaactcacgtccctatccccagactcccatctggcttaaaaacatg
ccaacacggggcctcaagctggccacggccagcgccaacattcacgtcccctatccccagactcccatctggcttaaaaacatggc
aaaaagacacagggactcaccgcttaacgccaagcgccttttgatcataatccagacaaatccggtccgagccatgcccgagctgccg
tcggcaacatacccgttcgatggatatgcgacacgcgcgacagcgccttcacaagattgaccgacgcgccctgtaatctctgagttgactgcact FIG. 20B (continued)

gtgtctacatgcacgccactcatcgatttgccgggatcgctgtacttcctacaagtggaaaatcagcagtgcgacatccattca
cattcaaacgtcgcgtactccgttccatcgagacagaaggtcgatcagtgagacatgatccactctcaaccgcatcagcctcccttcc
ttcgtagtttctgtttgtagttcgctgctacgtgcacagcgaaatgtgaaccaccgaaagaccacgttgtacatatccagcaaatcataa
cggggtaactttgccagacttatctagcactgccatgacgtgggcacaacatcttgccggcggagtggagttgctgatagctctggccg
tgctaattctggtaatagttacttgtgtgactttgagaaggtaaggatcagatcgctgtgctgtcttagttgccagccatctgttgttgccc
ctccccgtgccttcctgacctggaaggtgccactccactgtcctctaataaaatgaggaaattgcatcgcattgctgagtaggt
gtcattctattctgggggtgggtgggcaggacagcaaggtggagattgggacaagacaatagcaggcatgctggggatgcggt
gggctctatgggtacccagggtctgaagaattgacccgttcctctcctgggccagaagaagcaggcacatccccttctctgtgacaca
ccctgtccacgccctgttctttagttccagccccactcatagcgacactcatagctcaggaggggctccgccttcaatccaccccgctaa
agtacttggacgcggtctctccctccatcagcccaaccaaacatgtgaggaagtaatgagagaaatcatagaatttaaggccatgattaaggcca
tattaagtcagaagagggagagaaaatgcctccaacagttctcacgtctgcctcggtcgcctcgttcgagctgatcagctcactcaaggcg
tcatggcctaatcttccgctcatcagaggataacagggaaagaacatgtgagcaaaaggccagcaaaaggccaggaaccgtaaaa
aggccgcgttgctgcgtttccatagcctccgttcccccctggaagctccgcctcctgttccgaccctgccgcttaccggataccgt
cgacaggactataaagatccagccgtttccccctggaagctccctctcgtgcgctctctgttccgaccctgccgcttaccgatacctgt
ccgcctttctccccttcggaagcgtggcgctttctcatagctccatagctccatgtcgttaggtcgttctgtaggtcgttgctccaagctggg
ctgtgtgcacgaaccccccgttcagcccgaccgctgcgccttatccggtaactatcgtcttgagtccaacccggtaagacacgacttat
cgccactggcagcagccactggtaacaggattagcagagcgaggtatgtaggcggtgctacagagttcttgaagtggtggcctaact
acggctacactagaagaacagtattggtatctgcgctctgctgaagccagttaccttcggaaaaaagagttggtagctcttgatccggca
aacaaaccaccgctggtagcggtggttttttgttgcaagcagcagattacgcgcagaaaaaaaggatctcaagaagatcctttgatctt
tctacggggtctgacgctcagtggaacgaaaactcacgttaaggatttggtcatgagattatcaaaaaggatcttcacctagatccttt
taaattaaaaatgaagtttaaatcaatctaaagtatatgagtaaacttggtctgacagttaccaatgcttaatcagtgaggcacctatctc
agcgatctgtctatttcgttcatccatagttgcctgactccccgtcgtgtagataactacgatacgggagggcttaccatctggccccagtgctg
ataccagccactagaagaactaccagcagaaagtgaggagccacgttgtgatcgatcctccaactcagccaaaagttcgattattcaa
atttgaacttgttcggaacggtctgcgttgcgggaagatgctgatcgatcctccaactcagcgaaaagttcgattattcaa
caaagcccgcccgctcccgtcaagtcagcgtaatgctgcgaagatgctgagtttaccaattaaccaattctgattaaaaactctgatcagcatca
aatgaaactgcaaattattcatcaggattatcaggattatattttgtaaagcgtttctgtaataagagagaaaactcaccgaggcag FIG. 20B (continued)

ttccataaggatggcaagatcctggtatcggtctgcgattccgactcgtcgcaacatcaatacaacctattaattcccctcgtcaaaataag
gttatcaagtgagaaatcaccatgagtgacgactgaatccggtgagaatgcaaaagcttatgcattcttccagacttgttcaacaggc
cagccattacgctcgtcatcaaaatcactcgcatcaaccaaaccgttattcattcgtgattgcgcctgagcgagacgaaatacgcgatcg
ctgttaaaaggacaattacaaacaggaatcgaatgcaacgccagcgcgcatcaacaatatttcacctgaatcag
gatattctaataacctggatctgttttcccgggatcgcagtgtgagtaaccatgcatcatcaggagtacggataaaatgcttgat
ggtcggaagaggcataaattccgtcagccagttagtctgaccatcatcgtaacatcattggcaacgctaccttgccatgtttcagaa
acaactcggcgcatcggcttcccatacaaatcgatagattgtcgcacctgattgcccgacattatcgcgagcccattatacccataa
atcagcatccatgttggaatttaaatcgcggcctcgagccaagacgtttcccgttgaatatgctcataacacccctgtattactgtttatgta
agcagacagtttattgttcatgatgatataatttatcttgtgcaatgtaacatcagagattgagacaaacgtggcttccccccccccc
cattattgaagcattatcaggttattgtctcatgagcggatacatatttgaatgtatttagaaaaataacaaatagggttccgcgcatca
tttcccgaaaagtgccacctgacgtcaagaaccattattatcatgacattaacctataaaaatagcgtatcacgaggcccttcgtc

FIG. 21B

SEQ ID NO: 17 tcgcggcgttccgttgatgacgtgaaaacctctgacacatgcagctcccggagacgtcacagcttgtctgtaagcggatgccggga
gcagacaagcccgtcagggcgctcagcggtgttgggcgggtgtcgggtgtccttaactatgcggcatcagagcagattgtactg
agagtgcaccatatgcggtgtgaaaataccgcatgcgtaaggagagaaaataccgcatcagattgccattgccattgcatacgtg
tatccatcatcaatatatgtacattattatggctcatgtccaacattaccgccatgttgacattgattattgactagttattaatagtaatcaatta
cggggtcattagttcatagcccatatatggagttccgcgttacataacttacgtaaatggcccgcctggctgaccgcccaacgaccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatggacttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatggcggtaggcgtgtacggtgggaggtctatataagcaga
gctcgtttagtgaaccgtcagatcgcctggagacgccatccacgctgttttgacctccatagaagacaccgggaccgatcagcctcc
atcggctcgcatctctccttgaactcacgcccgcgtccgcgcgtctagttaaagctcgagttcttgtctcaactcagtacagactgagcct
tgtggtgcctcctgaactgcgtccgccgtctagttaaagttaaagcctgtaattgatccagctcagttcccgtgcccctccttggagcct
acctagactcagctcgcggctctccacgttgctgacctgcttgtcaactctagttaacggtctggggggcagtgagttctgagcagtact
cgttgctgccgcgcgcgcccacagacataatagctgacagactcgatatgacgtcttccttccatggtcttttctcgagtcaccgtcg
acacgtgatcagatatcgcggccgctctagaccaggcccgtctagaccaggccctggatccaccaaccaccagcgcctccaccaaaccttctatggtagacgatg
gagaccagcagacccagagatacatacccgctcactagtagcactagtggcagtgcactagtagcagtgaaacaagaagccccaagaagacaccac
cagcttggctgctcattgggcgcactagctcacaaccaagcagaaacaaaaagagcacagaagaagccccaagagacaccac
caccaaaaccagcaaaaagaccgctaagagagccctaaacaaccaagaacttgcgttaactgcat
gaagatcgagaatgactgcatcttccgttgatgctcgatgaaagttaacgcttacgcttgcttagtgggatctctgagaaac
cagtccatgtgaaggggcacgatcgacaatccagaactagccaaattgacattcaagaaaatcagcaagtatgatcctagaatgtctcaa
gtccgtatgcatgaaaatcagacgcatccaagttcaccatgagaaaccatggagacagtgtagccatggccacatggggcagtgcaa
tttagcaatgtctgggaggttaccattccgacgtctctggcaaacctggagcaccggcaacgtgtcaccttttttgacaataccggcaagtagta
gccatagtcgtgggagtgcaaatgaagaggggcccgaccactgtatataacagcactatcgtgtcctccaacttatcgttccgtgatgcac
acctgaagaatcagtgagtggtcggcgggcccgcactgnataacagcactactactaccgccgcactactactaccaaagtattatgaat

FIG. 21B (continued)

```
tacttgactcgacgatgcactgccacaaggaaggaagagacctaagagtcgttgcgcattcgaagcctacaaggctacgagaccgta
tataggtggtgcgcagattgtgactggcaggatcatgccaccatccctgagcatcgagcacgtctggagtgatgccgacgacgg
cgtactgaagatccaagtgtccatgcagatcgtatagctagataaaagcaatactattaaccacgctaagatacgttactatggtgccaatgg
agtacaggaggctgaacgctctacctaagtgtatccacaacagcaccatgtgacatctggcgacatggcgccatttcatcttggcc
gctgccgaccggcagtcaagttgaagtatcactaagtccgatccaagagctgctatgccgtacaacttactccatcagacagacttaacgaga
atggcaatgaaagtcccagcaccgagcaccgggcacaagacccgaattcctgcaaaactcctccatcagacagacttaacgaga
gaagagattacaaatgcatgaccgccgatgtcccatccaaggctagtgtccaataacaggtaagtcgtactcattagaccaaaga
cgaagaccatcaagtacaaatgcactgcggcgagactgtaaaagaaggtactgctacgacaacaaaatcacactgttcaattgtgacac
cgccccaaagtgttattacatatgcagtggataaccagtgtggcagtacaactcccatacgtgccccagtgccaagttacggagtg
aaaggaaagatccatgtgccttccctcgaccgacacgtgcagtcagcgtagcacctgaacgcaagtgacatacagactg
ggggaagtggagttccactccacctatgtaccccctctcccattaggagcctcggaaagtagtctggcagtatgtcaaccaacaccggtactgacta
tgggcacagagagctcatcgagcagcgcatgtaacctattagcataggtcttttcatgcttgtcagctcgctcgaaccaaatgcctaccacct
acagtactagcgagtcgagtcgtctaatagtcagtcttatagcactccgttccattattagtgcactacttatagccttgcgccacgcgcagacactttagatgattttc
atcaattagcaccaggcgcccaattaccacaccaaagccatgttttggctcaactggcatcccggttgcagctttcggcttccttatcctattgctgtagaaatcta
tacctgtggaccaacaacaagccatgtttttaggataaagcggctgtgtgtaattgcgacagcctacgagcactcaaccacgatgccgaatca
gcatgctgtatgaagattttttaggataagcggctgtgtgtaattgcgacagcctacgagcactcaaccacgatgccgaatca
ggtgggaataccgtttaaagcgtttgatagagcgaccaaggttacgcaggcctccgtatcttagtagtgattaagtcagaattagtccc
ctcattagttcaggattatattacctgcaactacaagactgtggtcccgtctccgtacattaaatgttgcgggaggcgctgagttgttcacaca
aaatgaagcgactataagtctcggttgttcacagggcgtgtaccggtttatgtgggaggcctcctactgctctgtgaccaccgaaaac
agtcagatgagtgaagtatacgattggaagagaactgaaccagaagaatcatgcgaggctgaccatcgcttacagtacacagcatcgctta
aggcacaagtaatgacaagtgcgattggagaactgaaccaaaccgtcgacgtgttgtcaacggacagtccagccagaatccaacaatc
aaagttcatacttggccgatatccagtcctggtcctcctttgatcaaggtgatcgtatacaaggtgatgaggtgtacaagacatc
gcaccgtacgcggatcccgcaagcaggcaggttcggagacatccaaagtagaactgttaacagactgattctatgccaaccaatt
tgaagcttaaaagaccggcttcaggcaatgtcatgtaccatacacgcaaaaccccttcggtttctcgtactgaaaaaaagagaaggga
gtaccattgaatcgaaacgccccctttgcctgtcatcatcaaagtcaatcagtacgtcgtcgaaaactgtgaaaactgtataccgatca
gtatggatatttgcgacgcgcacttcacaaggatcgatgaatcccgtctgtcgtcctgaaggcgtgaagtgcagtcctgcacttatt
```

FIG. 21B (continued)

```
catcggatttggcggagtagcgagcagcattcctacacatctaataagtaggtaagtgtgccatccacagccactgaactccgcaacg
atgaaggattctgtgcaggatgtccaggaagtccaggaaagcggccgccttgtcgacttcctgtgcgacttcctgtgcgagccgaacttcgtggtcaag
tgtgtaacgcgcggatcacttgccatgtaagttgtgaaccaccgaaagaccacatcgtaccatacgcagccaaaacaacacgacgccg
agttccatccatcctactacagcttgcaatggttgcaatggtcacacaccacctcaggccacctcaggccacctcagccacctgttgttgccctccccgtgctt
gttgtagtatccattgtatgtcaagacactagagatctgctgcctctagttgccagccatcgtgttgtttgcccctccccgtgctt
ccttgaccctgaaggtgccactccactgtccttcctaataaatgaggaaattgcatcgcattgctgagtagttgtcattcattctgg
gggggggtgggggcaggacagcaagggggaggattggaagaagaatatagcaggcatgctgggatgcggtggctctatgggta
cccaggtgctgaagaattgacccggttctcctgggccagaagaagaagcaggcacatccccttctgtgacacacctgtccacgcct
ctgttcttagttcagccccactcatagaccactcatagctcaggaggtccgcttcaatccccaccccgctaaagtactgcgaggt
ctctccctccctcatcagcccaccaaaaccaaactagcctccaagagtgggaagaaattaaagccaagataggctattaagtgcagagg
gagagaaaatgcctcaaacatgtgaggaagtaatgagagaaatcatagagaaattaaggccatgattaaggccatcatcatggccttaatctt
ccgcttcctcgctcactgactgctgcgtcggtcgcgagcggtatcagctcactcaaaagccgtaatacggttatcc
acagaatcaggggataaacgcaggaaagaacatgtgagcaagaaatggccagcaaaaggccaggaaccgtaaaaaggccgcgttgctg
gcgtttttccatagctccgccccccctgacgagcatcacaaaatcgacgctcaagtcagaggggggggggaaaaccgacaggactataa
agataccaggcgtttccccctggaagctccctcgtgcgctctcctgttccgaccctgccgcttaccggatacctgtccgcctttctccctt
cgggaagcgtggcgcttctcatagctcacgctgtagtctcagttcggtgtaggtcgttcgctccaagctggggctgtgtgcacgaac
cccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaa
gaacagtatttggtatctgcgctctgctgaagccagacagttaccttcggaaaaagagttggtagctcttgatccggcaaacaaaccaccgctg
gtagcggtggtttttttgtttgcaagcagcagattacgcgcagaaaaaaaggatctcaagaagatcctttgatctttctacggggtctgac
gctcagtggaacgaaaactcacgttaaggggattttggtcatgagattatcaaaaaggatcttcacctagatcctttaaattaaaatgaag
ttttaaatcaatctaaagtatatatgagtaaacttggtctgacagttaccaatgcttaatcagtgaggcacctatctcagcgatctgtctattc
gttcatccatagttgcctgactccccgtcgtgtagataactacgatacgggagggcttaccatctggccccagtgctgcaatgataccgcgagacccacgctc
accggctccagattttatcagcaataaaccagccagccggaagggccgagcgcagaagtggtcctgcaactttatccgcctccatccagtctattaattgttgccgggaagctagagtaagtagttcgccagttaatagtttgcgcaacgttgttgccattgctacaggcatcgtggtgtcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtc
```

FIG. 21B (continued)

agatcctggtatcggtctgcgattccgactccgatccaacatcaatacaaacctattaattccctcgtcaaaaataaggttatcaagtgagaa
atcaccatgagtgacgactgaatccggtgagaatggcaaaagctatgcatttcttccagactgttcaacagccagttcaacagccagccattacgctc
gtcatcaaaatcactcgccatcaaccaaaaccgttattcattcgtgattgcgcctgagcgagacgaaatacgcgatcgctgttaaaaggac
aattacaaacaggaatcgaatgcaaacggcgccaggaacactgccagtgccatcaacatgccagtaaccatgcatcatcaggagtacgagatcatcaggatattcttctaata
cctggaatgctgttttcccgggatcgcagtcggtgagtaaccatgcatcatcaggagtacggataaaatgcttgatgtcggaagagg
cataaaticcgtcagccagtttagtctgaccatctcatctgtaacatcattgccaacgctacctttgccatgttcagaaacactctggcg
catcgggcttcccatacaatcgatagattgtcgacctgattgcccgacattatcgcgagccattatacacccccttgattactgttatgtaagcagacagttt
gttggaattaatcgcggcctcgagcaagacgttcccgttgaaatgctcataacaccccttgattactgttatgtaagcagacagttt
tattgttcatgatgatatattttatctgtgcaatgtaacatcagagatttgagacacaaacgcggcttccccccccattattgaagca
tttatcaggttattgtcatgagcggatacatattgaattgatatgttagaaaataaacaaataggggttccgcgcacattcccgaaaa
gtgccacctgacgtctaagaaaaccattattcatgacattaaccctataaaaaataggcgtatcacgaggccttcgtc

FIG. 22B

SEQ ID NO: 18

```
tcgcgcggttcgtcgtgatgacggtgaaaacctctgacacagagctcccggagacggtcacagcttgtctgtaagcggatgccggga
gcagacaagcccgtcaggcgcgtcagcggtgttggccgggtgtcgggtgcttaactatgcggcatcagagcagattgtactg
agagtgcaccatatgcggtgtgaaaataccgcacagatgcgtaaggagaaaataccgcatcagattgccattgccattgcatacgttg
tatccatatcataatatgtacattatattggctcatgtcaatcatgtgcaaattaccgccatgttgacattgattattgactagttaatagtaatcaatta
cggggtcattagttcatagcccatatatggagttccgcgttacataacttacgtaaatggcccgcctggctgaccgcccaacgaccc
cgcccattgacgtcaataatgacgtatgttccatagtaacgccaataaggcactttccattgacgtcaatgggtggagtatttacgtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgatccagcctcc
atcggctcgcatctctccttcacgcgcccgccgccctaactgagtgcgccatccacgcctgagtgcgttcgcgtctgcgcctccgcc
tgtggtgcctctgaactcgctgcctgccgcgtctaggtaagtttaaagctcaactctagttaaacgtcagcagcagtgctgagcagtact
acctagactcagcagcgcctctccacgctttgcctgaccgctgcttgtcaacaatctagttaacgtgagggcagtgtagtcgtgagcagtact
cgtgctgcgcgcgcgccaccagacatatagtgcgaccagcataaatgctgacgaacgacactgttccttccatggtcttttctgcagtcaccgtcg
acacgtgtgatcagatatcgcggccgcacctgcccgaggtcttacaatccgttggccgagttgcctacgtcaactccaatagc
atggaggcaagtaggcaaggtaggcctgcaccgtgccctgcgcctgccgcgcctgctatccccggttgactaccccaagatccaacagtcactaggctgttagagc
tttggtgctggacaatgctacactgccagcgcccagcgcccggctctctgcacgcgcctgcggcctgcgaggaagccgaagactcaaaaaccttagccga
agaagcaaaaccagaaaccaccaacagcagaaggaaaatcagcccaacaacgcgaagaaaccgaagcccggtaaa
cgacagcgtaccgcctgaaattgaagcgcccgaccgacccgcacattgtcgggaaggaaatgaagaagcaagattatggaatacgccgttgcc
atggaaggaaagtgataaaaaccactacactgtaaaaggaaccattgaccaccccggccctagccgaaactcaaattcactaaatcttctct
tacgacatggagtttgctaaactaccgaccgaagatagcgacgcattcggtatacaacggaacaccccgaagtatttacaactg
gcatcacgcgagctgtcaaattttccggcggaaggtcaccatcccacaggagtcgaggcccggagagtagcggaaggctatact
ggataactccggaaaagtggtagccatagtcctaggagagctaatgaagtgccaagaacgcacttctgttgtcacctgaataag
aaggagccgctataaaacaccacgaagatactgtagagtgtcgcgtattaccgctatgtcatcctgcagaacgtcacatt
cccatgtgaccgaccgccaactgctataatcgtaatcctgacttgactgactgtaataacatgttggaaacaaatgtcaatcacccttcgtacgac
```

FIG. 22B (continued)

gttctgctggacgctgtctgaggtgcccacgagacggcacgtcagatcaacgcccacgatgactcactctcacagcaccgtacc
tcggcttgtcacagatgaagacgatgaagacgtacagccctataaaaatcgaaaaagtgtggatgatgccgatgacggagtt
ctccgtatacaagtaagtgcccagttagggtacaacagggcgggcactgcagctagcgcccgactccgttcatggccggaggagt
gcctccggaaatccaggagaggagagcaattgacgatttaaggtcttcacgtccaaaccatgttaccaccatcacataaggatactttgtc
attgtcaagtgcccctcctgttgatagtagtattacaaacatcattgaaagtgcatggctcgacaaaatacctgccttacctacgaaaggacacgagagt
acaagttcgtaggcaggagaaaaatatactctgccaccacaaatccatgaggacacaaaatccttgatgtgaagagagcgggaggagtgtacgta
aaagtcaggatacgtgaccatgcatgtccggacaacaatccataacctgatgtgaagagagcgggaggagtgtacgta
caaccgacagtgggcgaaacgtcacctacgagtgtaaatgcggaccacgtcaaatgggtgttaactccccgacttgatcaggcataccga
ggctgtacacagaaggggaaaaacaatgcattgcatatccgctacagcaggtcaatgtacagtaccaccgcgcaccttccagcgttaag
ccacacagcccaagagggaagttgcatatccgctacagcaggtcaatgtacagtaccaccgcgcaccttccagcgttaag
catgctatcgcagtgtctgacactgcacgctgagcatctccataaccatacaagggttcgagtatacttgggggaaatcagaaaccggtccga
cagaatgattgtcggagagtgtaactcgaaacttctccataaccatgctgccacatgaaatcgtacgccattactaccaccctctatccttctacacc
gtgtacgccaggaatcggcacctgccaatcctcatgctgccacatgaaatcgtacgccattactaccaccctctatccttctacacc
gttacagtgctgagccgcatggacatggcctctagtagtcgctggcttagtgtcatcagtagtatttatgctgctcaaaagcaagaaggattgccta
acacccttacacaactggcccgaacctaccgtaccattctggtaacattgtgttgctgtttccaacggactcagcggactcagcggatgaattaccg
ataccatgggtacctatgcaacacagtcaaacaaattgtctgatacaacaaatggtcatactcttagcagtcagtgatacttgttagatgt
tgctcctgtcgtctaccttttatgtgttgccagtcctccctaaacaaagcgacgcctacgaacataccgatactgctccccaaatgcgcgtt
gaactgtataaagcactagtggaacggcctggtatgccccttaataccgcaagcctggagtcatagaactgtcgaactgtcgaactgccgaaaggtg
ttaaaacgtgaatacattacctgcaggtaccacacggttcactggttgtccccttgaataccgcaagtcagaattcgcggtcgtatgccgaaagttg
aaaaagcagactataccgcaggtaccaggcctctgggggagaggagagcacagtgtttgcgactccgaaaacagtc
agcttagcgacaagtacgtgcgaactacgggaactgaacagtcaaacagatgccacagaccatgccgagcggttcagagtaccacacggcttccggtgaaat
cacagctccgaataaccacgggaactccacacagagacgtattgtcaacccgtgcgactccagcggaagcgcaaagacatga
aattgatagccggcgcccattactactacatttccccgtttgataataaggtcattataatcatggaagcgctataactatgacttccgga
atttggggccccgaaccctgagcttccggagatccatcaccaccggatccagatcctattagcaaacacagcaattcatt
gcagaggccggaagccagaaacatacacgtccccgtaccaccaagcgttcgaattcggagaataacaggtcag
cctttactgacacactgccccctttcggatcaaagtcaatgcaaagtacgtcagacaagtgtgccgtgggatcactcccgtatcc
gtggataaccgagcgcctgcatttcacggcccatgccagcccctgccatcagcatgcgatccaagtccgagcgctgctaagtgtcaccgttactagttgcacattactctaca FIG. 22B (continued)

gactatggcggagtgctcgtgttgacatacgagtcgcgggatcgcgcggggcaatgcgctgtacactcgcattcatcaaacagcggtactgc
gagaccatcggtatacgtcgagcaagaaggggagagactcacttaaattagtacgcgttcctgcaggcagacttcgaggtatcgatg
tgcggaacgagaaccacttgccatgccaatgtcaacaccaacggaacacgtaatgaacagaccccagaagtcgactccagactc
tcctcagcgatatccaaaacatcatggaactggactgcgcttatggggaattccagtataagctgctatagccgcaattgtctg
gtcatagcattagtattacagcacacagatgatcgacacagacccgatccagatcgctgtgcctctcagttgccagccatctg
ttgtttgcccctccccgtgccttcctgacccggaaggtgccactccactgccctgtccttcctaataaaatgaggaaattgcatcgcattgtc
tgagtaggtgtcattcattcctggggtggggggggggggcaggaacagcaagtgcaggattgggccagaacaatagcaggcatgctggg
gatgcggtgggtctctatgggtctccacgcccctggttcttagttccagcccactcatagaacactcataagctcaggaggctcccgccttcaatccca
gtgacacaccccgtccagcccctggttctctcccctcatcagcccccataaaccaaccctagcctccaagagtggaagaaattaaagca
agataggctattaagtgcagagggagagaaaatgcctccaacatgtgagaagtaatgagaaatcatagaaattttaaggcatgatt
taaggccatcatggccttaatcttccgctaatcttccgctcactgactcgctcggtcgttcggctgcgggcgagcggtatcagctcact
caaaggcggtaatacggttatccacagaatcaggggataaacgcaggaaagaacatgtgagcaaaaggccagcaaaaggccagga
accgtaaaaaggccgcgttgctggcgtttttccataggctccgcccccctgacgagcatcacaaaaatcgacgctcaagtcagaggtg
gcgaaacccgacaggactataaagataccaggcgtttccccctggaagctccctcgtgcgctctcctgttccgaccctgccgcttacc
ggatacctgtccgcctttctcccttcggaagcgtggcgctttctcatagctcacgctgtaggtatctcagttcggtgtaggtcgttcgctc
caagctgggctgtgtgcacgaaccccccgttcagcccgaccgctgcgccttatccggtaactatcgtcttgagtccaacccggtaaga
cacgacttatcgccactggcagcagccactggtaacaggattagcagagcgaggtatgtaggcggtgctacagagttcttgaagtggt
ggcctaactacggctacactagaagaacagtatttggtatctgcgctctgctgaagccagttaccttcggaaaaagagttggtagctctt
gatccggcaaacaaaccaccgctggtagcggtggtttttttgtttgcaagcagcagattacgcgcagaaaaaaaggatctcaagaaga
tcctttgatcttttctacggggtctgacgctcagtggaacgaaaactcacgttaaggggattttggtcatgagattatcaaaaaggatcttca
cctagatccttttaaattaaaaatgaagttttaaatcaatctaaagtatatatgagtaaacttggtctgacagttaccaatgcttaatcagtga
ggcacctatctcagcgatctgtctatttcgttcatccatagttgcctgactccccgtcgtgtagataactacgatacgggagggcttaccatctg
gccccagtgctgcaatgataccgcgagacccacgctcaccggctccagatttatcagcaataaaccagccagccggaagggccgagcgcagaagtggtcctgcaacttta
tccgcctccatccagtctattaattgttgccgggaagctagagtaagtagttcgccagttaatagtttgcgcaacgttgttgccattgctacaggcatcgtg
gtgtcacgctcgtcgtttggtatggcttcattcagctccggttcccaacgatcaaggcgagttacatgatcccccatgttgtgcaaaaaagt
ggctccactcgctccaagcaggaacccattcattcagctccggttcatggtcacgggataataccgcgccacatagcagaactttaaaagt
ccgactggttgttgccgggaagtctgcgcggggaagctaggaagctagcatcctccctcacggactattaatctgatagaaaaact
catcgagcatcaaatgaaactgcaatcattcaattcaggattatcaggattatcagcaggattatcattccgtctgtaatgaaggagaaaact FIG. 22B (continued)

caccgaggcagttccaaggatggcaagatcctgtatcgtctgcgattccgactcgtcgaatccgatctcgtccaacatcaatacaacctattaattccctc
gtcaaaaataaggttatcaagtgagaaatcaccatgagtgacgactgaatccgtgagaatggcaaaagcttatgcattcttccagac
tgttcaacaggccagccattacgctcgtcatcaaaatcactcgtcatcaaccaaaccgttattcattcgtgattgcgcctgagcgagacg
aaatacgcgatcgctgttaaaagacaattacaaacaggaatcgaatcaaccggccaggaaacactgccagcgcatcaacaatattt
tcacctgaatcaggatatcttctaatacctggaatgctgtttcccgggatcgagtggtgagtaaccatgcatcatcaggagtacgga
taaaatgcttgatgtcggaagagcataaattccgtcagccagtttagtctgaccatctcatcgtaacatcattggcaacgctacctttg
ccatgtttcagaaacaactctggcgcatcggcctttccatacaatcgatagattgtcgcacctgattgcccgacattatcgcgagccatt
tatacccatataaatcagcatccatgttggaattaatcggcctcgagcaagacgtttcccgttgaatatggctcataacaccccttgta
ttactgtttatgtaagcagacagttttattgttcatgatgatatttatctgtcaatgtaacatcagagatttgaatgtatttagaaaaataaacaaataggg
ccccccccccattattgaagcatttatcaggggttattgtctcatgagcggatacatatttgaatgtatttagaaaaataaacaaataggg
gttccgcgcacattcccgaaaagtgccacctgacgtctaagaaaccattattatcatgacattaacctataaaaatagcgtatcacga
ggcctttcgtc FIG. 23B (continued)

SEQ ID NO:19 atgagcctgcccctccggtcttgtgctgttggcaaacactacattccctgctctcagccgcttgcacacctgctgcgaaaggaacc
ggaaagcaccttggcatgctggaggacaacgtgatgagacacgtgacaacgtataaaagcatcgctgactgctctcccacgcc
aaagacgcagtactaaggacaattttaatgtctataaagccacagaccatatcagctcattgtcctgactgcggagaaggcattcgtgca
cagccctatcgcattggagcgcatcagaagaaatgaagcaacggacgaacgctgaaaatccaggtctcttgcagatcgggataagacagat
gacagccacgattggaccaagctgcgtatatgatagccatacgccagcgacgcggagcgagccggattgcttgtaaggacttcagcac
cgtgcacgatcaccgggaccatgtggacactggacacttattctcgcccgatgcccgaaaggagagacgctgacagtgggattacggacagcagaaa
gatcagccacacatgcacacaccgttcatcatgaaccacctgtgataggtaggagagaggttccactctgaccacaacatgtaaagagt
tacttgcagctacgtgcagagcaccgctgccactgcaaacaccacctgctgagagatagaggtgcatatgcccccagatactctgaccgcacgctgatg
acgcagtcttggcaacgtgaagatcacagttaatgggcagacggtgcgtacaagtgcaactgcggttggctcaaacgagggactgaca
accacagaacaaagtgataacaatgcaaaattgatcagtgccatgctgcagtcactaatcacaagaattggcaatacaactcccctttagtcc
cgcgcaacgtgaactcgggggaccgtaaaggaaagaatcacatccattccgcaaacgtgacttgcagagtgcaaaagcaagaa
acctacagtaacttacgaaaaaccaagtcacatgctgctatcctgaccatccgacactcttgctcttacgtaacatgggacaggaacc
aattaccacgaggagtgggtgacacaagaaggagagttacctgaccgtgcctactgaggtctgaggtctggagtcacttgggcaacaacgaa
ccatacaagtactgccgcagatgctacgaacggtactgctcatgtcaccacacagagataatcttgtactattgagctgtaccccactatg
actgtagtcattgtcgtgtggcctgttctgtgtcgatgggcacagcagtggaatgtgtgtgcgcacggccagatgcattaca
ccatatgaattaacaccaggagcacagcccctgttccctgctcagcctgatgctgcagaacgaccaaggcggccacatattacgaggctg
cggcatatctatgaacgaacagacgagccctgcttttttagccgtaatgagcatcggtgccacacactgtgagcgcgtacgaacacgtaacagtgatcccgaac
gccatgctgctgtaagaccctggcttttttagccgtaatgagcatcggtgccacacactgtgagcgcgtacgaacacgtaacagtgatcccgaac
acggtggagtacgctataagactcttgtcaacagacgcgggttacagccccatgggttgtgagatggagctacaatcagtcactgaacca
acactgtcacttgactacatcacgtgcgagtacaaaactgtcatccccccgtacgtgaagtgctgggtacagcagagtgcaaggacaag
agcctaccagactacagtgcaaggtctttactggagtctcaaaacagagtttgcatcggcctacagagcccacaccgcatcggcgtcggcgaagctc
gagcggcacatgtagagaaggtgccctacagagcgtgccacacgcgttcacagtaaaggacgccaagttgtgtgggc
cgcgtcctttaccaagaaacaacatttacgtagctgcctacgctaacgtgtacaaaggcgacgtgctacaacatgggacgtctacaaggcgtactcacacctttgcgcaggaa
ccaatgtcctccgcctggacacccttttgacaacacaaatgtggtgtacaaaaggcgacgtctacaacatggacgtctacaaaggcgtactcacacctttgcgcaggaa
gaccaggacaatttgtgacattcaaagtctgtacaccgaaaataaagacgtttatgccaacactcagttgttattggtactacaagaggcagca
ggcacgggtaccatgcaccatcctcggcaccatcctggcttcaagtattggctgaaggaacgaggagcatcgtacagcacacggcacccgtt

FIG. 23B (continued)

cggttgccagattgcgacaaacccgtaagagctgtaaattgcgctgtgggaacataccaattccatcgacataccggatgcggcctttact
agggttgtcgatgcaccctctgtaacgacatgtcatgcgaagtaccagcctgcactcactcctccgactttggggcgtcgccatcatcaaata
cacagctagcagaagaaagtaaatgtgcagtacattcgatgacgaacgccgttaccattcgagaagccgacgtagaagtagagggaactc
ccagctgcaaatatcctttctcaacagccctggcaagccgagtttcgtgcaagtgctccacacaagtacactgcgcagccgcatgcca
ccctccaaaggaccacatagtcaattaccagcatcacacaccaccctgggtccaggatatatccacaacggcaatgtcttgggtgcaga
agattacgggaggaggtaggattaattgttgctgctgccttaatttaattgtggtgctatgcgtcgttagcaggcac

SEQ ID NO: 20 atgagtcttgccatccagttatgtgcctgttggcaaacaccacgttccctgctcccagccctgctgctgtacgaaaggaacc
ggaggaaacctacgcatgtcttgaggacaaacgtcatgagacctggtactatcagctgctacaagcatccttaacatgttctcccaccgcca
gcgacgcagcaccaaggacaacttcaatgtctataaagccacaagacacatactagctcactgtccgactgtggaagggcactcgtgcc
atagtcccgtagcactagaaacgcatcagaaatgaagcgacagacgggacgtctccttgcaaatcgaatcaagtctccttgcaaatcgaataaagacgg
atgacagccacgattgaccaagctgcgttatatgtgacaaccacatgccagcagagaggcgcgggctatttgtaagaacatcag
caccgtgtacgattactggaacaatggccacactgcaccctcatcctggcccgatgtcaaaagggaaactctgacgtgtggggattcactgacagtagg
aagattagtcactcatgtacgcaccattccaccagaccctctgtataggtcggaaaaattccattccgaccgcagcacgcacgtaaagag
ctaccttgcacgtacgtgcagcaacgtaaagatcacagtcaagttgatcatgcccagacgtgccagacgtgccagaacgtgccccagacaccctgatcgcacata
atgtcacaacagtccggcaacgtaaagatcaatgaactcaagttgatcatgcccagacgtgccagacgtgccggtcaatgaaggactaa
caactacagacaagattgattaactgccgaaaggtaataactccaccagacgtgatcaatgcccaagtaactcacaaaagtggcagtataactccctctggt
ccgcgtaatgctgaacttgggaccgaaaagaaaattcacatccgtttcgctggcaaatgtaacatgcaggtgcctaaagcaagg
aaccccaccgtgacgtacggagaaaaccagtacatcatcatgtactactgtctcgtaccaccaacactctgtctccacggaatatgggagaaga
accaaactatcaagaagagtggggtgatgcataagaaggctgtcaaccgtgcgactagaaggctcgaggtcacgtggggcaaca
acgagccgtataagtattggccgcagttatctaccaaacgtggtacagccccatgccaccgtgagatagataattctgtattattgaccgctacccc
actatgactgtagtagttgtcagtgccacgttcatactcctgctgatgtgggattgcacgcatgtgtgcacgacgcagatgc
atcacacgtatgaactgacaccaggagctaccgtccctttcctgcttagcctaatatgctcatcagaaacagctaaagcggccacataccaa
gagggtgcgatataccctgtgaacgagcagcaaaacttgtttggctacagccctattccgctgcagccctgattgttcatgcaactgtctga
gactcttaccactgctgctaaaacgttggctttttagccgtaatgacgctgctccacactgtgagcgctacgaacacagtaacagtgatcc
cgaacacgtgggagtaccgtataagactctagtcaatagaccctcagtgatcaatagaccctcagtgattggagatgaactactgtcagtcactttgga

FIG. 23B (continued)

gccaacactatcgcttgattacatcacgtgcgagtacaaaacgtcatccgtctccgtacgtgaagtgctgcggtacagcagagtgcaagga
caaaaacctacctgactacagctgtaaggtcttcaccggcgtctaccatttatgtggggcggcctactgcttctgcgacgtgaaaacacg
cagttgagcgaagcacacgtggagaagtccgaatcatgcaaaacagaatttgcatcagcatacagggtcatactgcatctgcatcagctaa
gctccggctccttaccaaggaaataacatactgtaactgcctatgcaaacggcaacatgccgtcacagttaaggacgccaaattcattgtg
gggccaatgcttcagcctgacactttgcacaacaaaattgtggtgtacaaagtgacgtctataacatgactacaactgtactgcagagaccggc
gaagaccaggacaatttggcgatatccaaagtcgcacacctgagagtaaagacgtctatgctaaaagaaccgtctaaaagaaccgtagcagacgcag
tgtgggtacgtgcacgtgccatactctcaggcaccatctggcttaagtattgcaaaagaaccgggcgtgctgcagcacacagcacc
atttggctgcaaatagcaacaaaccggtaagagcggtgaactgcgccgtagggaactgccatctccatcgacacttttggggcgtgcgcattat
cttcactaggtgcgacgcgccctctttaacggacatgcgtgcgagttgcattcgatgactaacgccgtcacttattcggaagctgatagaagttgaaggg
taaatatgcagccagcaagaagcaagtgtgcggtgcattcgatgactaacgccgtcacttattcggaagctgatagaagttgaaggg
aattctcagctgcaaatctctttctgacggtcaactaccggcgtcacataccaccctcggggtccaggacatctccgctacggcgatgtcatgggtgc
caccccgaaggacacacatagtcaactaccggcgtcacataccaccctcggggtccaggacatctccgctacggcgatgtcatgggtgc
agaagatcacggggaggtgtgggactgtgttgcgtgttgcgcactacttgccgcactgattcaatcgtggtgcgtgtcgttcagcaggcac

SEQ ID NO: 21

Atggagttcatcccgaccgacgcaaacttttctataacagaaggtaccaacccgaccctggcccacccgccctacaattcaagtaattagacctagacca
cgtccacagaggcaggctgggcaactcgccagtgatctccgcagtcaacaaattgaccatgcgcggtacctcaacagaagcctcgcagaa
atcggaaaaacaagaagcaggcagaagcaggcagcaggcagcgccgcaaaagcaaccgccaaaagaagcaacccaccacaaagaagccggctc
aaaagaagaagaaaacaggcgtaggagagaagcggagaatgtgcatgaaatgtgacaccagacatgtgaaggaactatcgaagtcaagatgaaggcaaagtgatggg
ctacgcatgcctgtggggataaagtaatgcacagataccggtgcacagataccggtgaaaccagagtgtcgacatgaagctcgaagttcgaaacttgaaactgcctaaacgcgtaaactgcctttaagcggtc
gtctaataacgatgtcgatcttgaatgtgcagatattcagagggccggcgttcactatcccgaagttccacagaccgagaaaacccggagggtactataactgg
catcacggagcagtgcagtattcaggaggccggttcactatcccgaagttccacagaccgagaaaacccggagggtactataactgg
aaaggacggtgttggccatcgtcctaggaggggccaacgaaggtgcccgcaaggttgcccgcacggccctcgtggtgacgtgaacaaagacatcgtcaca
aaaattacccctgagggagccgaagagtgg FIG. 23B (continued)

SEQ ID NO: 22

Atggagttcatcccaaccacccaaacttttacaataggagtaccagcctcgcgccctactatccaagtcatcaggcccagaccg
cgccctcagaggcaagctgggcaacttgcccagctgatctcagcagttaataaactgacaatgcgcggtaccaacagaagccacgcagga
atcggaagaataagaagcaaaagcagcaaacagcaacaacagcagcagcaacctaaaagaaaccggctcaa
aagaaaaagaagccggctgggggacaaagtaatgaaaccagcacacgtaaaggggaccatcgataacgcggacctggccaaactggccttttaagcggtca
cgcgtgcctggtggggggacaaagtaatgaaaccagcacacgtaaaggggaccatcgataacgcggacctggccaaactggccttttaagcggtca
tctaagtatgacctgaatgcgcagatacccgtgcacatgaagttcgacgcttcgaagttcaccatgagaaaccgagcgggtactacaactgg
caccacgagcagcagtacagatccaggaggccgttcaccatcccacaggtgctggcaaaccaggggacaggcggcagaccgatcttcgacaac
aagggacgcgtggtggccatagtctaggaggagctaatgaaggagcccgtacagccctccggtggtgacctggtgacctggaataaagacattgtcactaa
aatcaccccgaggggggccgaagagtgg

FIG. 24

Seq ID NO: 23

```
   1 atggctgcgt gagacacacg tagcctacca gtttcttact gctctactct gcaaagcaag
  61 agattaataa cccatcatgg atcctgtgta cgtggacata gacgctgaca gcgcctttt
 121 gaaggccctg caacgtgcgt accccatgcgt tgaggtggaa ccaagcagg tcacaccgaa
 181 tgaccatgct aatgctagag cgttctcgca tctagctata aaactaatag agcaggaaat
 241 tgaccccgac tcaaccatcc tggatatcgg cagtgcgcca gcaaggagga tgatgtcgga
 301 caggaagtac cactcgtgtct gccgatgcg cagtgcgcag gatccgaga gactcgccaa
 361 ttatgcgaga aagctagcat ctgccgcagg aaaagtcctg gacagaaaca tctctgcctt
 421 gatcggggac ttacaagcag taatggccgt gccagacacg gagacgccaa cattctgctt
 481 acacagagac gtctcatgta gacacaacg gccagacacg gagacgccaa cgtctatgc
 541 tgtacacgca cccacgtcgc tatacccaca ggcgattaaa ggggtccgag tggcgtactg
 601 ggttggttc gacacaaccc cgtcatgta caatgccatg gcgggtgcct accctcata
 661 ctcgacaaac tgggcagatg agcaggtact gaagctaag aacataggat tatgttcaac
 721 agacctgacg gaagtagac gaggcaagtt gtctattatg agaggaaaaa agctaaaacc
 781 gtgcgaccgt gtgctgttct cagtagggtc aacgctctac ccggaaagcc gcaagctact
 841 taagagctgg cacctgccat cggtgttcca tttaaagggc aaactcagct tcacatgccg
 901 ctgtgataca gtgtttcgt gtgagggcta cgtcgttaag agaataacga tgagccagg
 961 cctttatgga aaaccaccag ggtatgcggt aaccaccacc tcggttgca catacgtgcc
1021 caagactacc gacacggttg acggcgaaag aatgtcattc gaagtcacgc cggaagatgc
1081 ggcgaccatt tgtgatcaaa tgaccggcat ccttgctaca aacggcagaa cgcaacgaa
1141 acagaactg ttgtgggggc tgaaccagag aatagtggtt aatagttgtt gtaagtgggc
1201 tacgaacacc atgaaaaatt atctgcttcc cgtgtcgcc aaaactcctg cagcctttca
1261 aaaggagtgc cggaagaca tggaagatga aaaactgctg gggtcagag acacggtggg
1321 gacctgctgc tgtctatggg cattcaagaa gcacaggtct acaagaggcc acagcttgac
1381 tgataccaga tcaattcaga aggttgtcaa agttcagac agctttgtgg tacgagtct
1441 gtggtcgtcc gggttgtcaa tccctttgag gactagaatc aaatggttgt taagcaaggt
1501 gccaaaaacc gacctgatcc catacacgg gaaagcccga acgcagaaa
1561 agaagcagag gaagacgag aagcagaact gacctaccac gccctaccac ctctacagc
```

FIG. 24 (continued)

```
1621 agcacaggaa gatgttcagg tcgaaatcga cgtggaacag cttgaggaca gagcgggcgc
1681 aggaataata gagactccga gaggagctat caaagttact gcccaaccaa cagaccacgt
1741 cgtgggagag tacctggtac tctccccgca gaccgtacta cgtagccaga agctcagtct
1801 gattcacgct ttggcggagc aagtgaagac gtgcacgcac aacggacgag cagggaggta
1861 tgcggtcgaa gcgtacgacg gccgagtcct agtgccctca ggctatgcaa tctcgcctga
1921 agacttccag agtctaagcg aaagcgcaac gatggtgtat aacgaaagag agttcgtaaa
1981 cagaaagcta caccatattg cgatgcacgg accagccctg aacaccgacg aagagtcgta
2041 tgagctggtg agggcagaga ggacagaaca cgagtacgtc tacgacgtgg atcagagaag
2101 atgctgtaag aaggaagaag ccgcaggact ggtactggtg ggcgacttga ctaatccgcc
2161 ctaccacgaa ttcgcatatg aagggctaaa aatccgccct gcctgcccat acaaaattgc
2221 agtcatagga gtcttcggag taccgggatc tggcaagtca gctattatca agaacctagt
2281 taccaggcag gacctggtga ctagagaaac tgccaagaaa tgccaagaaa tcaccacga
2341 cgtgatgaga cagagaggtc tagagatatc tgcacgtacg gtttgactcgc tgctctttgaa
2401 tggatgcaac agaccagtcg acgtgttgta cgtagacgag gcgtttgcgt gccactctgg
2461 aacgctactt gctttgatcg ccttgtgag accaaggcag aaagtgtac tttgtgtga
2521 cccgaagcag tgcggcttct tcaatatgat gcagatgaaa gtcaactata atcacaacat
2581 ctgcaccaca gtgtaccaca aaagtactc caggcggtgt acactgcctg tgaccgccat
2641 tgtgtcatcg ttgcattacg aagcaaaat gcgcactacg aatgagtaca acaagccgat
2701 tgtagtggac actacaggct caacaaaacc tgaccctgga gacctcgtgt taacgtgctt
2761 cagagggtgg gttaaacaac tgcaaattga ctatcgtgga gacctcgtgt ttgacagcag
2821 cgcatcccaa gggttaacca gaaaaggagt ttaacgcagt agacaaaaag ttaatgaaaa
2881 ccgctctat gcatcaacgt cagagcacgt caacgtactc ctaacgcgta cggaaggtaa
2941 actggtatgg aagacactt ccggcgacc gtggataaag acgctcagaa acgctaccga
3001 aggaaacttc aaagcaacta ttaaggatg ggaggtggag catgcatcaa aaagcaacg
3061 catctgcagt caccaaatga cctccatacc attccaaaat ctaaatgata tttgttggc
3121 gtccttg gtccctatcc tcgaaacacg gggatactca aaagccaacg ggcagtggtc
3181 tcagataatt caagccttca aagagacaa agcatactca cctgaagtag ccctgaatga
3241 aatatgtacg cgcatgtatg gggtggatct agacagcggg ctatttcta aaccgttggt
3301 gtctgtgtat tacgcggata accactggga taataggcct ggaggaaaa tgttcggatt
```

FIG. 24 (continued)

```
3361 taacccgag gcagcatcca ttctagaaag aaagtatcca ttcacaaaag ggaagtggaa
3421 catcaacaag cagatctgcg tgactaccag tgactaccag gaggatagaa gactttaacc ctaccaccaa
3481 catcataccg gccaacagga gactaccaca ctcattagtg ccgaacacc gcccagtaaa
3541 agggaaaga atggaatggc tggttaacaa gataacggc caccacgtgc tcctggtcag
3601 tggctataac cttgcactgc ctactaagag agtcactgg gtagcgcgt taggtgtccg
3661 cggagcggac tacacataca acctagagtt gggtctgcca gcaacgcttg gtaggtatga
3721 cctagtggtc ataaacatcc acacaccttt tcgcatacac cattaccaac agtgcgtcga
3781 ccacgcaatg aaactgcaaa tgctcgggg tgactcattg agactgctca aacggcggg
3841 ctctctattg atcagagcat atggttacgc agatagaacc agtgaacgag tcatctgcgt
3901 attggacgc aagtttagat cgtctagagc gttgaaacca ccatgtgtca tagtcaacgc
3961 tgagatgttt ttcctattca gcaactttga caatgcaga aggaatttca caatcatgt
4021 catgaacaat caactgaatg cagccttcgt aggacaggtc accgagcag gatgtgcacc
4081 gtcgtaccgg gtaaaacgca tggacatcgc tggatcgacg gaagagtgcg tagtcaacgc
4141 cgctaaccct cgcgggttac cgggtggcgg tgtttgcaag gcagtataca aaaaatggcc
4201 ggagtccttt aagacagtg caaccagt gggaaccgca aaaacagtta tgtgcgtaca
4261 gtatccagta atccacgctg gcagctgcct ttggaccaaa cttctctaat tattcggagt ctgaaggga
4321 ccgggaattg gcagctgcct atacctctcc atcgagaagt cgcaaaggaa gtaactaggc tgggagtaaa
4381 tagtgagct aaccacctct tctccacagg tgtatactca ggaggaaag acaggtgac
4441 ccagtcactg aaccacctct ttacagccat ggactcgacg gatgcagacg tggtcatcta
4501 ctgccgac aaagaaatggg agaagaaat atctgaggcc atacagatgc ggacccaagt
4561 agagctgctg gatgagcaca tctccataga ctgcgtgc acctgacag
4621 cagcttggca ggcagaaaag gatacagcac gataacagcc gcactgtact catatctaga
4681 agggacccgt ttcatcaga cggctgtgga cacggaaggc atacatacta tgtggccaaa
4741 gcaaacagag gccaatgagc aagtctgcct atatgccctg ggaaaagta ttgaatcgat
4801 caggcagaaa tgcccggtgg atgatcaga ggactcatct cccccaaaa ctgtccgtg
4861 cctttgccgt tacgctatga ctcccagaacg cgtcaccgg cttcgcatga accacgtcac
4921 aagcataatt gtgtgttctt cgtttcccct cccaaagtac aaaatagaag gagtgcaaaa
4981 agtcaaatgc tctaaggtaa tgctattga ccacaacgtg ccatcgcgcg taagtccaag
5041 ggaatataga tcttcccagg agtctgcaca ggaggcgagt acaatcacgt cactgacgca
```

FIG. 24 (continued)

```
5101 tagtcaattc gacctaagcg ttgatggcga gatactgccc gtccgtcag acctggatgc
5161 tgacgcccca gccctagaac cagcactaga cgacggggcg acacacgc tgccatccac
5221 aaccggaaac cttgcggccg tgtctgattg ggtaatgagc accgtacctg tcgcgccgcc
5281 cagaagaagg cgagggagaa acctgactgt gacatgtgac gagagagaag ggaatataac
5341 acccatggct agcgtccgat tctttagggc agagctgtgt ccggtcgtac aagaaacagc
5401 ggagacgcgt agcacagcaa tgtctcttca ggcaccgcca agtaccgcca cggaaccgaa
5461 tcatccgccg atctcctcg gagcatcaag cgagacgttc cccattacat ttgggactt
5521 caacgaagga gaaatcgaaa gcttgtcttc tgagctacta actttcgag acttcttacc
5581 aggagaagtg gatgacttga cagacgcga ctggtccacg ctgctcagaa cggacgacga
5641 gttaagacta gacaggcag gtgggtatat attctcgtcg gacaccggtc caggtcattt
5701 acaacagaag tcagtacgcc agtcagtgct gccggtgaac accctggagg aagtccacga
5761 ggagagagt taccaccta agctggatga agcaaaggag caactattac ttaagaaact
5821 ccaggagcag gcatccatgg ccaacagaag caggtatcag tcgcgcaaag tagaaaacat
5881 gaaagcagca atcatccaga gactaaacag aggctgtaga ctatacttaa tgtcagagac
5941 cccaaagtc cctacttacc ggactacata tccggcgcct gtgtactgc ctccgatcaa
6001 cgtccgattg tccaatcccg agtccgcagt ggcagcatgc aatgagttct tagctagaaa
6061 ctatccaact gtctcatcat accaaattac cgacgagtat gatgcatatc tagacatggt
6121 ggacgggtcg gagagttgcc tggaccgagc gacattcaat ccgtcaaaac tcaggagcta
6181 cccgaaacag cacgcttacc acgcgccctc gctgtaccgt cctgtaccgt ccccattcca
6241 gaacacacta cagaatgtac tggcagcagc catcagaagc aactgcaacg tcacacagat
6301 gagggaatta cccactttgg actcagcagt attcaacgtg gagtgtttca aaaaattcgc
6361 atgcaaccaa gaatactggg aagaattgc tgccagcagt attaggataa caactgagaa
6421 tttagcaacc tatgttacta aactaaaagg gccaaaagca gcagcgctat tcgcaaaaac
6481 ccataatcta ctgccactac aggaagtacc aatggatagg ttcacagtag atatgaaaag
6541 ggacgtaaag gtgactcctg gtacaaagca tacagaggaa agacctaagg tgcaggttat
6601 acaggcggct gaaccctgg cgacagcata cctatgtggg attcacacag agctggttag
6661 gaggctgaac gccgtcctcc tacccaatgt acatacacta tttgacatgt ctgccgagga
6721 tttcgatgcc atcatagccg cacactttaa gccaggagac actgttttgg aaacgacat
6781 agctcctt gataagagcc aagatgattc aagatgcttc actgcgctt actgctttga tgctgttaga
```

FIG. 24 (continued)

```
6841  ggattaggg  gtggatcact  ccctgctga  cttgatagag  gctgctttcg  gagagattc
6901  cagctgtcac  ctaccgacag  gtacgcgctt  caagttcggc  gccatgatga  aatcaggtat
6961  gttcctaact  ctgttcgtca  acacattgtt  aaacatcacc  atcgccagcc  gagtgctgga
7021  agatcgtctg  acaaaatccg  cgtgcgcggc  ctcatcggc  gacgacaaca  taatacatgg
7081  agtcgtctcc  gatgaattga  tggcagccag  atgtgccact  tggatgaaca  tggaagtgaa
7141  gatcatagat  gcagttgtat  ccctttactt  tgtggagggt  ttatactgca
7201  cgatactgtg  acaggaacag  cttgcagagt  ggcagaccg  ctaaaaaggc  ttttaaact
7261  gggcaaaccg  ctagcggcag  gtgacgaaca  agatgaagat  agaagacgag  cgctggctga
7321  cgaagtgatc  agatggcaac  gaacagggct  aattgatgag  ctggagaaag  cggtatactc
7381  taggtacgaa  gtgcaggggta  tatcagttgt  ggtaatgtcc  atggccacct  ttgcaagctc
7441  cagatccaac  ttcgagaagc  cgtcataact  ttgtacgcg  gtcctaaata
7501  ggtacgcact  acagctacct  attttgcaga  agtatctaa  acactaatca
7561  gctacaatgg  agttcatccc  aacccaaact  ggagtacca  gcctcgaccc
7621  tggactccgc  gcctactat  ccaagtcatc  cgcgccctca  gaggcaagct
7681  ggcaacttg  cccagctgat  ctcagcagtt  caatgcgcgc  ggtaccacaca
7741  cagaagccac  gcaggaatcg  gaagaataag  aataaactga  aaaacaaca  ggcgccacaa
7801  aacaacacaa  atcaaaagaa  gcagccacct  aaaagaaa  aaaaagaaag  gaaaaagaag
7861  ccgggccgca  gagagaggat  gtgcatgaaa  atcgaaaatg  cggtcaaaa  cgaagtcaag
7921  cacgaaggta  aggtaacagg  ttacgcgtgc  ctggtgggg  attgtatttt  gaaaccagca
7981  cacgtaaagg  ggaccatcga  taacgcggac  ctgcccaaac  acaaagtaat  gcggtcatct
8041  aagtatgacc  ttgaatgcgc  gcagatacc  gtgcacatga  tggcctttaa  gcggttcagg
8101  accatgaga  aaccggaggg  gtactacctac  tggcaccacg  agtccgacgc  gtactcagga
8161  ggccggttca  ccatccctac  aggtgctggt  gagcagtaca  gagcggcag  accgatcttc
8221  gacaacaagg  gacgcgtggt  ggccatagtc  gaataaagac  acaccaggag  agccgggtaca
8281  gccctctcgg  tggtgacctg  gaatacgttc  ttaggaggag  attgtcacta  agcccctgc
8341  gaagagtgga  gtcttgccat  cccagttatg  tgcctgttgg  aaatcaccc  gttccctgc
8401  tcccagcccc  cttgcacgcc  ctgctgctac  tgcctgctac  gaaaagcaac  cctacgcatg
8461  cttgaggaca  acgtcatgag  acctgggtac  tatcagctgc  tacaagcatc  cttaacatgt
8521  tctcccacc  gccagcgacg  cagcaccaag  cagaacttca  atgtctataa  agccacaaga
```

FIG. 24 (continued)

```
 8581 ccatacttag ctcactgtcc cgactgtgga gaaggcact cgtgccatag tccgtagca
 8641 ctagaacgca tcagaaatga agcgacagac gggacgctga aaatccaggt ctccttgcaa
 8701 atcggaataa agacgagag cagccacgat tggaccaagc tgcgttatat ggacaaccac
 8761 atgccagcag acgcagagag ggcgggcta tttgtaagaa catcagcacc gtgtacgatt
 8821 actggacaa tgggacactt catcctggcc cgatgtccaa aaggggaaac tctgacggtg
 8881 ggattcactg acagtaggaa gattagtcac tcatgtacgc acccattca ccacgaccct
 8941 cctgtgatag gtcgggaaaa attccattcc cgaccgcagc acggtaaaga gctaccttgc
 9001 agcacgtacg tgcagagcac cgccgcaact acggagaga tagaggtaca catgccccca
 9061 gacaccctg atcgcacatt aatgtcacaa cagtccggca acgtaaagat cacagtcaat
 9121 ggccacacgg tgcggtacaa gtgtaattgc cagtgctcaa atgaaggact aacaactaca
 9181 gacaaagtga ttaataactg caaggttgat tctgtcccg aacttgggga ccgaaaagga
 9241 aagtggcagt ataatcccc gctgcaaat cgtaatgctg gggtgcctaa agcaaggaac
 9301 aaattcaca tccgtttcc aaaccaagtc gtaacatgctac tgtatcctga ccacccaaca
 9361 cccacgtga cgtacggga accgaatat atcatgctac aagaagagtg ggtgatgcat
 9421 ctcctgtcct acccaagtcg cgtacggcta ccaaactatc agtgctcg gggcaacaac
 9481 aagaaggaag tcgtgctaag gggagagaa cgtgccgact cagcccatgg ccaccgcat
 9541 gagcgtata agtattggcc gcagttatct acaacggta ctgtagtagt tgtgtcagtg
 9601 gagataattc tgtattatta tgagctgtac cccactatga gatgcagcgg gtgtgcacga
 9661 gccacgttca tactcctgtc gatggtgggt atggcagcta cctgttagc ccgcttagc
 9721 cgcagatgca tcacacgta tgaactgaca ccagagacta ggatgcac gatatacctg
 9781 ctaatatgct gcatcagacg agcagcacg agccatac aaaggctgc agccctgatt
 9841 tggaacgagc agcaaccttt gttttggcta caagcccta tccgttggc tttttagcc
 9901 gttctatgca actgtctgag actcttacca tgctctgta aaacgtaaca acgtaacagt gatccgaac
 9961 gtaatgagcg tcggtgccca cactgtgagc gcgtacgta gctaacagcc catggattg
10021 acggtgggag taccgtatat catttcagt aaatagacct gcttgatta gcggtacagc
10081 gagatgaaat acttgcagt cactttggag ccaacactg gtgaagtgct gcgtacagc agagtgcaag
10141 gagtacaaaa ccgtcatccc gtctcccgtac ccaactaca catcacgttg
10201 gacaaaaacc tacctgacta cagctgtaag gtcttcaccg gcgtctaccc atttatgtgg
```

FIG. 24 (continued)

```
10261 gcggcgcct actgcttctg cgacgctgaa aacacgcagt tgagcgaagc acacgtggag
10321 aagtccgaat catgcaaaac agaatttgca tcagcataca gggctcatac cgcatctgca
10381 tcagctaagc tccgcgtcct ttaccaagga aataacatca ctgtaactgc ctatgcaaac
10441 ggcgaccatg ccgtcacagt taaggacgcc aaattcattg tgggccaat gtcttcagcg
10501 tggacaactt tgacaacaa aattgtggtg tacaaaggtg acgtctataa catggactac
10561 ccgcccttg gcgcaggaag accagacaa tttggcgata tccaaagtcg cacacctgag
10621 agtaaagacg tctatgctaa tacacaactg gtactgcaga gaccggctgt gggtacggta
10681 cacgtgccat actctcaggc accatctggc tttaagtatt ggctaaaaga acgcggggcg
10741 tcgctgcagc acacaggctg tacatagcaa caaacccggt aagagcggtg
10801 aactgcgccg taggaacat gcccatctcc atcgacatac cggaagcggc cttcactagg
10861 gtcgtcgacg cgccctcttt aacggacatg tcgtgcgagg taccagcctg caccattcc
10921 tcagactttg gggcgtcgc cattattaaa tatgcagcca gcaagaaagg caagtgtgcg
10981 gtgcattcga tgactaacgc cgtcactatt cgggaagctg agatagaagt tgaaggaat
11041 tctcagctgc aaatctcttt ctcgacggcc ttagccacgc ccgaattccg cgtacaagtc
11101 tgttctacac aagtacactg tgcagccgag tgccaccccc cgaaggacca catgtcaac
11161 tacccggcgt cacataccac cctcgggtc caggacatct gttgttgctg gatgtcatgg
11221 gtgcagaaga tcacggagg tgtgggactg cagcaggcac taacttgaca tttgccgcact gattctaatc
11281 gtggtgctat gcgtgtcgtt cagcaggcca gtacatagca attaatctat aggtatatg
11341 tgtccctaa gagacacact gtacatagca aataaattata agatctcat gctacgcaac
11401 ccctgaatag taacaaaata caaaatcact gtatgtaggt gataagcata aataagggg
11461 taggtatacg tgtcccctaa gagacacatt gaaaatcata aaaatcata aaatagaaaa
11521 ccgaataacc cctgaatagt aacaaaatat gaaaatcaat aaaaatcata aaacataaaa
11581 accataaaca gaagtagttc aaagggctat accataattg aatagtaaca aaacataaaa
11641 ttaataagc tcaaatgaat accataattg gcaaacgaa gagatgtagg tacttaagct
11701 tctctaaagc agccgaactc actttgaaa cataccgaac tcttccacga
11761 ttctccgaac ccacaggggac gtaggcatag ttattttgtt tttaatatt caaaaaaaa
11821 aaaaaaaaaa aaaaaaaaaa aaaaaaaaaa agcggccgct taattaatcg agggaatta
11881 attcttgaag acgaaagggc caggtgcac ttttcgggga aatgtgcgcg gaaccctat
11941 ttgttattt tctaaatac attcaaatat gtatccgctc atgagacaat aaccctgata
```

FIG. 24 (continued)

```
12001 aatgcttcaa taatattgaa aaaggaagag tatgagtatt caacatttcc gtgtcgccct
12061 tattccctttt tttgcggcat tttgccttcc tgttttttgct caccagaaa cgctggtgaa
12121 agtaaaagat gctgaagatc agttgggtgc acgagtgggt tacatcgaac tggatctcaa
12181 cagcggtaag atccttgaga gttttcgccc cgaagaacgt tttccaatga tgagcacttt
12241 taaagttctg ctatgtggcg cggtattatc ccgtgttgac gccgggcaag agcaactcgg
12301 tcgccgcata cactattctc agaatgactt ggttgagtac tcaccagtca cagaaaagca
12361 tcttacggat ggcatgacag taagagaatt atgcagtgct gccataacca tgagtgataa
12421 cactgcggcc aacttactc tgacaacgat cggaggaccg aaggagctaa ccgcttttt
12481 gcacaacatg ggggatcatg taactcgcct tgatcgttgg gaaccggagc tgaatgaagc
12541 cataccaaac gacgagcgtg acaccacgat gcctgtagca atggcaacaa cgttgcgcaa
12601 actattaact ggcgaactac ttactctagc ttcccggcaa caattaatag actggatgga
12661 ggcggataaa gttgcaggac cacttctgcg ctcggccctt ccggctggct ggtttattgc
12721 tgataaatct ggagccggtg agcgtgggtc tcgcggtatc attgcagcac tggggccaga
12781 tggtaagccc tcccgtatcg tagttatcta cacgacgggg agtcaggcaa ctatggatga
12841 acgaaataga cagatcgctg agataggtgc ctcactgatt aagcattggt aactgtcaga
12901 ccaagtttac tcatatatac tttagattga tttaaaactt cattttaat ttaaaaggat
12961 ctaggtgaag atccttttg ataatctcat gaccaaaatc ccttaacgtg agttttcgtt
13021 ccactgagcg tcagaccccg tagaaaagat caaaggatct tcttgagatc cttttttct
13081 gcgcgtaatc tgctgcttgc aaacaaaaaa accaccgcta ccagcggtgg tttgtttgcc
13141 ggatcaagag ctaccaactc tttttccgaa ggtaactggc ttcagcagag cgcagatacc
13201 aaatactgtc cttctagtgt agccgtagtt aggccaccac ttcaagaact ctgtagcacc
13261 gcctacatac ctcgctctgc taatcctgtt accagtggct gctgccagtg gcgataagtc
13321 gtgtcttacc gggttggact caagacgata gttaccggat aaggcgcagc ggtcgggctg
13381 aacggggggt tcgtgcacac agcccagctt ggagcgaacg acctacaccg aaactgagat
13441 acctacagcg tgagcattga gaaagcgcca cgcttcccga agggagaaag gcggacaggt
13501 atccggtaag cggcagggtc ggaacaggag agcgcacga gggagcttcc agggggaaacg
13561 cctggtatct ttatatcgtt cgggtttcg ccacctctga cttgagcgtc gatttttgtg
13621 atgctcgtca ggggggcgga gcctatggaa aaacgccagc aacgcggcct cgtatggaca
13681 tattgtcgtt agaacgcggc tacaattaat acataaggt atgtatcata caacatcgat
13741 ttaggtgaca ctatag
```

FIG. 25

Seq ID NO: 33

```
   1 atggctgcgt gagacacacg tagcctacca gtttcttact gctctactct gcttagcaag
  61 agacttgaga acccatcatg gatcccgtgt acgtggacat agacgccgac agcgccttt
 121 taaaggccct gcagcgtgcg taccccatgt ttgaggtgga accaaggcag gtcacaccga
 181 atgaccatgc caatgcgtaga gcattctcgc atctagctat aaaactaata gagcaggaaa
 241 ttgatcccga ctcaaccatc ctggacatag gcagcgcgcc agcaaggagg atgatgtcgg
 301 ataggaagta ccactgcgtt tgccctatgc gcagcgcaga agaccctgag agactcgcca
 361 actacgcgag aaaactagca tctgccgcag gaaaagtctt ggacagaaac atctccgaaa
 421 aaattggaga tctacaagca gtaatggctg taccagacgc agaaacgccc acattctgct
 481 tgcacactga cgtctcatgt agacaaaggg cggacgtcgc tataccag gatgtctacg
 541 ccgtgcatgc accaacatcg ctgtaccacc aggcgattaa aggagtccgt gtagcatact
 601 ggataggggtt tgatacaaacc ccgttcatgt ataatgccat ggcaggtgca taccctcgt
 661 actcgacaaa ctgggcagat gagcaggtgc tgaaggcaaa gaacatagga ttatgttcaa
 721 cagacctgac ggaaggtaga cgaggtaaat tgtctatcat gagaggaaaa aagatgaagc
 781 catgtgaccg cgtactgttc tcagtcgggt caacgcttta cccggagagc cgtaagcttc
 841 ttaagagttg gcacttacct tcagtgttcc atctaaaagg gaagctcagc ttcacgtgcc
 901 gctgtgatac agtggtttcg tgtgaaggct atgtcgttaa gagaataacg attagcccgg
 961 gcctctacgg taaaccaca gggtacgcag taacccacca tgcagacgga ttcctaatgt
1021 gcaaaacaac cgatacggta gatggcgaga gagtgtcatt ttcggtatgc acgtacgtac
1081 ccgcaaccat ttgtgatcaa atgacaggta ttcttgccac ggaggttaca ccggaggatg
1141 cacagaagct gctggtggga ctgaaccaga ggatagtggt caatggcaga acgcagagga
1201 acacgaacac aatgaagaat tacttgcttc ctgtagttgc ccaagccctc agtaagtggg
1261 caaaggaatg ccggaaaagat atggaaagtg aaaaacttt gggcatcaga gaaaggacac
1321 tgacatgctg ctgccttttgg gcgttcaaga agcagaaagac acacacgtc tacaagaggc
1381 ctgacactca gtcaattcag aaagtcccag ccgaatttga cagctttgtg gtaccaagtc
1441 tgtggtcatc tggactgtcg atcccgctac ggaccagaat caagtggctg ctaagcaaag
```

FIG. 25 (continued)

```
1501  tgccaaagac  tgatttgatc  ccttacagcg  gtgacgccaa  agaagcccgc  gacgctgaaa
1561  aagaagcaga  agaagaacga  gaagcggagc  taactcgcga  ggcactacca  ccactacagg
1621  cggcacagga  cgacgtccag  gtcgaaattg  acgtggaaca  gctcgaagac  agagctgggg
1681  caggaataat  tgaaactcca  agaggagcta  tcaaagtcac  tgcccaacca  acagaccacg
1741  tcgtgggaga  gtacttggta  ctttccccgc  agaccgtgtt  acgaagccag  aagctcagcc
1801  tgatccacgc  attggcggaa  caagtgaaga  catgcacaca  cagcggacgg  gcaggaaggt
1861  acgcggtcga  agcatatgac  ggcagaatcc  ttgtgccctc  aggctatgca  atatcacctg
1921  aagacttcca  gagcctgagc  gaaagtgcga  cgatggtgta  caacgaaagg  gagttcgtaa
1981  ataggaaatt  acaccatatc  gcgttgcacg  gaccagccct  gaacactgac  gaggagtcgt
2041  acgagctggt  aagggcagaa  aggacagagc  atgagtacgt  ctatgatgtg  gaccaaagaa
2101  ggtgctgcaa  gaaagaggag  gcagcccggc  tggtactggt  cggcgacttg  accaacccgc
2161  cctaccatga  gttcgcatat  gaagggctga  gaatccgccc  cgcctgccca  tacaagaccg
2221  cagtaatagg  gttctttgga  gtgccaggat  ccggcaaatc  agcaatcatt  aagaacctag
2281  ttaccaggca  agacctagtg  agaccagttg  accagtggaa  agaaagaaaa  ctgccaagaa  atctccaccg
2341  acgtgatgcg  acagagggaac  ctggagatat  ctgcacgcac  ggtcgactca  ctgctcttga
2401  acggatgcaa  tagaccagtc  gacgtgttgt  acgtcgacga  agcttttgcg  tgccattctg
2461  gcacgctact  tgctctgata  gccttggtga  gaccgaggca  gaaagtcgtg  ctatgcggtg
2521  atccgaaaca  gtgcggcttc  ttcaatatga  tgcagatgaa  agttaactac  aaccataaca
2581  tctgcaccca  agtgtaccat  aaaagtattt  ccaggcggtg  tacactgcct  gtgactgcca
2641  ttgtgtcctc  gttgcattac  gaaggcaaac  tgcgcacaac  aaatgagtac  aacaagccaa
2701  ttgtagtgga  tactacaggc  tcgacaaaac  ccgacccccgg  agaccttgtg  ctaacatgtt
2761  tcagagggtg  ggttaagcaa  ctgcaaattg  actatcgtgg  acacgaggtc  atgacagcag
2821  ctgcatctca  gggctaacc  agaaaagggg  tctatgccgt  caggcaaaaa  gttaatgaaa
2881  acccccttta  cgcatcaaca  tcagagcacg  tgaacgtgct  actgacgcgt  acgaaggca
2941  aactagtatg  gaagacactt  tctggagacc  catggataaa  gacactgcag  gacactgcag  aacccgccga
```

FIG. 25 (continued)

```
3001 aaggaaattt taaagcaaca attaaggaat gggaagtgga acatgcttca ataatggcgg
3061 gtatctgtaa ccaccaagtg acctttgaca cgttccagaa taaagccaat gtctgctggg
3121 cgaagagctt agtcccatc ctagaaacag caggataaa attaaacgac aggcagtggt
3181 cccagataat ccaggctttt aaagaagaca gagcatactc acccgaggtg gccctgaatg
3241 agatatgcac gcgcatgtac ggggtagacc tggacagcgg actgttctct aaaccactgg
3301 tgtccgtgca tcatgcggat aatcactggg acaacaggcc gggagggaag atgttcggat
3361 tcaacccga agcggcgtcc atactggaga ggaaataccc gtttacaaaa gggaagtgga
3421 ataccaacaa gcaaatctgt gtgactacta ggaggattga agatttaac ccgaacacca
3481 acattatacc tgccaacagg agattaccgc attcattggt ggccgaacat cgcccgtaa
3541 aagggagag gatggaatgg ttggtcaaca aaataaatgg ccaccatgtg ctcctggtca
3601 gcggctacaa cctcgttctg cccactaaga gagtcacctg ggtggccgcg ctggcattc
3661 ggggagctga ctacacatac acctagagt taggcctacc agcaacgctc ggtagatatg
3721 acctagtgat tataaacatc cacacaccct ttcgcataca tcattaccaa cagtgcgtgg
3781 atcacgcaat gaagctgcag atgctcggag gagactccct gagactgctc aagccgggtg
3841 gttcattact gatcaggca tacgctacg cagacagaac aagcgaacga gtagtctgcg
3901 tattgggacg caagtttcga tcatccagag cgttgaaacc gccgtgcgtc actagcaaca
3961 ccgagatgtt tttcttgttc agcaactttg ataacggcag aaggaacttt acgacgcacg
4021 taatgaacaa ccagctgaat gctgcttttg ttggtcaggc caaagaacga gggtgcgcac
4081 cgtcgtaccg ggttaaacgc atggacatcg caaagaacg tgaagagtgt gtagtcaacg
4141 ccgccaaccc tcgtggcta cgaggcgatg gcgtctgtaa agcagtatac aaaaaatggc
4201 cggagtcctt caagaacagt gcaacaccag tgggaaccgc aaagacagtc atgtgcggta
4261 cataccggt aatccatgca gtaggaccta atttctcaaa ttactctgag tccgaaggag
4321 accgggaatt ggcagctgct taccgagaag tcgctaagga ggtgactaga ctaggagtaa
4381 acagcgtagc tataccgctc ctttccaccg gtgtgtactc gacaggctga
4441 ctcagtcact aaaccacctt tttacagcat tagactcaac tgatgcagat gtggttatct
```

FIG. 25 (continued)

```
4501  actgccgcga caaggagtgg gagaagaaaa tagctgaggc catacaaatg aggacccaag
4561  tggaattact agacgaacac atctctgtag actgcgatat catccgagtg caccctgaca
4621  gcagtttggc agtagaaaa gggtacagca ctacagaagg ttcactgtac tcctacttgg
4681  aagggacacg gttccatcag acggcagtgg acatggcaga agtatacacc atgtgccaa
4741  agcagacgga ggctaatgaa caagtttgct tgtacgcatt ggggaaagt atagaatcaa
4801  tcaggcaaaa gtgcccagtg gatgacgcag atgcatcgtc gccccaaaa accgtcccgt
4861  gcctctgccg ttatgccatg acacccgaac gagtcaccag gcttcgtatg aaccatgtca
4921  caagcataat agtatgctca tcattccccc ttccaaagta taaaatagaa ggagtgcaga
4981  aagtcaagtg ttctaaagtg atgctgttcg accataacgt gccatcacgc gttagtccaa
5041  gggaatataa atcgcctcag gagaccgcac aagaagtaag ttcgaccacg tcactgacgc
5101  acagccaatt cgacccttagc gttgacggtg aggaactgcc cgctccgtct gacttggaag
5161  ctgacgctcc gattccggaa ccaacaccag acgacagagc ggtacttact ttgcctccca
5221  cgattgataa tttttcggct gtgtcagact gggtaatgaa taccgcgca gtcgaccac
5281  ccagaagaag acgtgggaaa aacttgaatg tcacctgcga cgagagagaa gggaacgtac
5341  ttcccatggc tagcgttcgg ttcttcagag cggatctgca ctccatcgta caggaaacgg
5401  cagagatacg cgatctcatt gcgtccctcc aggcgcccct gagtgtcgct acagaaccga
5461  atcaactgcc gatctcattt ggagcaccaa acgagactt cccataacg ttcggggatt
5521  ttgatgaagg ggagattgaa agcttgtcct ctgagttact gacctttggg gacttctgc
5581  cgggcgaagt ggatgacctg acagacagcg actggtccac gtgttcagac acggacgacg
5641  aattatgact agataggca ggtgggtaca tattctcatc tgacaccggc cccggccacc
5701  tgcaacagag gtctgtccgt cagacagtac tgccggtaaa taccttggag gaagttcagg
5761  aggagaaatg ttacccacct aagttggatg aagtgaaaga gcagttgtta cttaagaaac
5821  tccaggaaag tgcgtccatg gctaacagaa gcaggtacca atcccgcaaa gtagagaaca
5881  tgaaagcaac aatagtccaa aggctgaagg gtggttgcaa acttatttta atgtcggaga
5941  cccgaaagt tcctacctac cgaactacat atccggcacc agtgtactca ccccaatca
```

FIG. 25 (continued)

```
6001 atatccgact gtccaacccc gagtctgctg tggcagcgtg caatgagttc ctagcaagga
6061 actatccgac agttgcgtcg taccaaatca ccgatgagta cgatgcatac ctagacatgg
6121 tggacgggtc ggaaagttgc cttgaccggg cgacgttcaa cccatcaaag cttagaagtt
6181 atccaaaaca gcactcctac catgcaccca caatcagaag tgccgtacct tccccgttcc
6241 agaacacgct gcagaacgta ctggctgctg ccacgaaaag aaattgcaac gtcacacaga
6301 tgagagaact gcctactttg gattcagcgg tatttaatgt tgagtgcttt aaaaaatttg
6361 cgtgcaatca agaatactgg aaggaatttg ccgccagccc tattaggata acgactgaga
6421 acttgacaac ttatgtcaca aaactaaaag gaccaaaagc agcagcactg tttgccaaga
6481 cacataacct gctaccactg caggaggtgc cgatggacag gtttactgta gacatgaaaa
6541 gggacgtgaa ggtgactccg gggacgaagc acactgagga aagacctaaa gtgcaggtca
6601 tacaggcagc cgaacctttg gcaacagcat atctgtgtgg gatccacaga gagttggtca
6661 gaaggctgaa tgcagtcctt ctacctaatg tacacacgct gtttgacatg tctgccgagg
6721 actttgacgc cattattgcc gcgcacttca agccggggga cgccgtattg gaaaccgata
6781 tagcctcctt tgacaagagc caagacgact cattggcgct cactgctcta atgttgctag
6841 aggatttggg ggtggatcat cccctgttgg acttgatgaa ggctgccttc ggggagatct
6901 ccagctgcca cctaccgacg ggcaccgtt ttaagttcgg cgccatgatg aagtctggta
6961 tgttcctaac cctgttcgtc aaacatcac taaacatgc catagccagc cgagtgctgg
7021 aggaccgctt gacaaggtct gcgtgcgcgg cctttcatcgg cgacgacaat ataatacatg
7081 gggttgtctc tgacgaactg atggcagcaa ggtgtgctac atggatgaac atggaagtga
7141 agatcataga tgcggtcgtg tctcagaaaag cccgtactt ctgcggaggg tttatactgt
7201 atgacacagt agcaggcacg gcctgcagag tggcagacc gctaaagcgg ctgttcaagc
7261 tgggcaaacc gctggcagcg ggagatgaac aagacgacga cagaagacgt gcactggctg
7321 acgaagtggt tagatggcaa cgaacaggac taactgatga gctagaaaaa gcgtacact
7381 ccaggtatga agtgcagggc atatctgtcg tggtaatgtc tatgccaacc tttgcaagct
7441 ctagatctaa cttgagaag ctcagaggac ccgtcgtaac cctgtacggt ggtcctaaat
```

FIG. 25 (continued)

```
7501 aggtacgcac tacagctacc tatttcgtca gaaaccaatc gcagctactt gcatacctac
7561 cagctacaat ggagttcatc ccgacgcaaa ctttctataa cagaaggtac caacccgac
7621 cctggcccc acgccctaca attcaagtaa ttagacctag accacgtcca cagaggcagg
7681 ctgggcaact cgcccagctg atctccgcag tcaacaaatt gaccatgcgc gcggtacctc
7741 aacagaagcc tcgcagaaat cggaaaaaca agaagcaaag gcagaagaag caggcgccgc
7801 aaaacgaccc aaagcaaaag aagcaaccac cacaaaagaa gccggctcaa aagaagaaga
7861 aaccaggccg taggagaga atgtgcatga aaattgaaaa tgattgcatc ttcgaagtca
7921 agcatgaagg caaagtgatg ggctacgcat gcctggtggg ggataaagta atgaaaccag
7981 cacatgtgaa gggaactatc gacaatgccg atctggctaa actggccttt aagcggtcgt
8041 ctaaatacga tcttgaatgt gcacagatac cggtgcacat gaagtctgat gcctcgaagt
8101 ttacccacga gaaacccgag gggtactata actggcatca cggagcagtg cagtattcag
8161 gaggccggtt cactatcccg acgggtgcag gcaagccggg agacagcggc agaccgatct
8221 tcgacaacaa aggacgggtg gtggccatcg tcctaggagg gccaacgaa ggtgcccgca
8281 cggccctctc cgtggtgacg tggaacaaag acatcgtcac aaaaattacc cctgaggag
8341 ccgaagagtg gagcctcgcc ctcccggtct tgtgcctgtt ggcaaacact acattcccct
8401 gctctcagcc gcctttgcaca ccctgctgct acgaaaagga accggaaagc accttgcgca
8461 tgcttgagga caacgtgatg agaccggat actaccagct actaaaagca tcgctgactt
8521 gctctcccca ccgcgcggag cgagccggat cgcagtacta aggacaattt taatgtctat aaagccacaa
8581 gaccatatct agctcattgt cctgactgcg gagaagggca ttcgtgccac agccctatcg
8641 cattggagcg catcagaaat gaagcaacgct acggaacgct gaaaatccag gtctctttgc
8701 agatcggat aaagacagat gacaccacg attgaccaa gctgcgctat atggatagcc
8761 atacgccagc ggacgcggag cgagccggat tgcttgtaag gacttcagca ccgtgcacga
8821 tcaccgggac catgggacac tttattctcg cccgatgccc gaaaggagag acgctgacag
8881 tggatttac ggacagcaga aagatcagcc acacatgcac acacccgttc catcatgaac
8941 cacctgtgat aggtaggag aggttccact ctcgaccaca acatggtaaa gagttacctt
```

FIG. 25 (continued)

```
9001  gcagcacgta cgtgcagagc accgctgcca ctgctgagga gatagaggtg catatgcccc
9061  cagatactcc tgaccgcacg ctgatgacgc agcagtctgg caacgtgaag atcacagtta
9121  atgggcagac ggtgcggtac aagtcaact  gcggtggctc aaacgaggga ctgacaacca
9181  cagacaaagt gatcaataac tgcaaaattg atcagtgcca tgctgcagtc actaatcaca
9241  agaattggca atacaactcc cctttagtcc cgcgcaacgc tgaactcggg gaccgtaaag
9301  gaaagatcca catcccattc ccattggcaa acgtgacttg cagagtgcca aaagcaagaa
9361  accctacagt aacttacgga aaaaaccaag tcaccatgct gctgtatcct gaccatccga
9421  cactcttgtc ttaccgtaac atgggacagg aaccaaatta ccacgaggag tgggtgacac
9481  acaagaagga ggttaccttg accgtgccta ctgagggtct ggaggtcact tggggcaaca
9541  acgaaccata caagtactgg ccgcagatgt ctacgaacgg tactgctcat ggtcacccac
9601  atgagataat cttgtactat tatgagctgt accccactat gactgtagtc attgtgtcgg
9661  tggcctcgtt cgtgcttctg tcgatggtgg gcacagcagt gggaatgtgt gtgtgcgcac
9721  ggcgcagatg cattacacca tatgaattaa caccaggagc cactgttccc ttcctgctca
9781  gcctgctatg ctgcgtcaga acgaccaagg cggccacata ttacgaggct gcggcatatc
9841  tatgaacga acagcagccc ctgttctggt tgcaggctct tatcccgctg gccgccttga
9901  tcgtcctgtg caactgtctg aaactcttgc catgctgctg taagaccctg gctttttag
9961  ccgtaatgag catcggtgcc cacactgtga gcgcgtacga acacgtaaca gtgatcccga
10021 acacggtggg agtaccgtat aagactcttg tcaacagacc gggttacagc cccatggtgt
10081 tggagatgga gctacaatca gtcaccttgg aaccaacact gtcacttgac tacatcacgt
10141 gcgagtacaa aactgtcatc ccctcccgt  aaccaacact ctgtggtaca gcagagtgca
10201 aggacaagag cctaccagac tacagctgca aggtctttac tggagtctac ccattatgt
10261 ggggcgggcg ctactgcttt tgcgacgccg aaaatacgca attgagcgag gcacatgtag
10321 agaaatctga atcttgcaaa acagagtttg catcggccta cagagcccac accgcatcgg
10381 cgtcggcgaa gctccgcgtc ctttaccaag gaaacaacat taccgtagct gcctacgcta
10441 acggtgacca tgccgtcaca gtaaaggacg ccaagtttgt cgtgggccca atgtcctccg
```

FIG. 25 (continued)

```
10501  cctgacacc  ttttgacaac  aaaatcgtgg  tgtacaaagg  cgacgtctac  aacatggact
10561  accaccttt  tggcgcagga  agaccaggac  aatttggtga  cattcaaagt  cgtacaccgg
10621  aagtaaaga  cgtttatgcc  aacactcagt  tggtactaca  gaggccagca  gcaggcacgg
10681  tacatgtacc  atactctcag  gcaccatctg  gcttcaagta  ttggctgaag  gaacgaggag
10741  catcgctaca  gcacacggca  ccgttcggtt  gccagattgc  gacaaaccg  gtaagagctg
10801  taaattgcgc  tgtggggaac  ataccaattt  ccatcgacat  accggatgcg  gcctttacta
10861  gggttgtga  tgcaccctct  gtaacggaca  tgtcatgcga  agtaccagcc  tgcactcact
10921  cctccgactt  tggggcgtc  gccatcatca  aatacacagc  tagcaagaaa  ggtaaatgtg
10981  cagtacattc  gatgaccaac  gccgttacca  ttcgagaagc  cgacgtagaa  gtagagggga
11041  actcccagct  gcaaatatcc  ttctcaacag  ccctggcaag  cgccgagttt  cgcgtgcaag
11101  tgtgctccac  acaagtacac  tgcgcagccg  catgccaccc  tccaaaggac  cacatagtca
11161  attacccagc  atcacacacc  acccttgggg  tccaggatat  atccacaacg  gcaatgtctt
11221  gggtgcagaa  gattacggga  ggagtaggat  taattgttgc  tgttgctgcc  ttaattttaa
11281  ttgtggtgct  atgcgtgtcg  tttagcagc  actaaaccga  tgataaggca  cgaaataact
11341  aaatagcaaa  agtagaaagt  acataaccag  gtatatgtgc  cccttaagag  gcacaatata
11401  tatagctaag  cactattaga  tcaaagggct  atacaacccc  tgaatagtaa  caaaacacaa
11461  aaaccaataa  aaatcataaa  aagaaaaatc  tcataaaacag  gtataagtgt  cccctaagag
11521  acacattgta  tgtaggtagt  aagtatagat  caaagggcta  tattaacccc  tgaatagtaa
11581  caaaacacaa  aaacaataaa  aactacaaaa  tagaaaatct  ataaacaaaa  gtagttcaaa
11641  gggctacaaa  acccctgaat  agtaacaaaa  cataaaatgt  ataaaaaatt  aagtgtgtac
11701  ccaaaagagg  tacagtaaga  atcagtgaat  atcacaattg  gcaacgagaa  gagacgtagg
11761  tatttaagct  tcctaaaagc  agccgaactc  actttgagac  gtaggcatag  cataccgaac
11821  tcttccacta  ttctccgaac  ccacagggac  gtaggagatg  ttattttgtt  tttaatattt
11881  caaaaaaaa  aaaaaaaaa  aaaaaaaaa  aaaaaaaaa  agcggccgct  taattaatcg
11941  agggaatta  attcttgaag  acgaaaggc  caggtggcac  ttttcgggga  aatgtgcgcg
```

FIG. 25 (continued)

```
12001 gaaccctat ttgtttattt ttctaaatac attcaaatat gtatccgctc atgagacaat
12061 aaccctgata aatgcttcaa taatattgaa aaaggaagag tatgagtatt caacatttcc
12121 gtgtcgccct tattcccttt tttgcggcat tttgccttcc tgtttttgct cacccagaaa
12181 cgctggtgaa agtaaaagat gctgaagatc agttgggtgc acgagtgggt tacatcgaac
12241 tggatctcaa cagcggtaag atccttgaga gttttcgccc cgaagaacgt tttccaatga
12301 tgagcacttt taaagttctg ctatgtggcg cggtattatc ccgtgttgac gccgggcaag
12361 agcaactcgg tcgccgcata cactattctc agaatgactt ggttgagtac tcaccagtca
12421 cagaaaagca tcttacggat ggcatgacag taagagaatt atgcagtgct gccataacca
12481 tgagtgataa aacttacttc tgacaacgat cggaggaccg aaggagctaa
12541 ccgctttttt gcacaacatg gggatcatg taactcgcct tgatcgttgg gaaccggagc
12601 tgaatgaagc cataccaaac gacgagcgtg acaccacgat gcctgtagca atggcaacaa
12661 cgttgcgcaa actattaact ggcgaactac ttactctagc ttcccggcaa caattaatag
12721 actggatgga ggcggataaa gttgcaggac cacttctgcg ctcggccctt ccggctggct
12781 ggtttattgc tgataaatct ggagccggtg agcgtgggtc tcgcggtatc attgcagcac
12841 tggggccaga tggtaagccc tcccgtatcg tagttatcta cacgacgggg agtcaggcaa
12901 ctatggatga acgaaataga cagatcgctg agataggtgc ctcactgatt aagcattggt
12961 aactgtcaga ccaagtttac tcatatatac tttagattga tttaaaactt catttttaat
13021 ttaaaaggat ctaggtgaag atcctttttg ataatctcat gaccaaaatc ccttaacgtg
13081 agttttcgtt ccactgagcg tcagaccccg tagaaaagat caaaggatct tcttgagatc
13141 cttttttct gcgcgtaatc tgctgcttgc aaacaaaaaa accaccgcta ccagcggtgg
13201 tttgtttgcc ggatcaagag ctaccaactc tttttccgaa ggtaactggc ttcagcagag
13261 cgcagatacc aaatactgtc cttctagtgt agccgtagtt aggccaccac ttcaagaact
13321 ctgtagcacc gcctacatac ctcgctctgc taatcctgtt accagtggct gctgccagtg
13381 gcgataagtc gtgtcttacc gggttggact caagacgata gttaccggat aaggcgcagc
13441 ggtcgggctg aacggggggt tcgtgcacac agcccagctt ggagcgaacg acctacaccg
```

FIG. 25 (continued)

```
13501 aactgagata cctacagcgt gagcattgag aaagcgccac gcttcccgaa gggagaaagg
13561 cggacaggta tccggtaagc ggcagggtcg gaacaggaga gcgcacgagg gagcttccag
13621 ggggaaacgc ctggtatctt tatagtcctg tcgggtttcg ccacctctga cttgagcgtc
13681 gatttttgtg atgctcgtca gggggcgga gcctatggaa aaacgccagc aacgcgagct
13741 cgtatggaca tattgtcgtt agaacgcggc tacaattaat acataaccttt atgtatcata
13801 cacaatcgat ttaggtgaca ctatag
```

METHOD FOR PRODUCING CHIKUNGUNYA VIRUS (CHIKV) VIRUS-LIKE PARTICLES COMPRISING THE C, E2, AND E1 STRUCTURAL PROTEINS

CROSS-REFERENCE TO RELATED APPLICATIONS

This application is a divisional of U.S. patent application Ser. No. 16/520,113, filed Jul. 23, 2019, which is a divisional of U.S. patent application Ser. No. 15/145,483, filed May 3, 2016, now U.S. Pat. No. 10,369,208; which is a divisional of U.S. patent application Ser. No. 13/131,287, filed Sep. 19, 2011, now U.S. Pat. No. 9,353,353; which is the U.S. National Stage of International Patent Application No. PCT/US2009/006294, filed Nov. 24, 2009, which was published in English under PCT Article 21(2); which in turn claims the benefit of U.S. Provisional Application Nos. 61/118,206 and 61/201,118, filed on Nov. 26, 2008 and Dec. 5, 2008, respectively, the entire contents of each of which are incorporated herein by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by the Intramural Research Program, Vaccine Research Center, NIAID of the National Institute of Health. The Government has certain rights in this invention.

BACKGROUND OF THE INVENTION

Chikungunya virus (CHIKV), a mosquito-borne alphavirus in the family Togaviridae, was first isolated in Tanzania in 1952. Infection by this virus causes human disease that is characterized by rash, high fever and, its hallmark feature, severe arthritis that can persist for years. Chikungunya virus (CHIKV) has infected millions of people in Africa, Europe, and Asia since its re-emergence in Kenya in 2004. The evolution and spread of the virus into new geographic areas, and the disease severity present a serious public health in the absence of a vaccines or anti-viral therapies. Therefore, the development of anti-viral therapies for CHIKV and vaccine development remains a high priority. Phylogenetic analysis of CHIKV showed that there are three genotypes: Asian, East/Central/South African and West African. The Asian and East/Central/South African genotypes are most similar, whereas the West African strains are more divergent. Therapeutic and/or prophylactic methods for treating or preventing Chikungunya viral disease are urgently required.

SUMMARY OF THE INVENTION

As described below, the present invention features compositions and methods for the prevention or treatment of one or more strains of Chikungunya virus, as well as other alphavirus-mediated diseases.

In one aspect, the invention provides a virus-like particle (VLP) containing one or more 35 (e.g., one, two, three, four, five) Chikungunya virus structural polypeptides. In one embodiment, the structural polypeptides are any one or more of capsid and envelope proteins E3, E2, 6K and E1.

In another aspect, the invention provides an isolated polynucleotide encoding a virus-like particle of the previous aspect or any other VLP delineated herein. In one embodiment, the polynucleotide encodes a Chikungunya virus polyprotein containing C-E3-E2-6K-E1.

In a related aspect, the invention provides an expression vector containing a polynucleotide encoding one or more Chikungunya virus structural polypeptides.

In another aspect, the invention provides a prokaryotic or eukaryotic cell (e.g., mammalian, human, insect) containing the expression vector of any previous aspect or any other expression vector delineated herein. In one embodiment, the cell is in vitro.

In another aspect, the invention provides an immunogenic composition containing an effective amount of a virus-like particle of any previous aspect or any other VLP delineated herein.

In a related aspect, the invention provides an immunogenic composition containing an effective amount of a VLP containing a Chikungunya structural polyprotein containing C-E3-E2-6K-E1 and an adjuvant.

In another aspect, the invention provides an immunogenic composition containing an effective amount of an expression vector of any previous aspect or otherwise delineated herein (e.g., a DNA vaccine).

In another aspect, the invention provides a vaccine containing an effective amount of one or more Chikungunya virus structural polypeptides that is any one or more of capsid (C) and envelope proteins E1, E2, E3 and 6K.

In another aspect, the invention provides a vaccine containing an effective amount of a virus-like particle of any previous aspect or containing a polyprotein containing C-E3-E2-6K-E1.

In another aspect, the invention provides a vaccine containing a polynucleotide encoding a Chikungunya structural polyprotein or fragment thereof. In one embodiment, the Chikungunya structural polyprotein is encoded by an expression vector of any previous aspect. In one embodiment, the expression vector comprises a CMV/R promoter. In another embodiment, the vaccine is a DNA vaccine.

In another aspect, the invention provides a method of inducing an immune response against Chikungunya in a subject (e.g. human), the method involving administering to the subject an effective amount of an immunogenic composition of any previous aspect or any other immunogenic composition delineated herein. In one embodiment, the immunogenic composition contains one or more Chikungunya virus structural polypeptides that is any one or more of capsid (C) and envelope proteins E1, E2, E3 and 6K. In another embodiment, the immunogenic composition comprises a polyprotein containing C-E3-E2-6K-E1. In another embodiment, the method induces neutralizing antibodies in a subject.

In another aspect, the invention provides a method for treating or preventing a Chikungunya infection in a subject, the method involving administering to the subject an effective amount of a vaccine of any previous aspect or an immunogenic composition of any previous aspect. In one embodiment, wherein the vaccine or immunogenic composition is administered in one or more doses.

In another aspect, the invention provides a method for producing a virus-like particle, the method involves expressing in a cell one or more Chikungunya structural protein capable of self-assembly to form a virus-like particle. In one embodiment, the method further involves isolating the virus-like particle.

In another aspect, the invention provides a virus-like particle (VLP) containing one or more alphavirus structural polypeptides (e.g., capsid or envelope polypeptide). In one embodiment, the alphavirus is any one or more of Chikungunya virus, Sindbis virus, Eastern equine encephalitis (EEE) virus, Western equine encephalitis (WEE) virus, and Venezuelan equine encephalitis (VEE) virus.

In another aspect, the invention provides an isolated polynucleotide encoding a virus-like particle of the previous aspect or otherwise delineated herein.

In another aspect, the invention provides an expression vector containing a polynucleotide encoding one or more alphavirus structural polypeptides wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides an immunogenic composition containing an effective amount of a virus-like particle of any previous aspect or otherwise delineated herein.

In another aspect, the invention provides a vaccine containing an effective amount of one or more alphavirus structural polypeptides or a polynucleotide encoding one or more alphavirus structural proteins, wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides a method of inducing an immune response against an alphavirus in a subject, the method involving administering to the subject an effective amount of an immunogenic composition of a previous aspect. In one embodiment, the immunogenic composition contains one or more alphavirus structural polypeptides (e.g. envelope or capsid).

In another aspect, the invention provides a method for treating or preventing an alphavirus infection in a subject, the method involving administering to the subject an effective amount of a vaccine or an immunogenic composition of any previous aspect.

In another aspect, the invention provides a kit containing a VLP of any previous aspect, and instructions for use.

In another aspect, the invention provides a kit containing an immunogenic composition of any previous aspect, and instructions for use in a subject. In one embodiment, the immunogenic composition is provided in a first container and a second immunogenic composition is provided in a second container, and instructions for use in a prime boost immunization. In another embodiment, the immunogenic composition in the second container contains a VLP, viral polypeptide, or viral polynucleotide.

In another aspect, the invention provides a method for identifying inhibitors of Chikungunya virus entry into a eukaryotic cell, the method involving contacting a cell that expresses a Chikungunya virus receptor with a Chikungunya polypeptide selected from the group consisting of C, E3, E2, 6K, and E1 and a candidate compound, and assaying for viral entry, wherein a candidate compound that reduces viral entry in the cell relative to a control cell is identified as an inhibitor of Chikungunya virus entry. In one embodiment, the candidate inhibitor is an antibody, or fragment thereof or small molecule.

In another aspect, the invention provides a method for identifying inhibitors of Chikungunya viral entry involving contacting a cell that expresses a Chikungunya virus receptor with a candidate inhibitor and a pseudotyped virus containing a reporter gene; and measuring expression of the reporter gene in the cell, wherein a compound that reduces expression of the reporter gene relative to a control cell is identified as inhibiting viral entry. In one embodiment, the pseudotyped virus (e.g., lentivirus) contains one or more Chikungunya virus envelope proteins (e.g., E3, E2, 6K and E1). In one embodiment, the candidate inhibitor is an antibody, or fragment thereof or small molecule.

In another aspect, the invention provides a virus-like particle (VLP) containing one or more Chikungunya virus structural polypeptides for use in treating or preventing a Chikungunya infection.

In another aspect, the invention provides a method for treating or preventing a Chikungunya infection, the method involving administering a virus-like particle (VLP) containing one or more Chikungunya virus structural polypeptides prior to, subsequent to, concurrent with, or in any other sequence with the administration of one or more of another immunogenic composition, antiviral, or antibiotic agent.

In another aspect, the invention provides methods for treating or preventing a Chikungunya infection by administering neutralizing antibodies (e.g., mammalian, human) generated against a VLP of the invention to a subject (e.g., human).

In various embodiments of the above aspects or any other aspect of the invention delineated herein, the VLP contains one or more (1, 2, 3, 4) envelop proteins E3, E2, 6K and E1. In other embodiments, the VLP contains a polyprotein containing C-E3-E2-6K-E1 or a fragment thereof. In other embodiments of the above aspects or any other aspect of the invention delineated herein, a polynucleotide encodes one or more structural polypeptides that is any one or more of a alphavirus or Chikungunya virus capsid (C) and envelope proteins E3, E2, 6K and E1. In other embodiments, the polynucleotide encodes envelop proteins E3, E2, 6K and E1. In other embodiments, the polynucleotide encodes a Chikungunya virus polyprotein containing C-E3-E2-6K-E1. In still other embodiments, the expression vector is capable of expression in a prokaryotic or eukaryotic cell (e.g., mammal, human). In other embodiments, the structural polyprotein is derived from Chikungunya strain 37997 or LR2006. In other embodiments, the vector comprises the CMV/R promoter. In other embodiments, the expression vector is C-E37997 or C-EOPY-1. In other embodiments, the VLP induces an immune response (e.g., a protective immune response) in a subject. In other embodiments, the immune response treats or prevents a Chikungunya infection in a subject. In other embodiments of the above aspects, the VLP induces antibodies against homologous or heterologous strains of Chikungunya. In embodiments of the above aspects, the adjuvant is an immunostimulating agent (e.g., Ribi, aluminum salts, muramyl peptides, bacterial cell wall components, saponin adjuvants).

In other embodiments of the above aspects, the vaccine or immunogenic composition is administered in one or more priming immunizations and one or more boosting immunizations. In still another embodiment, the priming immunizations are administered at one, two, three, four, five, six, seven or eight week intervals. In still another embodiment, the boosting immunizations are administered two weeks, one month, two months or three months after the priming immunization. In other embodiments of the above aspects or any other aspect of the invention delineated herein, the immunization protects the subject against viremia or the inflammatory consequences of infection. In other embodiments, the method protects a subject from lethality. In other embodiments, the method induces neutralizing antibodies in the subject.

The invention provides immunogenic compositions featuring virus-like particles comprising Chikungunya polypeptides for the prevention or treatment of Chikungunya viral disease. Compositions and articles defined by the invention were isolated or otherwise manufactured in connection with the examples provided below. Other features and advantages of the invention will be apparent from the detailed description, and from the claims.

Definitions

By "alphavirus structural protein" is meant a polypeptide or fragment thereof having at least about 40% amino acid sequence identity to a naturally occurring viral capsid or envelope protein and having immunogenic activity in a mammal. In one embodiment, the alphavirus structural protein has at least about 85%, 90%, 95% or greater amino acid sequence identity with a Chikunguna virus structural protein or immunogenic fragment thereof. In one embodiment, the protein Exemplary alphaviruses include, but are not limited to, Western, Eastern, and Venezuelan equine encephalitis viruses, o'nyong-nyong virus, Ross River virus and Sindbis virus.

By "Chikungunya virus structural protein" is meant a polypeptide or fragment thereof having at least about 85% amino acid sequence identity to a naturally occurring Chikungunya virus capsid or envelope protein. In other embodiments, the amino acid sequence identity is at least about 90%, 95%, or more.

By "agent" is meant any small molecule chemical compound, antibody, nucleic acid molecule, or polypeptide, or fragments thereof.

As used herein, the term "adjuvant" is meant to refer to a compound that, when used in combination with a specific immunogen in a formulation, will augment, alter or modify the resultant immune response. In certain embodiments, the adjuvant is used in combination with a VLP. In other embodiments, the adjuvant is used in combination with a DNA vaccine. Modification of the immune response includes intensification or broadening the specificity of either or both antibody and cellular immune responses. Modification of the immune response can also mean decreasing or suppressing certain antigen-specific immune responses. In one embodiment, the adjuvant is Ribi adjuvant.

As used herein "alphavirus" is meant to refer to RNA-containing viruses that belong to the group IV Togaviridae family of viruses. Exemplary alphaviruses include but are not limited to Western, Eastern, and Venezuelan equine encephalitis viruses, o'nyong-nyong virus, Ross River virus and Sindbis virus.

As used herein "inducing immunity" is meant to refer to any immune response generated against an antigen. In one embodiment, immunity is mediated by antibodies against an infectious agent, which is exhibited by a vertebrate (e.g., a human), that prevents or ameliorates an infection or reduces at least one symptom thereof. VLPs or DNA vaccines of the invention can stimulate the production of antibodies that, for example, neutralize infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates an infection, for example CHIKV infection, or reduces at least one symptom thereof.

By "ameliorate" is meant decrease, suppress, attenuate, diminish, arrest, or stabilize the development or progression of a disease or a symptom thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include viral infections including but not limited to Western, Eastern, and Venezuelan equine encephalitis viruses, o'nyong-nyong virus, Ross River virus and Sindbis virus.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or prevent a diseases delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid molecule (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "structural polyprotein" is meant a composite amino acid molecule comprising at least two separable polypeptides that contribute to a viral capsid or envelope. In one embodiment, the polypeptides are susceptible to cleavage with a viral enzyme (e.g., capsid autoproteinase and signalases).

An exemplary structural polyprotein sequence is provided at Genbank Accession No. ABX40006.1, which is reproduced below.

(SEQ ID NO: 24)
MEFIPTQTFYNRRYQPRPWTPRPTIQVIRPRPRPQRQAGQLAQLISAVNK

LTMRAVPQQKPRRNRKNKKQKQKQQAPQNNTNQKKQPPKKKPAQKKKKPG

RRERMCMKIENDCIFEVKHEGKVTGYACLVGDKVMKPAHVKGTIDNADLA

KLAFKRSSKYDLECAQIPVHMKSDASKFTHEKPEGYYNWHHGAVQYSGGR

FTIPTGAGKPGDSGRPIFDNKGRVVAIVLGGANEGARTALSVVTWNKDIV

TKITPEGAEEWSLAIPVMCLLANTTFPCSQPPCTPCCYEKEPEETLRMLE

DNVMRPGYYQLLQASLTCSPHRQRRSTKDNFNVYKATRPYLAHCPDCGEG

HSCHSPVALERIRNEATDGTLKIQVSLQIGIKTDDSHDWTKLRYMDNHMP

ADAERAGLFVRTSAPCTITGTMGHFILARCPKGETLTVGFTDSRKISHSC

THPFHHDPPVIGREKFHSRPQHGKELPCSTYVQSTAATTEEIEVHMPPDT

PDRTLMSQQSGNVKITVNGQTVRYKCNCGGSNEGLTTTDKVINNCKVDQC

HAAVTNHKKWQYNSPLVPRNAELGDRKGKIHIPFPLANVTCRVPKARNPT

VTYGKNQVIMLLYPDHPTLLSYRNMGEEPNYQEEWVMHKKEVVLTVPTEG

LEVTWGNNEPYKYWPQLSTNGTAHGHPHEIILYYYELYPTMTVVVVSVAT

FILLSMVGMAAGMCMCARRRCITPYELTPGATVPFLLSLICCIRTAKAAT

YQEAAIYLWNEQQPLFWLQALIPLAALIVLCNCLRLLPCCCKTLAFLAVM

SVGAHTVSAYEHVTVIPNTVGVPYKTLVNRPGYSPMVLEMELLSVTLEPT

LSLDYITCEYKTVIPSPYVKCCGTAECKDKNLPDYSCKVFTGVYPFMWGG

AYCFCDAENTQLSEAHVEKSESCKTEFASAYRAHTASASAKLRVLYQGNN

ITVTAYANGDHAVTVKDAKFIVGPMSSAWTPFDNKIVVYKGDVYNMDYPP

FGAGRPGQFGDIQSRTPESKDVYANTQLVLQRPAVGTVHVPYSQAPSGFK

YWLKERGASLQHTAPFGCQIATNPVRAVNCAVGNMPISIDIPEAAFTRVV

DAPSLTDMSCEVPACTHSSDFGGVAIIKYAASKKGKCAVHSMTNAVTIRE

AEIEVEGNSQLQISFSTALASAEFRVQVCSTQVHCAAECHPPKDHIVNYP

ASHTTLGVQDISATAMSWVQKITGGVGLVVAVAALILIVVLCVSFSRH"

An exemplary expression vector encoding the structural polyprotein shown above is provided at Genbank Accession No. EU224268 (FIG. 24).

A second exemplary structural polyprotein sequence is provided at Genbank Accession No. ABX40011.1", which is reproduced below:

(SEQ ID NO: 25)
MEFIPTQTFYNRRYQPRPWAPRPTIQVIRPRPRPQRQAGQLAQLISAVNK

LTMRAVPQQKPRRNRKNKKQRQKKQAPQNDPKQKKQPPQKKPAQKKKKPG

RRERMCMKIENDCIFEVKHEGKVMGYACLVGDKVMKPAHVKGTIDNADLA

KLAFKRSSKYDLECAQIPVHMKSDASKFTHEKPEGYYNWHHGAVQYSGGR

FTIPTGAGKPGDSGRPIFDNKGRVVAIVLGGANEGARTALSVVTWNKDIV

TKITPEGAEEWSLALPVLCLLANTTFPCSQPPCTPCCYEKEPESTLRMLE

DNVMRPGYYQLLKASLTCSPHRQRRSTKDNFNVYKATRPYLAHCPDCGEG

HSCHSPIALERIRNEATDGTLKIQVSLQIGIKTDDSHDWTKLRYMDSHTP

ADAERAGLLVRTSAPCTITGTMGHFILARCPKGETLTVGFTDSRKISHTC

THPFHHEPPVIGRERFHSRPQHGKELPCSTYVQSTAATAEEIEVHMPPDT

PDRTLMTQQSGNVKITVNGQTVRYKCNCGGSNEGLTTTDKVINNCKIDQC

HAAVTNHKNWQYNSPLVPRNAELGDRKGKIHIPFPLANVTCRVPKARNPT

VTYGKNQVTMLLYPDHPTLLSYRNMGQEPNYHEEWVTHKKEVTLTVPTEG

LEVTWGNNEPYKYWPQMSTNGTAHGHPHEIILYYYELYPTMTVVIVSVAS

FVLLSMVGTAVGMCVCARRRCITPYELTPGATVPFLLSLLCCVRTTKAAT

YYEAAAYLWNEQQPLFWLQALIPLAALIVLCNCLKLLPCCCKTLAFLAVM

SIGAHTVSAYEHVTVIPNTVGVPYKTLVNRPGYSPMVLEMELQSVTLEPT

LSLDYITCEYKTVIPSPYVKCCGTAECKDKSLPDYSCKVFTGVYPFMWGG

AYCFCDAENTQLSEAHVEKSESCKTEFASAYRAHTASASAKLRVLYQGNN

ITVAAYANGDHAVTVKDAKFVVGPMSSAWTPFDNKIVVYKGDVYNMDYPP

FGAGRPGQFGDIQSRTPESKDVYANTQLVLQRPAAGTVHVPYSQAPSGFK

YWLKERGASLQHTAPFGCQIATNPVRAVNCAVGNIPISIDIPDAAFTRVV

DAPSVTDMSCEVPACTHSSDFGGVAIIKYTASKKGKCAVHSMTNAVTIRE

-continued

ADVEVEGNSQLQISFSTALASAEFRVQVCSTQVHCAAACHPPKDHIVNYP

ASHTTLGVQDISTTAMSWVQKITGGVGLIVAVAALILIVVLCVSFSRH

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "vaccine" refers to a formulation which contains VLPs or DNAs, or other gene-based vaccine vectors, of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or DNA vaccines. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses. In certain embodiments, a vaccine can also be a protein. For example, recombinant proteins have been produced by genetically engineering cells to produce one or more foreign genes, which in turn produce proteins that serve as the immunogen.

As used herein, the term "virus-like particle" (VLP) refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic representation of the CHIKV genome and CHIKV E expression vector used for incorporation of CHIKV E from strains 37997 and LR2006 OPY-1 into pseudotyped lentiviral vectors. The CHIKV genome consists of nonstructural polyproteins NS1, NS2, NS3 and NS4 and structural polyproteins capsid (C) and envelope (E: E3, E2, 6K and E1) (top). The polypeptide E genes from strains 37997 and LR2006 OPY-1 were inserted into an expression vector (bottom). FIG. 1B includes two graphs. The graph on the left shows the infectivity of the indicated pseudotyped lentiviral vectors in several CHIKV-permissive cell lines, including 293A human renal epithelial, HeLa cervical epithelial, Vero renal epithelial, A549 squamous epithelial and baby hamster kidney (BHK) cells. The pseudotyped vectors were standardized by HIV-1 Gag p24 (left) or the indicated concentration of p24 and used to infect 293A cells (right). After incubation with pseudotyped vectors for 24 hours, cells were lysed and luciferase activity was measured. The experiment was performed in triplicate. FIG. 1C includes two graphs that show the pH-dependent entry of CHIKV pseudotyped lentiviral vectors. Pseudotyped lentiviral vectors were incubated in the presence of the indicated amounts of ammonium chloride (left) and chloroquine (right). The experiment was performed in triplicate. Data are presented as the percentage of activity at the indicated dose relative to activity with no treatment. FIG. 1D is a graph showing neutralization measured with pseudotyped lentiviral vectors in sera from mice injected with CHIKV (strain S-27). Sera were incubated at the indicated dilutions with VSV-G, CHIKV strain 37997 or LR2006 OPY-1 E-pseudotyped lentiviral vectors and the mixture infected to 293A cells. Luciferase activity was analyzed 24 hours after infection. The experiment was performed in triplicate. No inhibition was observed with control non-immune antisera.

FIGS. 2A-2C show the schematic representation of plasmid expression vectors and characterization of CHIKV VLPs. FIG. 2A provides a schematic representation of CHIKV C-E or E expression vectors used for DNA vaccine and VLP production. The CHIKV structural polyproteins capsid plus envelope (C-E) or E alone from strains 37997 and LR2006 OPY-1 were inserted into an expression vector. 293T cells were transfected with each of the indicated plasmids. Expression was measured 48 h after transfection by Western blotting as described previously (29) with antisera reactive with CHIKV. FIG. 2B includes a graph, Western blot, and electron micrograph. VLPs were purified from the supernatants of 293F cells transfected with C-E expression vector $_{(C-E37997)}$ (left). The supernatants were harvested 72 hours after transfection followed by OptiPrep density gradient centrifugation. Each fraction was characterized for its buoyant density (left upper panel) and protein content (left lower panel) by Western blot analysis with antisera to CHIKV. The fractionated VLPs were observed by transmission electron microscopy with magnification 20,000× (left, bar 100 nm) (right). FIG. 2C provides a comparison of cryo-EM reconstructions of CHIKV VLP with Sindbis virus showing that CHIKV VLP is structurally similar to alphaviruses. Shaded-surface representation of the 3D density map of CHIKV VLP (left upper panel) and Sindbis virus (right upper panel) viewed along an icosahedral 2-fold axis. The white triangle marks the boundary of an icosahedral asymmetric unit. The numbers show the positions of the icosahedral 2-, 3-, and 5-fold axes limiting an asymmetric unit. The central cross-section through the cryo-EM maps of CHIKV VLP (left lower panel) and Sindbis virus (right lower panel). The orientations of the icosahedral (2-, 3-, and 5-fold) axes as well as the quasi-threefold (q3) axis are shown with white lines. Maps are calculated to 18 Å resolution.

FIG. 3C shows results from monkeys immunized with $_{VLP37997}$ or PBS (control) at 0, 4, and 24 weeks. A neutralizing assay was performed with CHIKV strain 37997 (left panel) or LR2006 OPY-1 (right panel) E pseudotyped lentiviral vectors in sera collected from immunized monkeys at 10 days after each immunization. The symbols show the average of the six monkeys and bars show the standard error of the mean. FIG. 3D shows the neutralizing activity against CHIKV LR2006 OPY-1 in immunized monkeys' sera after the 2nd and 3rd immunizations was confirmed by a standard plaque reduction neutralization test (PRNT). The symbols show the average of the six monkeys and bars show the standard error of the mean.

FIG. 4A quantitates results obtained in monkeys injected with PBS (Control) or immunized with $_{VLP37997}$. Monkeys were challenged with $10^{10}$ PFU of the CHIKV strain LR2006 OPY-1 15 weeks after the final boost. The peak viremia at 24 hours after challenge was measured by plaque assay. The serum dilutions started from 1:200 (limit of detection=1000 PFU/ml). Error bars represent the standard error of the mean. FIG. 4B is a graph showing the percentage of monocytes in the monkeys' white blood cells. Monocyte percentage was measured using a hematology analyzer before and 7 days after challenge with CHIKV. Error bars represent the standard error of the mean. A non-parametric two t-test was used for statistical analysis (Control vs. VLPs at 7 days, P=0.0036; Control at 0 days vs. 7 days, P=0.0015; VLPs at 0 days vs. 7 days, P>0.5). FIG. 4C shows the number of viral RNA copies present following passive transfer of purified IgG from a monkey immunized with VLPs (Immune) or a control monkey (Control IgG) into mice (2 mg of total IgG per mouse, n=5 per group). Recipient mice were challenged 24 hours after IgG transfer with a lethal LR2006 OPY-1 challenge (30 PFU) by intradermal injection. The viremia in the mice after challenge was measured by quantitative RT-PCR (limit of detection=40 RNA copies/ml). Error bars represent the standard error of the mean. FIG. 4D shows a survival curve of mice passively transferred with control IgG or CHIKV immunized IgG against lethal LR2006 OPY-1 challenge.

FIG. 7A shows the sequence of the insert (SEQ ID NO:1). FIG. 7B shows the sequence of the entire plasmid sequence (SEQ ID NO: 2).

FIG. 8B shows the sequence of the insert (SEQ ID NO:3). FIG. 8C shows the entire plasmid sequence (SEQ ID NO: 4).

FIG. 9A shows the CMV/R-Middleburg virus VLP plasmid. FIG. 9B shows the entire plasmid sequence (SEQ ID NO: 5).

FIG. 10B shows the entire plasmid sequence (SEQ ID NO: 6).

FIGS. 11A and 11B. FIG. 11A shows the CMV/R-Getah virus VLP plasmid. FIG. 11B shows the entire plasmid sequence (SEQ ID NO: 7).

FIG. 12A shows the CMV/R-Venezuelan equine encephalitis virus VLP plasmid.

FIG. 12B shows the entire plasmid sequence (SEQ ID NO: 8).

FIG. 13B shows the entire plasmid sequence (SEQ ID NO: 9).

FIG. 14B shows the entire plasmid sequence (SEQ ID NO: 10).

FIG. 15B shows the entire plasmid sequence (SEQ ID NO: 11).

FIG. 16B shows the entire plasmid sequence (SEQ ID NO: 12).

FIG. 17B shows the entire plasmid sequence (SEQ ID NO: 13).

FIG. 18B shows the entire plasmid sequence (SEQ ID NO: 14).

FIG. 19A shows the CMV/R-O'nyong-nyong virus VLP plasmid. FIG. 19B shows the entire plasmid sequence (SEQ ID NO: 15).

FIG. 20A shows the CMV/R-Mayaro virus VLP plasmid. FIG. 20B shows the entire plasmid sequence (SEQ ID NO: 16).

FIG. 21B shows the entire plasmid sequence (SEQ ID NO: 17).

FIG. 22B shows the entire plasmid sequence (SEQ ID NO: 18).

FIG. 24 shows the sequence of Genbank Accession No. EU224268, which is a Cloning vector pCHIKV-LR ic, complete sequence. See, Tsetsarkin. K., Higgs, S., McGee, C. E., DeLamballerie, X., Charrel, R. N. and Vanlandingham, D. L. Infectious clones of Chikungunya virus (La Reunion isolate) for vector competence studies, Vector Borne Zoonotic Dis. 6 (4), 325-337 (2006).

FIG. 25 shows the sequence of Genbank Accession No. EU224270, which is the complete sequence of the Cloning vector pCHIK-37997ic.

SEQUENCE LISTING

Figure 1A:
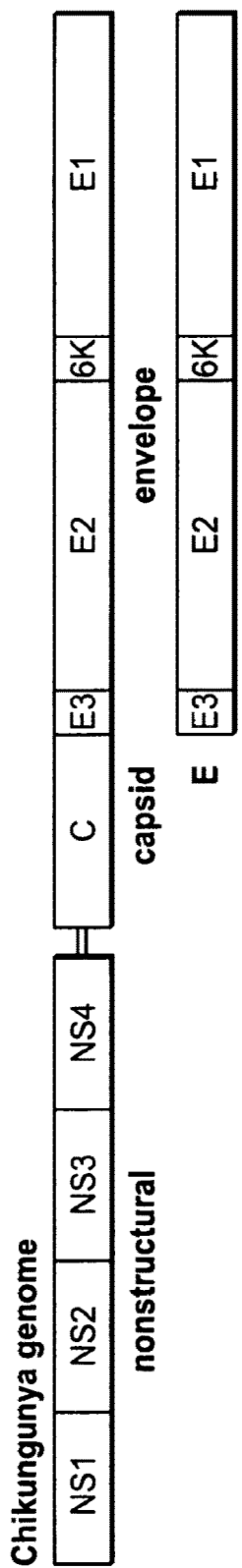
FIGS. 1A-1D show the characterization of CHIKV E pseudotyped lentiviral vectors.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file name "Sequence.txt" (~249 kb), which was created on Jun. 27, 2022, and which is incorporated by reference herein.

DETAILED DESCRIPTION OF THE INVENTION

Chikungunya virus (CHIKV) has infected millions of people in Africa, Europe, and Asia since its re-emergence in Kenya in 2004. The evolution and spread of the virus into new geographic areas, and the severity of the disease, present a serious public health threat in the absence of a vaccines or anti-viral therapies. The invention provides compositions and methods for inducing protective immunity. The invention is based, at least in part, on the discovery that a recombinant virus-like particle (VLP) vaccine protects against CHIKV infection in non-human primates. VLPs were generated by expression of viral structural proteins. These had similar buoyant density and morphology to replication-competent virus. Immunization with VLPs elicited neutralizing antibodies against homologous and heterologous envelope. Monkeys immunized with VLPs produced high titer cross-reactive neutralizing antibodies that protected against high dose challenge with emerging epidemic CHIKV. Furthermore, passive transfer of these antibodies from immune monkeys protected against lethal CHIKV challenge in immunodeficient mice, demonstrating that protection is mediated by the humoral immune response. Immunization with the VLP vaccine is a strategy that would prevent the infection and spread of CHIKV and related pathogenic viruses in humans.

Accordingly, the invention provides immunogenic compositions containing one or more alphavirus (e.g., Chikungunya virus) structural polypeptides. In particular, the immunogenic composition (e.g., vaccine) contains envelope or capsid polypeptides sufficient to form a virus-like particle. The invention further provides nucleic acid molecules encoding alphavirus (Chikungunya) structural polypeptides, expression vectors comprising these coding sequences, and methods of using these nucleic acid molecules for the preparation of virus-like particles. In other embodiments, the invention provides DNA vaccines that provide for the expression of one or more viral polypeptides in the cell of a subject.

Immunogenic Compositions

The invention provides compositions and methods for inducing an immunological response in a subject, particularly a human, which involves inoculating the subject with a VLP comprising one or more alphavirus or CHIKV polypeptides, or fragments thereof, in a suitable carrier for the purpose of inducing or enhancing an immune response. In one embodiment, an immune response protects the subject from a CHIKV infection, or inflammatory consequences thereof (e.g., arthritis). The administration of this immunological composition may be used either therapeutically in subjects already experiencing a CHIKV infection, or may be used prophylactically to prevent a CHIKV infection.

In certain embodiments, CHIKV candidate vaccines were developed by comparing the immunogenicity of gene products derived from two disparate strains, the 37997 strain from West Africa and the latest outbreak strain, OPY-1, of the East/Central/South African genotype, to develop CHIKV candidate vaccines. These strains share ~95% amino acid sequence similarity but have distinct biological differences, particularly related to their host range.

VLPs of the invention are useful for preparing vaccines and immunogenic compositions. One important feature of VLPs is the ability to express surface proteins so that the immune system of a vertebrate induces an immune response against said protein. However, not all proteins can be expressed on the surface of VLPs. There may be many reasons why certain proteins are not expressed, or be poorly expressed, on the surface of VLPs. One reason is that said protein is not directed to the membrane of a host cell or that said protein does not have a transmembrane domain.

The preparation of immunogenic compositions and vaccines is known to one skilled in the art. The vaccine includes a VLP comprising one or more CHIKV polypeptides, or fragments thereof. The invention also provides expression vectors encoding one or more CHIKV polypeptides or fragments thereof or variants thereof. Such an immunogenic composition is delivered in vivo in order to induce or enhance an immunological response in a subject, such as a humoral response.

For example, a VLP comprising one or more CHIKV polypeptides, or fragments or variants thereof are delivered in vivo in order to induce an immune response.

Typically vaccines are prepared in an injectable form, either as a liquid solution or as a suspension. Solid forms suitable for injection may also be prepared as emulsions, or with the polypeptides encapsulated in liposomes. Vaccine antigens are usually combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The VLP comprising one or more CHIKV polypeptides, or fragments or variants thereof may be administered in combination with an adjuvant (e.g., Ribi). Adjuvants are immunostimulating agents that enhance vaccine effectiveness. If desired, the VLP comprising one or more CHIKV polypeptides or fragments or variants thereof are administered in combination with an adjuvant that enhances the effectiveness of the immune response generated against the antigen of interest. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions, i.e. the VLP comprising one or more CHIKV polypeptides, pharmaceutically acceptable carrier and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The immunogenic compositions are typically administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

Immunogenic compositions are administered in a manner compatible with the dose formulation. The immunogenic composition comprises an immunologically effective amount of the VLP and other previously mentioned components. By an immunologically effective amount is meant a single dose, or a composition administered in a multiple dose schedule, that is effective for the treatment or prevention of an infection. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner, but typically range between 5 µg to 250 µg of antigen per dose.

The invention provides a VLP for use in treating or preventing an alphavirus infection (e.g., Chikungunya infection).

Polypeptide Expression

In general, VLPs comprising one or more CHIKV polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., supra). Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae*, *Kluyveromyces lactis* (*K. lactis*), species of *Candida* including *C. albicans* and *C. glabrata*, *Aspergillus nidulans*, *Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli*, *B. subtilis*, and mycobacteria.

Methods of cloning said proteins are known in the art. For example, the gene encoding a specific CHIKV or any alphavirus protein can be isolated by RT-PCR from polyadenylated mRNA extracted from cells which had been infected with said virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

The invention further provides nucleotides that encode proteins, including chimeric molecules, cloned into an expression vector that can be expressed in a cell that provides for the formation of VLPs. An "expression vector" is a vector, such as a plasmid, that is capable of promoting expression, as well as replication of a nucleic acid incorporated therein. Typically, the nucleic acid molecule to be expressed is "operably linked" to a promoter and/or enhancer, and is subject to transcription regulatory control by the promoter and/or enhancer.

In one embodiment, the VLP comprises one or more alphavirus envelope proteins, and in particular CHIKV virus envelope proteins. In another embodiment, the one or more envelope proteins are any one or more of E3, E2, 6K and E1. In another embodiment, the VLP further comprises a CHIKV virus capsid protein. In related embodiments, the Chikungunya virus capsid protein is used. In still another embodiment, the VLPs are comprised of capsid, E3, E2, 6K and E1. In another embodiment, the expression vector is a mammalian expression vector or baculovirus vector.

The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors provided herein comprise CHIKV polynucleotides that encode structural polypeptides, including envelope proteins or capsid proteins or portions thereof as described herein. The vector may be, for example, a phage, plasmid, viral, or retroviral vector. The constructs and/or vectors that comprise the nucleotides should be operatively linked to an appropriate promoter, such as the CMV promoter, phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, infect, or transform and can express viral proteins, including those described herein, into eukaryotic cells and/or prokaryotic cells. Thus, the invention provides for host cells which comprise a vector (or vectors) that contain nucleic acids which code for CHIKV structural genes, including capsid, E3, E2, 6K, and E1 or portions thereof, and/or any chimeric molecule described above, and permit the expression of CHIKV structural genes, including capsid E3, E2, 6K, and E1, or portions thereof, and/or any chimeric molecule described above in said host cell under conditions which allow the formation of VLPs.

In one embodiment, said vector is a recombinant baculovirus. In another embodiment, said recombinant baculovirus is transfected into an insect cell. In a preferred embodiment, said cell is an insect cell. In another embodiment, said insect cell is a SD cell.

In another embodiment, said vector and/or host cell comprise nucleotides that encode CHIKV genes, including capsid, E3, E2, 6K, and E1, or portions thereof as described herein. In another embodiment, said vector and/or host cell consists essentially of CHIKV capsid E3, E2, 6K, and E1, or portions thereof as described herein. In a further embodiment, said vector and/or host cell consists of CHIKV protein comprising capsid, E3, E2, 6K, and E1, or portions thereof, as described herein. These vector and/or host cell contain CHIKV core E3, E2, 6K, and E1, or portions thereof, as described herein, and may contain additional cellular constituents such as cellular proteins, baculovirus proteins, lipids, carbohydrates etc.

One particular bacterial expression system for polypeptide production is the E. coli pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from Schistosoma japonicum and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once a recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

CHIKV Polypeptides and Analogs

The invention provides VLPs comprising one or more CHIKV polypeptides. Also included in the invention are VLPs comprising one or more CHIKV polypeptides or fragments thereof that are modified in ways that enhance or do not inhibit their ability to modulate an immune response. In one embodiment, the invention provides methods for optimizing a CHIKV amino acid sequence or nucleic acid sequence by producing an alteration. Such alterations may include certain mutations, deletions, insertions, or post-translational modifications. The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues.

Alterations of a alphavirus or CHIKV polypeptide include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

In one embodiment, the invention provides polypeptide variants that differ from a reference polypeptide. The term "variant" refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. Desirably, variants show substantial biological activity. In one embodiment, a protein variant forms a VLP and elicits an antibody response when administered to a subject.

Natural variants can occur due to mutations in the proteins. These mutations may lead to antigenic variability within individual groups of infectious agents, for example CHIKV. Thus, a person infected with a particular strain develops antibody against that virus, as newer virus strains appear, the antibodies against the older strains no longer recognize the newer virus and reinfection can occur. The invention encompasses all antigenic and genetic variability of proteins from infectious agents for making VLPs.

Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "a fragment" means at least 5, 10, 13, or 15. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs having a chemical structure designed to mimic CHIKV VLPs or one or more CHIKV polypeptides functional activity can be administered according to methods of the invention. CHIKV analogs may exceed the physiological activity of native CHIKV. Methods of analog design are well known in the art, and synthesis of analogs can be carried out according to such methods by modifying the chemical structures such that the resultant analogs exhibit the immunomodulatory activity of a native CHIKV polypeptide. These chemical modifications include, but are not limited to, substituting alternative R groups and varying the degree of saturation at specific carbon atoms of the native CHIKV molecule. Preferably, the analogs are relatively resistant to in vivo degradation, resulting in a more prolonged therapeutic effect upon administration. Assays for measuring functional activity include, but are not limited to, those described in the Examples below.

CHIKV Polynucleotides

In general, the invention includes any nucleic acid sequence encoding a VLP comprising one or more CHIKV polypeptides or a fragment thereof, where the fragment induces an immune response. An isolated nucleic acid molecule is can be manipulated by recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. In certain exemplary embodiments, the vector comprises Chikungunya$_{37997}$ or Chikungunya$_{OPY-1}$ nucleic acid segments, or fragments thereof. The vector may further comprise a CMV/R promoter. The vector may also comprise the capsid protein, or a fragment thereof.

In other exemplary embodiments, the vector comprises an envelope protein selected from the group consisting of E3, E2, 6K, and E1. In certain examples, the vaccine may comprise capsid, E3, E2, 6K and E1. In other examples, the vaccine may comprise E3, E2, 6K and E1.

According to certain preferred embodiments of the invention, C-Env$_{37997}$ is set forth as SEQ ID NO:1; Env$_{37997}$ is set forth as SEQ ID NO:19; C-Env$_{OPY-1}$ is set forth as SEQ ID NO:3; Env$_{OPY-1}$ is set forth as SEQ ID NO: 20.

Shown below is the nucleotide sequence corresponding to the capsid (SEQ ID NO: 21) and E3, E2, 6K and E1 (SEQ ID NO: 19) of the CMV/R-CHIKV C-E3-E2-6K-E1 plasmid (Strain 37997). The CMV/R expression vector is described, for example, in U.S. Pat. No. 7,094,598, which is incorporated herein in its entirety.

E3-E2-6K-E1
SEQ ID NO: 19
Atgagcctcgccctcccggtcttgtgcctgttggcaaacactacattcc
cctgctctcagccgccttgcacaccctgctgctacgaaaaggaaccgga
aagcaccttgcgcatgcttgaggacaacgtgatgagaccgatactac
cagctactaaaagcatcgctgacttgctctccccaccgccaaagacgca
gtactaaggacaattttaatgtctataaagccacaagaccatatctagc
tcattgtcctgactgcggagaagggcattcgtgccacagccctatcgca
ttggagcgcatcagaaatgaagcaacggacggaacgctgaaaatccagg
tctctttgcagatcgggataaagacagatgacagccacgattggaccaa
gctgcgctatatggatagccatacgccagcggacgcggagcgagccgga
ttgcttgtaaggacttcagcaccgtgcacgatcaccgggaccatgggac
actttattctcgcccgatgccgaaggagagacgctgacagtgggatt
tacgacagcagaaagatcagccacacatgcacacacccgttccatcat
gaacccacctgtgataggtagggagaggttccactctcgaccacaacatg
gtaaagagttaccttgcagcacgtacgtgcagagcaccgctgccactgc
tgaggagatagaggtgcatatgcccccagatactcctgaccgcacgctg
atgacgcagcagtctggcaacgtgaagatcacagttaatgggcagacgg
tgcggtacaagtgcaactgcggtggctcaaacgagggactgacaaccac
agacaaagtgatcaataactgcaaaattgatcagtgccatgctgcagtc
actaatcacaagaattggcaatacaactccccttttagtcccgcgcaacg
ctgaactcggggaccgtaaaggaaagatccacatcccattcccattggc
aaacgtgacttgcagagtgccaaaagcaagaaacccctacagtaacttac
ggaaaaaaccaagtcaccatgctgctgtatcctgaccatccgacactct
tgtcttaccgtaacatgggacaggaaccaaattaccacgaggagtgggt
gacacacaagaaggaggttaccttgaccgtgcctactgagggtctggag
gtcacttggggcaacaacgaaccatacaagtactggccgcagatgtcta
cgaacggtactgctcatggtcacccacatgagataatcttgtactatta
tgagctgtacccactatgactgtagtcattgtgtcggtggcctcgttc
gtgcttctgtcgatggtgggcacagcagtgggaatgtgtgtgtgcgcac
ggcgcagatgcattacaccatatgaattaacaccaggagccactgttcc
cttcctgctcagcctgctatgctgcgtcagaacgaccaaggcggccaca
tattacgaggctgcggcatatctatggaacgaacagcagccctgttct
ggttgcaggctcttatcccgctggccgccttgatcgtcctgtgcaactg
tctgaaactcttgccatgctgctgtaagacctggcttttttagccgta
atgagcatcggtgcccacactgtgagcgcgtacgaacacgtaacagtga
tcccgaacacggtgggagtaccgtataagactcttgtcaacagaccggg
ttacagccccatggtgttggagatggagctacaatcagtcaccttggaa
ccaacactgtcacttgactacatcacgtgcgagtacaaaactgtcatcc
cctcccgtacgtgaagtgctgtggtacagcagagtgcaaggacaagag
cctaccagactacagctgcaaggtctttactggagtctacccatttatg
tggggcggcgcctactgcttttgcgacgccgaaaatacgcaattgagcg aggcacatgtagagaaatctgaatcttgcaaaacagagtttgcatcggc
ctacagagcccacaccgcatcggcgtcggcgaagctccgcgtccttttac
caaggaaacaacattaccgtagctgcctacgctaacggtgaccatgccg
tcacagtaaaggacgccaagtttgtcgtgggcccaatgtcctccgcctg
gacaccttttgacaacaaaatcgtggtgtacaaaggcgacgtctacaac
atggactacccacctttggcgcaggaagaccaggacaatttggtgaca
ttcaaagtcgtacaccggaaagtaaagacgtttatgccaacactcagtt
ggtactacagaggccagcagcaggcacggtacatgtaccatactctcag
gcaccatctggcttcaagtattggctgaaggaacgaggagcatcgctac
agcacacggcaccgttcggttgccagattgcgacaaacccggtaagagc
tgtaaattgcgctgtggggaacataccaatttccatcgacataccggat
gcggcctttactagggttgtcgatgcaccctctgtaacggacatgtcat
gcgaagtaccagcctgcactcactcctccgactttgggggcgtcgccat
catcaaatacacagctagcaagaaaggtaaatgtgcagtacattcgatg
accaacgccgttaccattcgagaagccgacgtagaagtagagggaact
cccagctgcaaatatccttctcaacagccctggcaagcgccgagtttcg
cgtgcaagtgtgctccacacaagtacactgcgcagccgcatgccaccct
ccaaaggaccacatagtcaattacccagcatcacacaccacccttgggg
tccaggatatatccacaacggcaatgtcttgggtgcagaagattacggg
aggagtaggattaattgttgctgttgctgccttaattttaattgtggtg
ctatgcgtgtcgtttagcaggcac Core
SEQ ID NO: 21
Atggagttcatcccgacgcaaactttctataacagaaggtaccaacccc
gaccctgggccccacgccctacaattcaagtaattagacctagaccacg
tccacagaggcaggctgggcaactcgcccagctgatctccgcagtcaac
aaattgaccatgcgcgcggtacctcaacagaagcctcgcagaaatcgga
aaaacaagaagcaaaggcagaagaagcaggcgccgcaaaacgacccaaa
gcaaagaagcaaccaccacaaaagaagccggctcaaaagaagaagaaa
ccaggccgtagggagagaatgtgcatgaaaattgaaaatgattgcatct
tcgaagtcaagcatgaaggcaaagtgatgggctacgcatgcctggtggg
ggataaagtaatgaaaccagcacatgtgaagggaactatcgacaatgcc
gatctggctaaactggcctttaagcggtcgtctaaatacgatcttgaat
gtgcacagataccggtgcacatgaagtctgatgcctcgaagtttaccca
cgagaaacccgaggggtactataactggcatcacggagcagtgcagtat
tcaggaggccggttcactatcccgacgggtgcaggcaagccgggagaca
gcggcagaccgatcttcgacaacaaaggacgggtggtggccatcgtcct
aggagggccaacgaaggtgcccgcacggccctctccgtggtgacgtgg
aacaaagacatcgtcacaaaaattacccctgagggagccgaagagtgg Shown below is the nucleotide sequence corresponding to the capsid (SEQ ID NO: 22) and E3, E2, 6K and E1 (SEQ ID NO: 20) of the CMV/R-CHIKV C-E3-E2-6K-E1 plasmid (Strain OPY-1).

E3-E2-6K-E1
SEQ ID NO: 20
Atgagtcttgccatcccagttatgtgcctgttggcaaacaccacgttcc
cctgctcccagccccttgcacgccctgctgctacgaaaaggaaccgga
ggaaaccctacgcatgcttgaggacaacgtcatgagacctgggtactat
cagctgctacaagcatccttaacatgttctccccaccgccagcgacgca
gcaccaaggacaacttcaatgtctataaagccacaagaccatacttagc
tcactgtcccgactgtggagaagggcactcgtgccatagtcccgtagca
ctagaacgcatcagaaatgaagcgacagacgggacgctgaaaatccagg
tctccttgcaaatcggaataaagacggatgacagccacgattggaccaa
gctgcgttatatggacaaccacatgccagcagacgcagagagggcgggg
ctatttgtaagaacatcagcaccgtgtacgattactggaacaatgggac
acttcatcctggcccgatgtccaaaaggggaaactctgacggtgggatt
cactgacagtaggaagattagtcactcatgtacgcacccatttcaccac
gaccctcctgtgataggtcgggaaaaattccattcccgaccgcagcacg
gtaaagagctaccttgcagcacgtacgtgcagagcaccgccgcaactac
cgaggagatagaggtacacatgccccagacacccctgatcgcacatta
atgtcacaacagtccggcaacgtaaagatcacagtcaatggccagacg
tgcggtacaagtgtaattgcggtggctcaaatgaaggactaacaactac
agacaaagtgattaataactgcaaggttgatcaatgtcatgccgcggtc
accaatcacaaaaagtggcagtataactcccctctggtcccgcgtaatg
ctgaacttggggaccgaaaaggaaaaattcacatcccgtttccgctggc
aaatgtaacatgcagggtgcctaaagcaaggaaccccaccgtgacgtac
gggaaaaaccaagtcatcatgctactgtatcctgaccacccaacactcc
tgtcctaccggaatatgggagaagaaccaaactatcaagaagagtgggt
gatgcataagaaggaagtcgtgctaaccgtgccgactgaagggctcgag
gtcacgtggggcaacaacgagccgtataagtattggccgcagttatcta
caaacggtacagcccatggccacccgcatgagataattctgtattatta
tgagctgtaccccactatgactgtagtagttgtgtcagtggccacgttc
atactcctgtcgatggtgggtatggcagcggggatgtgcatgtgtgcac
gacgcagatgcatcacaccgtatgaactgacaccaggagctaccgtccc
tttcctgcttagcctaatatgctgcatcagaacagctaaagcggccaca
taccaagaggctgcgatatacctgtggaacgagcagcaacctttgtttt
ggctacaagcccttattccgctggcagccctgattgttctatgcaactg
tctgagactcttaccatgctgctgtaaaacgttggcttttttagccgta
atgagcgtcggtgcccacactgtgagcgcgtacgaacacgtaacagtga
tcccgaacacggtgggagtaccgtataagactctagtcaatagacctgg
ctacagccccatggtattggagatggaactactgtcagtcactttggag
ccaacactatcgcttgattacatcacgtgcgagtacaaaaccgtcatcc
cgtctccgtacgtgaagtgctgcggtacagcagagtgcaaggacaaaaa
cctacctgactacagctgtaaggtcttcaccggcgtctacccattatg
tggggcggcgcctactgcttctgcgacgctgaaaacacgcagttgagcg
aagcacacgtggagaagtccgaatcatgcaaaacagaatttgcatcagc
atacagggctcataccgcatctgcatcagctaagctccgcgtcctttac
caaggaaataacatcactgtaactgcctatgcaaacggcgaccatgccg
tcacagttaaggacgccaaattcattgtggggccaatgtcttcagcctg
gacacctttcgacaacaaaattgtggtgtacaaaggtgacgtctataac
atggactacccgccctttggcgcaggaagaccaggacaatttggcgata
tccaaagtcgcacacctgagagtaaagacgtctatgctaatacacaact
ggtactgcagagaccggctgtgggtacggtacacgtgccatactctcag
gcaccatctggctttaagtattggctaaaagaacgcggggcgtcgctgc
agcacacagcaccatttggctgccaaatagcaacaaacccggtaagagc
ggtgaactgcgccgtagggaacatgcccatctccatcgacataccggaa
gcggccttcactagggtcgtcgacgcgccctcttaacggacatgtcgt
gcgaggtaccagcctgcacccattcctcagactttgggggcgtcgccat
tattaaatatgcagccagcaagaaaggcaagtgtgcggtgcattcgatg
actaacgccgtcactattcgggaagctgagatagaagttgaagggaatt
ctcagctgcaaatctctttctcgacggccttagccagcgccgaattccg
cgtacaagtctgttctacacaagtacactgtgcagccgagtgccacccc
ccgaaggaccacatagtcaactacccggcgtcacataccaccctcgggg
tccaggacatctccgctacggcgatgtcatgggtgcagaagatcacggg
aggtgtgggactggttgttgctgttgccgcactgattctaatcgtggtg
ctatgcgtgtcgttcagcaggcac Core
SEQ ID NO: 22
Atggagttcatcccaacccaaacttttttacaataggaggtaccagcctc
gaccctggactccgcgccctactatccaagtcatcaggcccagaccgcg
ccctcagaggcaagctgggcaacttgcccagctgatctcagcagttaat
aaactgacaatgcgcgcggtaccacaacagaagccacgcaggaatcgga
agaataagaagcaaaagcaaaaacaacaggcgccacaaaacaacacaaa
tcaaaagaagcagccacctaaaaagaaaccggctcaaaagaaaaagaag
ccggggccgcagagaggatgtgcatgaaaatcgaaaatgattgtatt
tcgaagtcaagcacgaaggtaaggtaacaggttacgcgtgcctggtggg
ggacaaagtaatgaaaccagcacacgtaaaggggaccatcgataacgcg
gacctggccaaactggcctttaagcggtcatctaagtatgaccttgaat
gcgcgcagatacccgtgcacatgaagtccgacgcttcgaagttcaccca
tgagaaaccggaggggtactacaactggcaccacggagcagtacagtac
tcaggaggccggttcaccatccctacaggtgctggcaaaccaggggaca
gcggcagaccgatcttcgacaacaagggacgcgtggtggccatagtctt
aggaggagctaatgaaggagcccgtacagccctctcggtggtgacctgg
aataaagacattgtcactaaaatcaccccgagggggccgaagagtgg
```

In a particular embodiment, a nucleic acid molecule set forth as SEQ ID NO: 1, 19, 3 or 20 includes a nucleotide sequence encoding a polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to a polypeptide encoding an envelope protein selected from capsid, E3, E2, 6K and E1 or E3, E2, 6K and E1.

In some embodiments of the invention proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host See U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. A person with skill in the art understands that various subcloning methods are available and are possible.

An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, as the term is used herein, because it is readily manipulatable by standard techniques known to those of ordinary skill in the art.

CHIKV VLP Production

The invention also provides constructs and methods for producing a VLP comprising CHIKV polypeptides, or fragments thereof, as well as compositions and methods that increase the efficiency of VLP production. For example, the addition of leader sequences to the CHIKV capsid, E3, E2, 6K, and E1 or portions thereof, that can improve the efficiency of protein transporting within the cell. In another example, a heterologous signal sequence can be fused to the CHIKV capsid, E3, E2, 6K, and E1 or portions thereof. In one embodiment, the signal sequence can be derived from the gene of an insect cell. Another method to increase efficiency of VLP production is to codon optimize the nucleotides that encode CHIKV capsid, E3, E2, 6K, and E1 or portions thereof, for a specific cell type.

Methods of cloning said proteins are known in the art. For example, the gene encoding a specific CHIKV or any alphavirus protein can be isolated by RT-PCR from polyadenylated mRNA extracted from cells which had been infected with said virus. The resulting gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the VLP comprises one or more alphavirus envelope proteins, and in particular CHIKV virus envelope proteins. In another embodiment, the one or more envelope proteins are selected from the group consisting of E3, E2, 6K and E1. In another embodiment, the VLP comprises a CHIKV virus capsid protein. In related embodiments, the Chikungunya virus capsid protein is used. In another embodiment, the VLPs are comprised of E3, E2, 6K and E1. In still another embodiment, the VLPs are comprised of capsid, E3, E2, 6K and E1. In another embodiment, the expression vector is a baculovirus vector.

The invention also provides methods of producing a VLP comprising CHIKV polypeptides, or fragments thereof. In one example, the method involves expressing in a cell a polynucleotide encoding a CHIKV polypeptide and culturing said cell, thereby producing VLPs. In one embodiment, a cell (e.g., human cell) is infected with a DNA vaccine, where the DNA vaccine is a DNA vector, comprising a nucleic acid segment encoding an alphavirus capsid protein or one or more alphavirus envelope proteins, or fragments thereof to produce an alphavirus VLP. In particular, the alphavirus is CHIKV.

Depending on the expression system and host cell selected, the VLPs are produced by growing host cells transformed by an expression vector under conditions whereby the recombinant proteins are expressed and VLPs are formed. In one embodiment, the invention comprises a method of producing a VLP, that involves transfecting vectors encoding at least one alphavirus protein into a suitable host cell and expressing said alphavirus protein under conditions that allow VLP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce VLPs of the invention include, but are not limited to, batch, batch-fed, continuous and perfusion cell culture techniques. In one embodiment, a cell comprising a CHIKV or alphavirus polynucleotide is grown in a bioreactor or fermentation chamber where cells propagate and express protein (e.g. recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The VLPs are isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. A person of skill in the art appreciates that there are additional methods that can be used to make and purify VLPs. Accordingly, the invention is not limited to the methods described herein.

In general, production of VLPs of the invention is accomplished by seeding a mammalian cell (e.g., human embryonic kidney (293T) cells) or Sf9 cells (non-infected) into shaker flasks, allowing the cells to expand and scaling up as the cells grow and multiply (for example from a 125-ml flask to a 50 L Wave bag). The medium used to grow the cells is formulated for the appropriate cell line (preferably serum free media, e.g. insect medium ExCell-420, JRH). Next, the cells are transfected or infected with an appropriate vector (e.g., mammalian expression vector or for SF (cells recombinant baculovirus at the most efficient multiplicity of infection (e.g. from about 1 to about 3 plaque forming units per cell). The polynucleotides, or portions thereof, are expressed in the cells where they self assemble into VLPs and are secreted from the cells approximately 24 to 72 hours post infection. Usually, transfection or infection is most efficient when the cells are in mid-log phase of growth (4-8.×$10^6$ cells/ml) and are at least about 90% viable.

VLPs of the invention are harvested approximately 48 to 120 hours post infection, when the levels of VLPs in the cell culture medium are near the maximum but before extensive cell lysis. The cell density and viability at the time of harvest can be about 0.5×$10^6$ cells/ml to about 1.5×$10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 µm filter cartridge or a similar device.

Next, VLPs in the clarified culture medium are concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4 C to about 10 C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or .beta.-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25 C to about 27 C. The baculovirus can also be inactivated by incubating the sample containing the VLPs at 0.05% BPL at 4 C for 3 days, then at 37 C for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

In certain embodiments, a DNA vaccine or VLP comprises agents, such as nucleic acid molecules, siRNA, microRNA, chemotherapeutic agents, imaging agents, and/or other agents that need to be delivered to a patient.

Accordingly, the present invention provides methods of treating viral diseases and/or disorders or symptoms thereof which comprise administering a therapeutically effective amount of a pharmaceutical composition comprising a VLP or DNA of the formulae herein to a subject (e.g., a mammal such as a human). Thus, one embodiment is a method of treating a subject suffering from or susceptible to a viral infection, viral disease or disorder or symptom thereof. The method includes the step of administering to the mammal a therapeutic or prophylactic amount of an amount of a compound herein sufficient to treat the disease or disorder or symptom thereof, under conditions such that the disease or disorder is prevented or treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, such as a VLP or DNA of a formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which an alphavirus may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with an alphavirus, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Compositions and Administration

The invention features pharmaceutical compositions that comprise VLPs of an alphavirus as described herein. The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

In particular embodiments, the invention encompasses an antigenic formulation comprising VLPs which comprises at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the pharmaceutical composition comprises VLPs of Chikungunya virus, and a pharmaceutically acceptable carrier. In other certain preferred embodiments, the pharmaceutical composition comprises VLPs of Chikungunya virus, an adjuvant, and a pharmaceutically acceptable carrier.

In one embodiment, the VLPs are comprised of Chikungunya virus envelope proteins, for example, the envelope proteins can be selected from the group consisting of E3, E2, 6K and E1. In another embodiment, the pharmaceutical composition further comprises a Chikungunya virus capsid protein. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

The invention also encompasses a vaccine formulation comprising VLPs that comprise at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the vaccine composition comprises VLPs of Chikungunya virus, and a pharmaceutically acceptable carrier. In other certain preferred embodiments, the vaccine composition comprises VLPs of Chikungunya virus, an adjuvant, and a pharmaceutically acceptable carrier. In one embodiment, the vaccine composition comprises VLPs of Chikungunya virus envelope proteins, for example, the envelope proteins can be selected from the group consisting of E3, E2, 6K and E1. In another embodiment, the vaccine composition further comprises a Chikungunya virus capsid protein and a pharmaceutically acceptable carrier or excipient. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the VLP composition is supplied in liquid form, for example in a sealed container indicating the quantity and concentration of the VLP composition. Preferably, the liquid form of the VLP composition is supplied in a hermetically sealed container at least about 50 µg/ml, more preferably at least about 100 µg/ml, at least about 200 µg/ml, at least 500 µg/ml, or at least 1 mg/ml.

Generally, VLPs or DNA vaccines of the invention are administered in an effective amount or quantity (as described herein) sufficient to stimulate an immune response against one or more strains of a virus a described here, for example an alphavirus, e.g. CHIKV. Preferably, administration of the VLP of the invention elicits immunity against a virus, for example an alphavirus, in particular example CHIKV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device.

Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, for example CHIKV.

Thus, the invention also comprises a method of formulating a vaccine or antigenic composition that induces immunity to an infection or at least one symptom thereof to a mammal, comprising adding to said formulation an effective dose of VLPs, e.g. CHIKV VLP. In one embodiment, the infection is an alphavirus infection, for example, but not limited to, Chikungunya virus, Sindbis virus, Eastern equine encephalitis (EEE) virus, Western equine encephalitis (WEE) virus, and Venezuelan equine encephalitis (VEE) virus.

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Prime Boost

The present methods also include a variety of prime-boost regimens. In these methods, one or more priming immunizations is followed by one or more boosting immunizations. The actual immunogenic composition can be the same or different for each immunization and the type of immunogenic composition (e.g., containing protein or expression vector), the route, and formulation of the immunogens can also be varied.

For example, in one embodiment, the prime comprises administering a DNA or gene-based vaccine as described herein and the boost comprises administering a VLP as described herein. In another embodiment, the prime comprises administering a VLP as described herein and the boost comprises administering a DNA or other gene-based vaccine as described herein.

One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

Methods of administering a composition comprising VLPs and/or DNA vaccines (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains of the virus. Administration can be intramuscular, subdermal, intraperitoneal. In one preferred embodiment, the administration is intramuscular.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals and/or antibiotics. A VLP may be administered concurrently, subsequent to, or sequentially with another immunogenic composition, antiviral, antibiotic, or any other agent that prevents or treats an alphavirus (e.g., Chikungunya infection).

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat, and non-human primates. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this invention.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween-80 emulsion also is contemplated. MF-59, Novasomes®, MHC antigens may also be used.

The VLPs of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the VLPs, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Delivery

The VLPs of the invention are useful for preparing compositions that stimulate an immune response. Such compositions are useful for the treatment or prevention or a viral infection (e.g., a CHIKV or other alphavirus infection). Both mucosal and cellular immunity may contribute to immunity to infectious agents and disease. In one embodiment, the invention encompasses a method of inducing immunity to a viral infection, for example Chikungunya virus infection in a subject, by administering to the subject a Chikungunya virus VLP or a DNA vaccine.

The invention also provides a method to induce immunity to viral infection or at least one symptom thereof in a subject, comprising administering at least one effective dose of a VLP or DNA vaccine as described herein, for example a VLP comprising one or more viral proteins, for example one or more CHIKV virus envelope proteins or a DNA vaccine comprising a nucleic acid segment encoding an alphavirus capsid protein or one or more alphavirus envelope proteins, or fragments thereof. In certain cases, the VLP further comprises a virus capsid protein. In another embodiment, the method comprises inducing immunity to a viral infection, e.g. CHIKV infection or at least one symptom thereof by administering said formulation in multiple doses.

VLPs of the invention can induce substantial immunity in a vertebrate (e.g. a human) when administered to said vertebrate. The substantial immunity results from an immune response against VLPs of the invention that protects or ameliorates infection or at least reduces a symptom of infection in said vertebrate. In some instances, if the said vertebrate is infected, said infection will be asymptomatic. The response may be not a fully protective response. In this case, if said vertebrate is infected with an infectious agent, the vertebrate will experience reduced symptoms or a shorter duration of symptoms compared to a non-immunized vertebrate.

In one embodiment, the invention comprises a method of inducing substantial immunity to alphavirus infection or at least one symptom thereof in a subject, comprising administering at least one effective dose of a VLP and/or a DNA vaccine comprising a nucleic acid segment encoding an alphavirus capsid protein or one or more alphavirus envelope proteins, or fragments thereof. In particular embodiments, the infection is CHIKV and the VLP comprises one or more CHIKV envelope protein as described herein. In another embodiment, the invention comprises a method of vaccinating a mammal against an alphavirus comprising administering to said mammal a protection-inducing amount of VLPs or DNA vaccines comprising at least one alphavirus protein. In one embodiment, said method comprises administering DNA vaccines comprising capsid, E3, E2, 6K and E1. In another embodiment, said method comprises administering DNA vaccines comprising E3, E2, 6K and E1. In another embodiment, said method comprises administering DNA vaccines comprising C-$Env_{37997}$ as set forth as SEQ ID NO:1. In another embodiment, said method comprises administering DNA vaccines comprising $Env_{37997}$ as set forth as SEQ ID NO:19. In another embodiment, said method comprises administering DNA vaccines comprising C-$Env_{OPY-1}$ as set forth as SEQ ID NO:3. In another embodiment, said method comprises administering DNA vaccines comprising $Env_{OPY-1}$ as set forth as SEQ ID NO:20. In one embodiment, said method comprises administering VLPs comprising capsid, E3, E2, 6K and E1. In another embodiment, said method comprises administering VLPs comprising E3, E2, 6K and E1. In one embodiment, said method comprises administering VLPs comprised of Chikungunya virus envelope proteins.

In another embodiment, the invention comprises a method of inducing a protective cellular response to a viral infection or at least one symptom thereof in a subject, comprising administering at least one effective dose of a DNA vaccine or a VLP.

As mentioned above, the VLPs of the invention prevent or reduce at least one symptom of an infection in a subject. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of viral infection or additional symptoms, a reduced severity of viral symptoms or a suitable assays (e.g. antibody titer and/or T-cell activation assay). The objective assessment comprises both animal and human assessments.

The invention also provides assays to identify inhibitors of viral entry comprising, in at least one embodiment, genetically modified target cells expressing at least one Chikungunya viral receptor, together with any co-receptors which might be required for infection or entry. These cells are genetically modified in the sense that they express a reporter gene, such as an affinity tag, a fluorogenic protein or an enzyme able to convert substrates into fluorogenic, chromogenic or luminometric products. Coupling this type of reporter signal to an inhibition of viral infection is accomplished by arranging the expression of the reporter gene to be strongly decreased (downregulated) upon infection with the virus of interest. In principle, this can be ensured by any suitable means, but especially preferred are:

The reporter gene product itself is fused to a cellular protein which, upon infection with the virus of interest is itself downregulated. For example, the reporter gene product can be fused to the corresponding viral receptor, which in many cases is downregulated upon infection.

Thus in one aspect a compound library may be screened for the ability to inhibit the infection of cells with Chikungunya virus (CHIKV). An appropriate indicator cell line is generated that stably expresses a reporter gene. In one example, these cells are seeded in microtiter plates and incubated with CHIKV particles in presence of different compounds, e.g., antibodies, in each well. Upon infection, the fusion protein is downregulated due to the expression of the viral genes. Consequently, only cells that have not been infected with CHIKV will express the reporter gene. Thus, wells that exhibit a positive reporter signal contain compounds that inhibit infection. Variations and modifications of these assays will be apparent from the relevant sections of the description which explain individual parts of the assay in more detail. Specifically, in one embodiment, the reporter gene can be expressed when infection occurs rather than the reporter gene being downregulated upon infection. In further embodiments, the viral particles are pseudotyped viral particles comprising one or more envelope protein and, optionally, the capsid protein from CHIKV.

In another embodiment, the invention provides methods for identifying inhibitors of viral entry using a reporter gene system as exemplified herein. Briefly, the invention provides recombinant lentiviral vectors expressing a reporter gene. Cells are incubated and co-transfected with an expression vector, e.g., $Env_{37997}$, $Env_{OPY-1}$, and a reporter plasmid using a standard techniques.

Cells are plated into one day prior to infection. CHIKV Env-pseudotyped lentiviral vectors encoding the reporter gene are first titrated by serial dilution. Similar amounts of pseudotyped vectors are then incubated with the candidate inhibitors prior to adding the virus. Cells are then lysed using cell lysis buffer and the reporter gene activity is measured. Inhibitors of viral entry are identified based on the expression of the reporter gene.

Kits

The invention also provides for a pharmaceutical pack or kit comprising one or more containers filled with one or more of the ingredients of the vaccine formulations of the invention. In a preferred embodiment, the kit comprises two containers, one containing VLPs and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject.

The invention also features a kit comprising a VLP as described herein. The invention also features kits comprising a DNA vaccine as described herein and instructions for use.

The invention also features a kit comprising a VLP in a first container and a DNA vaccine in a second container, and instructions for use in a prime boost immunization.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening,

EXAMPLES

Figure 1B:
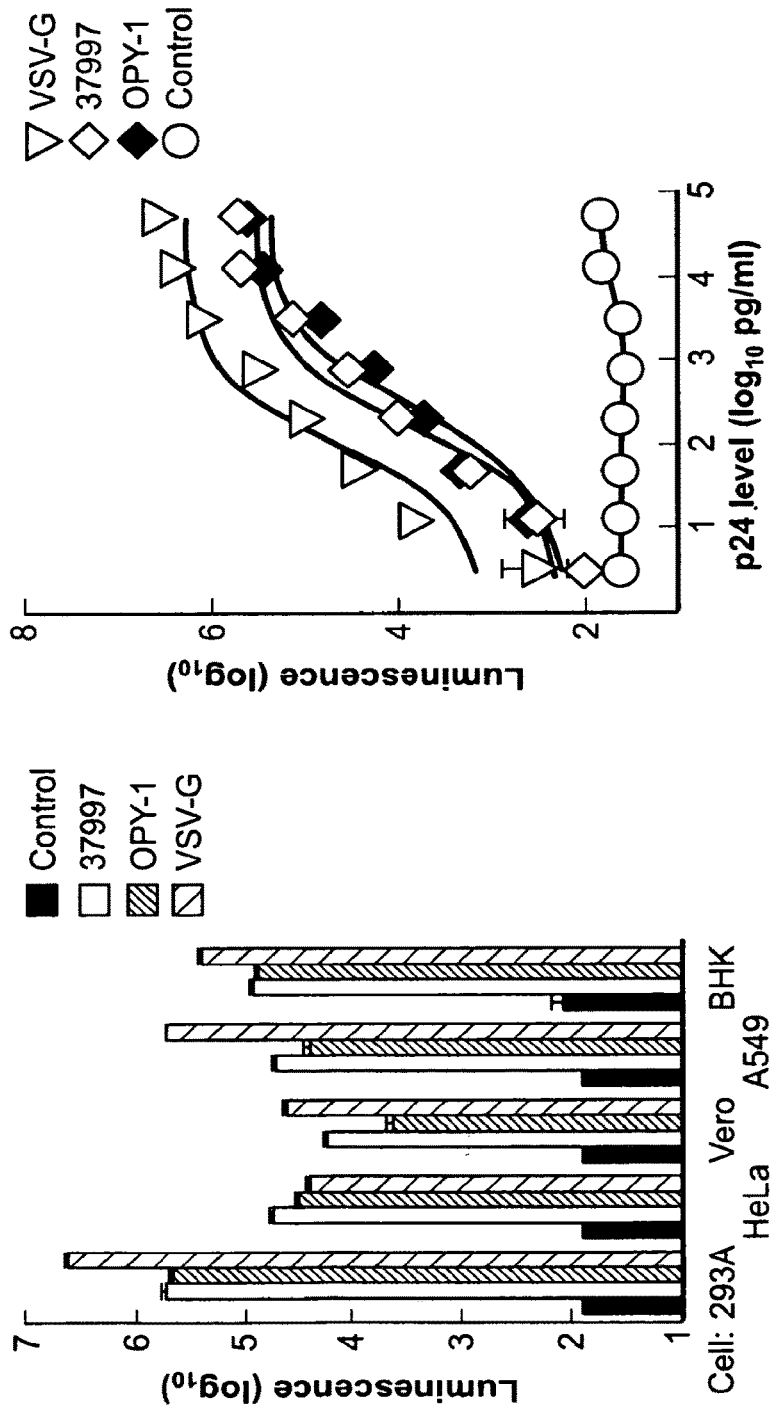
Figure 5:
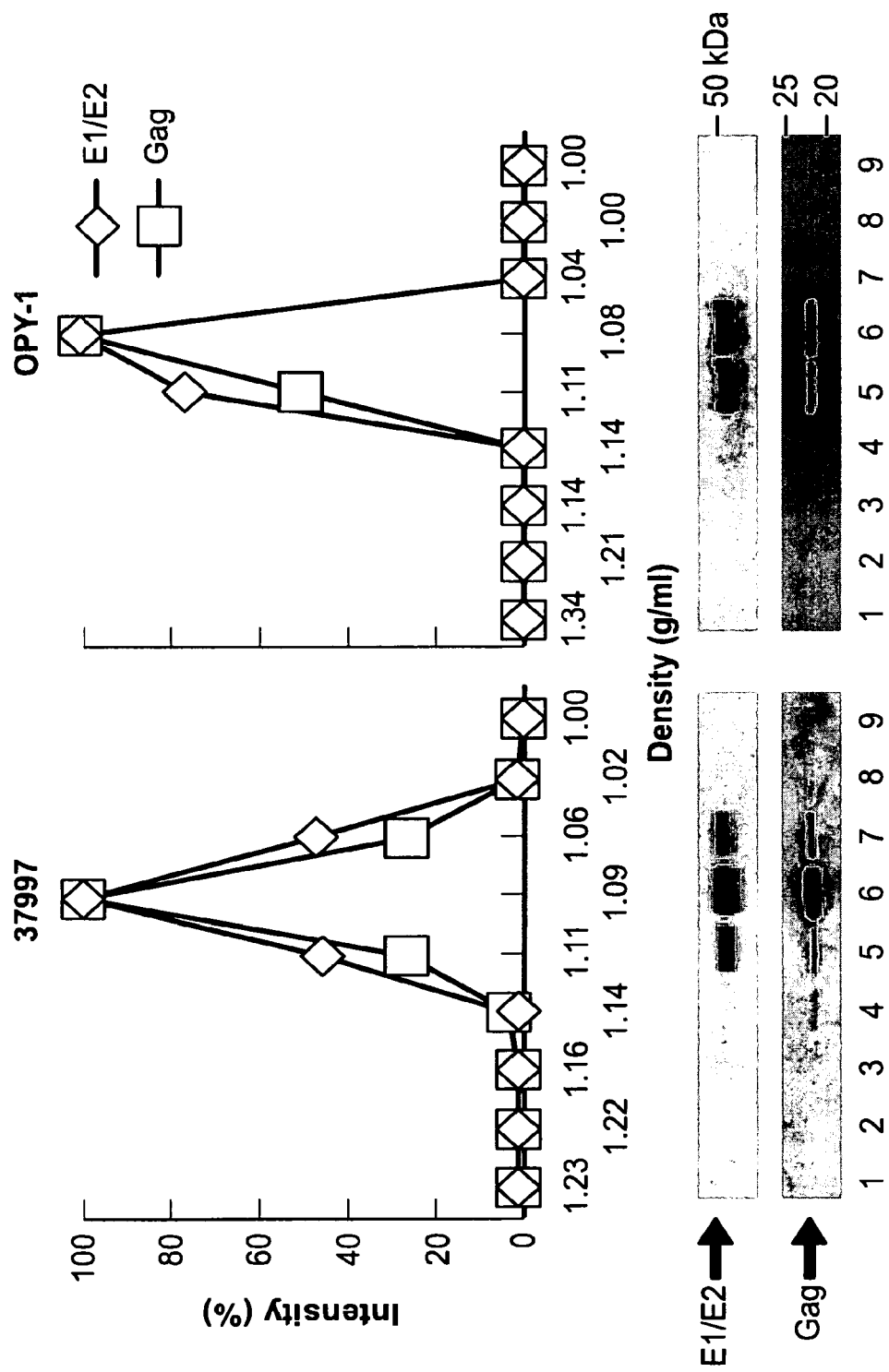
FIG. 5 shows the characterization of CHIKV E pseudotyped lentiviral vectors by buoyant density sedimentation and Western blot analysis. Plasmids encoding the indicated CHIKV Env strains were cotransfected with lentiviral expression vectors into 293T cells. Forty-eight hours after transfection, supernatants were harvested and run on sedimentation gradients as described previously. Quantification of gradient fractions is shown with the indicated strains, showing colocalization of Env with the Gag fraction of the expected buoyant density for lentiviral particles (1.08-1.1 g/ml) (upper panel). Western blot analysis of gradient fractions for CHIKV E1/E2 and Gag are shown (lower panel).
Figure 6:
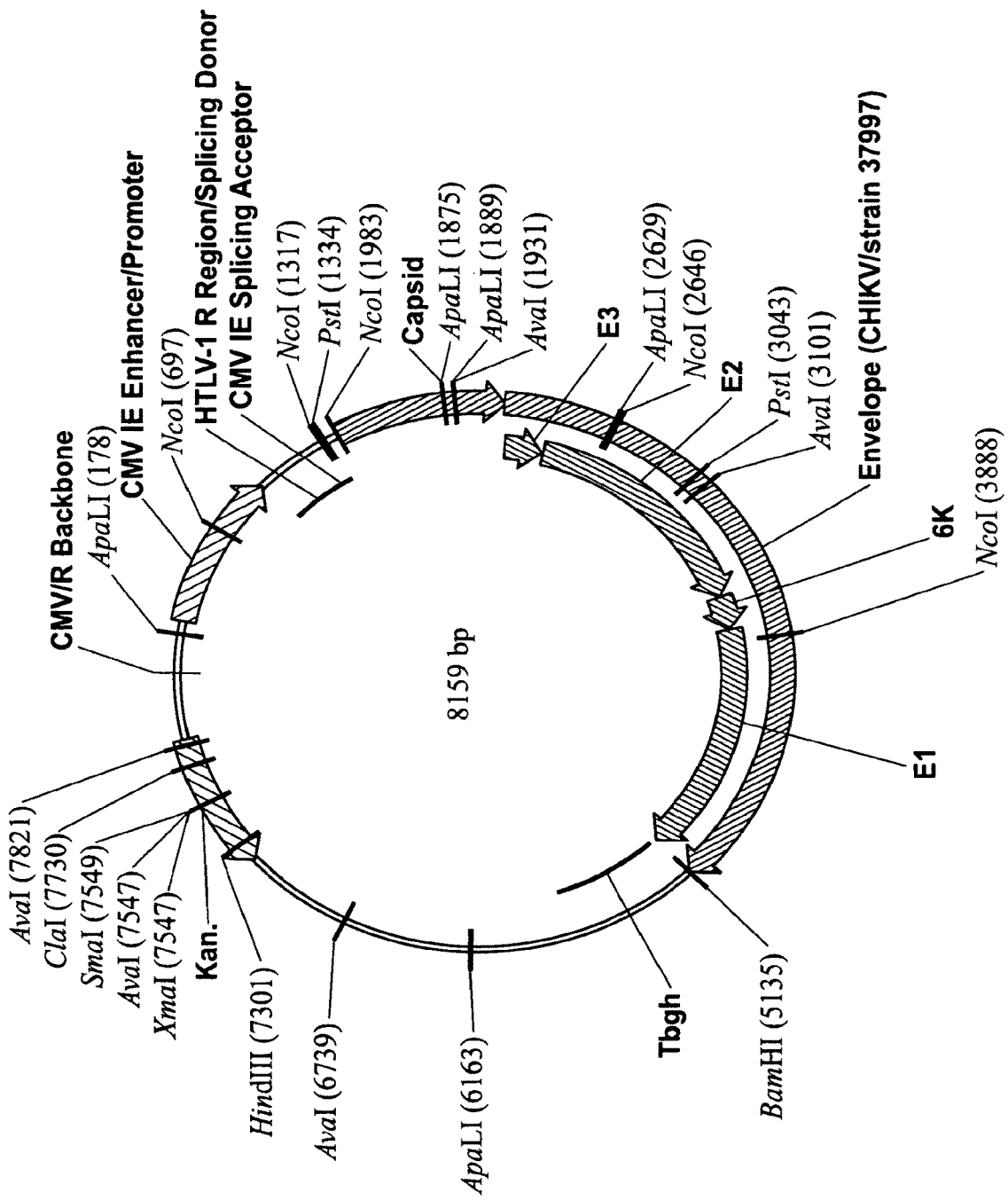
FIG. 6 shows the CMV/R-CHIKV C-E3-E2-6K-E1 plasmid (Strain 37997).
Figure 8A:
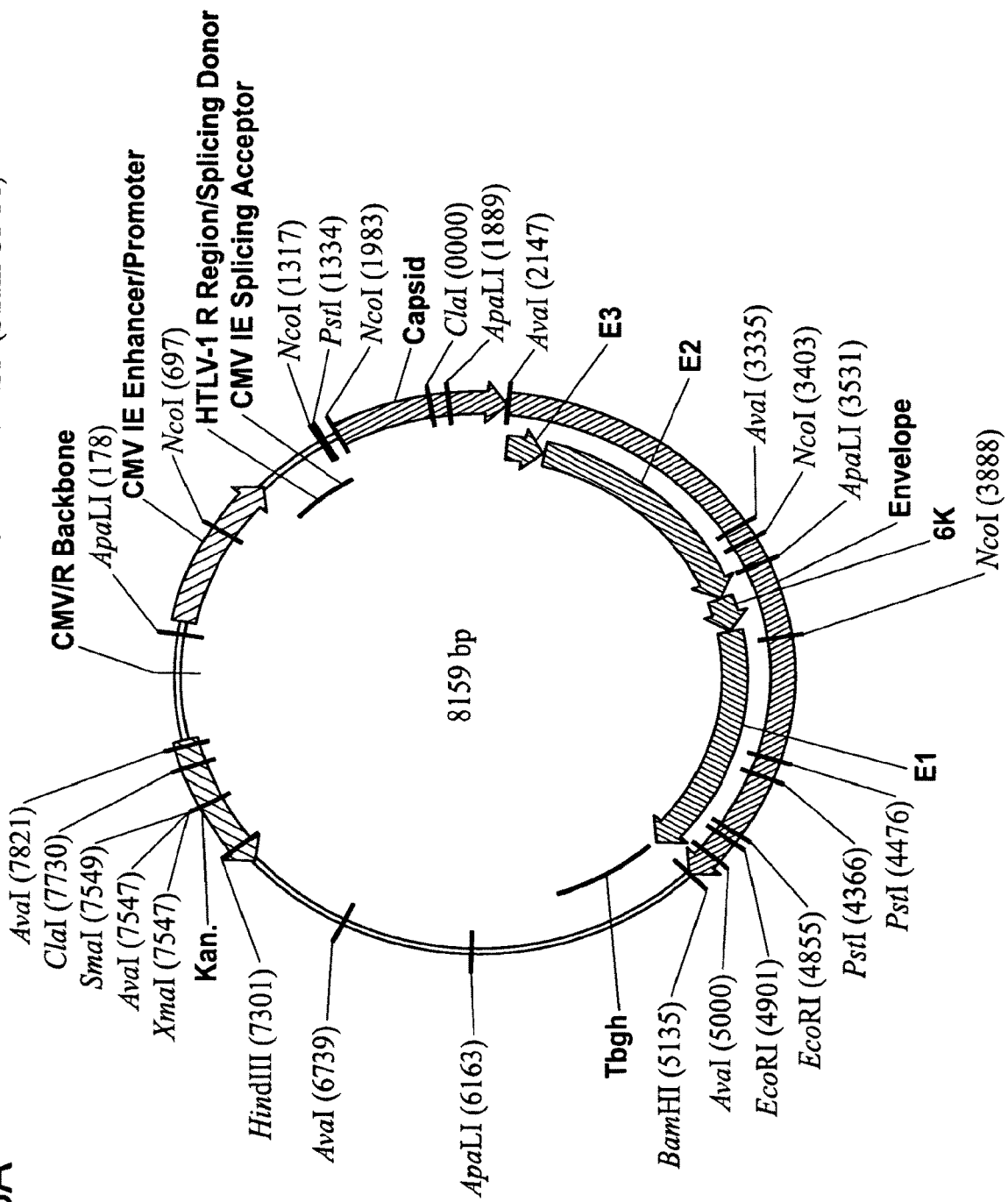
FIG. 8A shows the CMV/R-CHIKV C-E3-E2-6K-E1 plasmid (Strain OPY1).
Figure 10A:
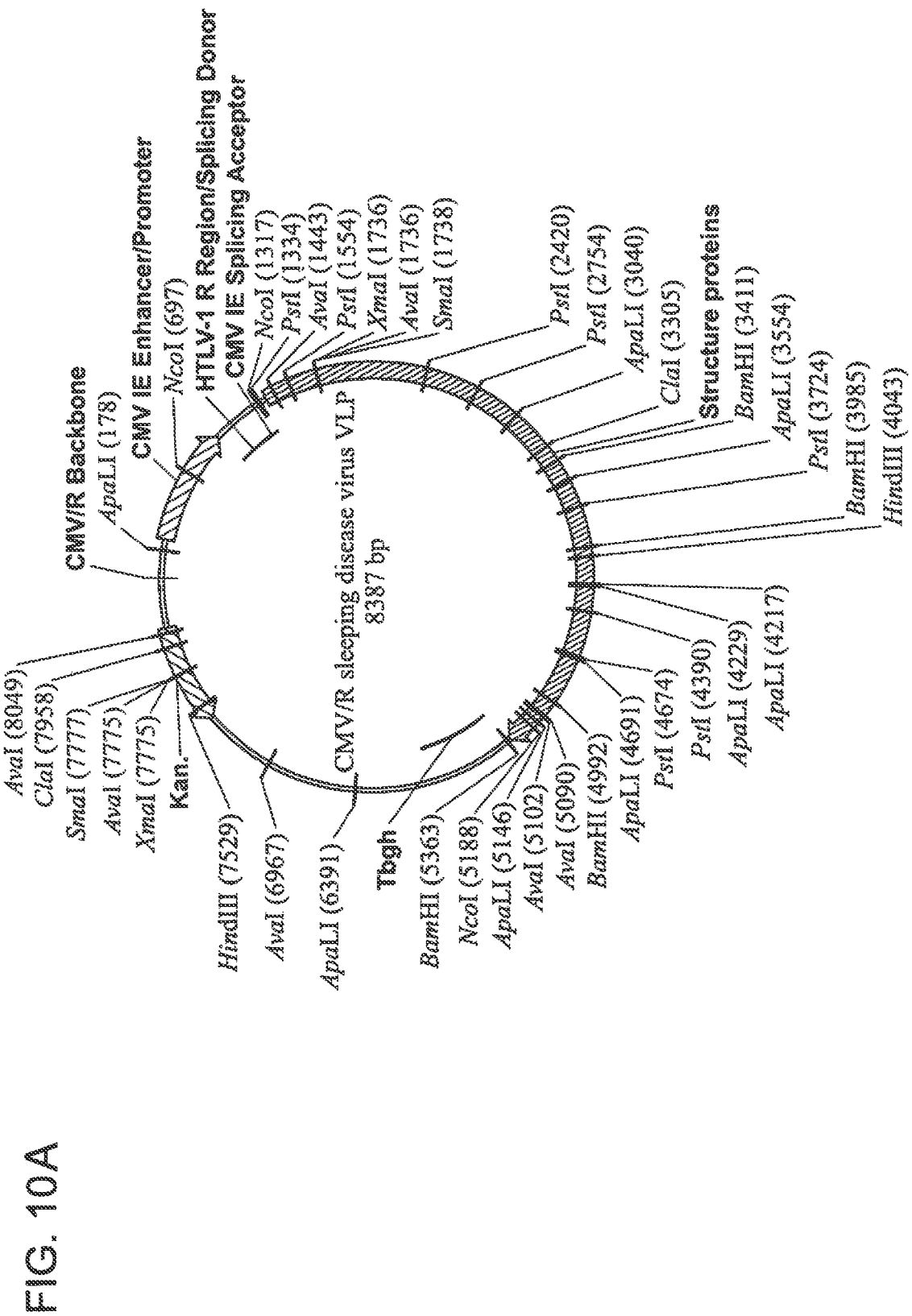
FIG. 10A shows the CMV/R-Sleeping disease virus VLP plasmid.
Figure 13A:
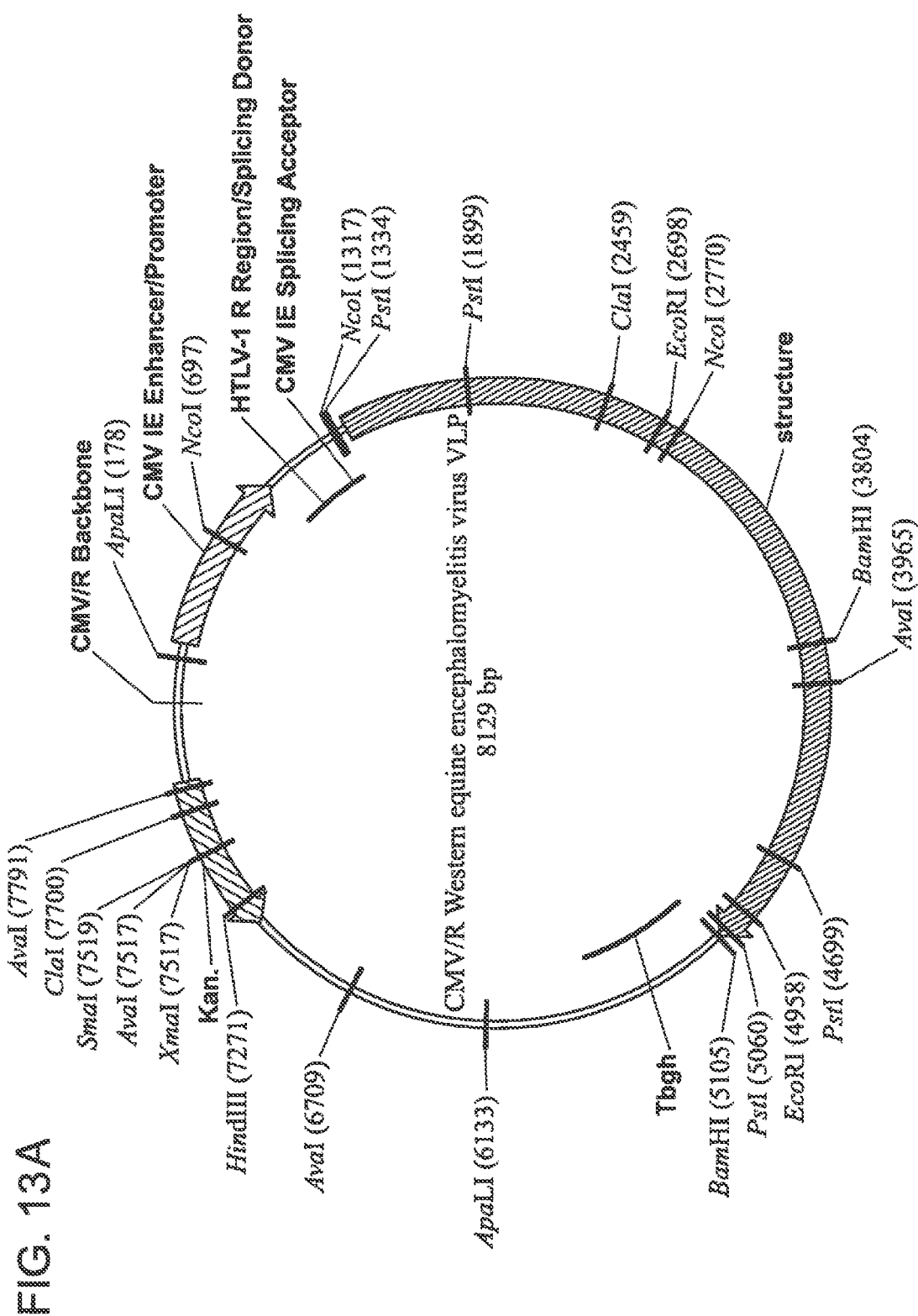
FIG. 13A shows the CMV/R-Western equine encephalitis virus VLP plasmid.
Figure 14A:
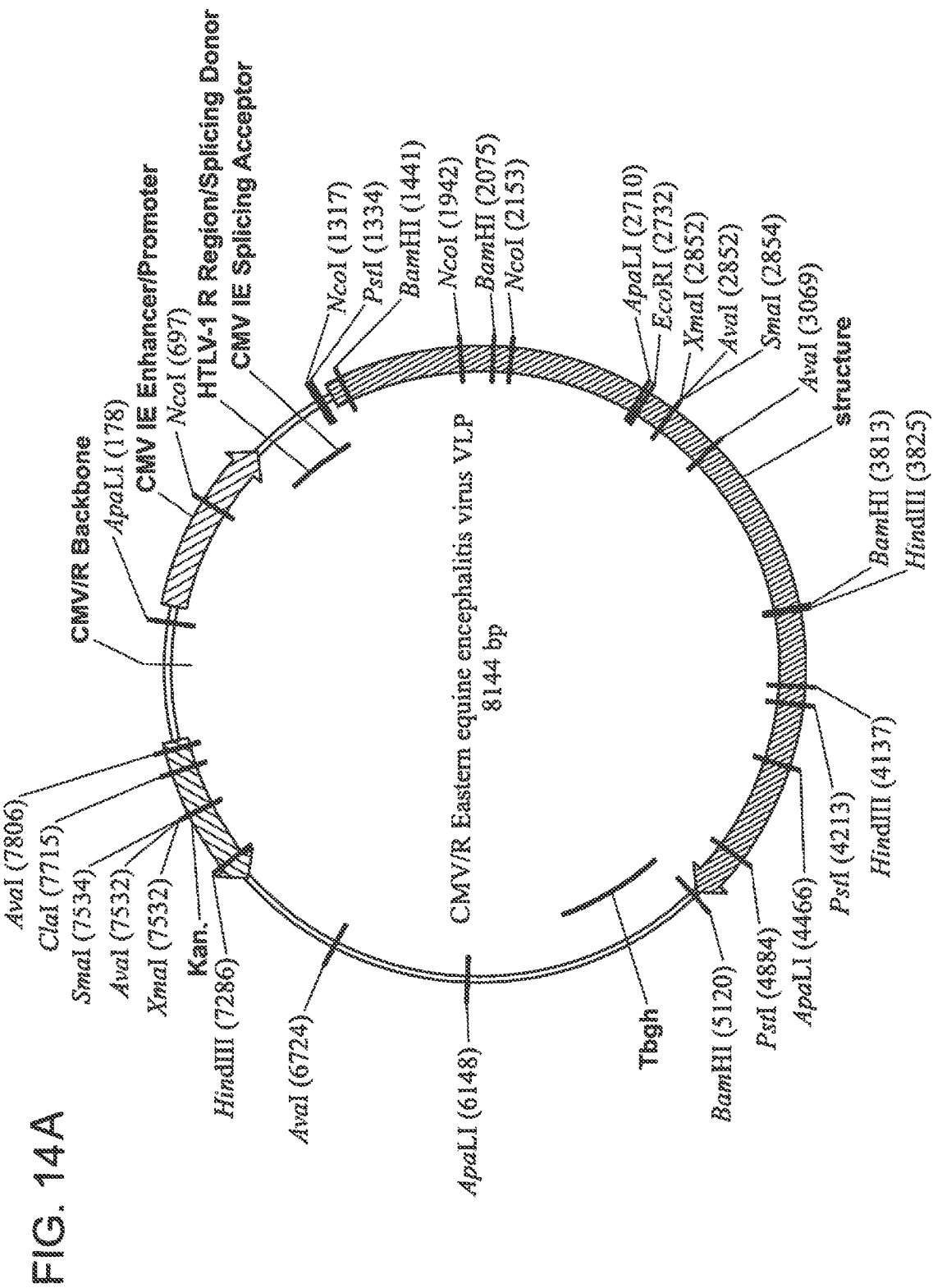
FIG. 14A shows the CMV/R-Eastern equine encephalitis virus VLP plasmid.
Figure 15A:
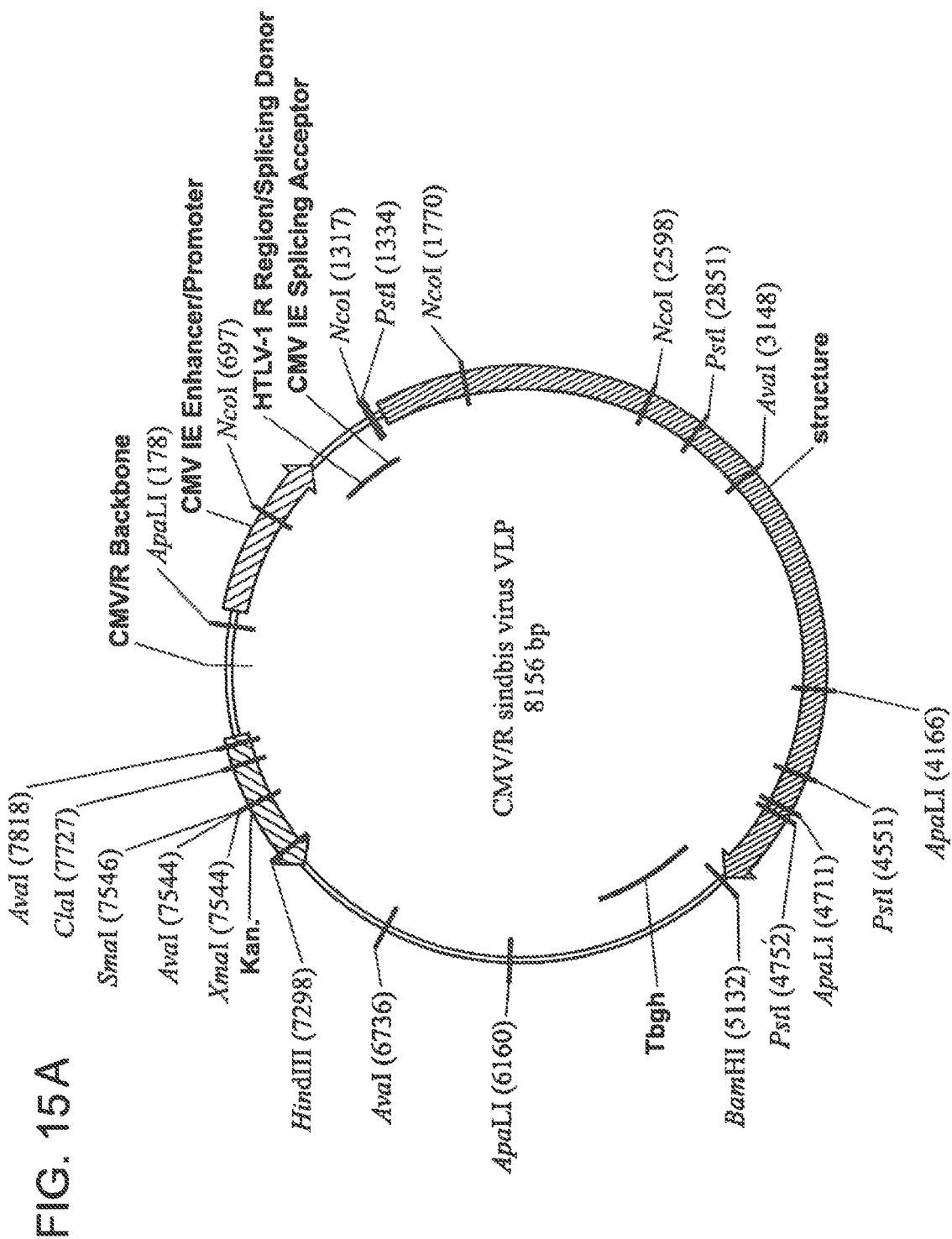
FIG. 15A shows the CMV/R-Sindbis virus VLP plasmid.
Figure 16A:
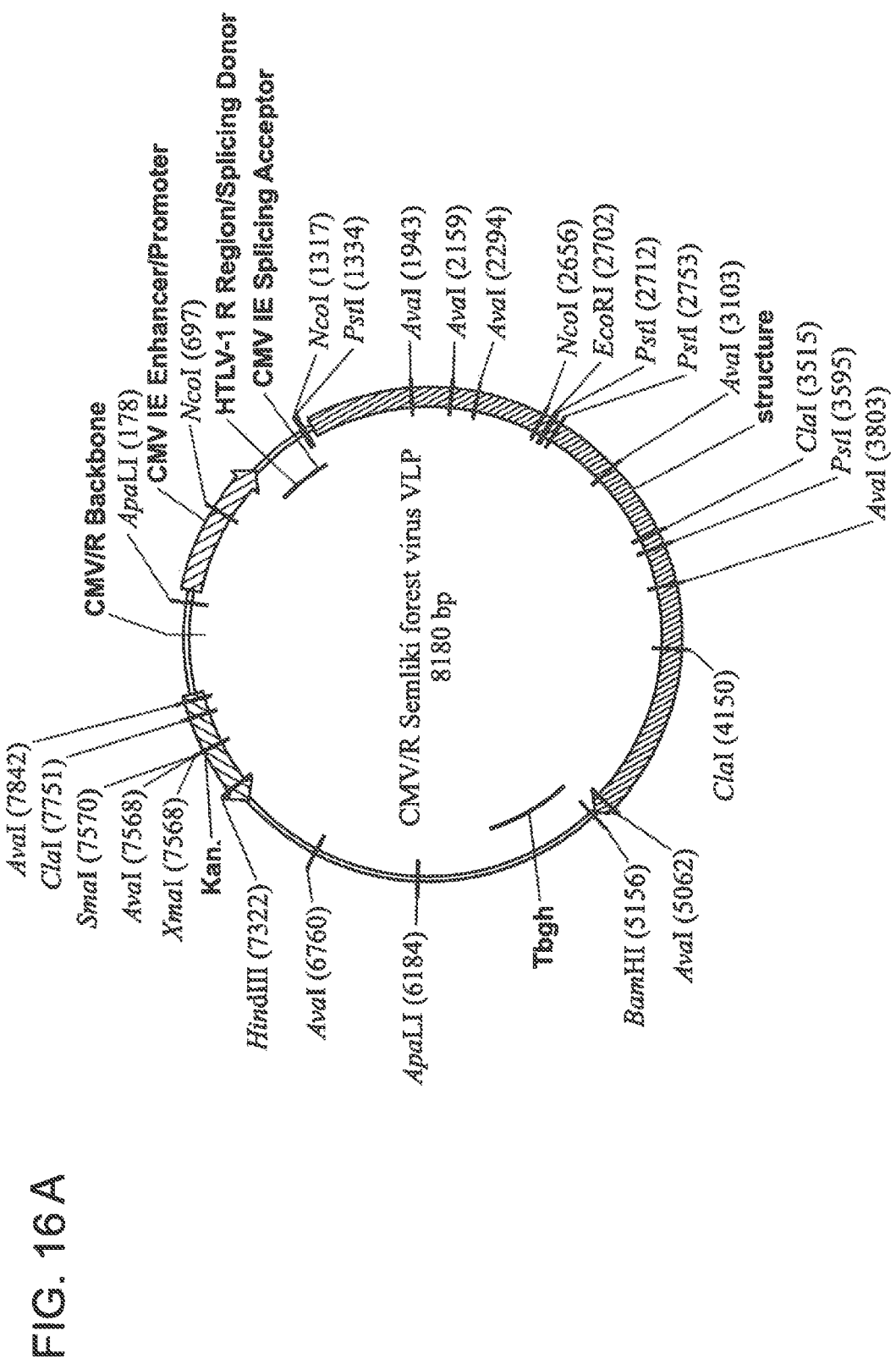
FIG. 16A shows the CMV/R-Semliki forest virus VLP plasmid.
Figure 17A:
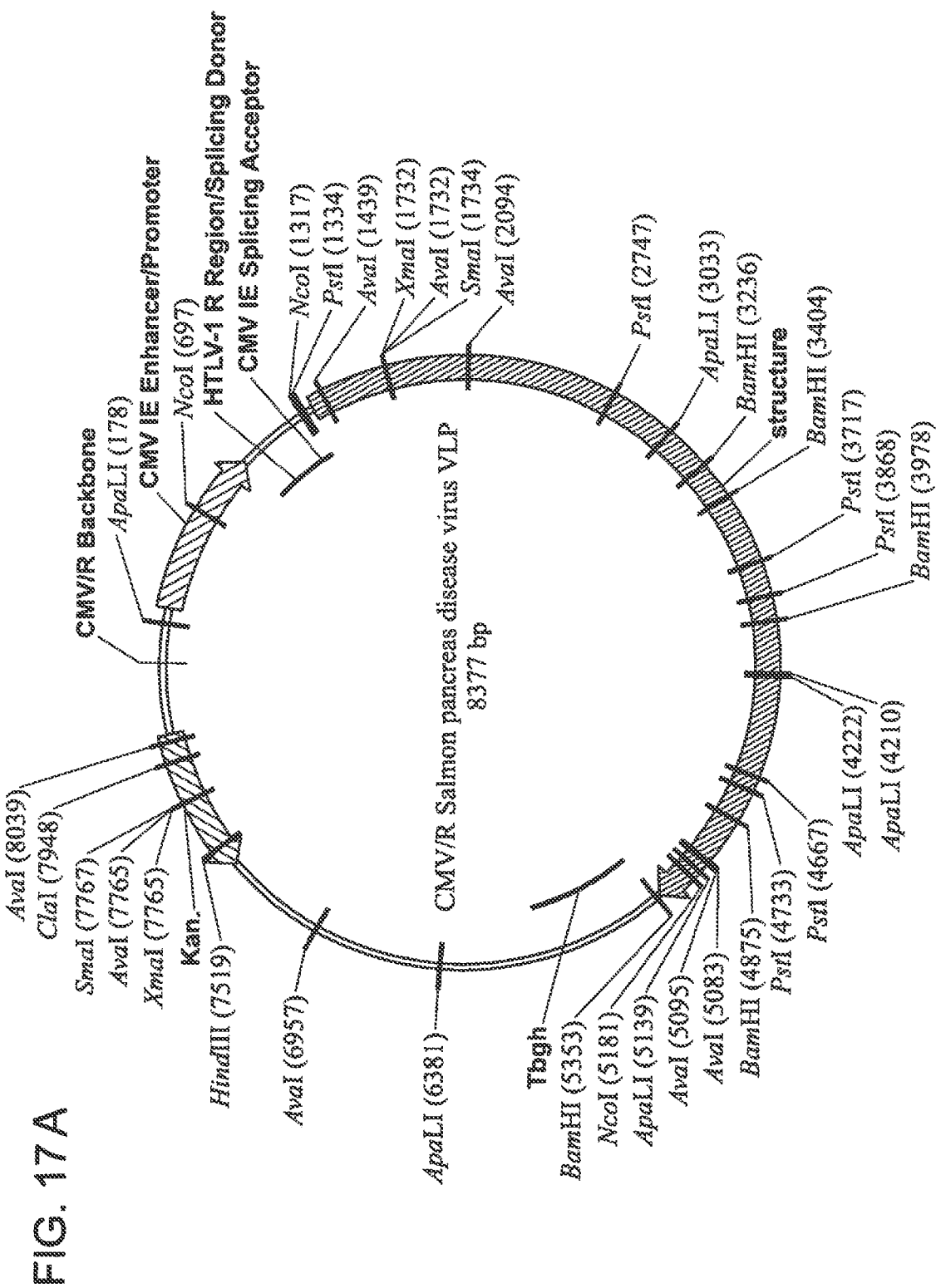
FIG. 17A shows the CMV/R-Salmon pancreas disease virus VLP plasmid.
Figure 18A:
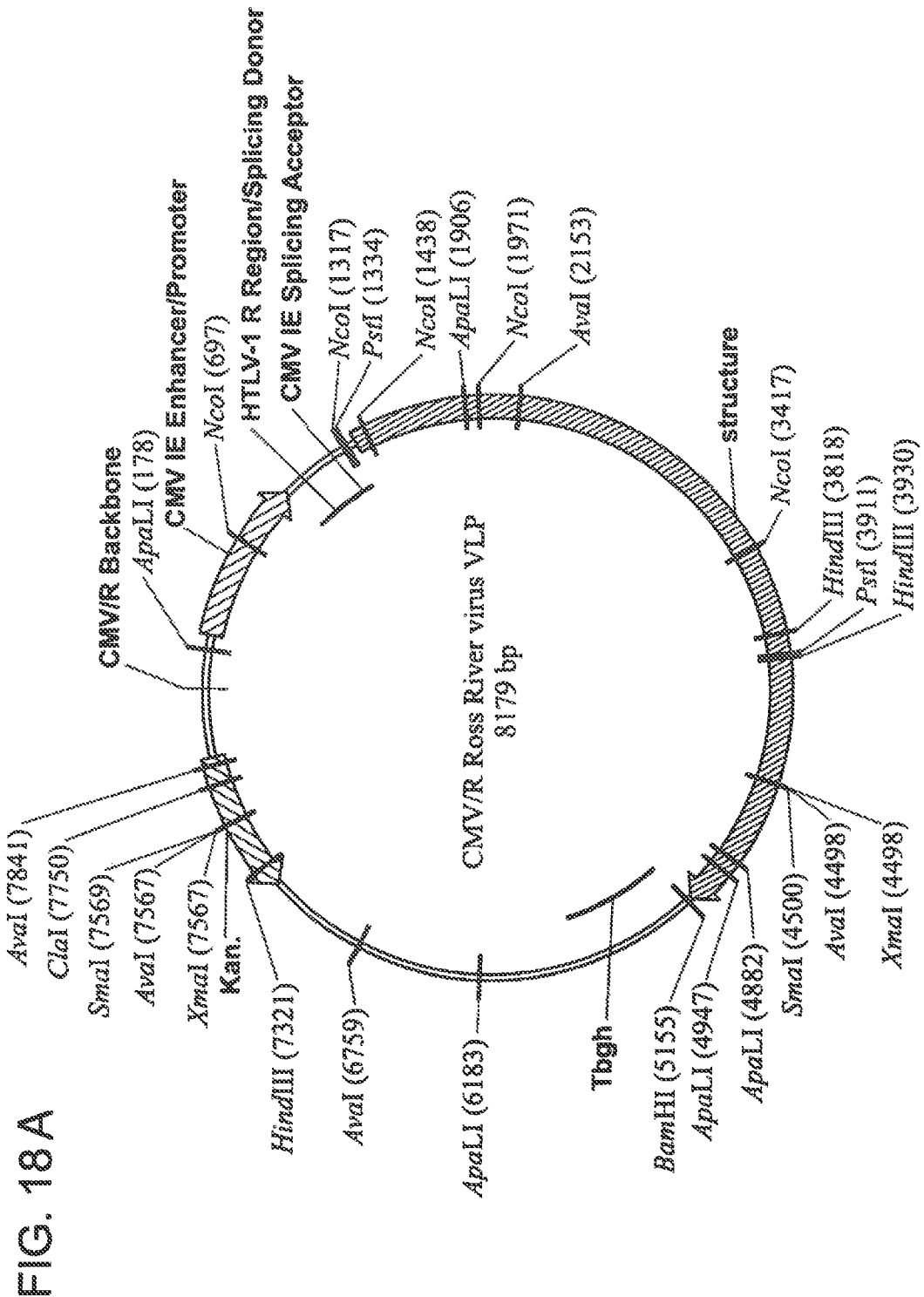
FIG. 18A shows the CMV/R-Ross River virus VLP plasmid.
Figure 21A:
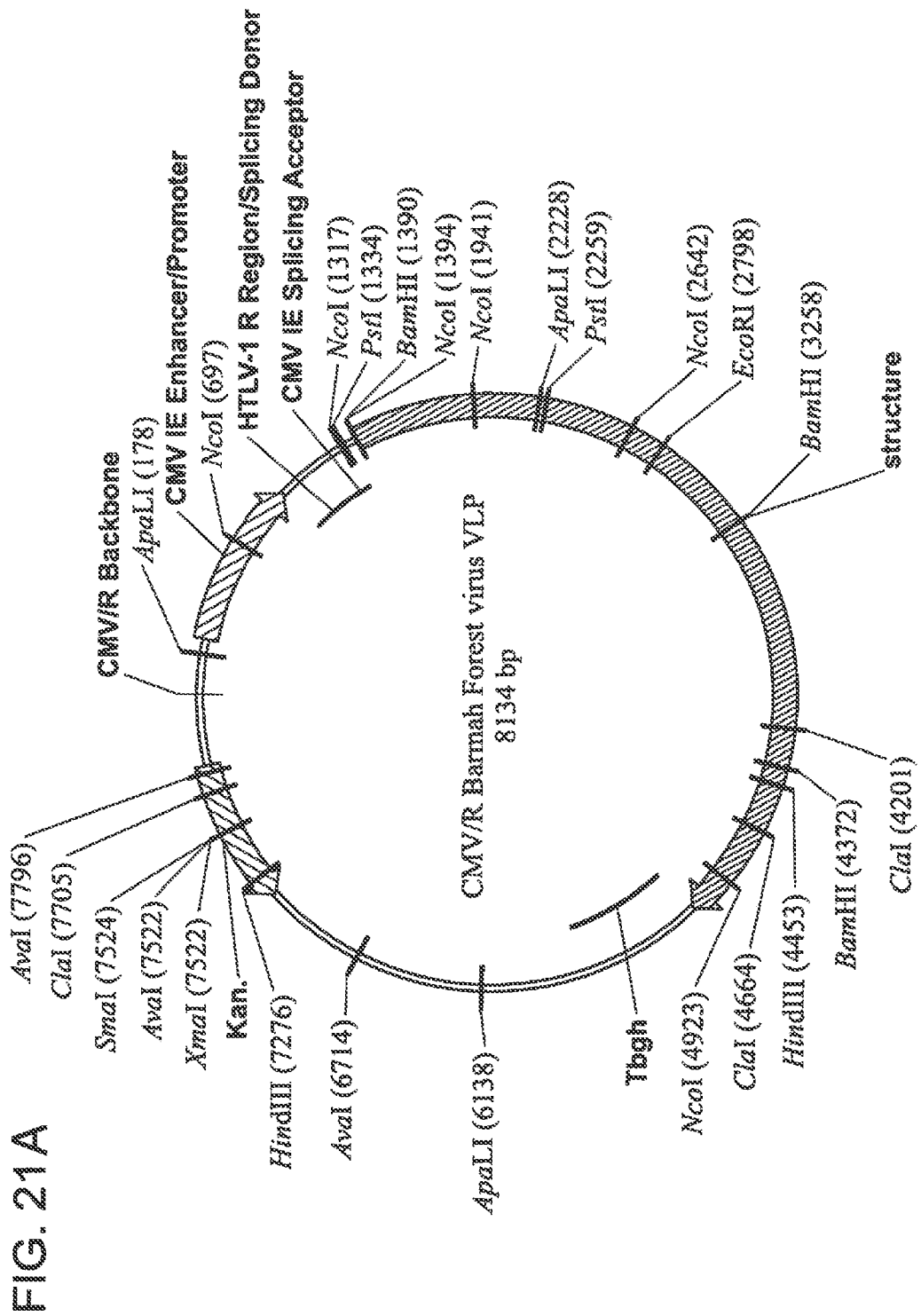
FIG. 21A shows the CMV/R-Barmah Forest virus VLP plasmid.
Figure 22A:
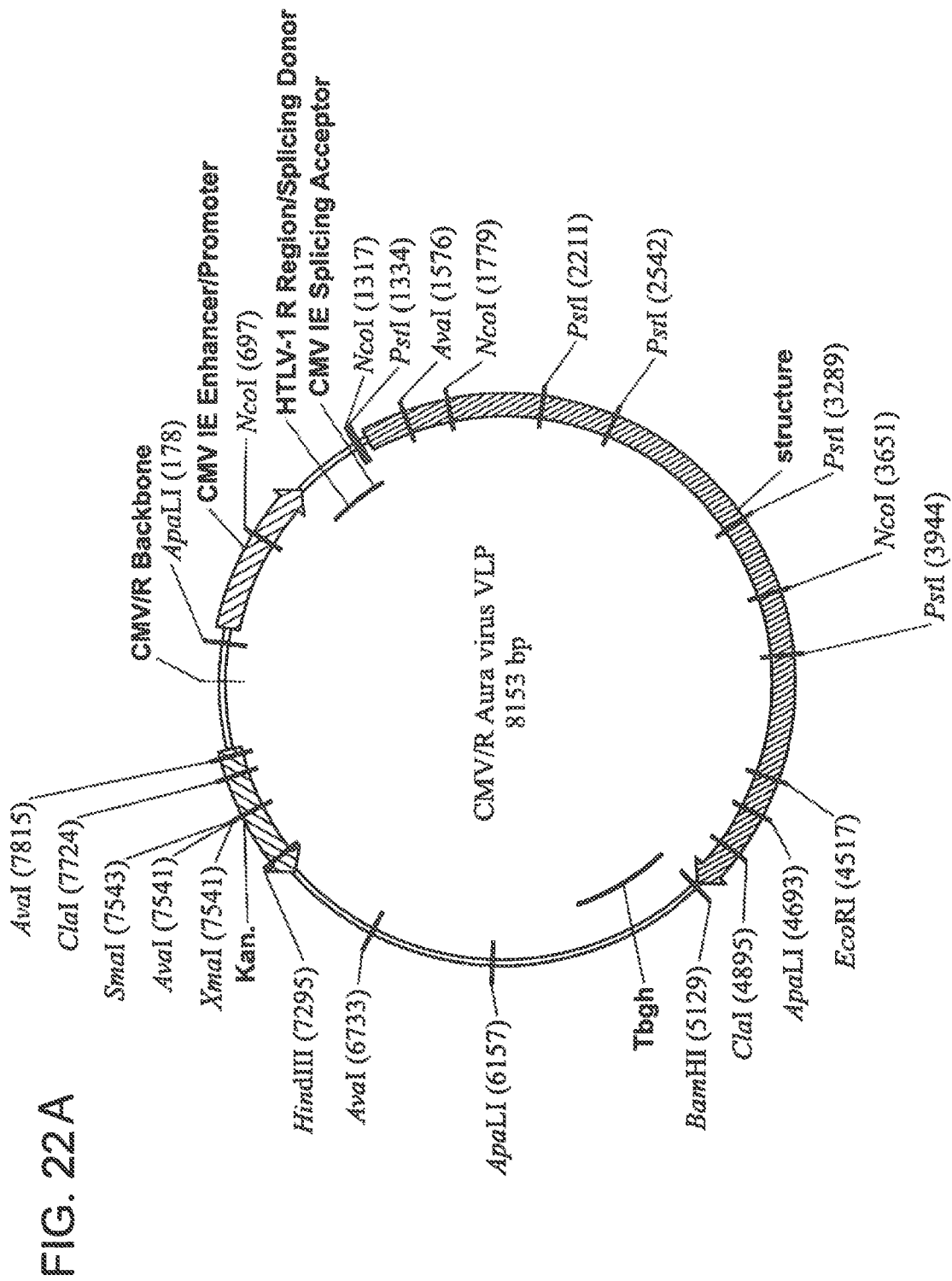
FIG. 22A shows the CMV/R-Aura virus VLP plasmid.
Figure 23A:
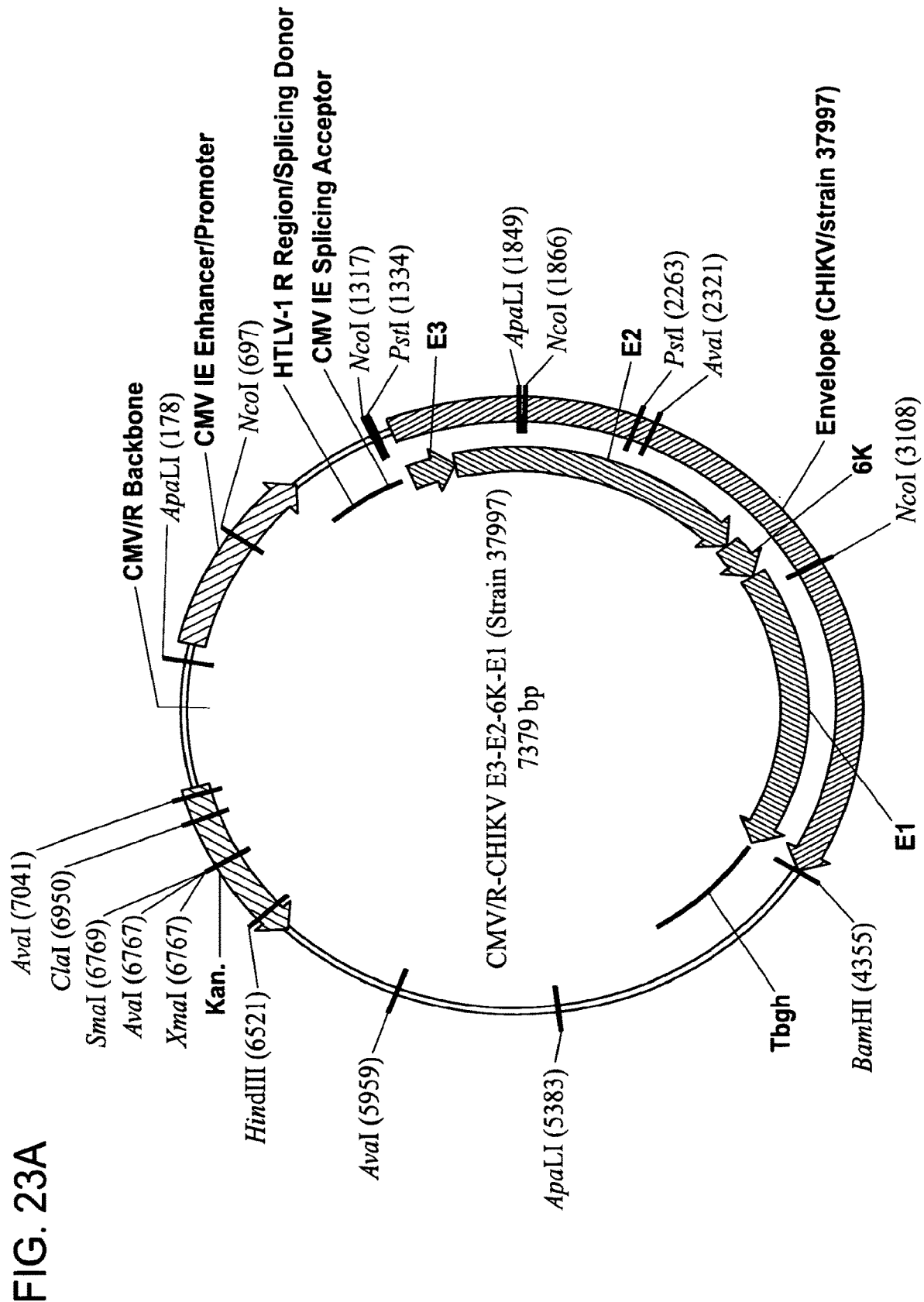
FIG. 23A shows the CMV/R-CHIKV E3-E2-6K-E1 plasmid (Strain 37997) and the sequence of the insert without the capsid (C) (SEQ ID NO:19).
Figure 23B:
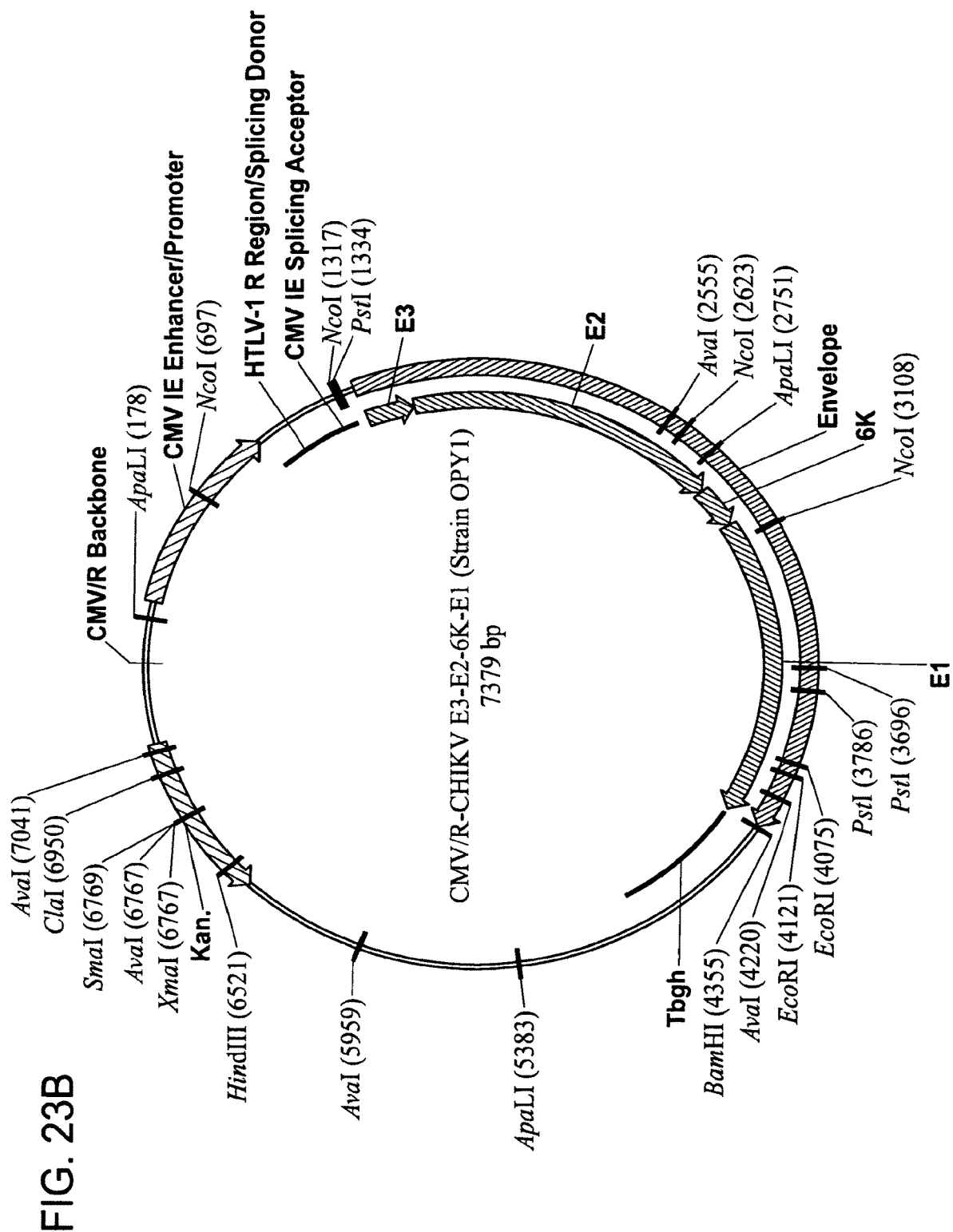
FIG. 23B shows the CMV/R-CHIKV E3-E2-6K-E1 plasmid (Strain OPY1) and the sequence of the insert without the capsid (C) (SEQ ID NO: 20).

Example 1: Lentiviral Vectors Pseudotyped with CHIKV Envelope Mediated Entry Through the Same Mechanism as Wild Type Virus To examine the mechanism and specificity of CHIKV cell entry, lentiviral vector reporters were pseudotyped with glycoproteins from different CHIKV strains that mediate entry into permissive cells. The CHIKV spike on the virion surface is formed by three E1-E2 heterodimers, where E1 glycoproteins mediate fusion and E2 glycoproteins interact with the host receptor. CHIKV E genes expressing the native polypeptide, E3-E2-6K-E1 polyprotein, for the 37997 and for LR2006 OPY-1 strains were inserted into an expression vector (E37997 and EOPY-1) (FIG. 1A, FIGS. 6, 7A, 7B, and 8A-8C). The incorporation of the two CHIKV Es into the pseudotyped lentiviral vectors was verified by buoyant density gradient sedimentation of the virus. Both CHIKV E and HIV-1 Gag had the same buoyant density as lentivirus particles (FIG. 5). The 37997 and LR2006 OPY-1 CHIKV pseudotyped lentiviral vectors infected several permissive cell lines (Sourisseau et al., *PLoS. Pathog.* 3, e89 (2007)) as measured by luciferase reporter activity, while a control devoid of CHIKV envelope proteins did not infect these cell lines (FIG. 1B, left), and infectivity was dose-dependent (FIG. 1B, right).

Figure 1C:
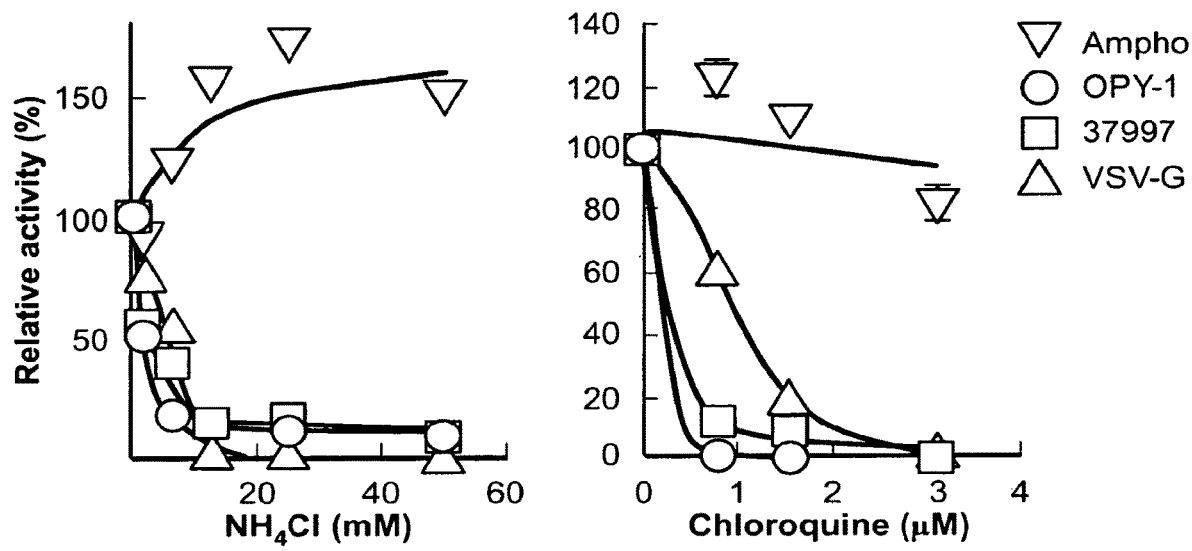
Figure 1D:
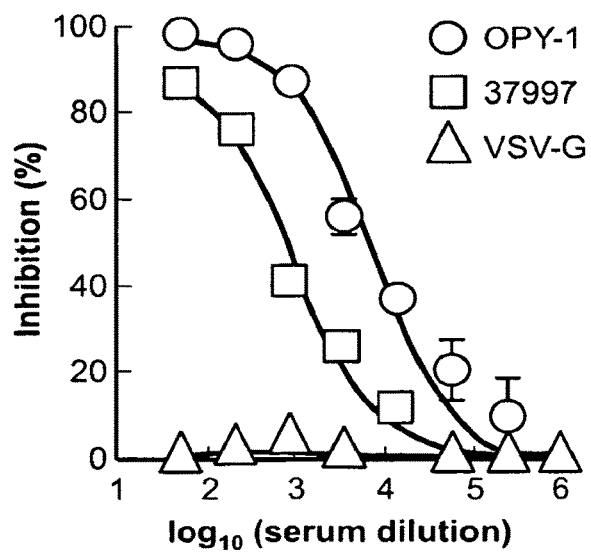

To determine whether entry occurred through the same mechanism as native virus, the pH and endosome dependence of entry was analyzed as described previously (Yang et al., *J. Virol.* 78, 5642 (2004)). CHIKV infects cells through a process of pH-dependent cell fusion. Thus, addition of ammonium chloride or chloroquine, which prevents acidification of the endosome, caused a dose-dependent reduction in CHIKV pseudotyped vector entry (FIG. 1C). Similar inhibition of entry was observed with VSV-G, known to enter in this fashion, but not with amphotropic murine leukemia virus (MuLV) glycoprotein 70, which enters in a pH-independent fashion. These findings demonstrated that lentiviral vectors pseudotyped with CHIKV envelope mediated entry through the same mechanism as wild type virus. Sera from mice injected with a CHIKV strain were next examined. Incubation of immune sera with the CHIKV pseudotyped lentiviral vector but not VSV-G pseudotyped vector inhibited entry (FIG. 1D). The specificity and potency of neutralizing antibodies could therefore be quantified without exposure to infectious virus.

Example 2: VLPs have Morphology of Wild Type Virus

Figure 2B:
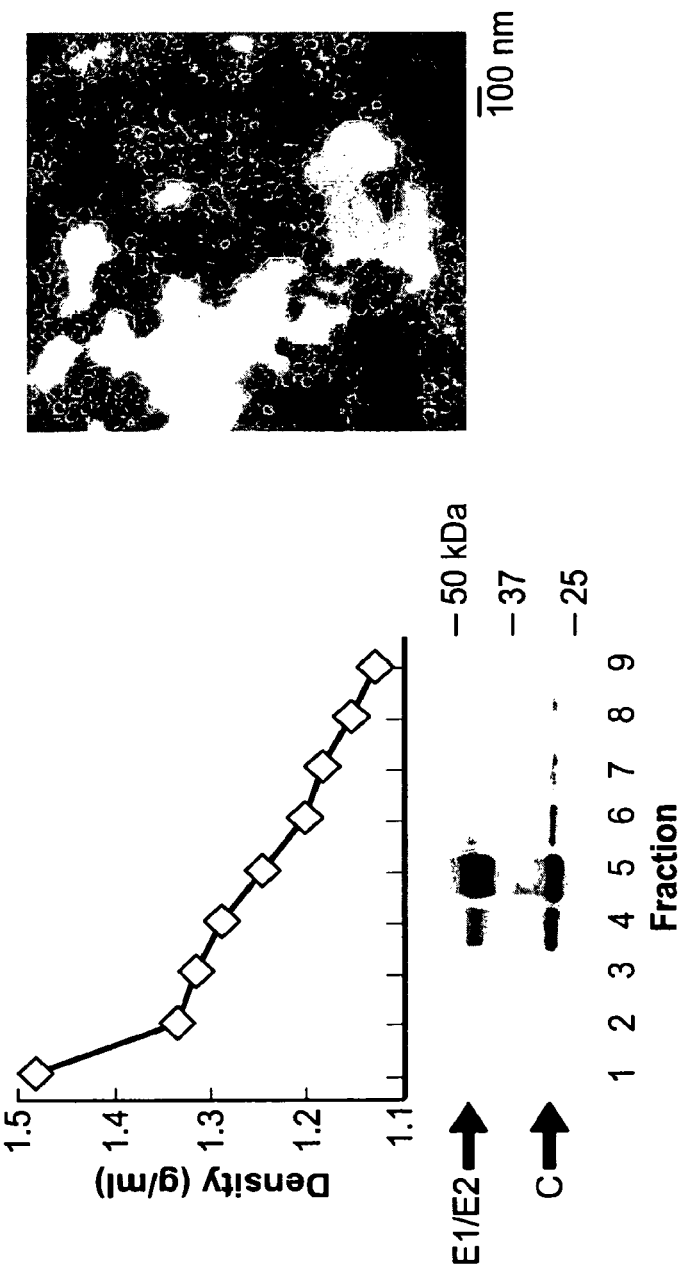

CHIKV encodes 4 nonstructural proteins, NS1, NS2, NS3 and NS4, which are involved in virus replication, and 5 structural proteins, which consist of capsid (C) and envelope proteins (E; E1, E2, E3 and 6K) that are synthesized as polyproteins and are cleaved by capsid autoproteinase and signalases (Strauss, *Microbiol. Rev.* 58, 491 (1994)). Eukaryotic expression vectors encoding C-E3-E2-6K-E1 from strains 37997 and LR2006 OPY-1 (C-E37997 and C-EOPY-1) were analyzed for their ability to give rise to VLP. The plasmids C-E37997 or C-EOPY-1 or the expression vectors described above, E37997 or EOPY-1 (FIG. 2A, upper panel), were transfected into human embryonic kidney (293T) cells, and expression was confirmed by Western blotting (FIG. 2A, lower panel). C and E1/E2 proteins were detected in the supernatant after transfection of the C-E37997 or C-EOPY-1 vector, suggesting that CHIKV VLPs had been generated. VLPs were purified by buoyant density gradient sedimentation. The yield of VLPs from strain 37997 was 10-20 mg/L, approximately 100 times higher than that from strain LR2006 OPY-1; strain 37997 was therefore chosen for further VLP characterization and development. Fractionation of clarified supernatant showed peak incorporation of E1/E2 at a density of 1.2 g/ml (FIG. 2B, left), comparable to the density of wild type CHIKV. Examination of the purified fraction from strain 37997 by electron microscopy revealed VLPs with the same morphologic appearance as wild type virus (FIG. 2B, right).

Cryoelectron microscopy and three dimensional image reconstruction assuming icosahedral symmetry showed that the VLPs had an external diameter of 65 nm and a core diameter of 40 nm (FIG. 2C, left). The potent immunogenic E1/E2 glycoproteins are organized into 240 heterodimers, assembled into 80 glycoprotein spikes arranged with T=4 quasi symmetry on the surface of the VLPs (FIG. 2C, left), closely similar to the structure of Sindbis virus (FIG. 2C, right). In addition, the organization of the nucleocapsid core is also remarkably similar to that of other alphaviruses.

Figure 3A:
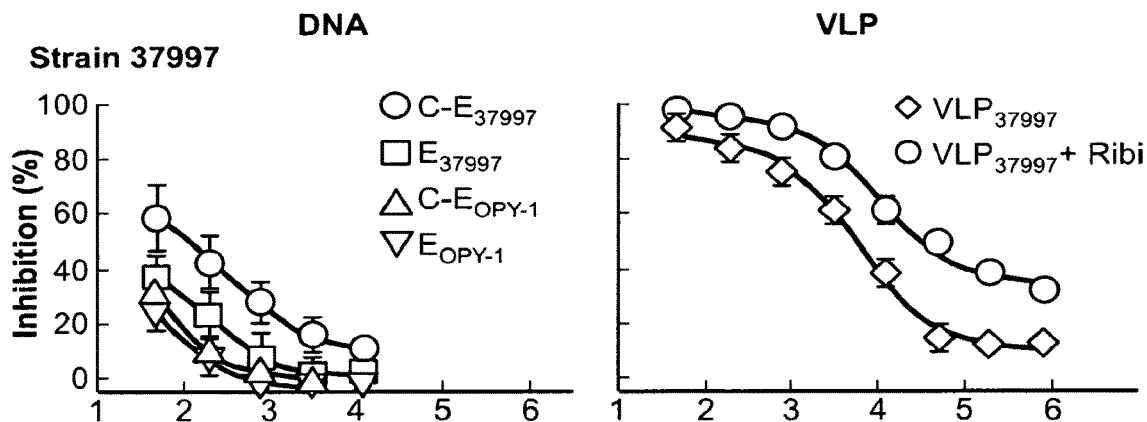
FIGS. 3A-3D are graphs showing the neutralization of CHIKV strains 37997 and LR2006 OPY-1 after DNA or VLP vaccination in mice and monkeys. Sera from immunized mice 10 days after the final immunization were tested with CHIKV strain 37997 (FIG. 3A) or LR2006 OPY-1 (FIG. 3B) E pseudotyped lentiviral vectors. Mice were immunized with the indicated DNA or $_{VLP37997}$. Each C-E or E (strain 37997 and LR2006 OPY-1, respectively) plasmid was injected at 0, 3 and 6 weeks. $_{VLP37997}$ with or without Ribi adjuvant was injected at 2 and 6 weeks. The experiment was performed in triplicate. The symbols show the average of the five mice and bars show the standard error of the mean. The curve fit was calculated by Prism software.
Figure 3B:
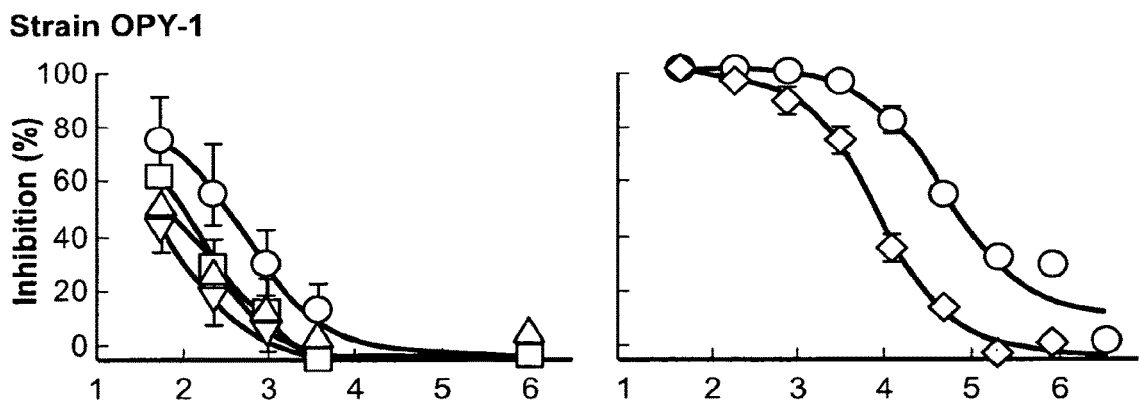

Example 3: VLPs Induced a More Potent Neutralizing Antibody Response to CHIKV than DNA Vaccines The immunogenicity of DNA and VLP vaccines was determined in mice immunized with DNA vaccines encoding C-E or E (strains 37997 and LR2006 OPY-1) or VLPs from strain 37997 (VLP37997) in the presence or absence of Ribi adjuvant. Mice injected with VLPs with adjuvant generated the highest titer neutralizing responses against both the homologous strain 37997 (FIG. 3A, right panel; IC50, 1:10, 703) and the heterologous strain LR2006 OPY-1 (FIG. 3B, right panel; IC50, 1:54, 600). While immunization with the plasmids encoding C-E and E from both strains elicited neutralizing responses, these responses were 100-fold lower than the VLP-immunized mice (FIG. 3A, B; left panel). These results indicate that VLPs elicited a more potent neutralizing antibody response than DNA vaccines.

Figure 3C:
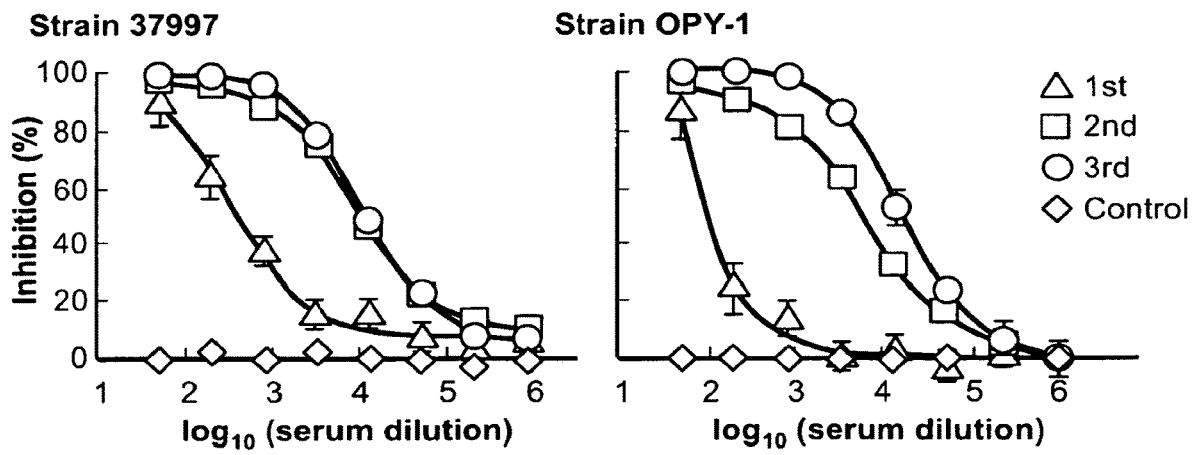
Figure 3D:
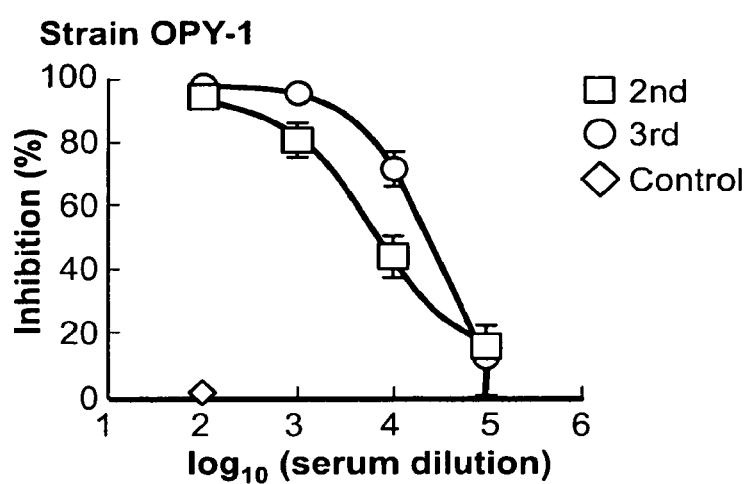

To characterize VLP-induced immune responses in a model with strong predictive value for humans, rhesus macaques were immunized with VLPs. Monkeys were injected with VLP37997 or PBS alone as a control. Sera from immunized and control monkeys were tested against CHIKV strain 37997 and LR2006 OPY-1 pseudotyped lentiviral vectors. All non-human primates (NHP) immunized with VLPs developed substantial neutralizing activity to both homologous and heterologous strains after primary immunization that increased after boosting (FIG. 3C; left panel: strain 37997, right panel: strain LR2006 OPY-1). To confirm that these antibodies neutralized infectious virus, a plaque reduction neutralization test (PRNT) was performed against the CHIKV LR2006 OPY-1. The antisera from the immunized monkeys elicited neutralizing antibody responses against LR2006 OPY-1 at titers that exceeded 1:40,000 (FIG. 3D). These data suggested that neutralizing antibodies using pseudotyped lentiviral vectors correlated with the PRNT assay, and that all immunized monkeys generated potent neutralizing antibody responses against CHIKV.

Figures 4A, 4B:
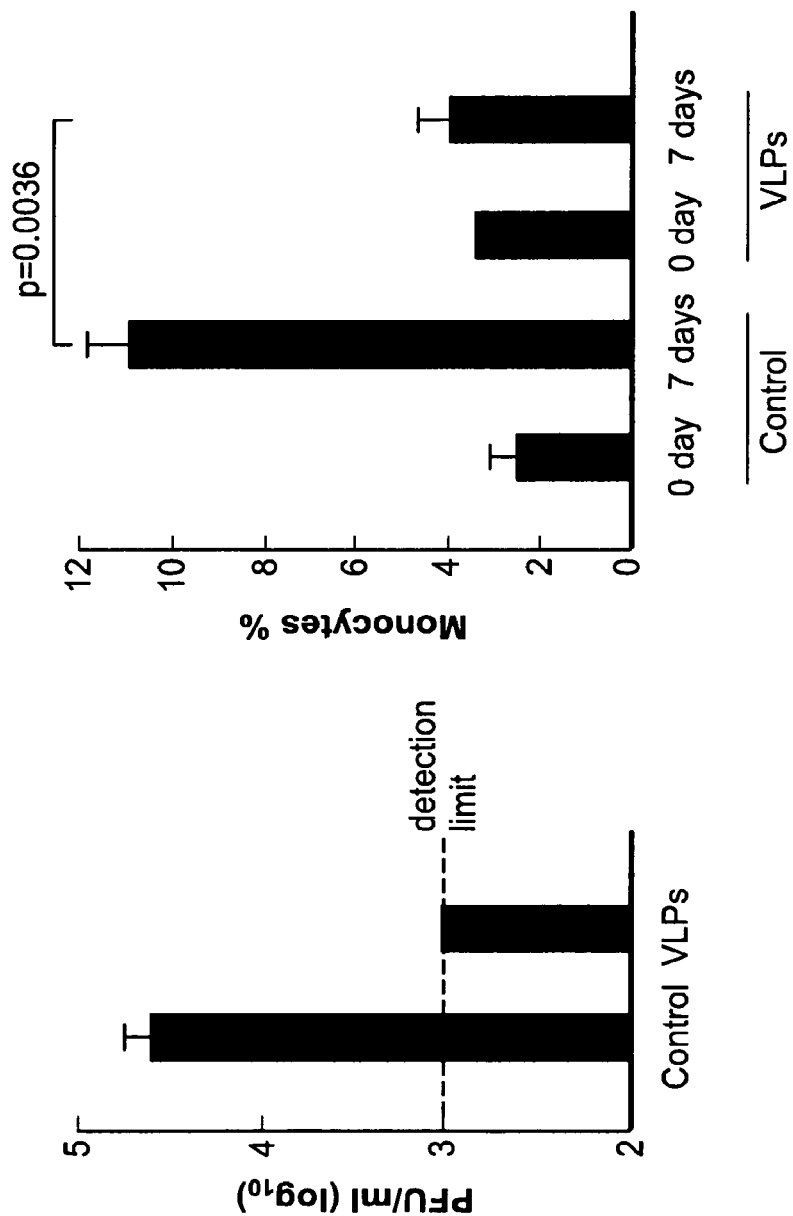
FIGS. 4A-4D are graphs showing protection against CHIKV LR2006 OPY-1 challenge in monkeys immunized with VLPs and in a CHIKV mouse model after passive transfer of purified IgG.

Example 4: Primate VLP Immunization Protected Against Viremia and Inflammatory Consequences of CHIKV Infection The ability of the VLP vaccine to protect against infection was determined by intravenous challenge of monkeys immunized with VLPs or controls using a high titer LR2006 OPY-1 virus stock 15 weeks after the final immunization. Similar to humans, infection in the NHP resulted in non-lethal viremia and a pro-inflammatory response as measured by an increase in monocyte counts. The control monkeys showed viremia beginning at 6 hours and lasting until 72 hours after challenge, while all of the immunized monkeys controlled the challenge virus completely (FIG. 4A). Similarly, the monocyte counts in control monkeys increased markedly relative to vaccinated monkeys by 4 days after challenge (FIG. 4B, Control vs. VLPs; p=0.0036). These data indicated that immunization protected against viremia as well as the inflammatory consequences of infection. To define the mechanism of protection in these animals, the question of whether immune IgG could protect against lethal challenge was examined using an adoptive transfer model.

Figures 4C, 4D:
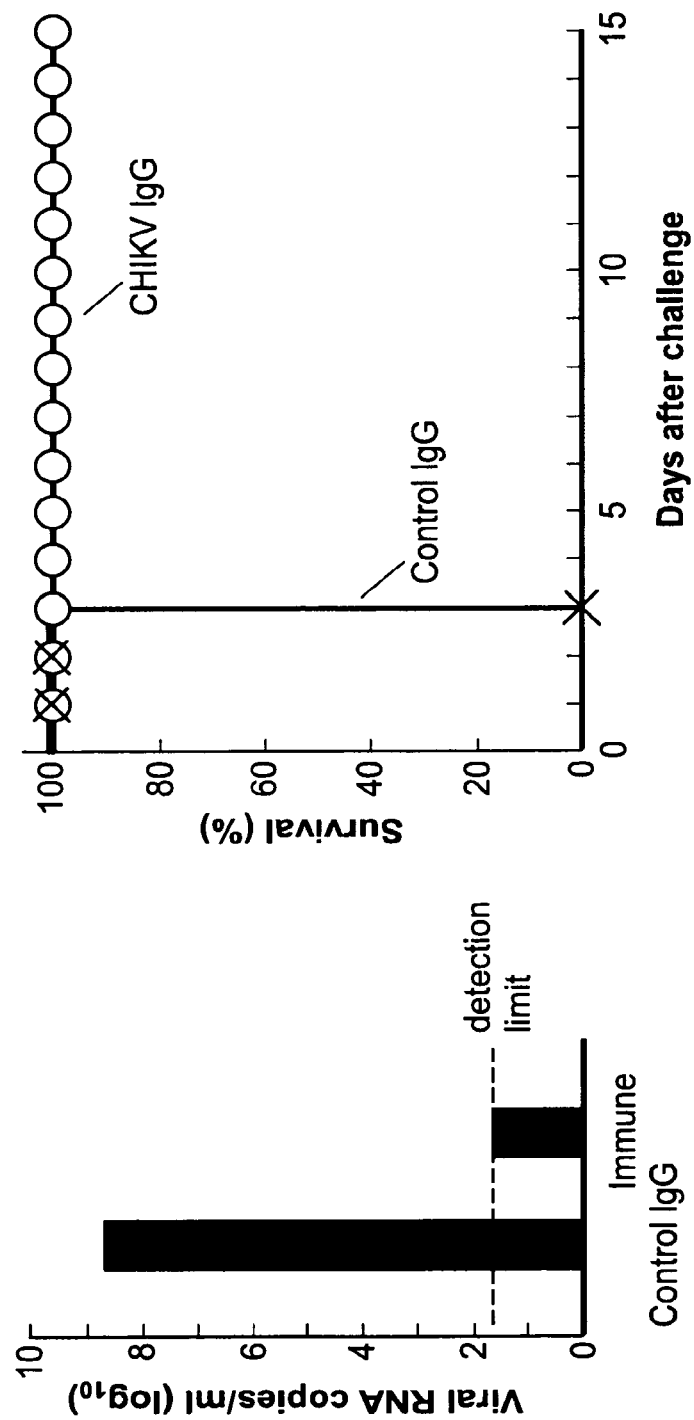

Example 5: Humoral Immune Responses Induced by CHIKV VLPs Conferred Protection Against CHIKV Infection Previous studies have shown that immunodeficient mice with defective type-I IFN signaling developed severe infection, displaying symptoms and tissue tropism analogous to humans, and providing a model to evaluate immune mechanisms of protection. Purified total IgG from immune or control monkeys was passively transferred into these mice. The recipient mice were challenged intradermally 24 hours after IgG transfer with a lethal dose of LR2006 OPY-1. Recipients of purified CHIKV immune IgG demonstrated no detectable viremia after infection and were completely protected from lethality (FIGS. 4C, D). In contrast, all mice that received purified IgG from control monkeys showed severe infection and viremia, and all died. These results indicate that humoral immune responses induced by CHIKV VLPs conferred protection against CHIKV infection.

As reported herein, VLPs and plasmid DNA vaccines against CHIKV were evaluated for their ability to elicit cross-strain neutralizing antibodies. Immunization with VLPs showed cross-strain reactivity and 100-fold higher titers than DNA vaccines, and monkeys showed protection against CHIKV infection at a dose higher than that likely to be encountered in the field. Moreover, passively transferred antibody from monkeys immunized with VLPs protected against a lethal challenge in a relevant murine model, which suggests that the humoral response is important for protection against CHIKV. The current outbreaks of CHIKV fever have occurred largely in Southern Asia and underscore the need for a human vaccine. These infections represent the spread of a virus first recognized in Kenya in 2004 before dissemination to several islands in the Indian Ocean in 2005-2006. The Reunion Island outbreak alone infected 244,000 people with an overall seroprevalence of 35%. The virus then spread to other continents, and by 2008 was reported in 37 countries with an estimated 1.4=6.5 million cases in India, Africa, Europe and Southeast Asia.

In 2009 the number of cases has continued to increase, in part because the current epidemic strain of CHIKV has adapted to a new vector, the Asian tiger mosquito, Ae. albopictus, which can survive in more temperate climates, including Europe and the United States. CHIKV continues to cause substantial morbidity and has resulted in significant economic losses. While there were no reports of mortality in previous chikungunya epidemics, more than 260 deaths during the latest outbreak were directly attributed to the virus. To date, there has been limited success in developing a safe and effective CHIKV vaccine. A live CHIKV vaccine candidate caused transient arthralagia in volunteers. Other efforts, which include a live attenuated vaccine, a formalin-killed vaccine, a Venezuelan equine encephalitis/CHIKV chimeric live attenuated vaccine and a consensus-based DNA vaccine (Muthumani et al., Vaccine 26, 5128 (2008)) have not yet proven to be both safe and effective. Although CHIKV strains vary widely, individual strains are antigenically related, so a vaccine that works against heterologous strains may be achieved (Harrison et al., Am. J Trop. Med. Hyg. 16, 786 (1967)). The safety and efficacy of VLP vaccines in general make them promising candidates for further study.

VLPs are known to be highly immunogenic and elicit higher titer neutralizing antibody responses than subunit vaccines based on individual proteins. Such VLPs authentically present viral spikes and other surface components in a repetitive array that effectively elicits recognition by B-cells to stimulate antibody secretion. This recognition leads to B cell signaling and MHC class II up-regulation that facilitates the generation of high titer specific antibodies. VLPs from other viruses, including hepatitis B virus (HBV) and human papillomavirus (HPV), elicit high titer neutralizing antibody responses that contribute to protective immunity in humans.

The vaccines described herein represent the first use of recombinant VLPs to prevent infection by alphaviruses. The spread of mosquito species worldwide has been aided by changes in trade, travel or global climate and may potentially cause other alphavirus outbreaks. This approach to vaccine development may prove useful for other alphaviruses of increasing concern, including Western, Eastern, and Venezuelan equine encephalitis viruses, o'nyong-nyong virus and Ross River virus.

The results reported herein were obtained using the following methods and materials.

Vector Construction

Plasmids encoding the structural polyproteins C, E1, E2, E3 and 6K (strains 37997 and LR2006 OPY-1, GenBank EU224270) (FIG. 25) and EU224268 (FIG. 24), respectively) were synthesized as previously described (Yang et al., Science 317, 825 (2007)) (GeneArt, Regensburg, Germany). Plasmids encoding the polyproteins E3, E2, 6K, and E1 were amplified by PCR using the sense primer 5' GCTCTAGACACCAT-GAGCCTCGCCCTCCCGGTCTTG 3' (SEQ ID NO:26) and antisense primer 5' TGGATCCTCATT-AGTGCCTGCTAAACGACA 3' (37997) (SEQ ID NO:27) and the sense primer 5' GCTCTAGACACCAT-GAGTCTTGCCATCCCAGTTATG 3' (SEQ ID NO:28) and antisense primer 5' TGGATCCTCATTAGTGCCTGCT-GAACGACA 3' (LR2006 OPY-1) (SEQ ID NO:29). XbaI and BamHI sites were inserted for cloning. Each fragment was digested with XbaI/BamHI and inserted into a eukaryotic expression vector under the control of a cytomegalovirus enhancer/promoter, CMV/R (Yang et al., Science 317, 825 (2007)) (C-E37997, E37997 and $_{EOPY-1}$). To confirm expression of CHIKV C and E proteins, 293T cells were transfected using a FuGENE™ 6 Transfection Reagent kit (Roche Diagnostics GmbH, Germany) with 3 μg of the plasmid DNAs, following the manufacturer's recommendations.

Cell Culture 293T and 293A (human embryonic kidney cells), Vero (African green monkey kidney epithelial cells), HeLa (human cervical adenocarcinoma), A549 (human lung carcinoma) and BHK (baby hamster kidney cells) were cultured in Dulbecco's modified Eagle's medium (DMEM; GIBCO BRL) containing 10% heat-inactivated fetal bovine serum (FBS) (GIBCO BRL).

Production of Pseudotyped Lentiviral Vectors

Lentiviral vectors expressing glycoproteins from different CHIKV strains were created. The recombinant lentiviral vectors expressing a luciferase reporter gene were produced as previously described (Naldini et al., *Proc. Natl. Acad. Sci. USA* 93, 11382 (1996), Yang et al., *Science* 317, 825 (2007)). Briefly, 293T cells were co-transfected with 500 ng CHIKV E plasmid from either strain ($_{E37997}$ or $E_{OPY-1}$), 7 μg of a transducing vector encoding a luciferase reporter gene (pHR'CMV-luciferase plasmid), and 7 μg of a packaging plasmid expressing human immunodeficiency virus-1 (HIV-1) structural proteins (pCMVAR8.2). 2 μg of vesicular stomatitis virus glycoprotein (VSV-G), 2 μg of pNGVL-4070A amphotropic MuLV gp70 expression vector or 500 ng of empty vector served as positive and negative controls for these pseudotyped reporters respectively. After a calcium phosphate transfection (Invitrogen, Carlsbad, CA) overnight, the culture media was replenished with fresh media. 48 hours later, supernatants were harvested, filtered through a 0.45 μm syringe filter, stored in aliquots, and frozen at −80° C. The viruses were standardized by the amount of HIV-1 Gag p24. CHIKV pseudotyped lentiviral vectors harvested 72 h after transfection were normalized according to HIV-1 Gag p24 levels before infection, as previously described (Yang et al., *Science* 317, 825 (2007)).

Neutralization of CHIKV E Pseudotyped Lentiviral Vectors by Mouse and Monkey Antisera The neutralization assay was performed as described previously (Yang et al., *Science* 317, 825 (2007)). A total of $10^4$ 293 A cells were plated into each well of a 96-well dish one day prior to infection. CHIKV E-pseudotyped lentiviral vectors encoding luciferase were first titrated by serial dilution. Similar amounts of pseudotyped lentiviral vectors (with p24 levels of approximately 50 ng/ml) were then incubated with the indicated dilutions of mouse antisera for 60 minutes at room temperature prior to adding the virus: sera solution to 293A cells ($10^4$ cells/well in a 96-well dish, 50 μl/well, in triplicate). Sera from non-immune mice or monkeys were used as a negative control. After a 24 hour incubation, cells were lysed using cell lysis buffer (Cell Signal) and the luciferase activity was measured using Microbeta® JET (PerkinElmer, Turku, Finland) following incubation with "Luciferase assay reagent" (Promega, Madison, WI), according to the manufacturer's protocol. Inhibition values were calculated as follows: inhibition (%)=[1−(luciferase activity (cps) in pseudotyped lentiviral vector infected cells incubated with the indicated dilutions of mouse antisera)/(luciferase activity (cps) in pseudotyped lentiviral vector infected cells incubated with the same dilutions of non-immune mouse serum)]×100. The $_{IC50}$ was calculated with Prism software (version 5).

Electron Microscopy

The morphology of the VLPs was examined by the Image Analysis Laboratory at the National Cancer Institute. VLPs were purified by Optiprep density centrifugation and were then fixed in 4% formaldehyde in PBS. Negative-stain electron microscopy for viral diagnosis has been described previously (Palmer and Martin, Electron Microscopy in Viral Diagnosis (CRC Press, Boca Raton, FL, 1988)). Briefly, 1.0 μl of the sample was placed onto a carbon-coated Formvar-filmed copper grid (Tousimis Research Corp., Rockville, MD) and VLPs allowed to attach. The VLPs were negatively stained by addition of 2 μl of 1% PTA solution (phosphotungstic acid, pH 7.0) (Fisher Scientific Co., Fairlawn, NJ). The grid was then examined by electron microscope (Hitachi H7000, Tokyo, Japan) operated at 75 kV. Digital images were taken by a CCD camera (AMT, Danvers, MA).

Cryo-Electron Microscopy and Image Analysis

Chikungunya VLPs were flash-frozen on holey grids in liquid ethane. Images were recorded at 47K magnification with a CM300 FEG microscope with electron dose levels of approximately 20 $e^{i}$/Å$^2$. All micrographs were digitized at 6.35 μm pixel$^{i1}$ using a Nikon scanner. Individual particle images were boxed using the program e2boxer in the EMAN2 package (Tang et al., *J Struct. Biol.* 157, 38 (2007)). CTF parameters were determined and phases were flipped using the CTFIT program from the EMAN package (Ludtke et al., *J Struct. Biol.* 128, 82 (1999)). An initial model was constructed in EMAN using assigned 2-, 3-, and 5-fold views and was refined in EMAN assuming icosahedral symmetry. The number of particles incorporated into the final reconstruction was 1489, giving a final resolution of 18 A based on a 0.5 Fourier shell correlation threshold.

Buoyant Density Gradient Sedimentation Analysis and Purification of VLPs

Buoyant density gradient analysis and purification of VLPs was performed as described previously (Akahata et al., *J. Virol.* 79, 626 (2005)). Briefly, a 293-derived suspension cell line, 293F ($2.5\times10^8$ cells) (Invitrogen) was transfected with 293fectin transfection reagent (Invitrogen) and 125 μg of $_{C\text{-}E37997}$ plasmid following the manufacturer's recommendations. The supernatants were harvested 72 h after transfection and filtered through a 0.45 ʒm pore size filter, then layered onto a 60% Optiprep (Iodixanol) medium (Invitrogen) and centrifuged at 50,000×g for 1.5 h with a Surespin 630 rotor (Sorvall). The supernatants were removed to leave 4 ml above the virus band and mixed to a 20% final concentration of OptiPrep. A density gradient was formed by centrifugation at 360,000×g for 3.5 hr with an NVT100 rotor (Beckman). 500 μl of each fraction was collected, weighed, and the densities of the fractions were plotted. 20 μl of each fraction was separated on a 4%-15% SDS-PAGE gel, transferred onto an Immobilon-P membrane, and blotted with sera from mice injected with the CHIKV strain S-27 (ATCC, VR-1241AF) and goat anti-mouse immunoglobulins linked to horseradish peroxidase (Santa Cruz Biotechnology).

Immunizations and Challenge of Mouse and Monkeys

Nineteen μg of VLPs (equivalent to approximately 10 μg of E1/E2) in 60 μl normal saline were mixed with 60 μl of Ribi solution (Sigma Adjuvant system, Sigma-Aldrich) per mouse following the manufacturer's recommendations. Female 6- to 8-week-old BALB/c mice were injected in the right and left quadriceps muscles with VLPs in normal saline or Ribi in 120 μl total volume, two times at weeks 2 and 6. For DNA vaccination groups, the mice were injected in the right and left quadriceps muscles with a total of 15 μg of purified plasmid C-$E_{37997}$, $E_{37997}$, C-$E_{OPY\text{-}1}$ or $E_{OPY\text{-}1}$ suspended in 100 μl of normal saline three times at weeks 0, 3 and 6. Five mice/group were injected. 10 days after the last injection, sera and spleen were collected.

In the monkey experiments, rhesus macaques (*Macaca mulatta*) weighing 3-4 kg were injected intramuscularly in the anterior quadriceps with either twenty μg of VLPs in 1 ml PBS (VLP group) or 1 ml PBS alone (control group) at weeks 0, 4 and 24. Six monkeys/group were injected. Blood was collected to measure antibody titers on days −14, 0, 10, 28, 38, 56, 70, 161 and 178. The monkeys (n=3 per group, randomly selected from each group) were challenged with $10^{10}$ PFU of CHIKV (strain LR2006 OPY-1) by intravenous injection. Blood was collected to measure viremia at 0, 6, 24, 48, 72, 96, 120 and 168 hours. The monkeys were sacrificed at 168 h after challenge. The whole blood cells were measured using a hematology analyzer (IDEXX Laboratories, Inc., Westbrook, Maine). Bleeds were EDTA-anticoagulated using 20-22 gauge needles and either syringes or vacuum tubes. The maximum blood volume removed did not exceed 20% (12 ml/kg) per month, with no more than 15% (9 ml/kg) removed during any single draw.

All animal experiments were reviewed and approved by the Animal Care and Use Committee, Vaccine Research Center (YRC), National Institute of Allergy and Infectious Diseases and performed in accordance with all relevant federal and National Institutes of Health guidelines and regulations.

Virus Preparation

CHIKV (strain LR2006 OPY-1) was prepared and the virus titers were determined as previously described (Tsetsarkin et al., PLoS. Pathog. 3, e201 (2007) and Pastorino et al., J Virol. Methods 124, 65 (2005)). Briefly, viral RNA transcribed from plasmid CHIK-LR is was transfected into BHK-21 cells by electroporation. The supernatants from the transfected cells were aliquotted and the stock virus was titrated and tissue culture infectious dose 50% ($TCID_{50}$) endpoint titers were determined using Vero cells. To produce virus for vertebrate challenge, C6/36 (*Aedes albopictus*) cells grown to confluence in T150 flasks were infected with stock virus at a multiplicity of infection of 0.03. Supernatants were harvested at 48 hrs post-infection, aliquotted and titrated to determine $TCID_{50}$ endpoint titers on Vero cells.

Plaque Assay

Serum samples were tested for CHIKV neutralizing antibody by a standard plaque reduction neutralization test (PRNT). Briefly, monkey sera were heat inactivated at 56° C. for 30 minutes and diluted in virus diluent (PBS/5% BSA). Diluted serum samples were mixed with an equal volume of 40 PFU CHIKV (strain LR2006 OPY-1) and incubated for 1 hr at 37° C. Six-well plates of confluent Vero cells were inoculated with 200 µl of the serum-virus mixtures in duplicate and incubated at 37° C. for 1 hr. Plates were overlaid with 3 ml of medium containing 0.9% agarose (Lonza Rockland, Rockland, ME) and incubated at 37° C. in a 5% $CO_2$ incubator for 2 days. A second overlay medium containing neutral red and 1% agarose was then added and the plates were incubated overnight before plaques were visualized and counted. The viremia in the monkeys after challenge was measured by plaque assay. Six-well plates of confluent Vero cells were inoculated with 200 µl of the serum-PBS mixtures in duplicate. The serum dilutions were 1:200, 1:400, 1:800, 1:1000, 1:10,000 and 1:100,000, since at lower dilutions toxicities were observed in the cells (detection limit 1:200 dilution=1000 PFU/ml).

Passive Transfer of Immunoglobulin and Challenge in IFNα/ßR$^{−/−}$ Mice

IFNα/ßR$^{−/−}$ mice were kindly given by Robert Seder and Daniel D. Pinschewer. IgG was purified from the serum in monkeys immunized with CHIKV VLPs or injected with PBS (control) using a HiTrap™ Protein G HP column (GE Healthcare) following the manufacturer's recommendations. IgG was further purified using a Melon Gel IgG Purification Kit (Pierce) following the manufacturer's recommendations. Purified IgG was dialyzed 3 times against PBS. 2 mg of purified IgG (from approximately 200 µl of serum) was administered intravenously into each recipient IFNα/ßR$^{−/−}$ mouse by tail vein injection 24 h before challenge. The mice were challenged with 30 PFU of CHIKV (strain LR2006 OPY-1) by intradermal injection.

Detection of CHIKV RNA by Quantitative RT-PCR

For RNA isolation, serum samples were spun down at 10,000×g for 1 hr, liquid poured off and 1 ml of RNA-STAT 60 (Isotex Diagnostics, Friendswood, TX) added. Samples were then incubated at RT for 5 min and resuspended in 250 µl of chloroform by vortexing. The samples were spun down at 10,000×g for 1 hr, the aqueous top-layer removed, 0.5 ml isopropanol and 10 µl tRNA (10 µg/ml) added and precipitated overnight at −20° C. Samples were spun down for 1 hr, washed with cold 75% ethanol and spun again for another hour. RNA was resuspended in 30 µl RNAse-free water. For RT-PCR, 10% RNA was added to TaqMan reagents (Applied Biosystems, Foster City, CA) along with primers and probe (listed below) and amplified in a 7700 Sequence Detection System (Applied Biosystems). Briefly, the sample was reverse-transcribed at 48° C. for 30 min., held at 95° C. for 10 min, then run for 40 cycles of 95° C. for 30 s and 60° C. for 1 min. The signal was compared to a standard curve of known concentrations of plasmid containing the LR2006 OPY-1 sequence starting at $10^7$ down to 1 copy/mL and multiplied by 10, giving a detection range from 40-$10^8$ copies/mL. All samples were performed in triplicate. The primers and probe were designed to bind to a highly conserved region on the E1 structural protein gene. Primer sequences: CHIK-F 5' AAGCTCCGCGTCCTTTACCAAG 3' (SEQ ID NO:30) and CHIK-R 5' CCAAATTGTC CTGGTCTTCCT3' (SEQ ID NO:31). Probe sequence: CHICK-P FAM-CCAATGTCTTCAGCCTGGACACCT-TTAMRA (SEQ ID NO:32) as described previously (Huang et al., *J. Virol.* 78, 12557 (2004); Pastorino et al., J Virol. Methods 124, 65 (2005)).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

SEQUENCE LISTING

<160> NUMBER OF SEQ ID NOS: 33

<210> SEQ ID NO 1
<211> LENGTH: 3747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | |
|---|---|---|---|---|---|
| atggagttca | tcccgacgca | aactttctat | aacagaaggt | accaaccccg | accctgggcc | 60 |
| ccacgccta | caattcaagt | aattagacct | agaccacgtc | cacagaggca | ggctgggcaa | 120 |
| ctcgcccagc | tgatctccgc | agtcaacaaa | ttgaccatgc | gcgcggtacc | tcaacgaag | 180 |
| cctcgcagaa | atcggaaaaa | caagaagcaa | aggcagaaga | agcaggcgcc | gcaaaacgac | 240 |
| ccaaagcaaa | agaagcaacc | accacaaaag | agccggctc | aaaagaagaa | gaaaccaggc | 300 |
| cgtagggaga | gaatgtgcat | gaaaattgaa | aatgattgca | tcttcgaagt | caagcatgaa | 360 |
| ggcaaagtga | tgggctacgc | atgcctggtg | ggggataaag | taatgaaacc | agcacatgtg | 420 |
| aagggaacta | tcgacaatgc | cgatctggct | aaactggcct | ttaagcggtc | gtctaaatac | 480 |
| gatcttgaat | gtgcacagat | accggtgcac | atgaagtctg | atgcctcgaa | gtttacccac | 540 |
| gagaaacccg | aggggtacta | taactggcat | cacggagcag | tgcagtattc | aggaggccgg | 600 |
| ttcactatcc | cgacgggtgc | aggcaagccg | ggagacagcg | gcagaccgat | cttcgacaac | 660 |
| aaaggacggg | tggtggccat | cgtcctagga | ggggccaacg | aaggtgcccg | cacggccctc | 720 |
| tccgtggtga | cgtggaacaa | agacatcgtc | acaaaaatta | cccctgaggg | agccgaagag | 780 |
| tggagcctcg | ccctcccggt | cttgtgcctg | ttggcaaaca | ctacattccc | ctgctctcag | 840 |
| ccgccttgca | caccctgctg | ctacgaaaag | gaaccggaaa | gcaccttgcg | catgcttgag | 900 |
| gacaacgtga | tgagacccgg | atactaccag | ctactaaaag | catcgctgac | ttgctctccc | 960 |
| caccgccaaa | gacgcagtac | taaggacaat | tttaatgtct | ataaagccac | aagaccatat | 1020 |
| ctagctcatt | gtcctgactg | cggagaaggg | cattcgtgcc | acagcccttat | cgcattggag | 1080 |
| cgcatcagaa | atgaagcaac | ggacggaacg | ctgaaaatcc | aggtctcttt | gcagatcggg | 1140 |
| ataaagacag | atgacagcca | cgattggacc | aagctgcgct | atatggatag | ccatacgcca | 1200 |
| gcggacgcgg | agcgagccgg | attgcttgta | aggacttcag | caccgtgcac | gatcaccggg | 1260 |
| accatgggac | actttattct | cgcccgatgc | ccgaaaggag | agacgctgac | agtgggattt | 1320 |
| acggacagca | gaaagatcag | ccacacatgc | acacacccgt | tccatcatga | accacctgtg | 1380 |
| ataggtaggg | agaggttcca | ctctcgacca | caacatggta | aagagttacc | ttgcagcacg | 1440 |
| tacgtgcaga | gcaccgctgc | cactgctgag | gagatagagg | tgcatatgcc | cccagatact | 1500 |
| cctgaccgca | cgctgatgac | gcagcagtct | ggcaacgtga | agatcacagt | taatgggcag | 1560 |
| acggtgcggt | acaagtgcaa | ctgcggtggc | tcaaacgagg | gactgacaac | cacagacaaa | 1620 |
| gtgatcaata | actgcaaaat | tgatcagtgc | catgctgcag | tcactaatca | caagaattgg | 1680 |
| caatacaact | ccccttttagt | cccgcgcaac | gctgaactcg | gggaccgtaa | aggaaagatc | 1740 |
| cacatcccat | tcccattggc | aaacgtgact | tgcagagtgc | caaaagcaag | aaaccctaca | 1800 |
| gtaacttacg | gaaaaaacca | agtcaccatg | ctgctgtatc | ctgaccatcc | cacactcttg | 1860 |
| tcttaccgta | acatgggaca | ggaaccaaat | taccacgagg | agtgggtgac | acacaagaag | 1920 |
| gaggttacct | tgaccgtgcc | tactgagggt | ctggaggtca | cttggggcaa | caacgaacca | 1980 |

| tacaagtact ggccgcagat gtctacgaac ggtactgctc atggtcaccc acatgagata | 2040 |
| atcttgtact attatgagct gtaccccact atgactgtag tcattgtgtc ggtggcctcg | 2100 |
| ttcgtgcttc tgtcgatggt gggcacagca gtgggaatgt gtgtgtgcgc acggcgcaga | 2160 |
| tgcattacac catatgaatt aacaccagga gccactgttc ccttcctgct cagcctgcta | 2220 |
| tgctgcgtca gaacgaccaa ggcggccaca tattacgagg ctgcggcata tctatggaac | 2280 |
| gaacagcagc ccctgttctg gttgcaggct cttatcccgc tggccgcctt gatcgtcctg | 2340 |
| tgcaactgtc tgaaactctt gccatgctgc tgtaagaccc tggcttttt agccgtaatg | 2400 |
| agcatcggtg cccacactgt gagcgcgtac aacacgtaa cagtgatccc gaacacggtg | 2460 |
| ggagtaccgt ataagactct tgtcaacaga ccgggttaca gccccatggt gttggagatg | 2520 |
| gagctacaat cagtcacctt ggaaccaaca ctgtcacttg actacatcac gtgcgagtac | 2580 |
| aaaactgtca tcccctcccc gtacgtgaag tgctgtggta cagcagagtg caaggacaag | 2640 |
| agcctaccag actacagctg caaggtcttt actggagtct acccatttat gtggggcggc | 2700 |
| gcctactgct tttgcgacgc cgaaaatacg caattgagcg aggcacatgt agagaaatct | 2760 |
| gaatcttgca aaacagagtt tgcatcggcc tacagagccc acaccgcatc ggcgtcggcg | 2820 |
| aagctccgcg tcctttacca aggaaacaac attaccgtag ctgcctacgc taacggtgac | 2880 |
| catgccgtca cagtaaagga cgccaagttt gtcgtgggcc caatgtcctc cgcctggaca | 2940 |
| ccttttgaca caaaatcgt ggtgtacaaa ggcgacgtct acaacatgga ctacccacct | 3000 |
| tttggcgcag aagaccagg acaatttggt gacattcaaa gtcgtacacc ggaaagtaaa | 3060 |
| gacgtttatg ccaacactca gttggtacta cagaggccag cagcaggcac ggtacatgta | 3120 |
| ccatactctc aggcaccatc tggcttcaag tattggctga aggaacgagg agcatcgcta | 3180 |
| cagcacacgg caccgttcgg ttgccagatt gcgacaaacc cggtaagagc tgtaaattgc | 3240 |
| gctgtgggga acataccaat ttccatcgac ataccggatg cggcctttac tagggttgtc | 3300 |
| gatgcaccct ctgtaacgga catgtcatgc gaagtaccag cctgcactca ctcctccgac | 3360 |
| tttgggggcg tcgccatcat caaatacaca gctagcaaga aggtaaatg tgcagtacat | 3420 |
| tcgatgacca acgccgttac cattcgagaa gccgacgtag aagtagaggg gaactcccag | 3480 |
| ctgcaaatat ccttctcaac agccctggca agcgccgagt ttcgcgtgca agtgtgctcc | 3540 |
| acacaagtac actgcgcagc cgcatgccac cctccaaagg accacatagt caattaccca | 3600 |
| gcatcacaca ccacccttgg ggtccaggat atatccacaa cggcaatgtc ttgggtgcag | 3660 |
| aagattacgg gaggagtagg attaattgtt gctgttgctg ccttaatttt aattgtggtg | 3720 |
| ctatgcgtgt cgtttagcag gcactaa | 3747 |

<210> SEQ ID NO 2
<211> LENGTH: 8159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |

```
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc     480
catagtaacg ccaatagggac ttttccattg acgtcaatgg gtggagtatt tacggtaaac   540
tgcccacttg gcagtacatc aagtgtatca tatgccaagt acgccccta ttgacgtcaa     600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatggagt tcatcccgac gcaaactttc tataacagaa ggtaccaacc ccgaccctgg   1440
gccccacgcc ctacaattca gtaattaga cctagaccac gtccacagag gcaggctggg    1500
caactcgccc agctgatctc cgcagtcaac aaattgacca tgcgcgcggt acctcaacag   1560
aagcctcgca gaaatcggaa aaacaagaag caaaggcaga agaagcaggc gccgcaaaac   1620
gacccaaagc aaaagaagca accaccacaa agaagccgg ctcaaaagaa gaagaaacca    1680
ggccgtaggg agagaatgtg catgaaaatt gaaaatgatt gcatcttcga agtcaagcat   1740
gaaggcaaag tgatgggcta cgcatgcctg gtggggata aagtaatgaa accagcacat    1800
gtgaagggaa ctatcgacaa tgccgatctg gctaaactgg cctttaagcg gtcgtctaaa   1860
tacgatcttg aatgtgcaca gataccggtg cacatgaagt ctgatgcctc gaagtttacc   1920
cacgagaaac ccgaggggta ctataactgg catcacggag cagtgcagta ttcaggaggc   1980
cggttcacta tcccgacggg tgcaggcaag ccgggagaca gcggcagacc gatcttcgac   2040
aacaaaggac gggtggtggc catcgtccta ggagggccaa acgaaggtgc ccgcacggcc   2100
ctctccgtgg tgacgtggaa caaagacatc gtcacaaaaa ttacccctga gggagccgaa   2160
gagtggagcc tcgccctccc ggtcttgtgc ctgttggcaa acactacatt cccctgctct   2220
cagccgcctt gcacaccctg ctgctacgaa aaggaaccgg aaagcacctt gcgcatgctt   2280
gaggacaacg tgatgagacc cggatactac cagctactaa aagcatcgct gacttgctct   2340
ccccaccgcc aaagacgcag tactaaggac aatttttaatg tctataaagc cacaagacca   2400
tatctagctc attgtcctga ctgcggagaa gggcattcgt gccacagccc tatcgcattg   2460
gagcgcatca gaaatgaagc aacggacgga acgctgaaaa tccaggtctc tttgcagatc   2520
gggataaaga cagatgacag ccacgattgg accaagctgc gctatatgga tagccatacg   2580
ccagcggacg cggagcgagc cggattgctt gtaaggactt cagcaccgtg cacgatcacc   2640
```

-continued

```
gggaccatgg gacactttat tctcgcccga tgcccgaaag gagagacgct gacagtggga    2700
tttacggaca gcagaaagat cagccacaca tgcacacacc cgttccatca tgaaccacct    2760
gtgataggta gggagaggtt ccactctcga ccacaacatg gtaaagagtt accttgcagc    2820
acgtacgtgc agagcaccgc tgccactgct gaggagatag aggtgcatat gcccccagat    2880
actcctgacc gcacgctgat gacgcagcag tctggcaacg tgaagatcac agttaatggg    2940
cagacggtgc ggtacaagtg caactgcggt ggctcaaacg agggactgac aaccacagac    3000
aaagtgatca ataactgcaa aattgatcag tgccatgctg cagtcactaa tcacaagaat    3060
tggcaataca actccccttt agtcccgcgc aacgctgaac tcggggaccg taaaggaaag    3120
atccacatcc cattcccatt ggcaaacgtg acttgcagag tgccaaaagc aagaaaccct    3180
acagtaactt acggaaaaaa ccaagtcacc atgctgctgt atcctgacca tccgacactc    3240
ttgtcttacc gtaacatggg acaggaacca aattaccacg aggagtgggt gacacacaag    3300
aaggaggtta ccttgaccgt gcctactgag ggtctggagg tcacttgggg caacaacgaa    3360
ccatacaagt actggccgca gatgtctacg aacggtactg ctcatggtca cccacatgag    3420
ataatcttgt actattatga gctgtacccc actatgactg tagtcattgt gtcggtggcc    3480
tcgttcgtgc ttctgtcgat ggtgggcaca gcagtgggaa tgtgtgtgtg cgcacggcgc    3540
agatgcatta caccatatga attaacacca ggagccactg ttcccttcct gctcagcctg    3600
ctatgctgcg tcagaacgac caaggcggcc acatattacg aggctgcggc atatctatgg    3660
aacgaacagc agcccctgtt ctggttgcag gctcttatcc cgctggccgc cttgatcgtc    3720
ctgtgcaact gtctgaaact cttgccatgc tgctgtaaga ccctggcttt tttagccgta    3780
atgagcatcg gtgcccacac tgtgagcgcg tacgaacacg taacagtgat cccgaacacg    3840
gtgggagtac cgtataagac tcttgtcaac agaccgggtt acagccccat ggtgttggag    3900
atggagctac aatcagtcac cttggaacca acactgtcac ttgactacat cacgtgcgag    3960
tacaaaactg tcatcccctc cccgtacgtg aagtgctgtg gtacagcaga gtgcaaggac    4020
aagagcctac cagactacag ctgcaaggtc tttactggag tctacccatt tatgtggggc    4080
ggcgcctact gcttttgcga cgccgaaaat acgcaattga gcgaggcaca tgtagagaaa    4140
tctgaatctt gcaaaacaga gtttgcatcg gcctacagag cccacaccgc atcggcgtcg    4200
gcgaagctcc gcgtccttta ccaaggaaac aacattaccg tagctgccta cgctaacggt    4260
gaccatgccg tcacagtaaa ggacgccaag tttgtcgtgg gcccaatgtc ctccgcctgg    4320 acacctttg acaacaaaat cgtggtgtac aaaggcgacg tctacaacat ggactaccca    4380 cctttggcg caggaagacc aggacaattt ggtgacattc aaagtcgtac accggaaagt    4440
aaagacgttt atgccaacac tcagttggta ctacagaggc cagcagcagg cacggtacat    4500
gtaccatact ctcaggcacc atctggcttc aagtattggc tgaaggaacg aggagcatcg    4560
ctacagcaca cggcaccgtt cggttgccag attgcgacaa acccggtaag agctgtaaat    4620
tgcgctgtgg ggaacatacc aatttccatc gacataccgg atgcggcctt tactagggtt    4680
gtcgatgcac cctctgtaac ggacatgtca tgcgaagtac cagcctgcac tcactcctcc    4740
gactttgggg gcgtcgccat catcaaatac acagctagca gaaaggtaa atgtgcagta    4800 cattcgatga ccaacgccgt taccattcga gaagccgacg tagaagtaga ggggaactcc    4860
cagctgcaaa tatccttctc aacagccctg gcaagcgccg agtttcgcgt gcaagtgtgc    4920
tccacacaag tacactgcgc agccgcatgc caccctccaa aggaccacat agtcaattac    4980
```

```
ccagcatcac acaccaccct tggggtccag gatatatcca caacggcaat gtcttgggtg    5040
cagaagatta cgggaggagt aggattaatt gttgctgttg ctgccttaat tttaattgtg    5100
gtgctatgcg tgtcgtttag caggcactaa tgaggatcca gatctgctgt gccttctagt    5160
tgccagccat ctgttgtttg cccctccccc gtgccttcct tgaccctgga aggtgccact    5220
cccactgtcc tttcctaata aaatgaggaa attgcatcgc attgtctgag taggtgtcat    5280
tctattctgg ggggtggggt ggggcaggac agcaagggg aggattggga agacaatagc     5340
aggcatgctg gggatgcggt gggctctatg gtacccagg tgctgaagaa ttgacccggt     5400
tcctcctggg ccagaaagaa gcaggcacat ccccttctct gtgacacacc ctgtccacgc    5460
ccctggttct tagttccagc cccactcata ggacactcat agctcaggag ggctccgcct    5520
tcaatcccac ccgctaaagt acttggagcg gtctctccct ccctcatcag cccaccaaac    5580
caaacctagc ctccaagagt gggaagaaat taaagcaaga taggctatta agtgcagagg    5640
gagagaaaat gcctccaaca tgtgaggaag taatgagaga aatcatagaa ttttaaggcc    5700
atgatttaag gccatcatgg ccttaatctt ccgcttcctc gctcactgac tcgctgcgct    5760
cggtcgttcg gctgcggcga gcggtatcag ctcactcaaa ggcggtaata cggttatcca    5820
cagaatcagg ggataacgca ggaaagaaca tgtgagcaaa aggccagcaa aaggccagga    5880
accgtaaaaa ggccgcgttg ctggcgtttt tccataggct ccgcccccct gacgagcatc    5940
acaaaaatcg acgctcaagt cagaggtggc gaaacccgac aggactataa agataccagg    6000
cgtttccccc tggaagctcc ctcgtgcgct ctcctgttcc gaccctgccg cttaccggat    6060
acctgtccgc ctttctccct tcgggaagcg tggcgctttc tcatagctca cgctgtaggt    6120
atctcagttc ggtgtaggtc gttcgctcca agctgggctg tgtgcacgaa ccccccgttc    6180
agcccgaccg ctgcgcctta tccggtaact atcgtcttga gtccaacccg gtaagacacg    6240
acttatcgcc actggcagca gccactggta acaggattag cagagcgagg tatgtaggcg    6300
gtgctacaga gttcttgaag tggtggccta actacggcta cactagaaga acagtatttg    6360
gtatctgcgc tctgctgaag ccagttacct tcggaaaaag agttggtagc tcttgatccg    6420
gcaaacaaac caccgctggt agcggtggtt tttttgtttg caagcagcag attacgcgca    6480
gaaaaaaagg atctcaagaa gatcctttga tcttttctac ggggtctgac gctcagtgga    6540
acgaaaactc acgttaaggg attttggtca tgagattatc aaaaaggatc ttcacctaga    6600
tccttttaaa ttaaaaatga agttttaaat caatctaaag tatatatgag taaacttggt    6660
ctgacagtta ccaatgctta atcagtgagg cacctatctc agcgatctgt ctatttcgtt    6720
catccatagt tgcctgactc cggggggggg ggcgctgagg tctgcctcgt gaagaaggtg    6780
ttgctgactc ataccaggcc tgaatcgccc catcatccag ccagaaagtg agggagccac    6840
ggttgatgag agctttgttg taggtggacc agttggtgat tttgaacttt tgctttgcca    6900
cggaacggtc tgcgttgtcg ggaagatgcg tgatctgatc cttcaactca gcaaagttc     6960
gatttattca acaaagccgc cgtcccgtca agtcagcgta atgctctgcc agtgttacaa    7020
ccaattaacc aattctgatt agaaaaactc atcgagcatc aaatgaaact gcaatttatt    7080
catatcagga ttatcaatac catatttttg aaaaagccgt ttctgtaatg aaggagaaaa    7140
ctcaccgagg cagttccata ggatggcaag atcctggtat cggtctgcga ttccgactcg    7200
tccaacatca atacaaccta ttaatttccc ctcgtcaaaa ataaggttat caagtgagaa    7260
atcaccatga gtgacgactg aatccggtga gaatggcaaa agcttatgca tttctttcca    7320
gacttgttca acaggccagc cattacgctc gtcatcaaaa tcactcgcat caaccaaacc    7380
```

```
gttattcatt cgtgattgcg cctgagcgag acgaaatacg cgatcgctgt taaaaggaca   7440
attacaaaca ggaatcgaat gcaaccggcg caggaacact gccagcgcat caacaatatt   7500
ttcacctgaa tcaggatatt cttctaatac ctggaatgct gttttcccgg ggatcgcagt   7560
ggtgagtaac catgcatcat caggagtacg gataaaatgc ttgatggtcg gaagaggcat   7620
aaattccgtc agccagttta gtctgaccat ctcatctgta acatcattgg caacgctacc   7680
tttgccatgt ttcagaaaca actctggcgc atcgggcttc ccatacaatc gatagattgt   7740
cgcacctgat tgcccgacat tatcgcgagc ccatttatac ccatataaat cagcatccat   7800 gttgaattt aatcgcggcc tcgagcaaga cgtttcccgt tgaatatggc tcataacacc   7860
ccttgtatta ctgtttatgt aagcagacag ttttattgtt catgatgata tattttatc   7920 ttgtgcaatg taacatcaga gattttgaga cacaacgtgg ctttcccccc cccccatta   7980 ttgaagcatt tatcagggtt attgtctcat gagcggatac atatttgaat gtatttagaa   8040
aaataaacaa atagggttc cgcgcacatt tccccgaaaa gtgccacctg acgtctaaga   8100
aaccattatt atcatgacat aacctataa aaataggcgt atcacgaggc cctttcgtc   8159
```

<210> SEQ ID NO 3
<211> LENGTH: 3744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
atggagttca tcccaaccca aacttttac aataggaggt accagcctcg accctggact    60 ccgcgccta ctatccaagt catcaggcc agaccgcgcc ctcagaggca agctgggcaa    120
cttgcccagc tgatctcagc agttaataaa ctgacaatgc gcgcggtacc acaacagaag   180
ccacgcagga atcggaagaa taagaagcaa agcaaaaac aacaggcgcc acaaaacaac   240
acaaatcaaa agaagcagcc acctaaaaag aaaccggctc aaaagaaaaa gaagccgggc   300
cgcagagaga ggatgtgcat gaaaatcgaa aatgattgta ttttcgaagt caagcacgaa   360
ggtaaggtaa caggttacgc gtgcctggtg ggggacaaag taatgaaacc agcacacgta   420
aaggggacca tcgataacgc ggaccctgcc aaactggcct ttaagcggtc atctaagtat   480
gaccttgaat gcgcgcagat accgtgcac atgaagtccg acgcttcgaa gttcacccat   540
gagaaaccgg aggggtacta caactggcac acggagcag tacagtactc aggaggccgg   600
ttcaccatcc ctacaggtgc tggcaaacca ggggacagcg gcagaccgat cttcgacaac   660
aagggacgcg tggtggccat agtcttagga ggagctaatg aaggagcccg tacagccctc   720
tcggtggtga cctggaataa agacattgtc actaaaatca cccccgaggg ggccgaagag   780
tggagtcttg ccatcccagt tatgtgcctg ttggcaaaca ccacgttccc ctgctcccag   840 ccccccttgca cgccctgctg ctacgaaaag gaaccggagg aaaccctacg catgcttgag   900
gacaacgtca tgagacctgg gtactatcag ctgctacaag catccttaac atgttctccc   960
caccgccagc gacgcagcac caaggacaac ttcaatgtct ataaagccac aagaccatac  1020
ttagctcact gtcccgactg tggagaaggg cactcgtgcc atagtcccgt agcactagaa  1080
cgcatcagaa atgaagcgac agacgggacg ctgaaaatcc aggtctcctt gcaaatcgga  1140 ataaagacg atgacagcca cgattggacc aagctgcgtt atatggacaa ccacatgcca  1200
gcagacgcag agagggcggg gctatttgta agaacatcag caccgtgtac gattactgga  1260
```

```
acaatgggac acttcatcct ggcccgatgt ccaaaagggg aaactctgac ggtgggattc    1320
actgacagta ggaagattag tcactcatgt acgcacccat ttcaccacga ccctcctgtg    1380
ataggtcggg aaaaattcca ttcccgaccg cagcacggta agagctacc ttgcagcacg     1440 tacgtgcaga gcaccgccgc aactaccgag agatagagg tacacatgcc cccagacacc     1500
cctgatcgca cattaatgtc acaacagtcc ggcaacgtaa agatcacagt caatggccag    1560
acggtgcggt acaagtgtaa ttgcggtggc tcaaatgaag gactaacaac tacagacaaa    1620
gtgattaata actgcaaggt tgatcaatgt catgccgcgg tcaccaatca caaaaagtgg    1680
cagtataact cccctctggt cccgcgtaat gctgaacttg gggaccgaaa aggaaaaatt    1740
cacatcccgt ttccgctggc aaatgtaaca tgcagggtgc ctaaagcaag gaaccccacc    1800
gtgacgtacg ggaaaaacca agtcatcatg ctactgtatc ctgaccaccc aacactcctg    1860
tcctaccgga atatgggaga agaaccaaac tatcaagaag agtgggtgat gcataagaag    1920
gaagtcgtgc taaccgtgcc gactgaaggg ctcgaggtca cgtggggcaa caacgagccg    1980
tataagtatt ggcccgcagtt atctacaaac ggtacagccc atggccaccc gcatgagata   2040
attctgtatt attatgagct gtaccccact atgactgtag tagttgtgtc agtggccacg    2100
ttcatactcc tgtcgatggt gggtatggca gcggggatgt gcatgtgtgc acgacgcaga    2160
tgcatcacac cgtatgaact gacaccagga gctaccgtcc cttcctgct tagcctaata     2220 tgctgcatca gaacagctaa agcggccaca taccaagagg ctgcgatata cctgtggaac    2280
gagcagcaac ctttgttttg gctacaagcc cttattccgc tggcagccct gattgttcta    2340
tgcaactgtc tgagactctt accatgctgc tgtaaaacgt tggcttttttt agccgtaatg   2400 agcgtcggtg cccacactgt gagcgcgtac gaacacgtaa cagtgatccc gaacacggtg    2460
ggagtaccgt ataagactct agtcaataga cctggctaca gccccatggt attggagatg    2520
gaactactgt cagtcacttt ggagccaaca ctatcgcttg attacatcac gtgcgagtac    2580
aaaaccgtca tcccgtctcc gtacgtgaag tgctgcggta cagcagagtg caaggacaaa    2640
aacctacctg actacagctg taaggtcttc accggcgtct acccatttat gtggggcggc    2700
gcctactgct tctgcgacgc tgaaaacacg cagttgagcg aagcacacgt ggagaagtcc    2760
gaatcatgca aaacagaatt tgcatcagca tacagggctc ataccgcatc tgcatcagct    2820
aagctccgcg tcctttacca aggaaataac atcactgtaa ctgcctatgc aaacggcgac    2880
catgccgtca cagttaagga cgccaaattc attgtggggc caatgtcttc agcctggaca    2940
cctttcgaca acaaaattgt ggtgtacaaa ggtgacgtct ataacatgga ctacccgccc    3000
tttggcgcag aagaccagg acaatttggc gatatccaaa gtcgcacacc tgagagtaaa    3060
gacgtctatg ctaatacaca actggtactg cagagaccgg ctgtgggtac ggtacacgtg    3120
ccatactctc aggcaccatc tggctttaag tattggctaa agaacgcgg ggcgtcgctg     3180 cagcacacag caccatttgg ctgccaaata gcaacaaacc cggtaagagc ggtgaactgc    3240
gccgtaggga acatgcccat ctccatcgac ataccggaag cggccttcac tagggtcgtc    3300
gacgcgccct ctttaacgga catgtcgtgc gaggtaccag cctgcaccca ttcctcagac    3360
tttgggggcg tcgccattat taaatatgca gccagcaaga aaggcaagtg tgcggtgcat    3420
tcgatgacta acgccgtcac tattcgggaa gctgagatag aagttgaagg gaattctcag    3480
ctgcaaatct ctttctcgac ggccttagcc agcgccgaat tccgcgtaca agtctgttct    3540
acacaagtac actgtgcagc cgagtgccac ccccgaagg accacatagt caactacccg    3600
```

| | |
|---|---|
| gcgtcacata ccaccctcgg ggtccaggac atctccgcta cggcgatgtc atgggtgcag | 3660 |
| aagatcacgg gaggtgtggg actggttgtt gctgttgccg cactgattct aatcgtggtg | 3720 |
| ctatgcgtgt cgttcagcag gcac | 3744 |

<210> SEQ ID NO 4
<211> LENGTH: 8159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctggc ttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca cgaccccccg cccattgacg tcaataatga cgtatgttcc | 480 |
| catagtaacg ccaataggga cttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccctacct gaggccgcca tccacgccgg ttgagtcgcg ttctgccgcc tcccgcctgt | 1080 |
| ggtgcctcct gaactgcgtc cgccgtctag gtaagtttaa agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgctctagac | 1380 |
| accatggagt tcatcccaac ccaaactttt acaatagga ggtaccagcc tcgaccctgg | 1440 |
| actccgcgcc ctactatcca agtcatcagg cccagaccgc gccctcagag caagctgggg | 1500 |
| caacttgccc agctgatctc agcagttaat aaactgacaa tgcgcgcggt accacaacag | 1560 |
| aagccacgca ggaatcggaa gaataagaag caaaagcaaa acaacaggc gccacaaaac | 1620 |
| aacacaaatc aaagaagca gccacctaaa aagaaaccgg ctcaaaagaa aaagaagccg | 1680 |
| ggccgcagag agaggatgtg catgaaaatc gaaatgatt gtattttcga agtcaagcac | 1740 |
| gaaggtaagg taacaggtta cgcgtgcctg tgggggaca agtaatgaa accagcacac | 1800 |
| gtaaagggga ccatcgataa cgcggacctg gccaaactgg cctttaagcg gtcatctaag | 1860 |

-continued

```
tatgaccttg aatgcgcgca gatacccgtg cacatgaagt ccgacgcttc gaagttcacc    1920
catgagaaac cggaggggta ctacaactgg caccacggag cagtacagta ctcaggaggc    1980
cggttcacca tccctacagg tgctggcaaa ccaggggaca gcggcagacc gatcttcgac    2040
aacaagggac gcgtggtggc catagtctta ggaggagcta atgaaggagc ccgtacagcc    2100
ctctcggtgg tgacctggaa taaagacatt gtcactaaaa tcaccccga ggggccgaa     2160
gagtggagtc ttgccatccc agttatgtgc ctgttggcaa acaccacgtt ccctgctcc    2220
cagccccctt gcacgccctg ctgctacgaa aaggaaccgg aggaaaccct acgcatgctt    2280
gaggacaacg tcatgagacc tgggtactat cagctgctac aagcatcctt aacatgttct    2340
ccccaccgcc agcgacgcag caccaaggac aacttcaatg tctataaagc cacaagacca    2400
tacttagctc actgtcccga ctgtggagaa gggcactcgt gccatagtcc cgtagcacta    2460
gaacgcatca gaaatgaagc gacagacggg acgctgaaaa tccaggtctc cttgcaaatc    2520
ggaataaaga cggatgacag ccacgattgg accaagctgc gttatatgga caaccacatg    2580
ccagcagacg cagagagggc ggggctattt gtaagaacat cagcaccgtg tacgattact    2640
ggaacaatgg gacacttcat cctggcccga tgtccaaaag gggaaactct gacggtggga    2700
ttcactgaca gtaggaagat tagtcactca tgtacgcacc catttcacca cgaccctcct    2760
gtgataggtc gggaaaaatt ccattcccga ccgcagcacg gtaaagagct accttgcagc    2820
acgtacgtgc agagcaccgc cgcaactacc gaggagatag aggtacacat gccccccagac   2880
acccctgatc gcacattaat gtcacaacag tccggcaacg taaagatcac agtcaatggc    2940
cagacggtgc ggtacaagtg taattgcggt ggctcaaatg aaggactaac aactacagac    3000
aaagtgatta ataactgcaa ggttgatcaa tgtcatgccg cggtcaccaa tcacaaaaag    3060
tggcagtata actcccctct ggtcccgcgt aatgctgaac ttggggaccg aaaaggaaaa    3120
attcacatcc cgtttccgct ggcaaatgta acatgcaggg tgcctaaagc aaggaacccc    3180
accgtgacgt acgggaaaaa ccaagtcatc atgctactgt atcctgacca cccaacactc    3240
ctgtcctacc ggaatatggg agaagaacca aactatcaag aagagtgggt gatgcataag    3300
aaggaagtcg tgctaaccgt gccgactgaa gggctcgagg tcacgtgggg caacaacgag    3360
ccgtataagt attggccgca gttatctaca aacggtacag cccatggcca cccgcatgag    3420
ataattctgt attattatga gctgtacccc actatgactg tagtagttgt gtcagtggcc    3480
acgttcatac tcctgtcgat ggtgggtatg gcagcgggga tgtgcatgtg tgcacgacgc    3540
agatgcatca caccgtatga actgacacca ggagctaccg tcccttcct gcttagccta    3600
atatgctgca tcagaacagc taaagcggcc acataccaag aggctgcgat atacctgtgg    3660
aacgagcagc aacctttgtt ttggctacaa gcccttattc cgctggcagc cctgattgtt    3720
ctatgcaact gtctgagact cttaccatgc tgctgtaaaa cgttggcttt tttagccgta    3780
atgagcgtcg tgcccacac tgtgagcgcg tacgaacacg taacagtgat cccgaacacg    3840
gtgggagtac cgtataagac tctagtcaat agacctggct acagcccat ggtattggag    3900
atggaactac tgtcagtcac tttggagcca acactatcgc ttgattacat cacgtgcgag    3960
tacaaaaccg tcatcccgtc tccgtacgtg aagtgctgcg gtacagcaga gtgcaaggac    4020
aaaaacctac ctgactacag ctgtaaggtc ttcaccggcg tctacccatt tatgtgggc    4080
ggcgcctact gcttctgcga cgctgaaaac acgcagttga gcgaagcaca cgtggagaag    4140
tccgaatcat gcaaaacaga atttgcatca gcatacaggg ctcataccgc atctgcatca    4200
gctaagctcc gcgtccttta ccaaggaaat aacatcactg taactgccta tgcaaacggc    4260
```

-continued

```
gaccatgccg tcacagttaa ggacgccaaa ttcattgtgg ggccaatgtc ttcagcctgg    4320
acacctttcg acaacaaaat tgtggtgtac aaaggtgacg tctataacat ggactacccg    4380 cccttttggcg caggaagacc aggacaattt ggcgatatcc aaagtcgcac acctgagagt    4440
aaagacgtct atgctaatac acaactggta ctgcagagac cggctgtggg tacggtacac    4500
gtgccatact ctcaggcacc atctggcttt aagtattggc taaaagaacg cggggcgtcg    4560
ctgcagcaca cagcaccatt tggctgccaa atagcaacaa acccggtaag agcggtgaac    4620
tgcgccgtag ggaacatgcc catctccatc gacataccgg aagcggcctt cactagggtc    4680
gtcgacgcgc cctctttaac ggacatgtcg tgcgaggtac cagcctgcac ccattcctca    4740
gactttgggg gcgtcgccat tattaaatat gcagccagca agaaaggcaa gtgtgcggtg    4800
cattcgatga ctaacgccgt cactattcgg gaagctgaga tagaagttga agggaattct    4860
cagctgcaaa tctctttctc gacggcctta gccagcgccg aattccgcgt acaagtctgt    4920
tctacacaag tacactgtgc agccgagtgc caccccccga aggaccacat agtcaactac    4980
ccggcgtcac ataccaccct cggggtccag gacatctccg ctacggcgat gtcatgggtg    5040
cagaagatca cggaggtgt gggactggtt gttgctgttg ccgcactgat tctaatcgtg    5100
gtgctatgcg tgtcgttcag caggcactaa tgaggatcca gatctgctgt gccttctagt    5160
tgccagccat ctgttgtttg cccctccccc gtgccttcct tgaccctgga aggtgccact    5220
cccactgtcc tttcctaata aaatgaggaa attgcatcgc attgtctgag taggtgtcat    5280
tctattctgg ggggtggggt ggggcaggac agcaagggg aggattggga agacaatagc    5340
aggcatgctg gggatgcggt gggctctatg ggtacccagg tgctgaagaa ttgacccggt    5400
tcctcctggg ccagaaagaa gcaggcacat ccccttctct gtgacacacc ctgtccacgc    5460
ccctggttct tagttccagc cccactcata ggacactcat agctcaggag ggctccgcct    5520
tcaatcccac ccgctaaagt acttggagcg gtctctccct ccctcatcag cccaccaaac    5580
caaacctagc ctccaagagt gggaagaaat taaagcaaga taggctatta agtgcagagg    5640
gagagaaaat gcctccaaca tgtgaggaag taatgagaga aatcatagaa ttttaaggcc    5700
atgatttaag gccatcatgg ccttaatctt ccgcttcctc gctcactgac tcgctgcgct    5760
cggtcgttcg gctgcggcga gcggtatcag ctcactcaaa ggcggtaata cggttatcca    5820
cagaatcagg ggataacgca ggaaagaaca tgtgagcaaa aggccagcaa aaggccagga    5880
accgtaaaaa ggccgcgttg ctggcgtttt tccataggct ccgcccccct gacgagcatc    5940
acaaaaatcg acgctcaagt cagaggtggc gaaacccgac aggactataa agataccagg    6000
cgtttccccc tggaagctcc ctcgtgcgct ctcctgttcc gaccctgccg cttaccggat    6060
acctgtccgc ctttctccct tcgggaagcg tggcgctttc tcatagctca cgctgtaggt    6120
atctcagttc ggtgtaggtc gttcgctcca agctgggctg tgtgcacgaa ccccccgttc    6180
agcccgaccg ctgcgcctta tccggtaact atcgtcttga gtccaacccg gtaagacacg    6240
acttatcgcc actggcagca gccactggta acaggattag cagagcgagg tatgtaggcg    6300
gtgctacaga gttcttgaag tggtggccta actacggcta cactagaaga acagtatttg    6360
gtatctgcgc tctgctgaag ccagttacct tcggaaaaag agttggtagc tcttgatccg    6420
gcaaacaaac caccgctggt agcggtggtt ttttgtttg caagcagcag attacgcgca    6480
gaaaaaaagg atctcaagaa gatcctttga tcttttctac ggggtctgac gctcagtgga    6540
acgaaaactc acgttaaggg attttggtca tgagattatc aaaaaggatc ttcacctaga    6600
```

-continued

```
tccttttaaa ttaaaaatga agttttaaat caatctaaag tatatatgag taaacttggt    6660
ctgacagtta ccaatgctta atcagtgagg cacctatctc agcgatctgt ctatttcgtt    6720
catccatagt tgcctgactc cggggggggg ggcgctgagg tctgcctcgt gaagaaggtg    6780
ttgctgactc ataccaggcc tgaatcgccc catcatccag ccagaaagtg agggagccac    6840
ggttgatgag agctttgttg taggtggacc agttggtgat tttgaacttt tgctttgcca    6900
cggaacggtc tgcgttgtcg ggaagatgcg tgatctgatc cttcaactca gcaaaagttc    6960
gatttattca acaaagccgc cgtcccgtca agtcagcgta atgctctgcc agtgttacaa    7020
ccaattaacc aattctgatt agaaaaactc atcgagcatc aaatgaaact gcaatttatt    7080
catatcagga ttatcaatac catattttg aaaaagccgt ttctgtaatg aaggagaaaa    7140
ctcaccgagg cagttccata ggatggcaag atcctggtat cggtctgcga ttccgactcg    7200
tccaacatca atacaaccta ttaatttccc ctcgtcaaaa ataaggttat caagtgagaa    7260
atcaccatga gtgacgactg aatccggtga gaatggcaaa agcttatgca tttctttcca    7320
gacttgttca acaggccagc cattacgctc gtcatcaaaa tcactcgcat caaccaaacc    7380
gttattcatt cgtgattgcg cctgagcgag acgaaatacg cgatcgctgt taaaaggaca    7440
attacaaaca ggaatcgaat gcaaccggcg caggaacact gccagcgcat caacaatatt    7500
ttcacctgaa tcaggatatt cttctaatac ctggaatgct gttttcccgg ggatcgcagt    7560
ggtgagtaac catgcatcat caggagtacg gataaaatgc ttgatggtcg aagaggcat    7620 aaattccgtc agccagttta gtctgaccat ctcatctgta acatcattgg caacgctacc    7680
tttgccatgt ttcagaaaca actctggcgc atcgggcttc ccatacaatc gatagattgt    7740
cgcacctgat tgcccgacat tatcgcgagc ccatttatac ccatataaat cagcatccat    7800
gttggaattt aatcgcggcc tcgagcaaga cgtttcccgt tgaatatggc tcataacacc    7860
ccttgtatta ctgtttatgt aagcagacag ttttattgtt catgatgata tatttttatc    7920
ttgtgcaatg taacatcaga gattttgaga cacaacgtgg ctttcccccc ccccccatta    7980
ttgaagcatt tatcagggtt attgtctcat gagcggatac atatttgaat gtatttagaa    8040
aaataaacaa ataggggttc cgcgcacatt tccccgaaaa gtgccacctg acgtctaaga    8100
aaccattatt atcatgacat taacctataa aaataggcgt atcacgaggc cctttcgtc     8159
```

<210> SEQ ID NO 5
<211> LENGTH: 8185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
```

```
catagtaacg ccaataggga cttccattg acgtcaatgg gtggagtatt tacggtaaac      540
tgcccacttg gcagtacatc aagtgtatca tatgccaagt acgcccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg agggcagta tagtctgagc agtactcgtt     1260
gctgccgcgc gcgccaccag acataatagc tgacagacta acagactgtt cctttccatg    1320
ggtcttttct gcagtcaccg tcgtcgacac gtgtgatcaa tgaattacat acctacgcag    1380
acgttctacg ccgccgatg gcgtcctcgc ccggcggccc gcccctgggt ggctccacca      1440
cccgtatact atccaccacc gccacccgtg cctgtcgacc cgcaagcgca gcaaatgcaa    1500
caacttattg ctgcggtcaa tacgctggct ataaggcaga atggcacccg aacacctgga    1560
caacaacgaa ggaaacgtca atcaaacaaa ccaaagagga acagacacc cccgaagaaa      1620
cagaacccgg cgaaaacaaa gaacaagcag aaaccgcaac cacccaagcc taagaaacgg    1680
aaacccggca agagagaaag gaaatgcatg aagatagaga atgattgcat attcgaggtc    1740
aagctcgaag gcaaggtcac tgggtacgcc tgcctggtag gagataaagt gatgaaacca    1800
gcacacgtga aaggagtcat agataaccct gaccttgcca agctagcttt taagaaatcg    1860
agcaagtatg accttgagtg tgcgcaaatt ccggtccaca tgaagtcaga tgcctcgcag    1920
ttcacccacg agaaaccaga aggacactac aactggcacc atggtgcagt acaatacctg    1980
aacggaagat ttaccatccc gacaggtgct gggaagccag gggacagcgg taggcctatc    2040
tttgacaaca agggtcgcgt agtggccatt gtgctggggg gagccaacga gggagcgagg    2100
acggctctat cggttgtcac ctggaacaaa gacatggtta cgcgcatcac cccagaagga    2160
actgaggagt ggactgccct ggtgacaact gcttgcatcc tgagcaatct gactttcgat    2220
tgcagcctgc caccatgtgc gccttgctgc tatgaaaaag acgcagaggg caccctgagg    2280
atgctggaga acaacgtcga taaccccgga tactacgatc tcctggctgc atcaacgcat    2340
tgtgacgccc cgcagcggcg tcgccgcagg gggctaactg aggactacga ggcttataaa    2400
ctcactaagc cgtacatagc ctattgctct gactgcggga acggacagtt ttgctacagc    2460
ccgatagcta ttgagagagt cagggccgag gcatcggacg gaatgctcaa gatacagatc    2520
tctgcgcaaa taggcctgca ggtggacgga gctcatgcgt ggacgaaaat cagatacatg    2580
aaagggcacg acgtggagga cacagacagg aactcactgg aggtgttcac caccggagag    2640
tgtacggtcc atggcaccat ggggcatttc atcgtagcta catgccccga aggtgactcc    2700
ttgacagtgg cgttcgttga caaacataag gtcaggcacg cttgcaggat agcatacaag    2760
catcgtgtcc ccgtatttggg cagagagcac tttacggtac ggccacatca tggagtagaa    2820
ttgccatgca ccacgtacgc catgagaaca tcagtcacta ccgaagaaat agaaatgcac    2880
```

```
gtggcgcatg acgtgcccga caacaccttt ctatccaaga ccggaaataa agtgaagata   2940
acgccaaaag gaaagtctat tcgctacaac tgcacgtgtg ggtctaagga gagcggtgtc   3000
acaaagcaag acaaagaatt tgacaactgc gaagtttcgc agtgccacac catggtgacc   3060
gcccacgata agtggcagtt taactctcct tatgtcccta gggcaggctc aggcaagaaa   3120
ggaaagatcc acgtaccctt tccactgagc aactctacgt gcagagttcc gttggcgcct   3180
ttaccgaaca ccatcccggc aaagaatgga atcacactgc agttgcatcc ggtcgccccg   3240
acgctactta cctaccgcac cctcggagag aaaccagaac accacacaga atggatatca   3300
gaaagttgcg aacgtacact ccccgtacct gaggaggggg tggagtacac atggggcaat   3360
cacgcccctg tgagactgtg ggcacaactg acgactaagg gttcagccca tgggatgccg   3420
cacgaaatct tctcatatta ctatggattg taccctgcca cgacggttgc agtgtgcgtg   3480
gggctagcgt gtgtgatctt gctggctctg tccgcgtcct gctgcctgtg cgtgtcagcg   3540
agaaataagt gcttgacccc gtacgcgttg acgccaggag ccgtggtgcc gtgcactttg   3600
agcttattgt gctgcgcccc cagagccaag gccgcaacgt tgcggagaca gcggcatat   3660
ctatgggacg agaaccagac ggtgttctgg atgcaattcg caatcccgt agcatgcttt   3720
atgatagtga catattgcct gcgccacttg atgctgtgct gtaggaccgc ttcttttta   3780
gtggcagtaa gcctgggaat gggggcgacc caggcgtatg agcatagtgt aacgctcccc   3840
aacgcggtcg gatttccgta cagagcccat gtagacagac cagggttctc tccattaacg   3900
ctccatatgg aggtagtctc cactagccta gagccgacgc tcgccctgga ttacgtcact   3960
tgcgagtaca aaacggtggt gccgtcgcct aaggtcacct gttgcggcat gtcggagtgt   4020
gcacaccagc aaaaagcgga cttttcaatgt aaagtctaca ccggcgtcta cccctttttg   4080
tggggcggtg cctactgctt ttgcaattcg gaaaacactc agctgagcga agcttatgtt   4140
gagcggagcg aggtgtgcaa acacgatcac gcagcggcgt atcgcgctca tacagccgca   4200
ttgaaggcta aaatcagagt gacctacggt tccacgaacg ggacggctga ggcgtttgtc   4260
aacggagaga gcaccgcacg aattggagac ctgaaaatga tcctaggtcc catatccacc   4320
gcgtggagcc cctttgaccc aaagatcgtc gtctacaagg acgaagtcta caatcaggat   4380
tatccaccgt acggatccgg gcaaccgggt agatttgggg acttacagag caggaccacc   4440
gagagtaacg atgtgtacgc caatactgca ctgaagctgg ctcgcccatc tgccggcacg   4500
gtgcacgttc catatacccc aacgccgtcc gggtttaagt attggctaaa agaaaagggg   4560
gacgcattga accacaaggc tcctttcggc tgcatcatca agacgaaccc cgtaagggca   4620
gaaaattgtg cagtcggaaa cataccagtg tctctagaca ttcccgacgc ggcttttaca   4680
cgcatagtcg acgcaccatc gctaaccggc ctgaagtgcg aggtggcgac ttgcacgcac   4740
tcatcggact ttggaggcac tttggtggtg gagtacaaga ccgacaaagt ggggacgtgc   4800
gccgtccact cagaatccaa cacggctgtt atgcaggaga cgagtctgtc cgtgacgatg   4860
gacggccgag gtacgttgca tttctccacc ggctcagcct caccgtcctt cgtactgaaa   4920
gtgtgcagta gcaaaaccac ttgcacagca aagtgcgtgc cgccaaagga ccacgtcgtc   4980
ccttttcctg ccaaccacaa caatgttgtg ttcccggact tttccagtac tgcagtgtct   5040
tggctcaccc acactatggg cggagctact gtggtgattg ctattgggat caccatattc   5100
ttaatagtta cttgcatagc ttttagtagg cactaggcgg ccgctctaga ccaggccctg   5160
gatccagatc tgctgtgcct tctagttgcc agccatctgt tgtttgcccc tcccccgtgc   5220
```

```
cttccttgac cctggaaggt gccactccca ctgtcctttc ctaataaaat gaggaaattg    5280
catcgcattg tctgagtagg tgtcattcta ttctgggggg tggggtgggg caggacagca    5340 aggggggagga ttgggaagac aatagcaggc atgctgggga tgcggtgggc tctatgggta    5400
cccaggtgct gaagaattga cccggttcct cctgggccag aaagaagcag gcacatcccc    5460
ttctctgtga cacaccctgt ccacgcccct ggttcttagt tccagcccca ctcataggac    5520
actcatagct caggagggct ccgccttcaa tcccacccgc taaagtactt ggagcggtct    5580
ctccctccct catcagccca ccaaaccaaa cctagcctcc aagagtggga agaaattaaa    5640
gcaagatagg ctattaagtg cagagggaga gaaaatgcct ccaacatgtg aggaagtaat    5700
gagagaaatc atagaatttt aaggccatga tttaaggcca tcatggcctt aatcttccgc    5760
ttcctcgctc actgactcgc tgcgctcggt cgttcggctg cggcgagcgg tatcagctca    5820
ctcaaaggcg gtaatacggt tatccacaga atcagggat aacgcaggaa agaacatgtg    5880
agcaaaaggc cagcaaaagg ccaggaaccg taaaaaggcc gcgttgctgg cgttttccca    5940
taggctccgc cccctgacg agcatcacaa aaatcgacgc tcaagtcaga ggtggcgaaa    6000
cccgacagga ctataaagat accaggcgtt tccccctgga agctccctcg tgcgctctcc    6060
tgttccgacc ctgccgctta ccggatacct gtccgccttt ctcccttcgg gaagcgtggc    6120
gctttctcat agctcacgct gtaggtatct cagttcggtg taggtcgttc gctccaagct    6180
gggctgtgtg cacgaacccc ccgttcagcc cgaccgctgc gccttatccg gtaactatcg    6240
tcttgagtcc aacccggtaa gacacgactt atcgccactg gcagcagcca ctggtaacag    6300
gattagcaga gcgaggtatg taggcggtgc tacagagttc ttgaagtggt ggcctaacta    6360
cggctacact agaagaacag tatttggtat ctgcgctctg ctgaagccag ttaccttcgg    6420
aaaaagagtt ggtagctctt gatccggcaa acaaaccacc gctggtagcg gtggtttttt    6480
tgtttgcaag cagcagatta cgcgcagaaa aaaggatct caagaagatc ctttgatctt    6540
ttctacgggg tctgacgctc agtggaacga aaactcacgt taagggattt tggtcatgag    6600
attatcaaaa aggatcttca cctagatcct tttaaattaa aaatgaagtt ttaaatcaat    6660
ctaaagtata tatgagtaaa cttggtctga cagttaccaa tgcttaatca gtgaggcacc    6720
tatctcagcg atctgtctat ttcgttcatc catagttgcc tgactcgggg ggggggggcg    6780
ctgaggtctg cctcgtgaag aaggtgttgc tgactcatac caggcctgaa tcgccccatc    6840
atccagccag aaagtgaggg agccacggtt gatgagagct ttgttgtagg tggaccagtt    6900
ggtgattttg aacttttgct ttgccacgga acggtctgcg ttgtcgggaa gatgcgtgat    6960
ctgatccttc aactcagcaa aagttcgatt tattcaacaa agccgccgtc ccgtcaagtc    7020
agcgtaatgc tctgccagtg ttacaaccaa ttaaccaatt ctgattagaa aaactcatcg    7080
agcatcaaat gaaactgcaa tttattcata tcaggattat caataccata tttttgaaaa    7140
agccgtttct gtaatgaagg agaaaactca ccgaggcagt tccataggat ggcaagatcc    7200
tggtatcggt ctgcgattcc gactcgtcca acatcaatac aacctattaa tttcccctcg    7260
tcaaaaataa ggttatcaag tgagaaatca ccatgagtga cgactgaatc cggtgagaat    7320
ggcaaaagct tatgcatttc tttccagact tgttcaacag gccagccatt acgctcgtca    7380
tcaaaatcac tcgcatcaac caaccgtta ttcattcgtg attgcgcctg agcgagacga    7440
aatacgcgat cgctgttaaa aggacaatta caaacaggaa tcgaatgcaa ccggcgcagg    7500
aacactgcca gcgcatcaac aatatttca cctgaatcag gatattcttc taatacctgg    7560
aatgctgttt tcccggggat cgcagtggtg agtaaccatg catcatcagg agtacggata    7620
```

```
aaatgcttga tggtcggaag aggcataaat tccgtcagcc agtttagtct gaccatctca    7680
tctgtaacat cattggcaac gctacctttg ccatgtttca gaaacaactc tggcgcatcg    7740
ggcttcccat acaatcgata gattgtcgca cctgattgcc cgacattatc gcgagcccat    7800
ttatacccat ataaatcagc atccatgttg gaatttaatc gcggcctcga gcaagacgtt    7860
tcccgttgaa tatggctcat aacacccctt gtattactgt ttatgtaagc agacagtttt    7920
attgttcatg atgatatatt tttatcttgt gcaatgtaac atcagagatt ttgagacaca    7980
acgtggcttt ccccccccc ccattattga agcatttatc agggttattg tctcatgagc    8040
ggatacatat ttgaatgtat ttagaaaaat aaacaaatag gggttccgcg cacatttccc    8100
cgaaaagtgc cacctgacgt ctaagaaacc attattatca tgacattaac ctataaaaat    8160
aggcgtatca cgaggccctt tcgtc                                          8185

<210> SEQ ID NO 6
<211> LENGTH: 8387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggA ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg agggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgccaccatg    1380
tttcccatgc aattcaccaa ctcagcctat cgccagatgg agcccatgtt cgcaccggct    1440
```

```
tctcgaggac aagtacagcc gtatcggccg cgcacaaagc gccgccaaga gccgcaagtc   1500
ggcaacgctg ctattgctgc cctcgcgaac cagatgagcg cgctccagct gcaggtggct   1560
ggacttgccg gccaggcaag ggtggaccgt cgtggaccga gacgtgttca gaaaaacaag   1620
cagaagaaga agaactcttc caacggagaa aaacccaagg agaagaagaa gaagcaaaaa   1680
caacaggaga agaaagggag cggcggtgaa aaagccaaga agccgcggaa ccggcccggg   1740
aaggaggtaa ggatctccgt aaagcgtgcc cgacagagcc ccttccccgt gtaccatgac   1800
ggtgccatat ccggctatgc ggtgctgatt ggctcccgcg tgtttaagcc agcgcacgtg   1860
aagggtaagt tcgaccaccc cgaactggcg gacatcaagt tccaggtcgc cgaggtcatg   1920
gacctcgaag cagccgcata ccctaagtgc atgcgagacc aggcggctga accagcaacc   1980
atgatggatg gagtgtacaa tggggagtac ggcaatattc aggagtggag acaattttg    2040
tattcgatgc gagcggcaga ggcaagccgg ggtgacagtg gcaggccatt caccgacaac   2100
tcaggaaagg ttgtcggtat cgtcctcgga ggaggacccg atggtaggcg cacacgtctc   2160
tccgtgatag gtttcgacaa gaagctgaag gccagagaga tcgcctacag cgaggccatc   2220
ccttggacac gcgcaccagc tctcctgctg ctgcctatgg tcatcgcctg cacctacaac   2280
tccaatacct ttgattgctc caaaccgtcc tgccaggatt gttgcattac tgctgaacca   2340
aagaaggcca tgactatgct gaaggacaac ctgaatgacc cgaactactg ggacctgctc   2400
attgccgtca ccacctgcag ttccgcccga aaaagaggg ctgtgtctac gtcgcctgtc    2460
gccgtttacg acacacaaat tctcgccgcc cacgcagctg cctccccgta tagggcgtac   2520
tgccccgatt gtgacggaac tgcctgcatc tcgccgatag ctatcgacga ggtggtaagt   2580
agcggtagtg accacgtcct tcgcatccgg gtcggttctc aatcgggagt gaccgctaaa   2640
ggcggtgcgg cgggtgaaac ctctctgcga tacctgggaa gggacggtaa ggtttacgcc   2700
gcggacaaca cgcggctcgt ggtgcgcacc actgcaaagt gtgacgtgct gcaggccact   2760
ggccactaca ttctggccaa ctgcccagtg gggcagagtc tcactgttgc ggccacactg   2820
gacggtaccc ggcatcaatg caccacggtt ttcgaacatc aagtaacgga gaagttcaca   2880
agagaacgca gcaagggcca ccacctgtcc gatctgacca gaaatgcac caggttctcc    2940
accacccga agaagtccgc gctctatctc gttgatgtgt atgatgctct gccgacttct    3000
gtagagatca gcaccgtggt gacatgcaac gaaagacagt gcacagtgag ggtgccaccc   3060
ggtaccacag tgaaattcga taagaggtgc aagaacgctg ccaaagagac cgtcaccttc   3120
accagcgact cccagacgtt tacgtgcgag agccggtcc taacggccgc cagcatcacc     3180
cagggcaagc cgcacctcag atcgtcaatg ttgcccagcg gaggcaaaga ggtgaaagcg   3240
aggattccat tcccgttccc gccagagact gcgacttgca gagtgagcat cgccccactg   3300
ccatcgatta cctatgagga aagcgatgtt ctgctggccg gcactgcgaa ataccccgtg   3360
ctgctaacta cacggaacct tggtttccat agcaacgcca catctgaatg gatccagggt   3420
aagtacctgc gccgcatccc ggtcacgccc caagggattg aactaatgtt gggaaacaac   3480
gcaccgctgc acttctggtc atctgtcagg tacgcatctg gagacgccga cgcgtacccc   3540
tgggaacttc tggtgcacca catcaagcac catccggagt acgcgtgggc gtttgtagga   3600
gttgcatgtg gcctgctggc cgttgcagca tgcatgttcg cgtgcgcatg caacagggtg   3660
cggtactctc tgctcgccaa cacgttcaac ccgaacccac caccattgac cgcactgact   3720
gcagcattgt gctgcatacc tggggctcgc gcggatcaac cctacctgga catcattgcc   3780
```

```
tacttgtgga ccaacagcaa agtggccttc gggctgcaat gcgcggcgcc cgtggcttgc    3840
atgctcatcg ttacatacgc ccttagacat tgcagattgt gctgcaattc tttttttaggg   3900 gtaagagggt ggtcggctct gctggtcatc cttgcgtatg tacagagctg caaggcgtac    3960
gaacacaccg tggtggtccc aatggatcca agagcccgt cgtacgaggc ggtgataaac     4020
cggaatgggt atgacccct gaagcttacc atcgcagtga actttaccgt catctcacca     4080
actacggctc tggaatactg gacctgtgca ggagtccctg tcgtcgagcc gccccatgtg    4140
ggctgctgca cgtcagtgtc ctgccctcc gacctctcca cgctgcacgc gttcaccggc     4200
aaagccgtct ccgacgtgca ctgcgatgtg cacacgaacg tgtaccctt gttgtgggt     4260 gcggctcact gcttctgttc cactgaaaac acgcaggtca gcgctgtggc cgccaccgtt    4320
tctgagttct gtgctcagga ctcagagcgc gccgaggcgt tcagcgttca cagcagctca    4380
gtcactgcag agattctggt gacgcttggt gaagtggtga cggcggtcca cgtttacgtg    4440
gacggggtaa catcagccag ggtaccgac ctcaagatcg tggctggccc aataacaact     4500
gactactccc cgtttgaccg caaagtagtc cgtatcggcg aagaggtcta taattacgac    4560
tggcctcctt acggggctgg tcgaccaggc acattcggag acattcaagc taggtcaacc    4620
aactatgtca aacccaatga tctgtacggg gacatcggaa ttgaagtact gcagccgact    4680
aatgaccacg tgcacgtggc ttacacgtat acgacctctg ggttgctgcg ttggttgcag    4740
gacgctccga aaccactcag tgtcacagca ccgcacggtt gtaagatcag tgctaacccg    4800
ctcctggccc tcgattgtgg ggttggtgcc gtcccatgt ccatcaacat tccggacgcg     4860
aagttcaccc gcaaactaaa ggacccgaaa ccttcggccc tgaaatgcgt ggtggacagt    4920
tgcgagtacg gggtggacta cggggggcgcc gccacgatca cctacgaggg ccacgaggct    4980
gggaagtgcg ggatccattc cctgacacca ggagtccctc tgagaacatc agtggttgaa    5040
gtagttgccg gcgctaatac cgtcaaaacg accttctcct cacccacgcc cgaggttaca    5100
ctcgaggtag agatctgttc ggcaatagtg aagtgcgcca gtgagtgcac tccaccgaag    5160
gaacacgtag tcgcagccag gcctcgccat ggcagcgaca ctggaggcta catctccggg    5220
cccgcaatgc gctgggccgg aaggattgta gggaacccta gtggtcctgt ttcctcatcc    5280
ttggccgtca cctactgcgt ggtgaagaag tgccgctcta aaagaatccg gatagtcaag    5340
agctaatcta gaccaggccc tggatccaga tctgctgtgc cttctagttg ccagccatct    5400
gttgtttgcc cctcccccgt gccttccttg accctggaag gtgccactcc cactgtcctt    5460
tcctaataaa atgaggaaat tgcatcgcat tgtctgagta ggtgtcattc tattctgggg    5520
ggtggggtgg ggcaggacag caaggggag gattgggaag acaatagcag gcatgctggg    5580
gatgcggtgg gctctatggg tacccaggtg ctgaagaatt gacccggttc ctcctgggcc    5640
agaaagaagc aggcacatcc ccttctctgt gacacaccct gtccacgccc ctggttctta    5700
gttccagccc cactcatagg acactcatag ctcaggaggg ctccgccttc aatcccaccc    5760
gctaaagtac ttggagcggt ctctcccctcc ctcatcagcc caccaaacca aacctagcct    5820
ccaagagtgg gaagaaatta aagcaagata ggctattaag tgcagaggga gagaaaatgc    5880
ctccaacatg tgaggaagta atgagagaaa tcatagaatt ttaaggccat gatttaaggc    5940
catcatggcc ttaatcttcc gcttcctcgc tcactgactc gctgcgctcg tcgttcggc     6000 tgcggcgagc ggtatcagct cactcaaagg cggtaatacg gttatccaca gaatcagggg    6060
ataacgcagg aaagaacatg tgagcaaaag gccagcaaaa ggccaggaac cgtaaaaagg    6120
ccgcgttgct ggcgtttttc cataggctcc gcccccctga cgagcatcac aaaaatcgac    6180
```

-continued

```
gctcaagtca gaggtggcga aacccgacag gactataaag ataccaggcg tttcccctg    6240 gaagctccct cgtgcgctct cctgttccga ccctgccgct taccggatac ctgtccgcct    6300
ttctcccttc gggaagcgtg gcgctttctc atagctcacg ctgtaggtat ctcagttcgg    6360
tgtaggtcgt tcgctccaag ctgggctgtg tgcacgaacc ccccgttcag cccgaccgct    6420
gcgccttatc cggtaactat cgtcttgagt ccaacccggt aagacacgac ttatcgccac    6480
tggcagcagc cactggtaac aggattagca gagcgaggta tgtaggcggt gctacagagt    6540
tcttgaagtg gtggcctaac tacggctaca ctagaagaac agtatttggt atctgcgctc    6600
tgctgaagcc agttaccttc ggaaaaagag ttggtagctc ttgatccggc aaacaaacca    6660
ccgctggtag cggtggtttt tttgtttgca agcagcagat tacgcgcaga aaaaaggat    6720 ctcaagaaga tcctttgatc ttttctacgg ggtctgacgc tcagtggaac gaaaactcac    6780
gttaagggat tttggtcatg agattatcaa aaaggatctt cacctagatc cttttaaatt    6840
aaaaatgaag ttttaaatca atctaaagta tatatgagta aacttggtct gacagttacc    6900
aatgcttaat cagtgaggca cctatctcag cgatctgtct atttcgttca tccatagttg    6960
cctgactcgg gggggggggg cgctgaggtc tgcctcgtga agaaggtgtt gctgactcat    7020
accaggcctg aatcgcccca tcatccagcc agaaagtgag ggagccacgg ttgatgagag    7080
ctttgttgta ggtggaccag ttggtgattt tgaacttttg ctttgccacg gaacggtctg    7140
cgttgtcggg aagatgcgtg atctgatcct tcaactcagc aaaagttcga tttattcaac    7200
aaagccgccg tcccgtcaag tcagcgtaat gctctgccag tgttacaacc aattaaccaa    7260
ttctgattag aaaaactcat cgagcatcaa atgaaactgc aatttattca tatcaggatt    7320
atcaatacca tatttttgaa aaagccgttt ctgtaatgaa ggagaaaact caccgaggca    7380
gttccatagg atggcaagat cctggtatcg gtctgcgatt ccgactcgtc caacatcaat    7440
acaacctatt aatttcccct cgtcaaaaat aaggttatca agtgagaaat caccatgagt    7500
gacgactgaa tccggtgaga atggcaaaag cttatgcatt tctttccaga cttgttcaac    7560
aggccagcca ttacgctcgt catcaaaatc actcgcatca accaaaccgt tattcattcg    7620
tgattgcgcc tgagcgagac gaaatacgcg atcgctgtta aaaggacaat acaaacagg    7680 aatcgaatgc aaccggcgca ggaacactgc cagcgcatca acaatatttt cacctgaatc    7740
aggatattct tctaatacct ggaatgctgt tttcccgggg atcgcagtgg tgagtaacca    7800
tgcatcatca ggagtacgga taaaatgctt gatggtcgga agaggcataa attccgtcag    7860
ccagtttagt ctgaccatct catctgtaac atcattggca acgctacctt tgccatgttt    7920
cagaaacaac tctggcgcat cgggcttccc atacaatcga tagattgtcg cacctgattg    7980
cccgacatta tcgcgagccc atttataccc atataaatca gcatccatgt tggaatttaa    8040
tcgcggcctc gagcaagacg tttcccgttg aatatggctc ataacacccc ttgtattact    8100
gtttatgtaa gcagacagtt ttattgttca tgatgatata ttttatctt gtgcaatgta    8160 acatcagaga ttttgagaca caacgtggct ttcccccccc ccccattatt gaagcattta    8220
tcagggttat tgtctcatga gcggatacat atttgaatgt atttagaaaa ataaacaaat    8280
agggggtccg cgcacatttc cccgaaaagt gccacctgac gtctaagaaa ccattattat    8340
catgacatta acctataaaa ataggcgtat cacgaggccc tttcgtc    8387
```

<210> SEQ ID NO 7
<211> LENGTH: 8166
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 7

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc      480
catagtaacg ccaatagga cttttccattg acgtcaatgg gtggagtatt tacggtaaac     540
tgcccacttg gcagtacatc aagtgtatca tatgccaagt acgccccta ttgacgtcaa      600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcac accatgaatt acattccaac    1380
tcaaaccttt tacggacgcc gttggcgacc acgcccggcg taccgtccat ggcgggtgcc    1440
gatgcagccg gccccaccca tggtgattcc tgagctgcaa actccgatcg tccaggccca    1500
acagatgcag cagctaatca gtgcagtttc tgccctgacg accaagcaaa atggcaaagc    1560
accgaagaag ccgaagaaaa agccgcaaaa agcgaaggct aagaaaaacg aacagcaaaa    1620
gaagaacgag aacaagaaac caccgcctaa gcagaagaat ccggctaaga agaagaaacc    1680
aggaaaaagg gaacgcatgt gcatgaagat agagaatgat tgcatcttcg aggtcaagct    1740
tgacggtaag gtcacgggat acgcctgcct agtcggggat aaagtgatga gccggcaca    1800
cgtcaaaggt gtgatcgaca accccgacct agcgaagctt acctacaaga atcgagcaa    1860
gtatgacctg gagtgcgccc agataccagt gcacatgaag tcagatgctt caaagtacac    1920
ccatgaaaaa ccagaagggc actacaattg gcatcacggt gcagtgcagt acagcggtgg    1980
caggttcaca atcccgacag gcgcaggtaa accaggagac agcggccggc cgatcttcga    2040
caacaaagga cgcgtggtgg ccattgtcct gggaggggcc aacgaaggag ccaggactgc    2100
cctatccgtc gtgacctgga ccaaagacat ggtcacacgg tacacccag aaggaacaga    2160
```

```
agaatggtcc gccgccttga tgatgtgcgt cttagccaac gttacattcc catgctcaga    2220
gcccgcgtgt gcaccctgtt gctatgaaaa acaaccagaa cagacactga ggatgttaga    2280
ggacaacgtg gaccgcccgg gctactacga cctgctcgag gccacgatga cgtgtaacaa    2340
tagtgcacgc caccgtcgca gtgtgacgaa acacttcaac gtctacaagg ccacgaaacc    2400
gtatctagcg tattgcgcgg actgcggaga cgggcagttc tgttacagcc cggtggctat    2460
agaaaaaatt agggatgagg cttccgatgg catgataaaa atccaggtcg cagcgcaaat    2520
tggcatcaac aaaggaggaa cacacgaaca caacaaaatc aggtacatcg ccgggcatga    2580
catgaaagag gcaaaccggg actctttaca agtgcatact tccggtgtgt gcgctattcg    2640
aggcacgatg ggccacttca tcgtggccta ctgccctcca ggggacgaac taaaggtcca    2700
gttccaagat gcagaatcgc acacccaggc ctgcaaagtg cagtacaaac acgcaccggc    2760
cccagtaggc agagaaaaat tcaccgtcag gccccacttc ggtatcgaag tgccatgcac    2820
aacgtaccag ctgactaccg caccgacgga ggaagagatc gacatgcata ccccaccgga    2880
tatcccagac ataacgttgc tgtcgcagca gtcaggtaat gtaaagatca cagcaggagg    2940
aaaaaccatc agatacaact gcacgtgtgg tagtggcaac gtgggcacca ccagtagcga    3000
caagactatc aattcgtgca aaatagcaca gtgccacgct gcggtgacta accacgataa    3060
gtggcagtac acctcctcgt ttgtccctag agccgaccag ttgtctcgca aggtaaagt    3120 gcacgtacct ttccctctga ccaactccac atgcagggtg cctgttgcac gtgcaccagg    3180
tgtcacatac ggaaagagag aactgacagt gaaactgcac ccagatcatc ccacgctgtt    3240
gacgtaccgg agtctaggag cagatccgcg cccgtatgag gagtggatag accgatacgt    3300
cgaacggacc ataccggtga ccgaagatgg gatcgagtac agatgggaa acaacccacc    3360 cgtgcgcttg tgggcccagc tgacaactga aggcaaaccc catgggtggc cgcacgagat    3420
catactctat tactatgggc tatacccagc agccaccatc gccgccgtct cagccgcggg    3480
tctcgcagtc gtactatcgc tgctggcgt atgttacatg ttcgccactg cacgccgcaa    3540
gtgcctgacc ccatacgccc tgacccccgg agctgtcgtc ccggtaacac taggagtact    3600
atgctgcgca ccacgagcgc atgccgcgtc atttgcggaa tctatggcgt atctatggga    3660
tgagaatcaa accctgtttt ggctggagct tgcaacgccg ctcgctgcca taatcatact    3720
tgtatgctgc ctgaagaacc tgctttgctg ctgcaaaccg ctttcttttt tagtgctggt    3780
gagcctggga actcccgtcg taaaatctta cgaacacacc gcaacgatcc cgaatgtggt    3840
gggattcccg tataaggctc acattgagag gaacggcttc tccccgatga ccctacagct    3900
tgaagtactt ggaaccagct tggaacccac gctaaactta gagtacataa cctgtgaata    3960
caagacagtc gtgccatcac cttatatcaa gtgctgcggg acatcagaat gcagatccat    4020
ggagcgcccc gactatcaat gccaggtcta cacaggagtg tacccatta tgtggggcgg    4080 cgcatactgc ttctgcgaca ctgagaacac ccagctgagt gaagcatacg ttgatagatc    4140
ggacgtatgc aagcacgacc atgccgccgc ctacaaggcg catactgcgg caatgaaagc    4200
caccatccga ataagctacg ggaacctcaa tcagacaaca acggcgttcg tcaacgggga    4260
gcacacagtg accgtcggag gcagcaggtt tacttttggt ccaatctcca ctgcctggac    4320
gcctttcgac aacaagatcg tcgtctacaa gaacgacgtc tacaaccagg acttcccacc    4380
ctacgggtca ggacaaccag ggaggttttg agacatccag agcaggacgg tagagagcaa    4440
ggacctgtat gccaacaccg ccctcaagtt gtcaagacct tcgtccggta ctgttcacgt    4500
gccttacaca cagaccccctt ctggctttaa gtactggata aaagagagag gcacgtcgct    4560
```

```
gaatgacaag gctcccttty gatgcgtaat caagaccaac ccagtcagag cagaaaattg    4620
cgccgttggc aacatcccag tctccatgga catcccggac accgcgttta cgcgcgtgat    4680
tgatgcacct gccgtcacaa acctggagtg ccaagtggcg gtctgcacgc actcatcgga    4740
cttcggcggg atcgcgactc tgactttcaa aactgacaaa cccggaaaat gtgctgtcca    4800
ttctcattcg aacgtagcca ccatacagga ggcagctgtg gacatcaaaa cagatggcaa    4860
gataaccctg catttctcta cagcatcagc atccccggca ttcaaggtat ctgtgtgcag    4920
tgccaaaacg acatgcatgg cagcgtgtga gccgccgaag gaccacatcg tcccttatgg    4980
ggcgagccat aacaaccaag ttttcctga catgtctggc acggcaatga catgggtgca    5040
gcgggtagcc ggcggactcg gcgggctaac actcgccgca gtggcagtac ttatactggt    5100
gacgtgtgtg actatgcgcc gctaatctag accaggccct ggatccagat ctgctgtgcc    5160
ttctagttgc cagccatctg ttgtttgccc ctccccgtg ccttccttga ccctggaagg    5220
tgccactccc actgtccttt cctaataaaa tgaggaaatt gcatcgcatt gtctgagtag    5280
gtgtcattct attctggggg gtggggtggg gcaggacagc aagggggagg attgggaaga    5340
caatagcagg catgctgggg atgcggtggg ctctatgggt acccaggtgc tgaagaattg    5400
acccggttcc tcctgggcca gaaagaagca ggcacatccc cttctctgtg acacccctg    5460 tccacgcccc tggttcttag ttccagcccc actcatagga cactcatagc tcaggagggc    5520
tccgccttca atcccacccg ctaaagtact tggagcggtc tctcctccc tcatcagccc    5580 accaaaccaa acctagcctc caagagtggg aagaaattaa agcaagatag gctattaagt    5640
gcagagggag agaaaatgcc tccaacatgt gaggaagtaa tgagagaaat catagaattt    5700
taaggccatg atttaaggcc atcatggcct taatcttccg cttcctcgct cactgactcg    5760
ctgcgctcgg tcgttcggct gcggcgagcg gtatcagctc actcaaaggc ggtaatacgg    5820
ttatccacag aatcagggga taacgcagga aagaacatgt gagcaaaagg ccagcaaaag    5880
gccaggaacc gtaaaaggc cgcgttgctg gcgtttttcc ataggctccg cccccctgac    5940
gagcatcaca aaaatcgacg ctcaagtcag aggtggcgaa acccgacagg actataaaga    6000
taccaggcgt ttccccctgg aagctccctc gtgcgctctc ctgttccgac cctgccgctt    6060
accggatacc tgtccgcctt tctcccttcg ggaagcgtgg cgctttctca tagctcacgc    6120
tgtaggtatc tcagttcggt gtaggtcgtt cgctccaagc tgggctgtgt gcacgaaccc    6180
cccgttcagc ccgaccgctg cgccttatcc ggtaactatc gtcttgagtc caacccggta    6240
agacacgact tatcgccact ggcagcagcc actggtaaca ggattagcag agcgaggtat    6300
gtaggcggtg ctacagagtt cttgaagtgg tggcctaact acggctacac tagaagaaca    6360
gtatttggta tctgcgctct gctgaagcca gttaccttcg gaaaaagagt tggtagctct    6420
tgatccggca acaaaccac cgctggtagc ggtggttttt tgtttgcaa gcagcagatt    6480 acgcgcagaa aaaaggatc tcaagaagat cctttgatct tttctacggg gtctgacgct    6540
cagtggaacg aaaactcacg ttaagggatt ttggtcatga gattatcaaa aaggatcttc    6600
acctagatcc ttttaaatta aaaatgaagt tttaaatcaa tctaaagtat atatgagtaa    6660
acttggtctg acagttacca atgcttaatc agtgaggcac ctatctcagc gatctgtcta    6720
tttcgttcat ccatagttgc ctgactcggg ggggggggc gctgaggtct gcctcgtgaa    6780
gaaggtgttg ctgactcata ccaggcctga atcgccccat catccagcca gaaagtgagg    6840
gagccacggt tgatgagagc tttgttgtag gtggaccagt tggtgatttt gaacttttgc    6900
```

```
tttgccacgg aacggtctgc gttgtcggga agatgcgtga tctgatcctt caactcagca    6960
aaagttcgat ttattcaaca aagccgccgt cccgtcaagt cagcgtaatg ctctgccagt    7020
gttacaacca attaaccaat tctgattaga aaaactcatc gagcatcaaa tgaaactgca    7080
atttattcat atcaggatta tcaataccat attttgaaa aagccgtttc tgtaatgaag    7140
gagaaaactc accgaggcag ttccatagga tggcaagatc ctggtatcgg tctgcgattc    7200
cgactcgtcc aacatcaata caacctatta atttcccctc gtcaaaaata aggttatcaa    7260
gtgagaaatc accatgagtg acgactgaat ccggtgagaa tggcaaaagc ttatgcattt    7320
ctttccagac ttgttcaaca ggccagccat tacgctcgtc atcaaaatca ctcgcatcaa    7380
ccaaaccgtt attcattcgt gattgcgcct gagcgagacg aaatacgcga tcgctgttaa    7440
aaggacaatt acaaacagga atcgaatgca accggcgcag gaacactgcc agcgcatcaa    7500 caatatttc acctgaatca ggatattctt ctaatacctg gaatgctgtt ttcccgggga    7560
tcgcagtggt gagtaaccat gcatcatcag gagtacggat aaaatgcttg atggtcggaa    7620
gaggcataaa ttccgtcagc cagtttagtc tgaccatctc atctgtaaca tcattggcaa    7680
cgctaccttt gccatgtttc agaaacaact ctggcgcatc gggcttccca tacaatcgat    7740
agattgtcgc acctgattgc ccgacattat cgcgagccca tttataccca tataaatcag    7800
catccatgtt ggaatttaat cgcggcctcg agcaagacgt ttcccgttga atatggctca    7860
taacacccct tgtattactg tttatgtaag cagacagttt tattgttcat gatgatatat    7920
ttttatcttg tgcaatgtaa catcagagat tttgagacac aacgtggctt tcccccccc    7980 cccattattg aagcatttat cagggttatt gtctcatgag cggatacata tttgaatgta    8040
tttagaaaaa taaacaaata ggggttccgc gcacatttcc ccgaaaagtg ccacctgacg    8100
tctaagaaac cattattatc atgacattaa cctataaaaa taggcgtatc acgaggccct    8160
ttcgtc                                                              8166

<210> SEQ ID NO 8
<211> LENGTH: 8186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc    480
catagtaacg ccaataggga cttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
```

```
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtctttcct gcagtcaccg tcgtcgacac gtgtgatcag atatcgcggc cgccaccatg   1380
ttcccgttcc aaccaatgta tccgatgcag ccaatgccct atcgtaaccc gttcgcggcc   1440
ccgcgcaggc cctggttccc cagaaccgac ccttttctgg cgatgcaggt gcaggaatta   1500
acccgctcga tggctaacct gacgttcaag caacgccggg acgcgccacc tgaggggcca   1560
cctgctaaga aacctaagag ggaggccccg caaaagcaaa aaggggggagg ccaagggaag   1620
aagaagaaga accaggggaa gaagaaggcc aagacggggc cgcctaatcc gaaggcacag   1680
agtggaaaca agaagaagcc caacaagaaa ccaggcaaga cagcgcat ggtcatgaaa    1740
ttggaatctg acaagacatt cccaattatg ctggaaggga agattaacgg ctacgcttgc   1800
gtggtcggag ggaagttatt caggccgatg cacgtggaag gcaagatcga caacgacgtt   1860
ctggccgcac ttaagacgaa gaaagcatcc aaatatgatc ttgagtatgc agatgtgcca   1920
cagaacatgc gggccgatac attcaagtac acccatgaga agccccaagg ctattacagc   1980
tggcatcatg gagcagtcca atatgaaaat gggcgtttca cggtgccaaa aggagttggg   2040
gccaagggag acagcggaag acccattctg gataatcagg acgggtggt cgctattgtg    2100
ctgggaggtg tgaatgaagg atctaggaca gccctttcag tcgtcatgtg aacgagaag    2160
ggagtaactg tgaagtatac tccggagaac tgcgagcaat ggtcactagt gaccactatg   2220
tgcctgctcg ccaatgtgac gttcccatgt gccgaaccac caatttgcta cgacagaaaa   2280
ccagcagaga ctttggccat gctcagcgtt aacgttgaca acccgggcta cgatgagctg   2340
ctggaagcag ctgttaagtg ccccggaaga aaaaggagat ctaccgagga gctgtttaag   2400
gagtataagc taacgcgccc ttacatggcc agatgcatca gatgtgccgt gggagctgc    2460
catagtccaa tagcaattga ggcagtgaag agcgacgggc acgacggcta tgttagactt   2520
cagacttcct cgcagtatgg cctggattcc tctggcaact taagggaag gactatgcgg    2580
tatgatatgc acgggaccat tgaagagata ccactacatc aagtgtcact ccacacatct   2640
cgcccgtgtc acattgtgga tgggcatggt tattttctgc ttgctaggtg cccggcaggg   2700
gactccatca ccatggaatt taagaaaggt tcagtcacac actcctgctc agtgccgtat   2760
gaagtgaaat ttaatcctgt aggcagagaa ctctacactc atccaccaga acacggagca   2820
gagcaagcgt gccaagtcta cgcgcacgat gcacagaaca gaggagctta tgtcgagatg   2880
cacctcccgg gctcagaagt ggacagcagt ttgatttcct tgagcggcag ttcagtcacc   2940
gtgacacctc ctgtcgggac tagcgccttg gtgaaatgca aagtgcggcgg cacaaagatc   3000
tccgaaacca tcaacaaggc aaaacagttc agccagtgca aagaagga gcagtgcaga    3060
gcatatcgac tgcagaatga caagtggtg tataattctg acaaactgcc caaagcagcg   3120
```

```
ggagccaccc taaaaggaaa actacacgtc ccgttcttgc tggcagacgg caaatgcacc   3180
gtgcctctag caccggaacc tatgataacc ttcggtttcc gatcagtgtc actgaaactg   3240
caccctaaga atcccacata tctgaccact cgccaacttg ctgatgagcc tcattacacg   3300
cacgagctca tatctgaacc agctgttagg aattttaccg tcactgaaaa ggggtgggag   3360
tttgtatggg gaaaccatcc gccgaaaagg ttttgggcac aggaaacagc acccggaaat   3420
ccacatgggc tgccacatga ggtgataact cattattacc acagatatcccc tatgtccacc   3480 atcctgggtt tgtcaatttg cgccgccatt gtaaccgttt ccgttgcagc gtccacctgg   3540
ctgttttgca aatccagagt ttcgtgccta actccttacc ggctaacacc taacgccagg   3600
atgccgcttt gcctggccgt gctttgctgc gcccgcactg cccgggccga ccacctgg    3660 gagtccttgg atcacctatg gaacaataac caacagatgt tctggattca attgctgatc   3720
cctctggccg ccttgattgt agtgactcgc ctgctcaagt gcgtgtgctg tgtagtgcct   3780
tttttagtcg tggccggcgc cgcaggcgcc ggcgcctacg agcacgcgac cacgatgccg   3840
agccaagcgg gaatctcgta taacaccata gtcaacagag caggctacgc gccactccct   3900
atcagcataa caccaacaaa gatcaagctg atacccacag tgaacttgga gtacgtcacc   3960
tgccactaca aaacaggaat ggattcacca gccatcaaat gctgcggatc tcaggaatgt   4020
actccaacta acaggcctga tgaacagtgc aaagtcttca caggggttta cccgttcatg   4080
tggggaggtg catattgctt ttgcgacact gagaatactc aggtcagcaa ggcctacgta   4140
atgaaatctg acgactgcct tgcggatcat gctgaagcat acaaagcgca cacagcctca   4200
gtgcaggcgt tcctcaacat cacagtgggg gaacactcta ttgtgaccac cgtgtatgtg   4260
aatggagaaa ctcctgtgaa cttcaatggg gtcaaactaa ctgcaggtcc actttccaca   4320
gcttggacac cctttgacag aaaaatcgtg cagtatgccg gggagatcta taattacgat   4380
tttcctgagt atggggcagg acaaccagga gcatttggag acatacaatc cagaacagtc   4440
tcaagctcag atctgtatgc caataccaac ctagtgctgc agagacccaa agcaggagcg   4500
atccatgtgc catacactca ggcaccatcg ggttttgagc aatggaagaa agataaagct   4560
ccgtcattga aattcaccgc ccctttcgga tgcgaaatat atacaaaccc cattcgcgcc   4620
gaaaattgtg ctgtagggtc aattccatta gcctttgaca ttcccgacgc cttgttcacc   4680
agggtgtcag aaacaccgac actttcagcg ccgaatgca ctcttaacga gtgcgtgtat   4740
tcatccgact ttggcgggat cgccacggtc aagtattcgg ccagcaagtc aggcaagtgc   4800
gcagtccatg tgccatcagg gactgctacc ctaaaagaag cagcagtcga gctaaccgag   4860
caagggtcgg cgaccattca tttctcgacc gcaaatatcc acccggagtt caggctccaa   4920
atatgcacat catatgtcac gtgcaaaggt gattgtcacc ccccgaaaga ccacattgtg   4980
acacaccccc agtatcacgc ccaaacattt acagccgcgg tgtcaaaaac cgcgtggacg   5040
tggttaacat ccctgctggg aggatcggcc gtaattatta aattggctt agtgctggct   5100 actattgtgg ccatgtacgt gctgaccaac cagaaacata attgatctag accaggccct   5160
ggatccagat ctgctgtgcc ttctagttgc cagccatctg ttgtttgccc ctcccccgtg   5220
ccttccttga ccctggaagg tgccactccc actgtccttt cctaataaaa tgaggaaatt   5280
gcatcgcatt gtctgagtag gtgtcattct attctggggg gtggggtggg gcaggacagc   5340
aagggggagg attgggaaga caatagcagg catgctgggg atgcgtggg ctctatgggt   5400 acccaggtgc tgaagaattg accccggttcc tcctgggcca gaaagaagca ggcacatccc   5460
```

```
cttctctgtg acacaccctg tccacgcccc tggttcttag ttccagcccc actcatagga    5520
cactcatagc tcaggagggc tccgccttca atcccacccg ctaaagtact tggagcggtc    5580
tctccctccc tcatcagccc accaaaccaa acctagcctc aagagtggg  aagaaattaa    5640 agcaagatag gctattaagt gcagagggag agaaaatgcc tccaacatgt gaggaagtaa    5700
tgagagaaat catagaattt taaggccatg atttaaggcc atcatggcct taatcttccg    5760
cttcctcgct cactgactcg ctgcgctcgg tcgttcggct gcggcgagcg gtatcagctc    5820
actcaaaggc ggtaatacgg ttatccacag aatcagggga taacgcagga agaacatgt    5880 gagcaaaagg ccagcaaaag gccaggaacc gtaaaaaggc cgcgttgctg gcgttttcc     5940 ataggctccg ccccctgac gagcatcaca aaatcgacg  ctcaagtcag aggtggcgaa    6000
acccgacagg actataaaga taccaggcgt ttccccctgg aagctccctc gtgcgctctc    6060
ctgttccgac cctgccgctt accggatacc tgtccgcctt ctcccttcg  ggaagcgtgg    6120 cgctttctca tagctcacgc tgtaggtatc tcagttcggt gtaggtcgtt cgctccaagc    6180
tgggctgtgt gcacgaaccc cccgttcagc ccgaccgctg cgccttatcc ggtaactatc    6240
gtcttgagtc caacccggta agacacgact tatcgccact ggcagcagcc actggtaaca    6300
ggattagcag agcgaggtat gtaggcggtg ctacagagtt cttgaagtgg tggcctaact    6360
acggctacac tagaagaaca gtatttggta tctgcgctct gctgaagcca gttaccttcg    6420
gaaaaagagt tggtagctct tgatccggca acaaaccac  cgctggtagc ggtggttttt    6480
ttgtttgcaa gcagcagatt acgcgcagaa aaaaggatc  tcaagaagat cctttgatct    6540
tttctacggg gtctgacgct cagtggaacg aaaactcacg ttaagggatt ttggtcatga    6600
gattatcaaa aaggatcttc acctagatcc ttttaaatta aaaatgaagt tttaaatcaa    6660
tctaaagtat atatgagtaa acttggtctg acagttacca atgcttaatc agtgaggcac    6720
ctatctcagc gatctgtcta tttcgttcat ccatagttgc ctgactcggg ggggggggc    6780 gctgaggtct gcctcgtgaa gaaggtgttg ctgactcata ccaggcctga atcgccccat    6840
catccagcca gaaagtgagg gagccacggt tgatgagagc tttgttgtag gtggaccagt    6900
tggtgatttt gaactttgc  tttgccacgg aacggtctgc gttgtcggga agatgcgtga    6960
tctgatcctt caactcagca aaagttcgat ttattcaaca aagccgccgt cccgtcaagt    7020
cagcgtaatg ctctgccagt gttacaacca attaaccaat tctgattaga aaaactcatc    7080
gagcatcaaa tgaaactgca atttattcat atcaggatta tcaataccat atttttgaaa    7140
aagccgtttc tgtaatgaag gagaaaactc accgaggcag ttccatagga tgcaagatc     7200 ctggtatcgg tctgcgattc cgactcgtcc aacatcaata caacctatta atttcccctc    7260
gtcaaaaata aggttatcaa gtgagaaatc accatgagtg acgactgaat ccggtgagaa    7320
tggcaaaagc ttatgcattt cttttccagac ttgttcaaca ggccagccat tacgctcgtc    7380
atcaaaatca ctcgcatcaa ccaaaccgtt attcattcgt gattgcgcct gagcgagacg    7440
aaatacgcga tcgctgttaa aaggacaatt acaaacagga atcgaatgca accggcgcag    7500
gaacactgcc agcgcatcaa caatattttc acctgaatca ggatattctt ctaatacctg    7560
gaatgctgtt ttcccgggga tcgcagtggt gagtaaccat gcatcatcag gagtacggat    7620
aaaatgcttg atggtcggaa gaggcataaa ttccgtcagc cagtttagtc tgaccatctc    7680
atctgtaaca tcattggcaa cgctacctt  gccatgtttc agaaacaact ctggcgcatc    7740
gggcttccca tacaatcgat agattgtcgc acctgattgc ccgacattat cgcgagccca    7800
tttatacccc tataaatcag catccatgtt ggaatttaat cgcggcctcg agcaagacgt    7860
```

```
ttcccgttga atatggctca taacacccct tgtattactg tttatgtaag cagacagttt    7920
tattgttcat gatgatatat ttttatcttg tgcaatgtaa catcagagat tttgagacac    7980
aacgtggctt tcccccccccc cccattattg aagcatttat cagggttatt gtctcatgag    8040
cggatacata tttgaatgta tttagaaaaa taaacaaata ggggttccgc gcacatttcc    8100
ccgaaaagtg ccacctgacg tctaagaaac cattattatc atgacattaa cctataaaaa    8160
taggcgtatc acgaggccct ttcgtc                                         8186
```

<210> SEQ ID NO 9
<211> LENGTH: 8129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta cagactgtt cctttccatg    1320 ggtcttttct gcagtcaccg tcgtcgacac gtgtgatcag atatcgcggc cgccaccatg    1380
tttccatacc ctcagctgaa ctttccacca gttaccccta caaatccgat ggcttaccga    1440
gatccaaacc ctcctaggcg ccgctggagg ccgtttcggc cccgctggc tgctcaaatc    1500 gaagatctta ggaggtcgat agtcaacttg actttcaaac aacgatcacc taatccgccg    1560
ccaggtccac cgccaaagaa gaagaagagt gctcctaagc caaaacctac tcagcctaaa    1620
aagaagaagc agcaagccaa gaggacgaaa cgcaagccta accagggaa cgacaacgt    1680
```

```
atgtgtatga agttggagtc ggacaagaca tttccgatca tgctgaacgg ccaagtgaat    1740
ggatatgcct gcgttgtcgg aggaaggctg atgaaaccac tccacgttga aggaaaaatt    1800
gataatgagc aattagcggc cgtgaaattg aagaaggcta gcatgtacga cttggagtac    1860
ggcgacgttc cccagaacat gaaatcagac acgctgcagt acaccagcga caaaccaccg    1920
ggcttctaca actggcacca cggcgcagtc cagtatgaga atgggagatt taccgtaccg    1980
agaggagtgg gcgggaaagg cgacagcgga agaccgatcc tggacaacag aggcagagtt    2040
gtggctattg ttctaggagg tgcaaatgag ggcacgcgta cggcgctttc agtggtcact    2100
tggaaccaga aaggggtgac cattagggat accccgaag gttctgaacc gtggtcacta    2160
gttacagcgc tatgcgtgct ttcgaatgtc acgttcccat gcgacaaacc acccgtgtgc    2220
tattcactga cgccagaacg aacactcgac gtgctcgaag agaacgtcga caatccaaat    2280
tacgacacgc tgctggagaa cgtcttgaaa tgtccatcac gccggcccaa acgaagcatt    2340
accgatgact tcacactgac cagtccctac ctggggttct gcccgtattg cagacactca    2400
acgccgtgtt tcagcccaat aaaaattgag aacgtgtggg acgaatctga tgatggatcg    2460
attagaatcc aggtctcggc acaattcggc tacaatcagg caggcactgc ggatgtcacc    2520
aaattccgtt acatgtcttt cgaccacgac catgacatca aggaagacag tatggagaaa    2580
atagctatca gcatctggg accctgccgt cgtcttggcc acaaagggta cttcctgtta    2640
gctcaatgtc ctccaggtga cagtgtaacc gtcagtatca cgagcggagc atctgagaat    2700
tcatgcaccg tggagaaaaa gatcaggagg aagtttgtcg gtagagagga gtacttgttc    2760
ccacccgtcc atggaaagct ggtaaagtgc cacgtttacg atcacttgaa ggagacgtct    2820
gccgggtaca taaccatgca caggccaggc ccacacgcgt ataagtccta tctggaggaa    2880
gcgtcaggcg aagtgtacat taaaccacct tctggcaaga acgtcaccta cgaatgtaag    2940
tgtggcgact acagcacagg tatcgtgagc acgcgaacga agatgaacgg ctgcactaaa    3000
gcaaaacagt gcattgccta caagagcgac caaacgaaat gggtcttcaa ctcgccggat    3060
cttattaggc acacagacca ctcagtgcaa ggtaaattgc acattccatt ccgcttgaca    3120
ccgacagtct gcccggttcc gttagctcac acgcctacag tcacgaagtg gttcaaaggc    3180
atcaccctcc acctgactgc aatgcgacca acattgctga caacgagaaa attggggctg    3240
cgagcagacg caacagcaga atggattaca gggtctacat ccaggaattt ttctgtgggg    3300
cgagaagggc tggagtacgt atggggtaac catgaaccag tcagagtctg gcccaggag     3360
tcggcaccag cgaccccaca tggatggcg catgagatca tcatccacta ttatcatcgg     3420
catccagtct acactgtcat tgtgctgtgt ggtgtcgctc ttgctatcct ggtaggcact    3480
gcatcatcag cagcttgcat cgccaaagca agaagagact gcctgacgcc atacgcgctt    3540
gcaccgaacg caacggtacc cacagcatta gcggttttgt gctgcattcg gccaaccaac    3600
gctgaaacat ttggagaaac tttgaaccat ctgtggttta caaccaacc gtttctctgg    3660
gcacagttgt gcattcctct ggcagcgctt gttattctgt tccgctgctt ttcatgctgc    3720
atgccttttt tattggttgc aggcgtctgc ctggggaagg tagacgcctt cgaacatgcg    3780
accactgtgc caaatgttcc ggggatcccg tataaggcgt tggtcgaacg cgcaggttac    3840
gcgccactta acctggagat cacggtcgtc tcatcggaat taacaccttc aactaacaag    3900
gagtacgtga cctgcaaatt ccacacagtc attccttcac cacaagttaa atgctgcggg    3960
tccctcgagt gcaaggcatc ctcaaaggcg gattacacat gccgcgtttt tggcggtgtg    4020
```

```
tacccttca    tgtggggagg    cgcacaatgc    ttctgtgaca    gtgagaacac    acaactgagt    4080
gaggcgtacg    tcgagttcgc    tccagactgc    actatagatc    acgcagtcgc    actaaaagtt    4140
cacacagctg    ctctgaaagt    cggcctgcgt    atagtatacg    gcaacaccac    cgcgcacctg    4200
gatacgtttg    tcaatggcgt    cacgccaggt    tcctcacggg    acctgaaggt    catagcaggg    4260
ccgatatcag    ccgcttttc    acccttgac    cataaggtcg    tcatcagaaa    ggggcttgtt    4320
tacaactacg    acttccctga    gtatggagct    atgaaaccag    gagcgttcgg    cgatattcaa    4380
gcatcctcgc    ttgatgctac    agacatagta    gcccgcactg    acatacggct    gctgaagcct    4440
tctgtcaaga    acatccacgt    ccctacacc    caagcagtat    cagggtatga    aatgtggaag    4500
aacaactcag    gacgaccct    gcaagaaaca    gcaccatttg    gatgtaaaat    tgaagtggag    4560
cctctgcgag    cgtctaactg    tgcttacggg    cacatcccta    tctcgattga    catccctgat    4620
gcagcttttg    tgagatcatc    agaatcacca    acaattttag    aagttagctg    cacagtagca    4680
gactgcattt    attctgcaga    ctttggtggt    tctctaacat    tacagtacaa    agctgacagg    4740
gagggacatt    gtccagttca    ctcccactcc    acgacagctg    ttttgaagga    agcgaccaca    4800
catgtgactg    ccgtaggcag    cataacacta    cattttagca    catcgagccc    acaagcaaat    4860
tttatagttt    cgctatgcgg    caagaagtcc    acctgcaatg    ctgaatgtaa    accaccggcc    4920
gaccacataa    ttggagaacc    acataaagtc    gaccaagaat    tccaggcggc    agtttccaaa    4980
acatcttgga    actggctgct    tgcactgttt    gggggagcat    catccctcat    tgttgtagga    5040
cttatagtgt    tggtctgcag    ctctatgctt    ataaacacac    gtagatgatc    tagaccaggc    5100
cctggatcca    gatctgctgt    gccttctagt    tgccagccat    ctgttgtttg    ccctccccc    5160 gtgccttcct    tgaccctgga    aggtgccact    cccactgtcc    tttcctaata    aaatgaggaa    5220
attgcatcgc    attgtctgag    taggtgtcat    tctattctgg    ggggtggggt    ggggcaggac    5280 agcaagggg    aggattggga    agacaatagc    aggcatgctg    gggatgcggt    gggctctatg    5340
ggtacccagt    gctgaagaa    ttgacccggt    tcctcctggg    ccagaaagaa    gcaggcacat    5400
ccccttctct    gtgacacacc    ctgtccacgc    cctggttct    tagttccagc    cccactcata    5460
ggacactcat    agctcaggag    ggctccgcct    tcaatcccac    ccgctaaagt    acttggagcg    5520
gtctctccct    ccctcatcag    cccaccaaac    caaacctagc    ctccaagagt    gggaagaaat    5580
taaagcaaga    taggctatta    agtgcagagg    gagagaaaat    gcctccaaca    tgtgaggaag    5640
taatgagaga    aatcatagaa    ttttaaggcc    atgatttaag    gccatcatgg    ccttaatctt    5700
ccgcttcctc    gctcactgac    tcgctgcgct    cggtcgttcg    gctgcggcga    gcggtatcag    5760
ctcactcaaa    ggcggtaata    cggttatcca    cagaatcagg    ggataacgca    ggaaagaaca    5820
tgtgagcaaa    aggccagcaa    aaggccagga    accgtaaaaa    ggccgcgttg    ctggcgtttt    5880
tccataggct    ccgcccct    gacgagcatc    acaaaaatcg    acgctcaagt    cagaggtggc    5940
gaaacccgac    aggactataa    agataccagg    cgtttcccc    tggaagctcc    ctcgtgcgct    6000
ctcctgttcc    gaccctgccg    cttaccggat    acctgtccgc    ctttctccct    tcgggaagcg    6060
tggcgctttc    tcatagctca    cgctgtaggt    atctcagttc    ggtgtaggtc    gttcgctcca    6120
agctgggctg    tgtgcacgaa    ccccccgttc    agcccgaccg    ctgcgcctta    tccggtaact    6180
atcgtcttga    gtccaacccg    gtaagacacg    acttatcgcc    actggcagca    gccactggta    6240
acaggattag    cagagcgagg    tatgtaggcg    gtgctacaga    gttcttgaag    tggtggccta    6300
actacggcta    cactagaaga    acagtatttg    gtatctgcgc    tctgctgaag    ccagttacct    6360
tcggaaaaag    agttggtagc    tcttgatccg    gcaaacaaac    caccgctggt    agcggtggtt    6420
```

```
ttttgtttg caagcagcag attacgcgca gaaaaaaagg atctcaagaa gatcctttga      6480
tcttttctac ggggtctgac gctcagtgga acgaaaactc acgttaaggg attttggtca      6540
tgagattatc aaaaaggatc ttcacctaga tccttttaaa ttaaaaatga agttttaaat      6600
caatctaaag tatatatgag taaacttggt ctgacagtta ccaatgctta atcagtgagg      6660
cacctatctc agcgatctgt ctatttcgtt catccatagt tgcctgactc ggggggggg       6720 ggcgctgagg tctgcctcgt gaagaaggtg ttgctgactc ataccaggcc tgaatcgccc      6780
catcatccag ccagaaagtg agggagccac ggttgatgag agctttgttg taggtggacc      6840
agttggtgat tttgaacttt tgctttgcca cggaacggtc tgcgttgtcg ggaagatgcg      6900
tgatctgatc cttcaactca gcaaaagttc gatttattca acaaagccgc cgtcccgtca      6960
agtcagcgta atgctctgcc agtgttacaa ccaattaacc aattctgatt agaaaaactc      7020
atcgagcatc aaatgaaact gcaatttatt catatcagga ttatcaatac catattttg       7080 aaaaagccgt ttctgtaatg aaggagaaaa ctcaccgagg cagttccata ggatggcaag      7140
atcctggtat cggtctgcga ttccgactcg tccaacatca atacaaccta ttaatttccc      7200
ctcgtcaaaa ataaggttat caagtgagaa atcaccatga gtgacgactg aatccggtga      7260
gaatggcaaa agcttatgca tttctttcca gacttgttca acaggccagc cattacgctc      7320
gtcatcaaaa tcactcgcat caaccaaacc gttattcatt cgtgattgcg cctgagcgag      7380
acgaaatacg cgatcgctgt taaaaggaca attacaaaca ggaatcgaat gcaaccggcg      7440
caggaacact gccagcgcat caacaatatt ttcacctgaa tcaggatatt cttctaatac      7500
ctggaatgct gttttccgg ggatcgcagt ggtgagtaac catgcatcat caggagtacg      7560
gataaaatgc ttgatggtcg gaagaggcat aaattccgtc agccagttta gtctgaccat      7620
ctcatctgta acatcattgg caacgctacc tttgccatgt ttcagaaaca actctggcgc      7680
atcgggcttc ccatacaatc gatagattgt cgcacctgat tgcccgacat tatcgcgagc      7740
ccatttatac ccatataaat cagcatccat gttggaattt aatcgcggcc tcgagcaaga      7800
cgtttcccgt tgaatatggc tcataacacc ccttgtatta ctgtttatgt aagcagacag      7860
ttttattgtt catgatgata tatttttatc ttgtgcaatg taacatcaga gattttgaga      7920
cacaacgtgg ctttcccccc ccccccatta ttgaagcatt tatcagggtt attgtctcat      7980
gagcggatac atatttgaat gtatttagaa aaataaacaa ataggggttc gcgcacatt       8040 tccccgaaaa gtgccacctg acgtctaaga accattatt atcatgacat aacctataa        8100 aaataggcgt atcacgaggc cctttcgtc                                        8129
```

<210> SEQ ID NO 10
<211> LENGTH: 8144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg       300
```

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccccg cccattgacg tcaataatga cgtatgttcc    480
```
 
```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgccaccatg   1380
ttcccatacc ctacacttaa ctacccgcct atggcgccga ttaacccgat ggcttaccgg   1440
gatcctaatc cgcctaggcg caggtggcgg ccctttaggc caccacttgc agctcaaatt   1500
gaggacctga gacgttccat cgctaacctg actttgaaac aacgagcacc taaccctcca   1560
gcaggaccgc ccgccaaacg caagaagcct gcgccaagcc taagcctgcg caggaaaaag   1620
aagcgaccac caccacctgc caagaaacaa aaacgtaaac ctaaaccagg caaacgacag   1680
cgaatgtgta tgaagctaga gtcagataaa acgtttccaa tcatgttgaa cggacaggtg   1740
aatggttacg cgtgcgtcgt gggtggacga gtgttcaaac cgctgcacgt agaaggcaga   1800
atagacaatg agcaactggc cgccatcaag ctgaagaagg ccagcatata tgaccttgag   1860
tatggtgatg tgccacaatg catgaaatca gataccctcc agtacaccag tgacaagcct   1920
cctggctttt ataactggca ccatggagct gtacagtatg agaacaatag gttcaccgta   1980
ccacgggggg tcgtggaaa gggtgacagc gggagaccta ttcttgacaa caaaggtaga   2040
gtcgtcgcaa ttgtcctggg tggagtcaac gaaggatcca ggacggctct atcagtggtg   2100
acatggaacc aaaaaggggt tacagtcaaa gatacaccag aggggtcaga gccatggtcg   2160
cttgccactg tcatgtgcgt cctggccaat atcacgtttc catgtgatca accaccctgc   2220
atgccatgct gttatgaaaa gaatccacac gaaacactca ccatgttgga acagaattac   2280
gacagccgag cctatgatca gctgctcgat gccgctgtga aatgtaatgc taggagaacc   2340
aggagagatt tggacactca tttcacccag tataagctgg cacgcccgta tattgctgat   2400
tgccctaact gtgggcatag tcggtgcgac agccctatag ctatagaaga agtcagaggg   2460
gatgcgcacg caggagtcat ccgcatccag acatcagcta tgttcggtct gaagacggat   2520
ggagttgatt tggcctacat gagtttcatg aacggcaaaa cgcagaaatc aataaagatc   2580
gacaacctgc atgtgcgcac ctcagcccct tgttccctcg tgtcgcacca cggctattac   2640
```

```
atcctggctc aatgcccacc agggacacg gttacagttg ggtttcacga cgggcctaac    2700
cgccatacgt gcacagttgc ccataaggta gaattcaggc cagtgggtag agagaaatac    2760
cgtcacccac ctgaacatgg agttgaatta ccatgcaacc gttacaccca aagcgtgca    2820
gaccaaggac actacgttga gatgcatcaa cccgggctag ttgccgacca ctctctcctt    2880
agcatccaca gtgccaaggt gaaaattacg gtaccgagcg gcgcccaagt gaaatactac    2940
tgcaagtgcc cagacgtacg agagggaact accagcagcg actatacaac cacctgcacg    3000
gatgtcaaac aatgcagggc ttacctgatt gacaacaaaa aatgggtgta caactctgga    3060
agactgcctc gaggagaggg cgacactttt aaaggaaaac ttcatgtgcc ctttgtgcct    3120
gttaaggcca agtgcatcgc cacgctggca ccagagcctc tagttgagca caaacaccgc    3180
accctgattt tacacctgta cccgaccac ccgaccttgc tgacgaccag gtcacttgga    3240
agtgatgcaa atccaactcg acaatggatt gagcgaccaa caactgtcaa tttcacagtc    3300
accggagaag ggttggagta tacctgggga aaccatccac caaaaagagt atgggctcaa    3360
gagtcaggag aagggaatcc acatggatgg ccgcacgaag tggtagtcta ttactacaac    3420
agatacccat taaccacaat tatcgggtta tgcacctgtg tggctatcat catggtctct    3480
tgtgtcacat ccgtgtggct cctttgcagg actcgcaatc tttgcataac cccgtataaa    3540
ctagccccga acgctcaagt cccaatactc ctggcgttac tttgctgcat taagccgacg    3600
agggcagatg acaccttgca agtgctgaat tacctgtgga caacaatca aaactttttc    3660
tggatgcaga cgcttatccc acttgcagcg cttattgtat gcatgcgcat gctgcgctgc    3720
ttattttgct gtgggccggc tttttttactt gtctgcggcg ccttgggcgc cgcagcgtac    3780
gaacacacag cagtgatgcc gaacaaggtg gggatcccgt acaaagcttt agtcgaacgc    3840
ccaggttatg cacccgttca cctacagata cagctggtta ataccaggat aattccatca    3900
actaacctgg agtacatcac ctgcaagtat aagacaaaag tgccttctcc agtagtgaaa    3960
tgctgcggtg ccactcaatg tacctccaaa ccccatcctg actatcagtg tcaggtgttt    4020
acaggtgttt acccattcat gtggggagga gcctactgct tctgcgacac tgaaaacacc    4080
cagatgagcg aggcgtatgt agagcgctcg aagagtgcct ctattgacca cgcaaaagct    4140
tataaagtac acacaggcac tgttcaggca atggtgaaca taacttatgg gagcgtcagc    4200
tggagatctg cagatgttta cgtcaatggt gaaactcccg cgaaaatagg agatgccaaa    4260
ctcatcatag gtccactgtc atctgcgtgg tccccattcg ataacaaggt ggtggttcat    4320
gggcatgaag tgtataatta cgactttcct gagtacggca ccggcaaagc aggctctttt    4380
ggagacctgc aatcacgcac atcaaccagc aacgatctgt acgcaaacac caacttgaag    4440
ctacaacgac cccaggctgg tatcgtgcac acaccttca cccaggcgcc ctccggcttc    4500
gaacgatgga aagggacaa aggggcaccg ttgaacgacg tagccccgtt tggctgttcg    4560
attgccctgg agccgctccg tgcagaaaat tgtgcagtgg aagcatccc tatatctata    4620
gatatacccg atgcggcttt taccagaata tctgaaacac cgacagtctc agacctggaa    4680
tgcaaaatta cggagtgtac ttatgcctcc gatttcggtg gtatagccac cgttgcctac    4740
aaatccagta agcaggaaa ctgtccaatt cattctccat caggtgttgc agttattaaa    4800
gagaatgacg tcactcttgc tgagagcgga tcatttacat tccacttctc cactgcaaac    4860
atccatcctg cttttaagct gcaggtctgc actagtgcag ttacctgcaa aggagattgt    4920
aagccaccga aagaccacat cgtcgattat ccagcacaac atactgaatc ctttacgtcg    4980
gcgatatccg ccactgcgtg gtcgtggcta aaagtgctgg taggaggaac atcagcattt    5040
```

```
atcgttctgg ggcttattgc tacagcagtg gttgccctag ttctgttctt ccatagacat    5100
taatctagac caggccctgg atccagatct gctgtgcctt ctagttgcca gccatctgtt    5160
gtttgcccct cccccgtgcc ttccttgacc ctggaaggtg ccactccac tgtcctttcc     5220 taataaaatg aggaaattgc atcgcattgt ctgagtaggt gtcattctat tctgggggat    5280
ggggtggggc aggacagcaa gggggaggat tgggaagaca atagcaggca tgctggggat    5340
gcggtgggct ctatgggtac ccaggtgctg aagaattgac ccggttcctc ctgggccaga    5400
aagaagcagg cacatcccct tctctgtgac acaccctgtc cacgcccctg gttcttagtt    5460
ccagccccac tcataggaca ctcatagctc aggagggctc cgccttcaat cccacccgct    5520
aaagtacttg gagcggtctc tccctccctc atcagcccac caaaccaaac ctagcctcca    5580
agagtgggaa gaaattaaag caagataggc tattaagtgc agagggagag aaaatgcctc    5640
caacatgtga ggaagtaatg agagaaatca tagaatttta aggccatgat ttaaggccat    5700
catggcctta atcttccgct tcctcgctca ctgactcgct gcgctcggtc gttcggctgc    5760
ggcgagcggt atcagctcac tcaaaggcgg taatacggtt atccacagaa tcagggata    5820 acgcaggaaa gaacatgtga gcaaaaggcc agcaaaaggc caggaaccgt aaaaaggccg    5880
cgttgctggc gtttttccat aggctccgcc cccctgacga gcatcacaaa aatcgacgct    5940
caagtcagag gtggcgaaac ccgacaggac tataaagata ccaggcgttt ccccctggaa    6000
gctccctcgt gcgctctcct gttccgaccc tgccgcttac cggatacctg tccgcctttc    6060
tcccttcggg aagcgtggcg ctttctcata gctcacgctg taggtatctc agttcggtgt    6120
aggtcgttcg ctccaagctg ggctgtgtgc acgaaccccc cgttcagccc gaccgctgcg    6180
ccttatccgg taactatcgt cttgagtcca acccggtaag acacgactta tcgccactgg    6240
cagcagccac tggtaacagg attagcagag cgaggtatgt aggcggtgct acagagttct    6300
tgaagtggtg gcctaactac ggctacacta agaacagt atttggtatc tgcgctctgc    6360
tgaagccagt taccttcgga aaaagagttg gtagctcttg atccggcaaa caaaccaccg    6420
ctggtagcgg tggtttttt gtttgcaagc agcagattac gcgcagaaaa aaaggatctc    6480
aagaagatcc tttgatcttt tctacggggt ctgacgctca gtggaacgaa aactcacgtt    6540
aagggatttt ggtcatgaga ttatcaaaaa ggatcttcac ctagatcctt ttaaattaaa    6600
aatgaagttt taaatcaatc taagtatat atgagtaaac ttggtctgac agttaccaat    6660
gcttaatcag tgaggcacct atctcagcga tctgtctatt tcgttcatcc atagttgcct    6720
gactcggggg gggggggcgc tgaggtctgc ctcgtgaaga aggtgttgct gactcatacc    6780
aggcctgaat cgccccatca tccagccaga aagtgaggga gccacggttg atgagagctt    6840
tgttgtaggt ggaccagttg gtgatttga acttttgctt tgccacggaa cggtctgcgt    6900
tgtcgggaag atgcgtgatc tgatccttca actcagcaaa agttcgattt attcaacaaa    6960
gccgccgtcc cgtcaagtca gcgtaatgct ctgccagtgt tacaaccaat taaccaattc    7020
tgattagaaa aactcatcga gcatcaaatg aaactgcaat ttattcatat caggattatc    7080
aataccatat ttttgaaaaa gccgtttctg taatgaagga gaaaactcac cgaggcagtt    7140
ccataggatg caagatcct ggtatcggtc tgcgattccg actcgtccaa catcaataca    7200
acctattaat ttcccctcgt caaaaataag gttatcaagt gagaaatcac catgagtgac    7260
gactgaatcc ggtgagaatg gcaaaagctt atgcatttct ttccagactt gttcaacagg    7320
ccagccatta cgctcgtcat caaaatcact cgcatcaacc aaaccgttat tcattcgtga    7380
```

```
ttgcgcctga gcgagacgaa atacgcgatc gctgttaaaa ggacaattac aaacaggaat   7440
cgaatgcaac cggcgcagga acactgccag cgcatcaaca atattttcac ctgaatcagg   7500
atattcttct aatacctgga atgctgtttt cccggggatc gcagtggtga gtaaccatgc   7560
atcatcagga gtacggataa aatgcttgat ggtcggaaga ggcataaatt ccgtcagcca   7620
gtttagtctg accatctcat ctgtaacatc attggcaacg ctacctttgc catgtttcag   7680
aaacaactct ggcgcatcgg gcttcccata caatcgatag attgtcgcac ctgattgccc   7740
gacattatcg cgagcccatt tatacccata taaatcagca tccatgttgg aatttaatcg   7800
cggcctcgag caagacgttt cccgttgaat atggctcata cacccccttg tattactgtt   7860
tatgtaagca gacagtttta ttgttcatga tgatatattt ttatcttgtg caatgtaaca   7920
tcagagattt tgagacacaa cgtggctttc cccccccccc cattattgaa gcatttatca   7980
gggttattgt ctcatgagcg gatacatatt tgaatgtatt tagaaaaata aacaaatagg   8040
ggttccgcgc acatttcccc gaaaagtgcc acctgacgtc taagaaacca ttattatcat   8100
gacattaacc tataaaaata ggcgtatcac gaggcccttt cgtc                   8144
```

<210> SEQ ID NO 11
<211> LENGTH: 8156
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 11

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga cttttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960 tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg agggcagtg tagtctgagc agtactcgtt   1260
```

-continued

```
gctgccgcgc gcgccaccag acataatagc tgacagacta acagactgtt cctttccatg     1320
ggtcttttct gcagtcaccg tcgtcgacac gtgtgatcag atatcgcggc cgccaccatg     1380
aatagaggat tctttaacat gctcggccgc cgcccttcc cggccccac tgccatgtgg      1440 aggccgcgga gaaggaggca ggcggccccg atgcctgccc gcaacgggct ggcttctcaa     1500
atccagcaac tgaccacagc cgtcagtgcc ctagtcattg acaggcaac tagacctcaa     1560 cccccacgtc cacgcccgcc accgcgccag aagaagcagg cgcccaagca accaccgaag     1620
ccgaagaaac caaaaacgca ggagaagaag aagaagcaac ctgcaaaacc caaacccgga     1680
aagagacagc gcatggcact taagttggag gccgacagat tgttcgacgt caagaacgag     1740
gacggagatg tcatcgggca cgcactggcc atggaaggaa aggtaatgaa acctctgcac     1800
gtgaaaggaa ccatcgacca ccctgtgcta tcaaagctca aatttaccaa gtcgtcagca     1860
tacgacatgg agttcgcaca gttgccagtc aacatgagaa gtgaggcatt cacctacacc     1920
agtgaacacc ccgaaggatt ctataactgg caccacggag cggtgcagta tagtggaggt     1980
agatttacca tccctcgcgg agtaggaggc agaggagaca gcggtcgtcc gatcatggat     2040
aactccggtc gggttgtcgc gatagtcctc ggtggcgctg atgaaggaac acgaactgcc     2100
ctttcggtcg tcacctggaa tagtaaaggg aagacaatta agacgacccc ggaagggaca     2160
gaagagtggt ccgcagcacc actggtcacg gcaatgtgtt tgctcggaaa tgtgagcttc     2220
ccatgcgacc gcccgcccac atgctatacc gcgaaccctt ccagagccct cgacatcctt     2280
gaagagaacg tgaaccatga ggcctacgat accctgctca atgccatatt gcggtgcgga     2340
tcgtctggca gaagcaaaag aagcgtcatt gacgacttta ccctgaccag ccctacttg     2400 ggcacatgct cgtactgcca ccatactgta ccgtgcttca gccctgttaa gatcgagcag     2460
gtctgggacg aagcggacga taacaccata cgcatacaga cttccgccca gtttggatac     2520
gaccaaagcg gagcagcaag cgcaaacaag taccgctaca tgtcgcttaa gcaggatcac     2580
accgttaaag aaggcaccat ggatgacatc aagattagca cctcaggacc gtgtagaagg     2640
cttagctaca aaggatactt tctcctcgca aaatgccctc aggggacag cgtaacggtt     2700 agcatagtga gtagcaactc agcaacgtca tgtacactgg cccgcaagat aaaaccaaaa     2760
ttcgtgggac gggaaaaata tgatctacct cccgttcacg gtaaaaaaat tccttgcaca     2820
gtgtacgacc gtctgaaaga acaactgca ggctacatca ctatgcacag gccgagaccg     2880
cacgcttata catcctacct ggaagaatca tcagggaaag tttacgcaaa gccgccatct     2940
gggaagaaca ttacgtatga gtgcaagtgc ggcgactaca agaccggaac cgtttcgacc     3000
cgcaccgaaa tcactggttg caccgccatc aagcagtgcg tcgcctataa gagcgaccaa     3060
acgaagtggg tcttcaactc accggacttg atcagacatg acgaccacac ggcccaaggg     3120
aaattgcatt tgcctttcaa gttgatcccg agtacctgca tggtccctgt tgcccacgcg     3180
ccgaatgtaa tacatggctt taaacacatc agcctccaat tagatacaga ccacttgaca     3240
ttgctcacca ccaggagact aggggcaaac ccggaaccaa ccactgaatg gatcgtcgga     3300
aagacggtca gaaacttcac cgtcgaccga gatggcctgg aatacatatg ggaaaatcat     3360
gagccagtga gggtctatgc ccaagagtca gcaccaggag accctcacgg atggccacac     3420
gaaatagtac agcattacta ccatcgccat cctgtgtaca ccatcttagc cgtcgcatca     3480
gctaccgtgg cgatgatgat tggcgtaact gttgcagtgt tatgtgcctg taaagcgcgc     3540
cgtgagtgcc tgacgccata cgccctgccc caaaacgccg taatcccaac ttcgctggca     3600
ctcttgtgct gcgttaggtc ggccaatgct gaaacgttca ccgagaccat gagttacttg     3660
```

```
tggtcgaaca gtcagccgtt cttctgggtc cagttgtgca tacctttggc cgctttcatc    3720
gttctaatgc gctgctgctc ctgctgcctg ccttttttag tggttgccgg cgcctacctg    3780
gcgaaggtag acgcctacga acatgcgacc actgttccaa atgtgccaca gataccgtat    3840
aaggcacttg ttgaaagggc agggtatgcc ccgctcaatt tggagatcac tgtcatgtcc    3900
tcggaggttt tgccttccac caaccaagag tacattacct gcaaattcac cactgtggtc    3960
ccctccccaa aaatcaaatg ctgcggctcc ttggaatgtc agccgccgc tcatgcagac    4020 tatacctgca aggtcttcgg aggggtctac ccctttatgt ggggaggagc gcaatgtttt    4080
tgcgacagtg agaacagcca gatgagtgag gcgtacgtcg aattgtcagc agattgcgcg    4140
tctgaccacg cgcaggcgat taaggtgcac actgccgcga tgaaagtagg actgcgtatt    4200
gtgtacggga acactaccag tttcctagat gtgtacgtga acggagtcac accaggaacg    4260
tctaaagact tgaaagtcat agctggacca atttcagcat cgtttacgcc attcgatcat    4320
aaggtcgtta tccatcgcgg cctggtgtac aactatgact tcccggaata tggagcgatg    4380
aaaccaggag cgtttggaga cattcaagct acctccttga ctagcaagga tctcatcgcc    4440
agcacagaca ttaggctact caagccttcc gccaagaacg tgcatgtccc gtacacgcag    4500
gcctcatcag gatttgagat gtggaaaaac aactcaggcc gcccactgca ggaaaccgca    4560
cctttcgggt gtaagattgc agtaaatccg ctccgagcgg tggactgttc atacgggaac    4620
attcccattt ctattgacat cccgaacgct gcctttatca ggacatcaga tgcaccactg    4680
gtctcaacag tcaaatgtga agtcagtgag tgcacttatt cagcagactt cggcgggatg    4740
gccaccctgc agtatgtatc cgaccgcgaa ggtcaatgcc ccgtacattc gcattcgagc    4800
acagcaactc tccaagagtc gacagtacat gtcctggaga aaggagcggt gacagtacac    4860
tttagcaccg cgagtccaca ggcgaacttt atcgtatcgc tgtgtgggaa gagacaaca    4920 tgcaatgcag aatgtaaacc accagctgac catatcgtga gcaccccgca caaaatgac    4980 caagaatttc aagccgccat ctcaaaaaca tcatggagtt ggctgtttgc ccttttcggc    5040
ggcgcctcgt cgctattaat tataggactt atgattttg cttgcagcat gatgctgact    5100
agcacacgaa gatgatctag accaggccct ggatccagat ctgctgtgcc ttctagttgc    5160
cagccatctg ttgtttgccc ctccccgtg ccttccttga ccctggaagg tgccactccc    5220
actgtccttt cctaataaaa tgaggaaatt gcatcgcatt gtctgagtag tgtcattct    5280 attctggggg gtggggtggg gcaggacagc aaggggagg attgggaaga caatagcagg    5340
catgctgggg atgcggtggg ctctatgggt acccaggtgc tgaagaattg acccggttcc    5400
tcctgggcca gaaagaagca ggcacatccc cttctctgtg acacaccctg tccacgcccc    5460
tggttcttag ttccagcccc actcatagga cactcatagc tcaggagggc tccgccttca    5520
atcccacccg ctaaagtact tggagcggtc tctccctccc tcatcagccc accaaaccaa    5580
acctagcctc caagagtggg aagaaattaa agcaagatag gctattaagt gcagagggag    5640
agaaaatgcc tccaacatgt gaggaagtaa tgagagaaat catagaattt taaggccatg    5700
atttaaggcc atcatggcct taatcttccg cttcctcgct cactgactcg ctgcgctcgg    5760
tcgttcggct gcggcgagcg gtatcagctc actcaaaggc ggtaatacgg ttatccacag    5820
aatcagggga taacgcagga aagaacatgt gagcaaaagg ccagcaaaag gccaggaacc    5880
gtaaaaaggc cgcgttgctg gcgttttttcc ataggctccg ccccctgac gagcatcaca    5940 aaaatcgacg ctcaagtcag aggtggcgaa acccgacagg actataaaga taccaggcgt    6000
```

```
ttccccctgg aagctccctc gtgcgctctc ctgttccgac cctgccgctt accggatacc    6060
tgtccgcctt tctcccttcg ggaagcgtgg cgctttctca tagctcacgc tgtaggtatc    6120
tcagttcggt gtaggtcgtt cgctccaagc tgggctgtgt gcacgaaccc cccgttcagc    6180
ccgaccgctg cgccttatcc ggtaactatc gtcttgagtc caacccggta agacacgact    6240
tatcgccact ggcagcagcc actggtaaca ggattagcag agcgaggtat gtaggcggtg    6300
ctacagagtt cttgaagtgg tggcctaact acggctacac tagaagaaca gtatttggta    6360
tctgcgctct gctgaagcca gttaccttcg gaaaagagt tggtagctct tgatccggca     6420
aacaaaccac cgctggtagc ggtggttttt tgtttgcaa gcagcagatt acgcgcagaa     6480 aaaaggatc tcaagaagat cctttgatct tttctacggg gtctgacgct cagtggaacg     6540
aaaactcacg ttaagggatt ttggtcatga gattatcaaa aaggatcttc acctagatcc    6600
ttttaaatta aaaatgaagt tttaaatcaa tctaaagtat atatgagtaa acttggtctg    6660
acagttacca atgcttaatc agtgaggcac ctatctcagc gatctgtcta tttcgttcat    6720
ccatagttgc ctgactcggg ggggggggc gctgaggtct gcctcgtgaa gaaggtgttg     6780
ctgactcata ccaggcctga atcgccccat catccagcca gaaagtgagg gagccacggt    6840
tgatgagagc tttgttgtag gtggaccagt tggtgatttt gaacttttgc tttgccacgg    6900
aacggtctgc gttgtcggga agatgcgtga tctgatcctt caactcagca aaagttcgat    6960
ttattcaaca aagccgccgt cccgtcaagt cagcgtaatg ctctgccagt gttacaacca    7020
attaaccaat tctgattaga aaaactcatc gagcatcaaa tgaaactgca atttattcat    7080
atcaggatta tcaataccat attttgaaa agccgtttc tgtaatgaag gagaaaactc      7140
accgaggcag ttccatagga tggcaagatc ctggtatcgg tctgcgattc cgactcgtcc    7200
aacatcaata caacctatta atttcccctc gtcaaaaata aggttatcaa gtgagaaatc    7260
accatgagtg acgactgaat ccggtgagaa tggcaaaagc ttatgcattt cttccagac     7320 ttgttcaaca ggccagccat tacgctcgtc atcaaaatca ctcgcatcaa ccaaaccgtt    7380
attcattcgt gattgcgcct gagcgagacg aaatacgcga tcgctgttaa aggacaatt    7440 acaaacagga tcgaatgca accggcgcag gaacactgcc agcgcatcaa caatatttc      7500 acctgaatca ggatattctt ctaatacctg gaatgctgtt ttcccgggga tcgcagtggt    7560
gagtaaccat gcatcatcag gagtacggat aaaatgcttg atggtcggaa gaggcataaa    7620
ttccgtcagc cagtttagtc tgaccatctc atctgtaaca tcattggcaa cgctacctt     7680 gccatgtttc agaaacaact ctggcgcatc gggcttccca tacaatcgat agattgtcgc    7740
acctgattgc ccgacattat cgcgagccca tttatacca tataaatcag catccatgtt    7800
ggaatttaat cgcggcctcg agcaagacgt ttcccgttga atatggctca taacacccct    7860
tgtattactg tttatgtaag cagacagttt tattgttcat gatgatatat ttttatcttg    7920
tgcaatgtaa catcagagat tttgagacac aacgtggctt tcccccccc cccattattg     7980 aagcatttat cagggttatt gtctcatgag cggatacata tttgaatgta tttagaaaaa    8040
taaacaaata ggggttccgc gcacatttcc ccgaaaagtg ccacctgacg tctaagaaac    8100
cattattatc atgacattaa cctataaaaa taggcgtatc acgaggccct ttcgtc         8156
```

<210> SEQ ID NO 12
<211> LENGTH: 8180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcagattgg | 240 |
| ctattggcca | ttgcatacgt | tgtatccata | tcataatatg | tacatttata | ttggctcatg | 300 |
| tccaacatta | ccgccatgtt | gacattgatt | attgactagt | tattaatagt | aatcaattac | 360 |
| ggggtcatta | gttcatagcc | catatatgga | gttccgcgtt | acataactta | cggtaaatgg | 420 |
| cccgcctggc | tgaccgccca | acgacccccg | cccattgacg | tcaataatga | cgtatgttcc | 480 |
| catagtaacg | ccaataggga | ctttccattg | acgtcaatgg | gtggagtatt | tacggtaaac | 540 |
| tgcccacttg | gcagtacatc | aagtgtatca | tatgccaagt | acgccccta | ttgacgtcaa | 600 |
| tgacggtaaa | tggcccgcct | ggcattatgc | ccagtacatg | accttatggg | actttcctac | 660 |
| ttggcagtac | atctacgtat | tagtcatcgc | tattaccatg | gtgatgcggt | tttggcagta | 720 |
| catcaatggg | cgtggatagc | ggtttgactc | acggggattt | ccaagtctcc | accccattga | 780 |
| cgtcaatggg | agtttgtttt | ggcaccaaaa | tcaacgggac | tttccaaaat | gtcgtaacaa | 840 |
| ctccgcccca | ttgacgcaaa | tgggcggtag | gcgtgtacgg | tgggaggtct | atataagcag | 900 |
| agctcgttta | gtgaaccgtc | agatcgcctg | gagacgccat | ccacgctgtt | ttgacctcca | 960 |
| tagaagacac | cgggaccgat | ccagcctcca | tcggctcgca | tctctccttc | acgcgcccgc | 1020 |
| cgccctacct | gaggccgcca | tccacgccgg | ttgagtcgcg | ttctgccgcc | tcccgcctgt | 1080 |
| ggtgcctcct | gaactgcgtc | cgccgtctag | gtaagtttaa | agctcaggtc | gagaccgggc | 1140 |
| ctttgtccgg | cgctcccttg | gagcctacct | agactcagcc | ggctctccac | gctttgcctg | 1200 |
| accctgcttg | ctcaactcta | gttaacggtg | gagggcagtg | tagtctgagc | agtactcgtt | 1260 |
| gctgccgcgc | gcgccaccag | acataatagc | tgacagacta | acagactgtt | cctttccatg | 1320 |
| ggtcttttct | gcagtcaccg | tcgtcgacac | gtgtgatcag | atatcgcggc | cgccaccatg | 1380 |
| aattacatcc | ctacgcaaac | gttttacggc | cgccggtggc | gcccgcgccc | ggcggcccgt | 1440 |
| ccttggccgt | tgcaggccac | tccggtggct | cccgtcgtcc | ccgacttcca | ggcccagcag | 1500 |
| atgcagcaac | tcatcagcgc | cgtaaatgcg | ctgacaatga | gacagaacgc | aattgctcct | 1560 |
| gctaggcctc | ccaaaccaaa | gaagaagaag | acaaccaaac | caaagccgaa | aacgcagccc | 1620 |
| aagaagatca | acggaaaaac | gcagcagcaa | aagaagaaag | acaagcaagc | cgacaagaag | 1680 |
| aagaagaaac | ccgaaaaaag | agaagaatg | tgcatgaaga | ttgaaaatga | ctgtatcttc | 1740 |
| gaagtcaaac | acgaaggaaa | ggtcactggg | tacgcctgcc | tggtgggcga | caaagtcatg | 1800 |
| aaacctgccc | acgtgaaagg | agtcatcgac | aacgcggacc | tggcaaagct | agctttcaag | 1860 |
| aaatcgagca | agtatgacct | tgagtgtgcc | cagataccag | ttcacatgag | gtcggatgcc | 1920 |
| tcaaagtaca | cgcatgagaa | gcccgaggga | cactataact | ggcaccacgg | ggctgttcag | 1980 |
| tacagcggag | gtaggttcac | tataccgaca | ggagcgggca | aaccgggaga | cagtggccgg | 2040 |
| cccatctttg | acaacaaggg | agggtagtc | gctatcgtcc | tgggcggggc | caacgagggc | 2100 |
| tcacgcacag | cactgtcggt | ggtcacctgg | aacaaagata | tggtgactag | agtgaccccc | 2160 |
| gagggtccg | aagagtggtc | cgcccgctg | attactgcca | tgtgtgtcct | tgccaatgct | 2220 |
| accttcccgt | gcttccagcc | cccgtgtgta | ccttgctgct | atgaaaacaa | cgcagaggcc | 2280 |

-continued

```
acactacgga tgctcgagga taacgtggat aggccagggt actacgacct ccttcaggca   2340
gccttgacgt gccgaaacgg aacaagacac cggcgcagcg tgtcgcaaca cttcaacgtg   2400
tataaggcta cacgcccttacatcgcgtac tgcgccgact gcggagcagg gcactcgtgt    2460
catagccccg tagcaattga agcggtcagg tccgaagcta ccgacgggat gctgaagatt   2520
cagttctcgg cacaaattgg catagataag agtgacaatc atgactacac gaagataagg   2580
tacgcagacg ggcacgccat tgagaatgcc gtccggtcat ctttgaaggt agccacctcc   2640
ggagactgtt tcgtccatgg cacaatggga catttcatac tggcaaagtg cccaccgggt   2700
gaattcctgc aggtctcgat ccaggacacc agaaacgcgg tccgtgcctg cagaatacaa   2760
tatcatcatg accctcaacc ggtgggtaga gaaaaattta caattagacc acactatgga   2820
aaagagatcc cttgcaccac ttatcaacag accacagcgg agaccgtgga ggaaatcgac   2880
atgcatatgc cgccagatac gccggacagg acgttgctat cacagcaatc tggcaatgta   2940
aagatcacag tcggaggaaa gaaggtgaaa tacaactgca cctgtggaac cggaaacgtt   3000
ggcactacta attcggacat gacgatcaac acgtgtctaa tagagcagtg ccacgtctca   3060
gtgacggacc ataagaaatg gcagttcaac tcaccttttcg tcccgagagc cgacgaaccg   3120
gctagaaaag gcaaagtcca tatcccattc ccgttggaca acatcacatg cagagttcca   3180
atggcgcgcg aaccaaccgt catccacggc aaaagagaag tgacactgca ccttcaccca   3240
gatcatccca cgctcttttc ctaccgcaca ctgggtgagg acccgcagta tcacgaggaa   3300
tgggtgacag cggcggtgga acggaccata cccgtaccag tggacgggat ggagtaccac   3360
tggggaaaca acgacccagt gaggctttgg tctcaactca ccactgaagg gaaaccgcac   3420
ggctggccgc atcagatcgt acagtactac tatgggcttt acccggccgc tacagtatcc   3480
gcggtcgtcg ggatgagctt actggcgttg atatcgatct tcgcgtcgtg ctacatgctg   3540
gttgcggccc gcagtaagtg cttgaccct tatgctttaa caccaggagc tgcagttccg   3600
tggacgctgg ggatactctg ctgcgccccg cgggcgcacg cagctagtgt ggcagagact   3660
atggcctact tgtgggacca aaaccaagcg ttgttctggt tggagtttgc ggcccctgtt   3720
gcctgcatcc tcatcatcac gtattgcctc agaaacgtgc tgtgttgctg taagagcctt   3780
tcttttttag tgctactgag cctcggggca accgccagag cttacgaaca ttcgacagta   3840
atgccgaacg tggtggggtt cccgtataag gctcacattg aaaggccagg atatagcccc   3900
ctcactttgc agatgcaggt tgttgaaacc agcctcgaac caacccttaa tttggaatac   3960
ataacctgtg agtacaagac ggtcgtcccg tcgccgtacg tgaagtgctg cggcgcctca   4020
gagtgctcca ctaaagagaa gcctgactac caatgcaagg tttacacagg cgtgtacccg   4080
ttcatgtggg gagggcata ttgcttctgc gactcagaaa acacgcaact cagcgaggcg   4140
tacgtcgatc gatcggacgt atgcaggcat gatcacgcat ctgcttacaa agcccataca   4200
gcatcgctga aggccaaagt gaggggttatg tacggcaacg taaaccagac tgtggatgtt   4260
tacgtgaacg gagaccatgc cgtcacgata gggggtactc agttcatatt cgggccgctg   4320
tcatcggcct ggaccccgtt cgacaacaag atagtcgtgt acaaagacga agtgttcaat   4380
caggacttcc cgccgtacgg atctgggcaa ccagggcgct cggcgacat ccaaagcaga   4440 acagtggaga gtaacgacct gtacgcgaac acggcactga agctggcacg cccttcaccc   4500
ggcatggtcc atgtaccgta cacacagaca ccttcagggt tcaaatattg gctaaaggaa   4560
aaagggacag ccctaaatac gaaggctcct tttggctgcc aaatcaaaac gaaccctgtc   4620
```

```
agggccatga actgcgccgt gggaaacatc cctgtctcca tgaatttgcc tgacagcgcc    4680
tttacccgca ttgtcgaggc gccgaccatc attgacctga cttgcacagt ggctacctgt    4740
acgcactcct cggatttcgg cggcgtcttg acactgacgt acaagaccaa caagaacggg    4800
gactgctctg tacactcgca ctctaacgta gctactctac aggaggccac agcaaaagtg    4860
aagacagcag gtaaggtgac cttacacttc tccacggcaa gcgcatcacc ttcttttgtg    4920
gtgtcgctat gcagtgctag ggccaccgtg tcagcgtcgt gtgagccccc gaaagaccac    4980
atagtcccat atgcggctag ccacagtaac gtagtgtttc cagacatgtc gggcaccgca    5040
ctatcatggg tgcagaaaat ctcgggtggt ctgggggcct tcgcaatcgg cgctatcctg    5100
gtgctggttg tggtcacttg cattgggctc cgcagataat ctagaccagg ccctggatcc    5160
agatctgctg tgccttctag ttgccagcca tctgttgttt gccctcccc cgtgccttcc    5220 ttgaccctgg aaggtgccac tcccactgtc ctttcctaat aaaatgagga aattgcatcg    5280
cattgtctga gtaggtgtca ttctattctg ggggtgggg tgggcagga cagcaagggg    5340 gaggattggg aagacaatag caggcatgct ggggatgcgg tgggctctat gggtacccag    5400
gtgctgaaga attgacccgg ttcctcctgg gccagaaaga agcaggcaca tccccttctc    5460
tgtgacacac cctgtccacg cccctggttc ttagttccag ccccactcat aggacactca    5520
tagctcagga gggctccgcc ttcaatccca cccgctaaag tacttggagc ggtctctccc    5580
tccctcatca gcccaccaaa ccaaacctag cctccaagtg tgggaagaaa ttaaagcaag    5640
ataggctatt aagtgcagag ggagagaaaa tgcctccaac atgtgaggaa gtaatgagag    5700
aaatcataga atttttaaggc catgatttaa ggccatcatg gccttaatct tccgcttcct    5760
cgctcactga ctcgctgcgc tcggtcgttc ggctgcggcg agcggtatca gctcactcaa    5820
aggcggtaat acggttatcc acagaatcag gggataacgc aggaaagaac atgtgagcaa    5880
aaggccagca aaaggccagg aaccgtaaaa aggccgcgtt gctggcgttt ttccataggc    5940 tccgccccc tgacgagcat cacaaaaatc gacgctcaag tcagaggtgg cgaaacccga    6000
caggactata aagataccag gcgtttcccc ctggaagctc cctcgtgcgc tctcctgttc    6060
cgaccctgcc gcttaccgga tacctgtccg cctttctccc ttcgggaagc gtggcgcttt    6120
ctcatagctc acgctgtagg tatctcagtt cggtgtaggt cgttcgctcc aagctgggct    6180
gtgtgcacga accccccgtt cagcccgacc gctgcgcctt atccggtaac tatcgtcttg    6240
agtccaaccc ggtaagacac gacttatcgc cactggcagc agccactggt aacaggatta    6300
gcagagcgag gtatgtaggc ggtgctacag agttcttgaa gtggtggcct aactacggct    6360
acactagaag aacagtattt ggtatctgcg ctctgctgaa gccagttacc ttcggaaaaa    6420
gagttggtag ctcttgatcc ggcaaacaaa ccaccgctgg tagcggtggt ttttttgttt    6480
gcaagcagca gattacgcgc agaaaaaaag gatctcaaga agatcctttg atcttttcta    6540
cggggtctga cgctcagtgg aacgaaaact cacgttaagg gattttggtc atgagattat    6600 caaaaggat cttcacctag atccttttaa attaaaaatg aagttttaaa tcaatctaaa    6660
gtatatatga gtaaacttgg tctgacagtt accaatgctt aatcagtgag gcacctatct    6720
cagcgatctg tctatttcgt tcatccatag ttgcctgact cggggggggg gggcgctgag    6780
gtctgcctcg tgaagaaggt gttgctgact cataccaggc ctgaatcgcc ccatcatcca    6840
gccagaaagt gagggagcca cggttgatga gagctttgtt gtaggtggac cagttggtga    6900
ttttgaactt ttgctttgcc acggaacggt ctgcgttgtc gggaagatgc gtgatctgat    6960
ccttcaactc agcaaaagtt cgatttattc aacaaagccg ccgtcccgtc aagtcagcgt    7020
```

```
aatgctctgc cagtgttaca accaattaac caattctgat tagaaaaact catcgagcat    7080
caaatgaaac tgcaatttat tcatatcagg attatcaata ccatattttt gaaaaagccg    7140
tttctgtaat gaaggagaaa actcaccgag gcagttccat aggatggcaa gatcctggta    7200
tcggtctgcg attccgactc gtccaacatc aatacaacct attaatttcc cctcgtcaaa    7260
aataaggtta tcaagtgaga atcaccatg agtgacgact gaatccggtg agaatggcaa    7320
aagcttatgc atttctttcc agacttgttc aacaggccag ccattacgct cgtcatcaaa    7380
atcactcgca tcaaccaaac cgttattcat tcgtgattgc gcctgagcga gacgaaatac    7440
gcgatcgctg ttaaaaggac aattacaaac aggaatcgaa tgcaaccggc gcaggaacac    7500
tgccagcgca tcaacaatat tttcacctga atcaggatat tcttctaata cctggaatgc    7560
tgttttcccg gggatcgcag tggtgagtaa ccatgcatca tcaggagtac ggataaaatg    7620
cttgatggtc ggaagaggca taaattccgt cagccagttt agtctgacca tctcatctgt    7680
aacatcattg gcaacgctac ctttgccatg tttcagaaac aactctggcg catcgggctt    7740
cccatacaat cgatagattg tcgcacctga ttgcccgaca ttatcgcgag cccatttata    7800
cccatataaa tcagcatcca tgttggaatt taatcgcggc ctcgagcaag acgtttcccg    7860
ttgaatatgg ctcataacac cccttgtatt actgtttatg taagcagaca gttttattgt    7920
tcatgatgat atattttat cttgtgcaat gtaacatcag agattttgag acacaacgtg    7980
gctttccccc cccccccatt attgaagcat ttatcagggt tattgtctca tgagcggata    8040
catatttgaa tgtatttaga aaaataaaca aataggggtt ccgcgcacat ttccccgaaa    8100
agtgccacct gacgtctaag aaaccattat tatcatgaca ttaacctata aaaataggcg    8160
tatcacgagg ccctttcgtc                                                 8180
```

<210> SEQ ID NO 13
<211> LENGTH: 8377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggg ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
```

```
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc cgcgccaccag acataatagc tgacagacta acagactgtt cctttccatg   1320
ggtcttttct gcagtcaccg tcgtcgacac gtgtgatcag atatcgcggc cgcatgtttc   1380
ccatgcaatt caccaactca gcctatcgcc agatggagcc catgtttgca ccgggttccc   1440
gaggacaagt acagccgtac cggccgcgca ctaagcgccg ccaggagccg caagtcggca   1500
acgccgccat tactgccctc gcgaaccaga tgagtgcgct ccagttgcag gtagctggac   1560
ttgccggcca ggcaagggtg gaccgccgtg ggccaagacg tgttcagaag aacaagcaga   1620
agaagaagaa ctcttccaac ggagaaaaac ccaaagagaa gaagaagaag caaaacaac    1680
aggagaagaa gggaagcggt ggcgaaaaag tcaagaagac taggaaccga cccgggaagg   1740
aggtaaggat ctccgtaaag tgtgcccgac agagcacctt ccccgtgtac cacgaaggtg   1800
ctatatccgg ctacgctgtg ctgattggat ctcgcgtatt caagccggca cacgtgaagg   1860
gtaagatcga ccaccctgaa ctggcagaca tcaagttcca ggtcgccgag gacatggacc   1920
tcgaagcagc tgcgtacccg aagagcatgc gagaccaagc ggctgaacca gcgaccatga   1980
tggacagagt gtacaactgg gagtatggca ctatcagagt ggaggataat gtcataatcg   2040
acgcaagcgg tagggggcaag ccgggtgaca gtggcagggc catcaccgac aactcgggaa   2100
aggttgttgg tattgtcctc ggaggaggac ccgatggcag gcgcacacgc ctctccgtga   2160
taggtttcga caagaagatg aaggctaggg agatcgccta cagtgatgcc ataccttgga   2220
cacgcgctcc ggccctcctg ctgctgccta tggttattgt ctgcacctac aattccaaca   2280
ccttcgattg ctccaaaccg tcctgccagg actgctgcat tactgctgaa ccagagaagg   2340
ccatgaccat gctgaaggac aatctgaacg acccgaacta ctgggaccta ctcattgctg   2400
tcaccacctg tggctccgcc cggagaaaga gggctgtgtc tacgtcgcct gccgcctttt   2460
acgacacaca gatcctcgcc gcccacgcag ctgcctcccc atacagggcg tactgccccg   2520
attgtgacgg aacagcgtgt atctcgccga tagccatcga cgaggtggtg agcagtggca   2580
gcgaccacgt cctccgcatg cgggttggtt ctcaatcggg agtgaccgct aagggtggtg   2640
cggcgggtga aacctctctg cgatacctgg gaagggacgg gaaggttcac gccgcagaca   2700
acacgcgact cgtggtgcgc acgactgcaa agtgcgacgt gctgcaggcc actggccact   2760
acatcctggc caactgccca gtggggcaga gcctaaccgt tgcggccaca ctggatggca   2820
cccggcatca atgcaccacg gttttcgaac accaagtaac ggagaagttc accagagaac   2880
gcagcaaggg ccaccatctg tccgacatga ccaagaaatg caccagattt tccactacac   2940
caaaaaagtc cgccctctac ctcgttgatg tgtatgacgc tctgccgatt tctgtagaga   3000
ttagcaccgt cgtaacatgc agcgacagcc agtgcacagt gagggtgcca cctggtacca   3060
cagtgaaatt cgacaagaaa tgcaagagcg ctgactcggc aaccgtcact ttcaccagcg   3120
actcccagac gtttacgtgt gaggagccag tcctaacggc tgccagtatc acccagggca   3180
```

```
agccacacct cagatcggca atgttgccta gcggaggcaa ggaagtgaaa gcaaggatcc   3240
cgttcccgtt cccgccggaa accgcaactt gcagagtgag tgtagcccca ctgccgtcga   3300
tcacctacga ggaaagcgat gtcctgctag ccggtaccgc aaaataccct gtgctgctaa   3360
ccacacggaa ccttggtttc catagcaacg ccacatccga atggatccag ggcaagtacc   3420
tgcgccgcat cccggtcacg cctcaaggga tcgagctaac atggggaaac aacgcgccga   3480 tgcactttg gtcatccgtc aggtacgcat ccggggacgc tgatgcgtac ccctgggaac    3540
ttctggtgta ccacaccaag caccatccag agtacgcgtg ggcgtttgta ggagttgcat   3600
gcggcctgct ggctatcgca gcgtgcatgt ttgcgtgcgc atgcagcagg gtgcggtact   3660
ctctggtcgc caacacgttc aactcgaacc caccaccatt gaccgcactg actgcagcac   3720
tgtgttgcat accaggggct cgcgcggacc aaccctactt ggacatcatt gcctacttgt   3780
ggaccaacag caaagtggcc ttcgggctac aatttgcggc gcccgtggcc tgtgtgctca   3840
tcattacata cgcccttagg cactgcagat tgtgctgcaa gtcttttta ggggtaagag    3900 ggtggtcagc cctgctggtc atccttgcgt atgtacagag ctgcaagagc tacgaacaca   3960
ccgtggtggt cccaatggat ccaagagccc cgtcgtacga agcagtgata aaccggaatg   4020
ggtatgatcc attgaagctg accatctcag tgaatttcac cgtcatctca ccaactacgg   4080
ctctggaata ttggacctgc gcaggagtcc ccatcgtcga gccgcccat gtgggctgct    4140 gcacgtcggt gtcctgcccc tctgacctct ctacgctgca tgcgtttact ggcaaagctg   4200
tctccgacgt gcactgcgat gtgcacacaa acgtgtaccc cttgttgtgg ggcgcggctc   4260
actgcttctg ttccaccgag aatacacagg tcagcgctgt ggcagccacc gtttctgagt   4320
tctgtgccca ggactcagag cgtgccgaag cgttcagcgt acacagcagc tcagtcaccg   4380
ctgaggtcct ggtgacgctt ggtgaagtgg tgacggcagt ccacgtttac gtggacgggg   4440
taacatcagc cagggcact gacctcaaga tcgtggctgg accaataaca accgactact    4500
ccccattcga tcgcaaagta gtccgcatcg gcgaagaggg ctataactat gactggcctc   4560
cttacggggc tggccgacca ggcacattcg gagacattca agctaggtca accaactatg   4620
tcaaacccaa cgatctgtat ggggacatcg gaattgaagt actgcagccg actaacgacc   4680
acgtacatgt ggcttacacg tatacgacct ctgggttact gcgttggctg caggacgctc   4740
cgaaaccact cagtgtcaca gcaccgcacg gttgtaagat cagtgccaat ccgctcctgg   4800
ccctcgattg tggggttggt gccgtcccca tgtccatcaa cattccggac gcgaagttta   4860
cccgcaaatt aaaggatccg aaaccatcgg ccctgaaatg cgtggtggac agctgcgagt   4920
acggggtgga ctacgggggc gccgccacga tcacctacga gggccacgag gccgggaagt   4980
gcgggattca ttccctgaca ccaggagtcc ccctgagaac atcggtggtt gaagtggttg   5040
ctggcgccaa taccgtcaaa acgaccttct cctcacccac gcccgaggtt gcactcgagg   5100
tagagatctg ttcggcaata gtgaagtgcg ctggtgagtg cactccaccg aaggaacatg   5160
tggtcgcaac caggcctcgc catggcagcg accctggagg ctacatctcc gggcccgcaa   5220
tgcgctgggc cggagggatt gtagggaccc tagtggtcct gttccttatc cttgccgtca   5280
tctactgcgt ggtgaagaag tgccgctcca aaagaatccg gatagtcaag agctaatcta   5340
gaccaggccc tggatccaga tctgctgtgc cttctagttg ccagccatct gttgtttgcc   5400
cctcccccgt gccttccttg accctggaag gtgccactcc cactgtcctt tcctaataaa   5460
atgaggaaat tgcatcgcat tgtctgagta ggtgtcattc tattctgggg ggtggggtgg   5520
ggcaggacag caaggggag gattgggaag acaatagcag gcatgctggg gatgcggtgg   5580
```

```
gctctatggg tacccaggtg ctgaagaatt gacccggttc ctcctgggcc agaaagaagc    5640
aggcacatcc ccttctctgt gacacaccct gtccacgccc ctggttctta gttccagccc    5700
cactcatagg acactcatag ctcaggaggg ctccgccttc aatcccaccc gctaaagtac    5760
ttggagcggt ctctccctcc ctcatcagcc caccaaacca aacctagcct caagagtgg    5820 gaagaaatta aagcaagata ggctattaag tgcagaggga gagaaatgc ctccaacatg     5880 tgaggaagta atgagagaaa tcatagaatt ttaaggccat gatttaaggc catcatggcc    5940
ttaatcttcc gcttcctcgc tcactgactc gctgcgctcg gtcgttcggc tgcggcgagc    6000
ggtatcagct cactcaaagg cggtaatacg gttatccaca gaatcagggg ataacgcagg    6060
aaagaacatg tgagcaaaag gccagcaaaa ggccaggaac cgtaaaaagg ccgcgttgct    6120
ggcgtttttc cataggctcc gcccccctga cgagcatcac aaaaatcgac gctcaagtca    6180
gaggtggcga acccgacag gactataaag ataccaggcg tttccccctg gaagctccct    6240
cgtgcgctct cctgttccga ccctgccgct taccggatac ctgtccgcct ttctcccttc    6300
gggaagcgtg gcgctttctc atagctcacg ctgtaggtat ctcagttcgg tgtaggtcgt    6360
tcgctccaag ctgggctgtg tgcacgaacc ccccgttcag cccgaccgct gcgccttatc    6420
cggtaactat cgtcttgagt ccaacccggt aagacacgac ttatcgccac tggcagcagc    6480
cactggtaac aggattagca gagcgaggta tgtaggcggt gctacagagt tcttgaagtg    6540
gtggcctaac tacggctaca ctagaagaac agtatttggt atctgcgctc tgctgaagcc    6600
agttaccttc ggaaaaagag ttggtagctc ttgatccggc aaacaaacca ccgctggtag    6660
cggtggtttt tttgtttgca agcagcagat tacgcgcaga aaaaaaggat ctcaagaaga    6720
tcctttgatc ttttctacgg ggtctgacgc tcagtggaac gaaaactcac gttaagggat    6780
tttggtcatg agattatcaa aaaggatctt cacctagatc cttttaaatt aaaaatgaag    6840
ttttaaatca atctaaagta tatatgagta aacttggtct gacagttacc aatgcttaat    6900
cagtgaggca cctatctcag cgatctgtct atttcgttca tccatagttg cctgactcgg    6960 ggggggggg cgctgaggtc tgcctcgtga agaaggtgtt gctgactcat accaggcctg    7020
aatcgcccca tcatccagcc agaaagtgag ggagccacgg ttgatgagag ctttgttgta    7080
ggtggaccag ttggtgattt tgaacttttg ctttgccacg gaacggtctg cgttgtcggg    7140
aagatgcgtg atctgatcct tcaactcagc aaaagttcga tttattcaac aaagccgccg    7200
tcccgtcaag tcagcgtaat gctctgccag tgttacaacc aattaaccaa ttctgattag    7260
aaaaactcat cgagcatcaa atgaaactgc aatttattca tatcaggatt atcaatacca    7320
tatttttgaa aaagccgttt ctgtaatgaa ggagaaaact caccgaggca gttccatagg    7380
atggcaagat cctggtatcg gtctgcgatt ccgactcgtc caacatcaat acaacctatt    7440
aatttcccct cgtcaaaaat aaggttatca agtgagaaat caccatgagt gacgactgaa    7500
tccggtgaga atggcaaaag cttatgcatt tctttccaga cttgttcaac aggccagcca    7560
ttacgctcgt catcaaaatc actcgcatca accaaaccgt tattcattcg tgattgcgcc    7620
tgagcgagac gaaatacgcg atcgctgtta aaaggacaat acaaacagg aatcgaatgc    7680 aaccggcgca ggaacactgc cagcgcatca acaatatttt cacctgaatc aggatattct    7740
tctaatacct ggaatgctgt tttcccgggg atcgcagtgg tgagtaacca tgcatcatca    7800
ggagtacgga taaaatgctt gatggtcgga agaggcataa attccgtcag ccagtttagt    7860
ctgaccatct catctgtaac atcattggca acgctacctt tgccatgttt cagaaacaac    7920
```

| | |
|---|---|
| tctggcgcat cgggcttccc atacaatcga tagattgtcg cacctgattg cccgacatta | 7980 |
| tcgcgagccc atttataccc atataaatca gcatccatgt tggaatttaa tcgcggcctc | 8040 |
| gagcaagacg tttcccgttg aatatggctc ataacacccc ttgtattact gtttatgtaa | 8100 |
| gcagacagtt ttattgttca tgatgatata tttttatctt gtgcaatgta acatcagaga | 8160 |
| ttttgagaca caacgtggct ttccccccccc ccccattatt gaagcattta tcagggttat | 8220 |
| tgtctcatga gcggatacat atttgaatgt atttagaaaa ataaacaaat aggggttccg | 8280 |
| cgcacatttc cccgaaaagt gccacctgac gtctaagaaa ccattattat catgacatta | 8340 |
| acctataaaa ataggcgtat cacgaggccc tttcgtc | 8377 |

```
<210> SEQ ID NO 14
<211> LENGTH: 8179
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1645)..(1646)
<223> OTHER INFORMATION: a, c, t, g, unknown or other
<220> FEATURE:
<221> NAME/KEY: modified_base
<222> LOCATION: (1993)..(1994)
<223> OTHER INFORMATION: a, c, t, g, unknown or other
<220> FEATURE:
<221> NAME/KEY: modified_base
<222> LOCATION: (2072)..(2072)
<223> OTHER INFORMATION: a, c, t, g, unknown or other
<220> FEATURE:
<221> NAME/KEY: modified_base
<222> LOCATION: (2426)..(2427)
<223> OTHER INFORMATION: a, c, t, g, unknown or other
<220> FEATURE:
<221> NAME/KEY: modified_base
<222> LOCATION: (2713)..(2713)
<223> OTHER INFORMATION: a, c, t, g, unknown or other
<220> FEATURE:
<221> NAME/KEY: modified_base
<222> LOCATION: (3081)..(3081)
<223> OTHER INFORMATION: a, c, t, g, unknown or other
<220> FEATURE:
<221> NAME/KEY: modified_base
<222> LOCATION: (3253)..(3253)
<223> OTHER INFORMATION: a, c, t, g, unknown or other
<220> FEATURE:
<221> NAME/KEY: modified_base
<222> LOCATION: (3618)..(3620)
<223> OTHER INFORMATION: a, c, t, g, unknown or other
<220> FEATURE:
<221> NAME/KEY: modified_base
<222> LOCATION: (3706)..(3722)
<223> OTHER INFORMATION: a, c, t, g, unknown or other
<220> FEATURE:
<221> NAME/KEY: modified_base
<222> LOCATION: (3888)..(3890)
<223> OTHER INFORMATION: a, c, t, g, unknown or other
<220> FEATURE:
<221> NAME/KEY: modified_base
<222> LOCATION: (3926)..(3927)
<223> OTHER INFORMATION: a, c, t, g, unknown or other
<220> FEATURE:
<221> NAME/KEY: modified_base
<222> LOCATION: (4415)..(4415)
<223> OTHER INFORMATION: a, c, t, g, unknown or other
<220> FEATURE:
<221> NAME/KEY: modified_base
<222> LOCATION: (4761)..(4763)
<223> OTHER INFORMATION: a, c, t, g, unknown or other
<220> FEATURE:
<221> NAME/KEY: modified_base
<222> LOCATION: (4893)..(4897)
```

<223> OTHER INFORMATION: a, c, t, g, unknown or other

<400> SEQUENCE: 14

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgcatgaatt    1380
acataccaac ccagactttt tacggacgcc gttggcggcc tcgcccggcg ttccgtccat    1440
ggcaggtgcc gatgcagccg acacctacta tggttacacc catgctgcaa gcaccggacc    1500
tacaggctca acagatgcaa caactgatca gcgcagtctc tgcactaacc accaaacaga    1560
atgtaaaagc accaaagggg caacggaaac agaaacagca gaaaccaaag gaaaagaagg    1620
aaaaacagaa gaaaaagccg acgcnnaaga agaagcagca gcagaaacca aaaccacagg    1680
ctaagaagaa gaaaccaggg agaagagaaa gaatgtgcat gaagatcgag aatgactgca    1740
tattcgaggt caaactggac ggcaaggtta ccggctatgc gtgcctagtc ggagataagg    1800
tcatgaagcc ggctcacgtt aaaggcacaa ttgataaccc agaccttgcg aagttgactt    1860
acaagaaatc cagtaagtat gacctcgaat gcgcccagat cccagtgcac atgaagtccg    1920
acgcctccaa gtacacacat gaaaagcccg aaggtcatta caattggcac catggagcag    1980
tgcagtacag cgnnggaagg tttaccatcc ccacaggcgc cggcaaacca ggagatagcg    2040
gtaggcctat ttttgacaac aaagggcgag tngtggccat cgtgttaggc ggggccaacg    2100
aaggtgcccg cactgcgctg tctgtggtga cgtggacaaa agacatggtc actcgggtaa    2160
cgccagaagg aaccgaagag tggtctgccg cgctgatgat gtgtatcctt gccaacacct    2220
cttttccatg ctcgtcacct ccctgctacc cctgctgcta cgaaaaacag ccagaacaga    2280
```

```
cactgcggat gctggaagac aacgtgaata gacctgggta ctatgagtta ctggaagcgt   2340
ccatgacatg cagaaacaga tcacgccacc gccgcagtgt aatagagcac ttcaatgtgt   2400
ataaggctac tagaccgtac ttagcnnact gcgctgactg cggggacggg tacttctgct   2460
atagcccggt tgctatcgag aagatccgag atgaggcgtc tgatggcatg ctcaagatcc   2520
aagtctccgc ccaaataggt ctggacaagg caggtaccca cgcccacacg aagatgcgat   2580
atatggctgg tcatgatgtt caggaatcta agagagattc cttgagggtg tatacgtccg   2640
cagcgtgctc tatacatggg acgatgggac acttcatcgt cgcacactgt ccaccaggcg   2700
actacctcaa ggnttcgttc gaggacgcaa attcacacgt gaaggcatgt aaggtccaat   2760
acaagcacga cccattgccg gtgggtagag agaagtttgt ggttagacca cactttggcg   2820
tagagctgcc atgcacctca taccagctga caacggctcc caccgacgag gagattgaca   2880
tgcatacacc gccagatata ccggatcgca ccctgctatc acagacggcg ggcaacgtca   2940
aaataacagc aggcggcagg actatcaggt acaattgtac ctgcggccgt gacaacgtag   3000
gcactaccag tactgacaag accatcaaca catgcaagat agaccaatgc catgctgccg   3060
ttaccagcca tgacaaatgg naatttacct ctccatttgt tcccagggct gatcagacag   3120
ccaggaaagg caaagtgcat gttccattcc ctttgactaa cgtcacctgc cgagtgccgt   3180
tggcacgagc gccggatgtc acctatggta agaaggaggt gaccctaaga ttacacccag   3240
atcatccgac gcncttctcc tataggagtt taggagccgt accgcacccg tacgaggaat   3300
gggttgacaa gttctctgag cgcatcatcc cagtgacgga agaagggatt gagtaccagt   3360
ggggtaacaa cccgccggtc cgcctgtggg cgcaactgac gactgagggt aaaccccatg   3420
gctggccaca tgaaatcatt cagtactatt atggactata ccccgccgcc actattgccg   3480
cagtatccgg ggcgagtctg atggccctcc taactctagc ggccacatgc tgcatgctgg   3540
ccaccgcgag gagaaagtgc ctaacaccgt acgctttgac gccaggagcg gtggtaccgt   3600
tgacattggg gctgcttnnn tgcgcaccga gggcgaacgc agcatcattt gctgagacta   3660
tggcctatct gtgggacgag aacaaaaccc tcttttggat ggaatnnnnn nnnnnnnnnn   3720
nngcgcttgc tttgctggca tgctgtatca aaagcctgat ctgctgttgt aagccatttt   3780 ctttttagt gttactgagc ctgggagcct ccgcaaaagc ttatgagcac acagccacaa   3840
ttccgaacgt ggtggggttc ccgtataagg ctcacattga aaggaatnnn ttctcgccca   3900
tgactctgca gcttgaagtg gtgganncaa gcttggaacc cacacttaac ctggagtaca   3960
ttacctgcga atacaagacg gtggtccctt cgccatttat caaatgttgc ggaacatcag   4020
aatgctcatc taaagagcag ccagactacc aatgcaaggt gtacacgggt gtataccctt   4080
tcatgtgggg tggagcttac tgtttctgcg actccgagaa cacgcagctt agcgaggcct   4140
atgtcgacag gtcagacgtt tgcaaacatg atcatgcatt ggcctacaag gcacacacgg   4200
cctctctaaa agcaacaatc aggatcagct acggcaccat caaccagacc accgaggcct   4260
tcgtcaatgg agaacacgcg gtcaacgtgg gcggaagcaa gttcatcttt ggaccgatct   4320
caacagcttg gtcaccgttc gacaataaaa ttgtcgtgta aaagatgat gtctacaacc   4380 aggacttccc acccctacgga tcaggccagc cgggnagatt cggagacatc cagagcagga   4440
cagtggagag caaagacttg tatgctaata cggccctaaa actctcaaga ccatcacccg   4500
gggttgtgca tgtgccatac acgcagacac catccggatt taagtattgg ctgaaggaga   4560
aaggatcttc attgaataca aaggcccctt ttggctgcaa gataaagacc aatccagtca   4620
```

```
gagctatgga ttgtgcagtt ggcagtatac ctgtgtcgat ggacatacct gacagtgcat    4680
tcacacgagt ggtagatgcc ccggctgtaa cagacctgag ctgccaggta gctgtctgta    4740
cacactcctc cgatttcgga nnngttgcca cattgtctta caagacggac aaacccggca    4800
agtgcgccgt tcactcacat tccaacgtcg caacgttgca agaggcgacg gtggatgtca    4860
aggaggatgg caaggtcaca gtgcactttt ctnnnnngtc cgcctccccg gcattcaaag    4920
tgtccgtctg tgacgcaaaa acaacgtgca cggcggcgtg cgagcctccg aaagaccaca    4980 tcgtcccta tggggcgagc cataacaacc aggtctttcc ggacatgtca ggaactgcga    5040
tgacgtgggt acagaggatg gccagtgggt taggtgggct ggccctcatc gcggtggttg    5100
tgctggtctt ggtaacctgc ataacaatgc gtcggtaatc tagaccaggc cctggatcca    5160
gatctgctgt gccttctagt tgccagccat ctgttgtttg cccctccccc gtgccttcct    5220
tgaccctgga aggtgccact cccactgtcc tttcctaata aaatgaggaa attgcatcgc    5280
attgtctgag taggtgtcat tctattctgg ggggtggggt ggggcaggac agcaagggg    5340 aggattggga agacaatagc aggcatgctg gggatgcggt gggctctatg ggtacccagg    5400
tgctgaagaa ttgacccggt tcctcctggg ccagaaagaa gcaggcacat ccccttctct    5460
gtgacacacc ctgtccacgc ccctggttct tagttccagc cccactcata ggacactcat    5520
agctcaggag ggctccgcct tcaatcccac ccgctaaagt acttggagcg gtctctccct    5580
ccctcatcag cccaccaaac caaacctagc ctccaagagt gggaagaaat taaagcaaga    5640
taggctatta agtgcagagg gagagaaaat gcctccaaca tgtgaggaag taatgagaga    5700
aatcatagaa ttttaaggcc atgatttaag gccatcatgg ccttaatctt ccgcttcctc    5760
gctcactgac tcgctgcgct cggtcgttcg gctgcggcga gcggtatcag ctcactcaaa    5820
ggcggtaata cggttatcca cagaatcagg ggataacgca ggaaagaaca tgtgagcaaa    5880
aggccagcaa aaggccagga accgtaaaaa ggccgcgttg ctggcgtttt tccataggct    5940
ccgcccccct gacgagcatc acaaaaatcg acgctcaagt cagaggtggc gaaacccgac    6000
aggactataa agataccagg cgtttccccc tggaagctcc ctcgtgcgct ctcctgttcc    6060
gaccctgccg cttaccggat acctgtccgc ctttctccct tcgggaagcg tggcgctttc    6120
tcatagctca cgctgtaggt atctcagttc ggtgtaggtc gttcgctcca agctgggctg    6180
tgtgcacgaa ccccccgttc agcccgaccg ctgcgcctta tccggtaact atcgtcttga    6240
gtccaacccg gtaagacacg acttatcgcc actggcagca gccactggta acaggattag    6300
cagagcgagg tatgtaggcg gtgctacaga gttcttgaag tggtggccta actacggcta    6360
cactagaaga acagtatttg gtatctgcgc tctgctgaag ccagttacct tcggaaaaag    6420
agttggtagc tcttgatccg gcaaacaaac caccgctggt agcggtggtt tttttgtttg    6480
caagcagcag attacgcgca gaaaaaaagg atctcaagaa gatcctttga tcttttctac    6540
ggggtctgac gctcagtgga acgaaaactc acgttaaggg attttggtca tgagattatc    6600
aaaaaggatc ttcacctaga tccttttaaa ttaaaaatga gttttaaat caatctaaag    6660 tatatatgag taaacttggt ctgacagtta ccaatgctta atcagtgagg cacctatctc    6720
agcgatctgt ctatttcgtt catccatagt tgcctgactc ggggggggg ggcgctgagg    6780 tctgcctcgt gaagaaggtg ttgctgactc ataccaggcc tgaatcgccc catcatccag    6840
ccagaaagtg agggagccac ggttgatgag agctttgttg taggtggacc agttggtgat    6900
tttgaacttt tgctttgcca cggaacggtc tgcgttgtcg ggaagatgcg tgatctgatc    6960
cttcaactca gcaaaagttc gatttattca acaaagccgc cgtcccgtca agtcagcgta    7020
```

-continued

```
atgctctgcc agtgttacaa ccaattaacc aattctgatt agaaaaactc atcgagcatc    7080
aaatgaaact gcaatttatt catatcagga ttatcaatac catattttg aaaaagccgt     7140
ttctgtaatg aaggagaaaa ctcaccgagg cagttccata ggatggcaag atcctggtat    7200
cggtctgcga ttccgactcg tccaacatca atacaaccta ttaatttccc ctcgtcaaaa    7260
ataaggttat caagtgagaa atcaccatga gtgacgactg aatccggtga gaatggcaaa    7320
agcttatgca tttctttcca gacttgttca acaggccagc cattacgctc gtcatcaaaa    7380
tcactcgcat caaccaaacc gttattcatt cgtgattgcg cctgagcgag acgaaatacg    7440
cgatcgctgt taaaggaca attacaaaca ggaatcgaat gcaaccggcg caggaacact     7500
gccagcgcat caacaatatt tccacctgaa tcaggatatt cttctaatac ctggaatgct    7560
gttttccccgg ggatcgcagt ggtgagtaac catgcatcat caggagtacg ataaaatgc    7620
ttgatggtcg aagaggcat aaattccgtc agccagttta gtctgaccat ctcatctgta     7680
acatcattgg caacgctacc tttgccatgt ttcagaaaca actctggcgc atcgggcttc    7740
ccatacaatc gatagattgt cgcacctgat tgcccgacat tatcgcgagc ccatttatac    7800
ccatataaat cagcatccat gttggaattt aatcgcggcc tcgagcaaga cgtttcccgt    7860
tgaatatggc tcataacacc ccttgtatta ctgtttatgt aagcagacag ttttattgtt    7920
catgatgata tatttttatc ttgtgcaatg taacatcaga gattttgaga cacaacgtgg    7980
cttttccccccc cccccatta ttgaagcatt tatcagggtt attgtctcat gagcggatac    8040
atatttgaat gtatttagaa aaataaacaa ataggggttc cgcgcacatt tccccgaaaa    8100
gtgccacctg acgtctaaga aaccattatt atcatgacat taacctataa aaataggcgt    8160
atcacgaggc cctttcgtc                                                 8179
```

<210> SEQ ID NO 15
<211> LENGTH: 8145
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
```

-continued

```
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctcca tcggctcgca tctctccttc acgcgcccgc     1020
cgccctacct gaggccgcca tccacgccgg ttgagtcgcg ttctgccgcc tcccgcctgt     1080
ggtgcctcct gaactgcgtc cgccgtctag gtaagtttaa agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcgtcgacca ccatggagtt cataccagca caaacttact     1380
acaatagaag ataccagcct agaccctgga ctcaacgccc tactatccag gtgatcaggc     1440
caaaaccacg ccgaagaagg cctgcaggac aactcgcaca actgatatcc gcagtcagca     1500
gactagcact gcgtacagtt ccccagaaac cacgccggac ccgaaaaatt aagaagcaaa     1560
agcaagtaaa gcaagaacaa cagagtacta cgaaccagaa gaaaaaggcg ccgaaacaaa     1620
agcagaccca aaagaaaaag agaccaggac gaagggaaag gatgtgcatg aagattgaaa     1680
atgactgcat cttcgaagtc agacatgaag gaaaagtaac ggggtatgca tgcctagtag     1740
gtgataaggt aatgaaacca gcacacgtga aaggaactat tgacaacgca gacctagcga     1800
agttggcgtt caaaagatca tccaaatatg atctagagtg cgcacagata ccagtgcaca     1860
tgaaatcgga cgcctcaaag ttcacccatg aaaaaccaga aggctattac aactggcatc     1920
acggagcagt acagtattct ggagggaggt tcacgatccc tacaggcgca ggaaagcctg     1980
gggacagcgg aagaccaatc tttgacaaca aggggcgtgt cgtggctatt gttctaggcg     2040
gagcaaacga aggaaccagg acagcactat ctgtagtgac ttggaataaa gacatagtca     2100
caaaaatcac accagagggg tcagttgaat ggagccttgc cctccctgtc atgtgcctgt     2160
tggcaaatac aaccttccca tgttcccaac cgccttgcgc gccgtgctgc tacgaaaaga     2220
aaccggaaga aaccttgaga atgctggagg acaacgtcat gcaaccagga tattaccagt     2280
tactcgattc agcattggcc tgctcacaac gtcgtcaaaa acgtaatgca agagaaaact     2340
tcaatgtcta caaagtcact aggccgtact agcccactg tcctgactgc ggggagggac      2400
actcatgcca cagcccaata gcattagaac ggatcagaag tgaggcaaca gatggtacct     2460
tgaaaatcca ggtatctctg caaatcggaa taaagacaga cgacagccac gattggacga     2520
agctacggta tatggatagc catacacctg tggatgcaga ccgatccggg ttgtttgtca     2580
gaacgtcagc accgtgcacc atcacgggaa cgatgggaca tttcatacta gcacgctgtc     2640 cgaaggagagacgctgacg gtaggatttg tagacagtag aaggatcagt cacacgtgca     2700
tgcacccgtt ccgccacgag ccaccgctga tagggagaga gaagtttcac tcccgcccgc     2760
agcatggcaa agaactacct tgcagtacat acgtccatac cacagcggca actgctgagg     2820
aaatagaagt gcatatgccg ccagatacc ctgactacac gctgatgaca cagcaagcgg     2880
gaaacgttaa gatcacagtt gacggccaga cggtacgata caagtgcaaa tgtgacggct     2940
ccaatgaagg attaataacc gctgacaaag tcataaataa ctgcaaagta gaccaatgcc     3000
acacagcggt tacaaaccac aagaaatggc aatacaattc accgctgacc ccgcggaact     3060
ccgaacaagg agatagaaaa ggtaagatcc atatcccatt tccactggtg aacacaacct     3120
gcagggtacc aaaagcaaga aatccgactg tcacatacgg taaaaacaga gtcactctgc     3180
```

-continued

```
tgttacatcc agaccaccca acactccttt cgtaccgcgc catgggaagg atcccggatt    3240
accatgaaga gtggataaca aacaagaagg aaataagtat cacagtacca gcagaaggct    3300
tagaggttac gtggggtaat aatgacccat acaaatattg gccccaactg tctacaaatg    3360
gtactgcgca cggcaccca catgaaataa tcctctatta ctatgagctg tacccaacta    3420
ccacaattgc tgtactagct gctgcttcta tcgtaataac atctttggta ggtctatcat    3480
taggcatgtg catatgcgcg agacgcaggt gcatcacgcc atatgagctg actccaggag    3540
ctaccatccc attcctccta ggtgtactat gctgtgccag gactgcaaaa gcagcatcgt    3600
actacgaagc tgcaacatac ctctggaatg agcaacaacc attattttgg ttacagcttc    3660
taatccctct gtcagctgca attgttgtgt gtaattgcct aaaactttta ccatgctgct    3720
gcaaaacatt gacttttta gccgtcatga gcatcggtgc ccgcactgtg accgcgtacg    3780
agcacgcaac agtgatcccg aacacggtgg gagtaccgtg taagactctt gttagcagac    3840
cagggtacag ccctatggtc ttagaaatgg agctacagtc ggtcactctg gaaccagcat    3900
tatccttgga ttacattacg tgtgagtata aacaatcac accgtccccg tacgtaaaat    3960
gctgtggtac agctgaatgt aaggccaaga acctgccaga ttataactgc aaagtattca    4020
caggcgtcta cccatttatg tggggaggag catactgctt ctgtgacgca gagaacacac    4080
agctcagcga ggcacacgtt gagaaatcag aatcatgcaa aactgagttt gcatcagcct    4140
acagagccca cacagcttca gtatcagcta aactacgtgt cttttaccaa gggaataata    4200
tcaccgtgtc tgcatacgcc aatggtgatc atgcagttac ggtggaagac gcgaagtttg    4260
tcatcggtcc actatcgtcc gcctggtcac catttgataa taagatcgtg gtgtacaaag    4320
gcgaagtcta caatatggac tatccaccttc tcggcgcagg gaggccagga cagttcggtg    4380
acatccagag ccgcacgcca gacagcaagg acgtctatgc gaatacgcag ttaatactgc    4440
aaagaccagc ggcaggagca atacacgtgc cttactccca ggcaccttcg ggctttaagt    4500
actggctcaa ggaaaaaggg gcatcattgc agcatactgc accatttggc tgtcagatag    4560
caacaaaccc ggtaagagca gtgaactgtg cagtgggcaa cataccagtc tccattgaca    4620
tcccagatga agctttcacc agggtcactg acgctccttc catcacagac atgtcctgcg    4680
aagtagcttc gtgtacccat tcatctgatt ttggaggtgc cgcagtcata agtacacag    4740 ctagtaaaaa aggaaaatgc gccgtgcact ctgtaacaaa tgcggtcact atccgcgaac    4800
ctaacgtaga tgtcaaggga acagcacaat tgcaaattgc cttctcgacc gcactagcta    4860
gtgcggaatt caaggtgcag atctgctcca cactggtaca ctgctcagcg acgtgccatc    4920
ctcctaaaga ccatatagtc aattacccgt cacctcacac cacactagga gtgcaggaca    4980
tttcaacgac agctatgtct tgggtccaga agattacagg aggagtggga ctcgtggttg    5040
ctatagctgc tttgatctta attatagttc tctgcgtatc atttagcaga cactaagcgg    5100
ccgctctaga ccaggccctg gatccagatc tgctgtgcct tctagttgcc agccatctgt    5160
tgtttgcccc tccccgtgc cttccttgac cctggaaggt gccactccca ctgtccttt     5220 ctaataaaat gaggaaattg catcgcattg tctgagtagg tgtcattcta ttctgggggg    5280
tggggtgggg caggacagca aggggaggga ttgggaagac aatagcaggc atgctgggga    5340
tgcggtgggc tctatgggta cccaggtgct gaagaattga cccggttcct cctgggccag    5400
aaagaagcag gcacatcccc ttctctgtga cacaccctgt ccacgcccct ggttcttagt    5460
tccagcccca ctcataggac actcatagct caggagggct ccgccttcaa tcccaccgc    5520 taaagtactt ggagcggtct ctccctccct catcagccca ccaaaccaaa cctagcctcc    5580
```

```
aagagtggga agaaattaaa gcaagatagg ctattaagtg cagagggaga gaaaatgcct    5640
ccaacatgtg aggaagtaat gagagaaatc atagaatttt aaggccatga tttaaggcca    5700
tcatggcctt aatcttccgc ttcctcgctc actgactcgc tgcgctcggt cgttcggctg    5760
cggcgagcgt atcagctca ctcaaaggcg gtaatacggt tatccacaga atcaggggat    5820
aacgcaggaa agaacatgtg agcaaaaggc cagcaaaagg ccaggaaccg taaaaaggcc    5880
gcgttgctgg cgttttttcca taggctccgc ccccctgacg agcatcacaa aaatcgacgc    5940
tcaagtcaga ggtggcgaaa cccgacagga ctataaagat accaggcgtt ccccctggaa    6000
agctccctcg tgcgctctcc tgttccgacc ctgccgctta ccggatacct gtccgccttt    6060
ctcccttcgg gaagcgtggc gctttctcat agctcacgct gtaggtatct cagttcggtg    6120
taggtcgttc gctccaagct gggctgtgtg cacgaaccc ccgttcagcc cgaccgctgc    6180
gccttatccg gtaactatcg tcttgagtcc aacccggtaa gacacgactt atcgccactg    6240
gcagcagcca ctggtaacag gattagcaga gcgaggtatg taggcggtgc tacagagttc    6300
ttgaagtggt ggcctaacta cggctacact agaagaacag tatttggtat ctgcgctctg    6360
ctgaagccag ttaccttcgg aaaaagagtt ggtagctctt gatccggcaa acaaaccacc    6420
gctggtagcg gtggtttttt tgtttgcaag cagcagatta cgcgcagaaa aaaggatct    6480 caagaagatc ctttgatctt ttctacgggg tctgacgctc agtggaacga aaactcacgt    6540
taagggattt tggtcatgag attatcaaaa aggatcttca cctagatcct tttaaattaa    6600
aaatgaagtt ttaaatcaat ctaaagtata tatgagtaaa cttggtctga cagttaccaa    6660
tgcttaatca gtgaggcacc tatctcagcg atctgtctat ttcgttcatc catagttgcc    6720
tgactcgggg ggggggggcg ctgaggtctg cctcgtgaag aaggtgttgc tgactcatac    6780
caggcctgaa tcgccccatc atccagccag aaagtgaggg agccacggtt gatgagagct    6840
ttgttgtagg tggaccagtt ggtgattttg aacttttgct ttgccacgga acggtctgcg    6900
ttgtcgggaa gatgcgtgat ctgatccttc aactcagcaa aagttcgatt tattcaacaa    6960
agccgccgtc ccgtcaagtc agcgtaatgc tctgccagtg ttacaaccaa ttaaccaatt    7020
ctgattagaa aaactcatcg agcatcaaat gaaactgcaa tttattcata tcaggattat    7080
caataccata tttttgaaaa agccgtttct gtaatgaagg agaaaactca ccgaggcagt    7140
tccataggat ggcaagatcc tggtatcggt ctgcgattcc gactcgtcca acatcaatac    7200
aacctattaa tttccccctcg tcaaaaataa ggttatcaag tgagaaatca ccatgagtga    7260
cgactgaatc cggtgagaat ggcaaaagct tatgcatttc tttccagact tgttcaacag    7320
gccagccatt acgctcgtca tcaaaatcac tcgcatcaac caaaccgtta ttcattcgtg    7380
attgcgcctg agcgagacga atacgcgat cgctgttaaa aggacaatta caaacaggaa    7440
tcgaatgcaa ccggcgcagg aacactgcca gcgcatcaac aatattttca cctgaatcag    7500
gatattcttc taatacctgg aatgctgttt tcccggggat cgcagtggtg agtaaccatg    7560
catcatcagg agtacggata aaatgcttga tggtcggaag aggcataaat tccgtcagcc    7620
agtttagtct gaccatctca tctgtaacat cattggcaac gctacctttg ccatgtttca    7680
gaaacaactc tggcgcatcg gcttcccat acaatcgata gattgtcgca cctgattgcc    7740
cgacattatc gcgagccat ttatacccat ataaatcagc atccatgttg gaatttaatc    7800
gcggcctcga gcaagacgtt tcccgttgaa tatggctcat aacaccccctt gtattactgt    7860 ttatgtaagc agacagtttt attgttcatg atgatatatt tttatcttgt gcaatgtaac    7920
```

```
atcagagatt ttgagacaca acgtggcttt cccccccccc ccattattga agcatttatc   7980
agggttattg tctcatgagc ggatacatat ttgaatgtat ttagaaaaat aaacaaatag   8040
gggttccgcg cacatttccc cgaaaagtgc cacctgacgt ctaagaaacc attattatca   8100
tgacattaac ctataaaaat aggcgtatca cgaggcccdt tcgtc                  8145
```

<210> SEQ ID NO 16
<211> LENGTH: 8132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca cgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa     600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgccaccatg   1380
gacttcctac caactcaagt gttctatggc agacgctgga gaccacgaat gccgccacgc   1440
ccttggagac cacgcatgcc tacaatgcag agaccagacc aacaggcccg acaaatgcag   1500
caattgattg cagcggttag cacgcttgcc ctgaggcaga atgcagccgc ccctcagcgt   1560
ggaaagaaga agcagccacg cagaaagaaa ccaaaaccgc agcccgagaa accaaagaag   1620
caagaacaga agccgaagca aaagaaggcc cctaaacgaa gccagggag aagagaacgc     1680 atgtgcatga agattgagca tgattgcatc ttcgaggtta agcacgaagg taaagtcacg   1740
ggttacgcct gccttgtcgg tgacaaggta atgaagccag cacacgttcc cggggtgata   1800
```

```
gacaatgcag atcttgcacg cctgtcgtac aagaaatcca gtaagtacga tctggaatgt    1860
gcacaaatac ccgtggctat gaagtcagat gcttcgaagt acacccatga gaaacccgag    1920
ggtcattaca actggcacta cggcgccgtc cagtacacgg gaggaagatt cacggtgccc    1980
acaggagtgg gtaagcctgg cgacagcggt cggcccatct ttgacaacaa agggccggtt    2040
gtcgcaatag tgctgggagg agccaacgaa ggtaccagaa ccgcccttc cgttgtgaca    2100 tggaataaag acatggtcac gaagattaca cctgaaggca ctgtggagtg ggcagcctcg    2160
acagtgacag ccatgtgtct tttgacaaat atatccttcc catgtttcca accgagctgt    2220
gcaccgtgct gctatgaaaa ggggcctgag ccgacgctga ggatgctgga ggagaacgta    2280
aattcagaag gatattacga cctgctgcac gctgccgtgt actgtagaaa cagttcaagg    2340
tcgaagagaa gcactgcaaa tcattttaat gcgtataagt tgacccgtcc atatgtggct    2400
tactgcgcag actgcggtat gggtcattct tgccacagcc cagccatgat cgaaaatatt    2460
caggcggatg caacagatgg cacgctaaaa attcagtttg cttcccaaat tggcctgacc    2520
aaaacggaca cgcacgatca cacaaagatt agatatgctg aaggacacga cattgcagag    2580
gctgccagat caacccttaa ggtacacagt agcagtgagt gcacggtaac cggcacaatg    2640 ggacactta tcctggccaa atgtccacct ggcgaacgaa tcagtgtctc atttgttgat    2700
tcgaaaaacg aacaccggac ctgccggata gcctaccacc atgaacagag gttaataggg    2760
cgagaaagat tcacggtgcg accgcatcat ggaattgagc taccttgcac cacttatcaa    2820
ttgactaccg ccgaaaccct gaagaaatt gatatgcaca tgccgccgga cattccggat    2880
agaactatcc tttcccaaca atcaggaaat gttaagataa cggtgaatgg acgaaccgtc    2940
aggtacagct cttcttgcgg ttcccaagcc gtcgggacaa caaccacaga caagaccatt    3000
aatagctgta ccgttgacaa atgtcaggct tacgtcacga gccacacaaa atggcaattc    3060
aattcacctt ttgtcccacg tcggatgcaa gcagagcgca agggcaaagt gcatatcccc    3120
tttcccctta ttaacaccac ctgccgtgta ccgctggctc ccgaggccct tgttaggagc    3180
ggtaaacgcg aagctacact ttcattgcac cctatccacc ccacattgct aagttacaga    3240
acatttggag cggagcgggt cttttgacgag cagtggatca ccgcccagac ggaggtaacg    3300
atcccggtac ctgtggaggg agtggagtac cagtggggca accataaacc tcaacgtttt    3360
gtggtcgcac tgacgactga aggcaaagca catggatggc ctcatgaaat tattgaatac    3420
tactacggac tgcatcctac gacaaccatt gtcgtggtga ttcgtgtctc agtggtggtg    3480
cttctgtcat tcgccgcctc ggtctacatg tgcgtggtag cacgaaccaa atgtctgaca    3540
ccatatgcac tcacgccggg agctgttgtt cctgttacca ttggggtgct gtgttgcgca    3600
ccgaaagcac atgcagccag tttcgcagaa ggtatggcct atctgtggga taacaatcag    3660
tcgatgttct ggatggagct gaccggacca ttggccctcc ttattctggc tacatgctgc    3720
gcccgatcac tgctttcctg ctgcaagggg tctttttag tcgcaatgag catcgggagt    3780
gccgttgcca gtgcttacga gcacacggca attattccga accaagtggg attcccgtat    3840
aaggctcatg ttgcgcgtga aggttacagt cctttgaccc tgcagatgca ggtgatagag    3900
accagccttg agccaacact caacctggag tatatcactt gcgattacaa aacaaaagtt    3960
ccatcaccat acgtaaagtg ctgcggcacg gcagaatgcc gcacacagga caagcctgag    4020
tacaaatgtg cagtgttcac aggtgtgtat cctttttatgt ggggaggtgc atactgttt    4080 tgtgattcgg agaacacaca gatgagcgaa gcctacgtgg agcgcgctga cgtgtgtaaa    4140
cacgaccacg cagctgccta ccgtgcccac accgcatccc ttagagcaaa aattaaggtg    4200
```

```
acatacggta ctgtgaacca gacagttgag gcgtatgtga acggtgacca tgccgtaacg    4260
attgccggaa caaaatttat tttgggcca gtgtcaacgc cttggacacc gttcgataca    4320
aaaattctgg tttacaaagg ggagttatac aatcaggact tcccacggta tggtgccggg    4380
cagcctggaa gatttgggga cattcagagc cggacgctgg atagtcgaga cctatatgcc    4440
aacacgggcc tcaagctggc acgaccggca gccggcaaca ttcacgtccc ctatacccag    4500
actccatctg gctttaaaac atggcaaaaa gacagggact caccgcttaa cgccaaggcg    4560
ccttttggat gcataatcca gacaaatccg gtccgagcca tgaactgcgc cgtcggcaac    4620
atacccgttt cgatggatat cgccgacagc gccttcacaa gattgaccga cgcgcctgta    4680
atctctgagt tgacgtgcac tgtgtctaca tgcacgcact catcggattt tggcgggatc    4740
gctgtacttt cctacaaggt ggaaaaatca ggcaggtgcg acatccattc acattcaaac    4800
gtcgcggtac tccaggaagt ttccatcgag acagaaggtc gatcagtgat ccacttctca    4860
accgcatcag cctccccttc cttcgtagtt tctgtttgta gttcgcgtgc tacgtgcaca    4920
gcgaaatgtg aaccaccgaa agaccacgtt gttacatatc cagcaaatca taacgggta    4980 actttgccag acttatctag cactgccatg acgtgggcac aacatcttgc cggcggagtt    5040
gggttgctga tagctctggc cgtgctaatt ctggtaatag ttacttgtgt gactttgaga    5100
aggtaaggat ccagatctgc tgtgccttct agttgccagc catctgttgt ttgcccctcc    5160
cccgtgcctt ccttgaccct ggaaggtgcc actcccactg tcctttccta ataaaatgag    5220
gaaattgcat cgcattgtct gagtaggtgt cattctattc tggggggtgg ggtggggcag    5280
gacagcaagg gggaggattg gaagacaat agcaggcatg ctggggatgc ggtgggctct    5340
atgggtaccc aggtgctgaa gaattgaccc ggttcctcct gggccagaaa gaagcaggca    5400
catccccttc tctgtgacac accctgtcca cgccctggt tcttagttcc agccccactc    5460
ataggacact catagctcag gagggctccg ccttcaatcc cacccgctaa agtacttgga    5520
gcggtctctc cctccctcat cagcccacca aaccaaacct agcctccaag agtgggaaga    5580
aattaaagca agataggcta ttaagtgcag agggagagaa aatgcctcca acatgtgagg    5640
aagtaatgag agaaatcata gaattttaag gccatgattt aaggccatca tggccttaat    5700
cttccgcttc ctcgctcact gactcgctgc gctcggtcgt tcggctgcgg cgagcggtat    5760
cagctcactc aaaggcggta atacggttat ccacagaatc aggggataac gcaggaaaga    5820
acatgtgagc aaaaggccag caaaaggcca ggaaccgtaa aaaggccgcg ttgctggcgt    5880
ttttccatag gctccgcccc cctgacgagc atcacaaaaa tcgacgctca agtcagaggt    5940
ggcgaaaccc gacaggacta taaagatacc aggcgtttcc ccctggaagc tccctcgtgc    6000
gctctcctgt tccgaccctg ccgcttaccg gatacctgtc cgcctttctc ccttcgggaa    6060
gcgtggcgct ttctcatagc tcacgctgta ggtatctcag ttcggtgtag gtcgttcgct    6120
ccaagctggg ctgtgtgcac gaaccccccg ttcagcccga ccgctgcgcc ttatccggta    6180
actatcgtct tgagtccaac ccggtaagac acgacttatc gccactggca gcagccactg    6240
gtaacaggat tagcagagcg aggtatgtag gcggtgctac agagttcttg aagtggtggc    6300
ctaactacgg ctacactaga agaacagtat ttggtatctg cgctctgctg aagccagtta    6360
ccttcggaaa aagagttggt agctcttgat ccggcaaaca accaccgct ggtagcggtg    6420 gtttttttgt ttgcaagcag cagattacgc gcagaaaaaa aggatctcaa gaagatcctt    6480
tgatcttttc tacggggtct gacgctcagt ggaacgaaaa ctcacgttaa gggattttgg    6540
```

| | |
|---|---|
| tcatgagatt atcaaaaagg atcttcacct agatccttt aaattaaaaa tgaagtttta | 6600 |
| aatcaatcta agtatatat gagtaaactt ggtctgacag ttaccaatgc ttaatcagtg | 6660 |
| aggcacctat ctcagcgatc tgtctatttc gttcatccat agttgcctga ctcgggggg | 6720 |
| gggggcgctg aggtctgcct cgtgaagaag gtgttgctga ctcataccag gcctgaatcg | 6780 |
| ccccatcatc cagccagaaa gtgagggagc cacggttgat gagagctttg ttgtaggtgg | 6840 |
| accagttggt gattttgaac ttttgctttg ccacggaacg gtctgcgttg tcgggaagat | 6900 |
| gcgtgatctg atccttcaac tcagcaaaag ttcgatttat tcaacaaagc cgccgtcccg | 6960 |
| tcaagtcagc gtaatgctct gccagtgtta caaccaatta accaattctg attagaaaaa | 7020 |
| ctcatcgagc atcaaatgaa actgcaattt attcatatca ggattatcaa taccatattt | 7080 |
| ttgaaaaagc cgtttctgta atgaaggaga aaactcaccg aggcagttcc ataggatggc | 7140 |
| aagatcctgg tatcggtctg cgattccgac tcgtccaaca tcaatacaac ctattaattt | 7200 |
| cccctcgtca aaaataaggt tatcaagtga gaaatcacca tgagtgacga ctgaatccgg | 7260 |
| tgagaatggc aaaagcttat gcatttcttt ccagacttgt tcaacaggcc agccattacg | 7320 |
| ctcgtcatca aaatcactcg catcaaccaa accgttattc attcgtgatt gcgcctgagc | 7380 |
| gagacgaaat acgcgatcgc tgttaaaagg acaattacaa acaggaatcg aatgcaaccg | 7440 |
| gcgcaggaac actgccagcg catcaacaat attttcacct gaatcaggat attcttctaa | 7500 |
| tacctggaat gctgttttcc cggggatcgc agtggtgagt aaccatgcat catcaggagt | 7560 |
| acggataaaa tgcttgatgg tcggaagagg cataaattcc gtcagccagt ttagtctgac | 7620 |
| catctcatct gtaacatcat tggcaacgct acctttgcca tgtttcagaa acaactctgg | 7680 |
| cgcatcgggc ttcccataca atcgatagat tgtcgcacct gattgcccga cattatcgcg | 7740 |
| agcccattta tacccatata atcagcatc catgttggaa tttaatcgcg gcctcgagca | 7800 |
| agacgtttcc cgttgaatat ggctcataac accccttgta ttactgttta tgtaagcaga | 7860 |
| cagttttatt gttcatgatg atatatttt atcttgtgca atgtaacatc agagattttg | 7920 |
| agacacaacg tggctttccc cccccccca ttattgaagc atttatcagg gttattgtct | 7980 |
| catgagcgga tacatatttg aatgtattta gaaaaataaa caaataggggg ttccgcgcac | 8040 |
| atttccccga aaagtgccac ctgacgtcta agaaaccatt attatcatga cattaaccta | 8100 |
| taaaaatagg cgtatcacga ggccctttcg tc | 8132 |

```
<210> SEQ ID NO 17
<211> LENGTH: 8134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (2169)..(2169)
<223> OTHER INFORMATION: a, c, t, g, unknown or other

<400> SEQUENCE: 17
```

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccg cccattgacg tcaataatga cgtatgttcc     480
catagtaacg ccaataggga cttccattg acgtcaatgg gtggagtatt tacggtaaac     540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
cttttgtccg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caggccctgg atccatggat ttcatcccca cccaaacctt ctatggtaga cgatggagac   1440
cagcaccagt ccagagatac ataccccaac cccaaccacc agcgcctcca cgccgtagga   1500
gaggaccatc tcaactccaa cagcttgtgg ctgcattggg cgcactagct ctacaaccca   1560
agcagaaaca aaaagagca cagaagaagc caagaagac accaccacca aaaccaaaaa     1620
agacccagaa gcctaagaaa ccaacccaaa agaagaagtc caaacccggc aaacgtatgc   1680
gtaactgcat gaagatcgag aatgactgca tcttccggt gatgctcgat ggaaaggtta    1740
acggctacgc ttgcttagtg ggggataaag tcatgaaacc agctcatgtg aagggcacga   1800
tcgacaatcc agaactagcc aaattgacat tcaagaaatc tagcaagtat gatctagaat   1860
gtgctcaagt gccggtatgc atgaaaatcag acgcatccaa gttcacccat gagaaaccag   1920
aaggacatta caactggcac catggggcag tgcaatttag caatggtagg tttaccattc   1980
cgacgggctc tggcaaacct ggagacagtg gtaggcctat ttttgacaat accggcaagg   2040
tagtagccat agtgctggga ggtgcaaatg aagggcccg gacagcccta tccgtggtca    2100
cctggaataa ggatatggtg acccgcataa cacctgaaga atcagtggag tggtcggcgg   2160
ccgcactgna tataacagca ctatgtgtcc tccagaactt atcgttcccg tgtgatgcac   2220
caccatgtgc accatgctgt tacgaaaaag accctgcagg gaccctaaga ttgctgtctg   2280
accactacta ccacccaag tattatgaat tacttgactc gacgatgcac tgcccacaag    2340
gaaggagacc taagaggtct gttgcgcatt tcgaagccta caaggctacg agaccgtata   2400
tagggtggtg cgcagattgt ggactggcag gatcatgccc atccctgtg agcatcgagc    2460 acgtctggag tgatgccgac gacggcgtac tgaagatcca agtgtccatg cagatcggta   2520
tagctaaaag caatactatt aaccacgcta agatacgtta catgggtgcc aatggagtac   2580
aggaggctga acgtctacc ctaagtgtat ccacaacagc accatgtgac atcttggcga    2640
ccatgggcca tttcatcttg gcccgctgcc gacccggcag tcaagttgaa gtatcactaa   2700
```

```
gcaccgatcc aaagctgcta tgccgtacac cattctccca caagcccagg tttattggca    2760
atgaaaagtc cccagcaccc accgggcaca agacccgaat tccctgcaaa acttactccc    2820
atcagacaga cttaacgaga gaagagatta caatgcatgt accgccggat gtccccatcc    2880
aagggctagt gtccaataca ggtaagtcgt actcattaga cccaaagacg aagaccatca    2940
agtacaaatg cacttgcggc gagactgtaa aagaaggtac tgctacgaac aaaatcacac    3000
tgttcaattg tgacaccgcc ccaaagtgta ttacatatgc agtggataac acagtgtggc    3060
agtacaactc ccaatacgtg cccaggtccg aagttacgga ggtgaaagga agatccatg    3120
tgcctttccc tctgaccgac agcacgtgtg cagtcagcgt agcacctgaa ccgcaagtga    3180
catacagact gggggaagtg gagttccact tccaccctat gtaccccacc ctcttctcca    3240
ttaggagcct cggaaaggat ccgagccaca gtcaagaatg gatagataca cccatgagca    3300
agacaatcca agttggggca gaaggcgtgg agtatgtctg gggaaacaac aacccggtac    3360
gactatgggc acagaagagc tcatcgagca gcgcgcatgg taaccctatt agcatagtct    3420
cacattacta tgacctgtac ccttactgga ccatcacagt actagcgagt ctaggcttgc    3480
taatagtgat tagttccggt ttttcatgct ttttgtgttc agtcgctcga accaaatgcc    3540
ttacacccta tcaattagca ccaggcgccc aattacccac atttatagca ctcctttgct    3600
gcgctaagtc tgcacgcgca gacactttag atgattttc ctacctgtgg accaacaacc    3660
aagccatgtt ttggctccaa ctggcatctc cggttgcagc gttcttgtgc ttatcctatt    3720
gctgtagaaa tctagcatgc tgtatgaaga tttttttagg gataagcggc ctgtgtgtaa    3780
ttgccacgca ggcctacgag cactcaacca cgatgccgaa tcaggtggga ataccgttta    3840
aagccttgat agagcgacca ggttacgcag gcctcccgct atctttagta gtgattaagt    3900
cagaattagt cccctcatta gttcaggatt atattacctg caactacaag actgtggtcc    3960
cgtctccgta cattaaatgt tgcggaggcg ctgagtgttc acacaaaaat gaagcggact    4020
ataagtgctc ggtgttcaca ggcgtgtacc cgtttatgtg gggaggcgcc tactgcttct    4080
gtgacaccga aaacagtcag atgagtgaag tatacgtaac cagagaagaa tcatgcgagg    4140
ctgaccatgc catcgcttat caggtacaca cagcatcgct taaggcacaa gtaatgatat    4200
cgattggaga actgaaccaa accgtcgacg tgtttgtcaa cggagacagt ccagccagaa    4260
tccaacaatc aaagttcata cttgggccga tatccagtgc ctggtctcct tttgatcaca    4320
aggtgatcgt atacagggat gaggtgtaca atgaagacta cgcaccgtac ggatccggcc    4380
aagcaggcag gttcggagac atccaaagta gaactgttaa cagcactgat gtctatgcca    4440
acaccaattt gaagcttaaa agaccggctt caggcaatgt tcatgtacca tacacgcaaa    4500
cccttcggg tttctcgtac tggaaaaaag agaagggagt accattgaat cgaaacgccc    4560
cttttggctg tatcatcaaa gtcaatccag tacgtgctga aaactgcgta tatggcaaca    4620
taccgatcag tatggatatt gcggacgcgc acttcacaag gatcgatgaa tccccgtctg    4680
tgtccttgaa ggcgtgtgaa gtgcagtcct gcacttattc atcggatttt ggcggagtag    4740
cgagcatttc ctacacatct aataaggtag gtaagtgtgc catccacagc cactcgaact    4800
ccgcaacgat gaaggattct gtgcaggatg tccaggaaag cggcgccttg tcgcttttct    4860
ttgcgacttc ctctgtcgag ccgaacttcg tggtccaagt gtgtaacgcg cggatcactt    4920
gccatggtaa gtgtgaacca ccgaaagacc acatcgtacc atacgcagcc aaacacaacg    4980
acgccgagtt tccatccatc tctactacag cttggcaatg gttggcacac accacctcag    5040
```

```
ggccactcac catacttgtg gtagctatta tagtcgttgt tgtagtatcc attgtagtat   5100
gtgcaagaca ctagagatct gctgtgcctt ctagttgcca gccatctgtt gtttgccoct   5160 cccccgtgcc ttccttgacc ctggaaggtg ccactcccac tgtcctttcc taataaaatg   5220
aggaaattgc atcgcattgt ctgagtaggt gtcattctat tctgggggt ggggtggggc    5280 aggacagcaa gggggaggat tgggaagaca atagcaggca tgctggggat gcggtgggct   5340
ctatgggtac ccaggtgctg aagaattgac ccggttcctc ctgggccaga agaagcagg    5400 cacatcccct tctctgtgac acccctgtc cacgcccctg gttcttagtt ccagcccac     5460 tcataggaca ctcatagctc aggagggctc cgccttcaat cccacccgct aaagtacttg   5520
gagcggtctc tccctccctc atcagcccac caaaccaaac ctagcctcca agagtgggaa   5580
gaaattaaag caagataggc tattaagtgc agagggagag aaaatgcctc caacatgtga   5640
ggaagtaatg agagaaatca tagaattta aggccatgat ttaaggccat catgccctta    5700
atcttccgct tcctcgctca ctgactcgct gcgctcggtc gttcggctgc ggcgagcggt   5760
atcagctcac tcaaaggcgg taatacggtt atccacagaa tcaggggata acgcaggaaa   5820
gaacatgtga gcaaaaggcc agcaaaaggc caggaaccgt aaaaaggccg cgttgctggc   5880 gttttccat aggctccgcc ccctgacga gcatcacaaa aatcgacgct caagtcagag     5940
gtggcgaaac ccgacaggac tataaagata ccaggcgttt ccccctggaa gctccctcgt   6000
gcgctctcct gttccgaccc tgccgcttac cggatacctg tccgcctttc tcccttcggg   6060
aagcgtggcg ctttctcata gctcacgctg taggtatctc agttcggtgt aggtcgttcg   6120
ctccaagctg ggctgtgtgc acgaaccccc cgttcagccc gaccgctgcg ccttatccgg   6180
taactatcgt cttgagtcca acccggtaag acacgactta tcgccactgg cagcagccac   6240
tggtaacagg attagcagag cgaggtatgt aggcggtgct acagagttct tgaagtggtg   6300
gcctaactac ggctacacta gaagaacagt atttggtatc tgcgctctgc tgaagccagt   6360
taccttcgga aaaagagttg gtagctcttg atccggcaaa caaaccaccg ctggtagcgg   6420 tggtttttt gtttgcaagc agcagattac gcgcagaaaa aaaggatctc aagaagatcc   6480
tttgatcttt tctacggggt ctgacgctca gtggaacgaa aactcacgtt aagggatttt   6540
ggtcatgaga ttatcaaaaa ggatcttcac ctagatcctt ttaaattaaa aatgaagttt   6600
taaatcaatc taaagtatat atgagtaaac ttggtctgac agttaccaat gcttaatcag   6660
tgaggcacct atctcagcga tctgtctatt tcgttcatcc atagttgcct gactcggggg   6720 ggggggcgc tgaggtctgc ctcgtgaaga aggtgttgct gactcatacc aggcctgaat   6780
cgccccatca tccagccaga aagtgaggga gccacggttg atgagagctt tgttgtaggt   6840
ggaccagttg gtgattttga cttttgctt tgccacggaa cggtctgcgt tgtcggaag    6900 atgcgtgatc tgatccttca actcagcaaa agttcgattt attcaacaaa gccgccgtcc   6960
cgtcaagtca gcgtaatgct ctgccagtgt tacaaccaat taaccaattc tgattagaaa   7020
aactcatcga gcatcaaatg aaactgcaat ttattcatat caggattatc aataccatat   7080
ttttgaaaaa gccgtttctg taatgaagga gaaaactcac cgaggcagtt ccataggatg   7140
gcaagatcct ggtatcggtc tgcgattccg actcgtccaa catcaataca acctattaat   7200
ttcccctcgt caaaaataag gttatcaagt gagaaatcac catgagtgac gactgaatcc   7260
ggtgagaatg gcaaaagctt atgcatttct ttccagactt gttcaacagg ccagccatta   7320
cgctcgtcat caaaatcact cgcatcaacc aaaccgttat tcattcgtga ttgcgcctga   7380
gcgagacgaa atacgcgatc gctgttaaaa ggacaattac aaacaggaat cgaatgcaac   7440
```

```
cggcgcagga acactgccag cgcatcaaca atattttcac ctgaatcagg atattcttct    7500
aatacctgga atgctgtttt cccggggatc gcagtggtga gtaaccatgc atcatcagga    7560
gtacggataa aatgcttgat ggtcggaaga ggcataaatt ccgtcagcca gtttagtctg    7620
accatctcat ctgtaacatc attggcaacg ctacctttgc catgtttcag aaacaactct    7680
ggcgcatcgg gcttcccata caatcgatag attgtcgcac ctgattgccc gacattatcg    7740
cgagcccatt tatacccata taaatcagca tccatgttgg aatttaatcg cggcctcgag    7800
caagacgttt cccgttgaat atggctcata acacccctgg tattactgtt tatgtaagca    7860
gacagtttta ttgttcatga tgatatattt ttatcttgtg caatgtaaca tcagagattt    7920
tgagacacaa cgtggctttc cccccccccc cattattgaa gcatttatca gggttattgt    7980
ctcatgagcg gatacatatt tgaatgtatt tagaaaaata acaaataggg gttccgcgc    8040 acatttcccc gaaaagtgcc acctgacgtc taagaaacca ttattatcat gacattaacc    8100
tataaaaata ggcgtatcac gaggccctt cgtc                                8134
```

<210> SEQ ID NO 18
<211> LENGTH: 8153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga cttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttc tcaactcta gttaacggtg gagggcagtg tagtctgagc agtactcgtt   1260
gctgccgcgc gcgccaccag acataatagc tgacagacta acagactgtt cctttccatg   1320
```

```
ggtcttttct gcagtcaccg tcgtcgacac gtgtgatcag atatcgcggc cgccaccatg    1380
aactctgtct tttacaatcc gtttggccga ggtgcctacg ctcaacctcc aatagcatgg    1440
aggccaagac gtagggctgc acctgcgcct cgaccatccg ggttgactac ccagatccaa    1500
cagctcacta gggctgttag agctttggtg ctggacaatg ctacacgtcg ccagcgcccg    1560
gctcctcgca cgcgcccgag gaagccgaag actcaaaaac ctaagccgaa gaagcaaaac    1620
cagaaaccac cacaacagca gaagaaaggg aaaaatcagc cccaacaacc gaagaaaccg    1680
aagcccggta acgacagcg taccgccctg aaatttgaag ccgaccgcac atttgtcggg    1740
aagaatgaag acggcaagat tatgggatac gccgttgcca tggaagggaa agtgataaaa    1800
ccactacatg taaaaggaac cattgaccac ccggccctag cgaaacttaa attcactaaa    1860
tcttcttctt acgacatgga gtttgctaaa ctaccgaccg aaatgaaaag cgacgcattc    1920
gggtatacaa cggaacaccc cgaagtattt tacaactggc atcacggagc tgtccaattt    1980
tccggcggaa ggttcaccat ccctacagga gtcggaggcc ccggagatag cggaaggcct    2040
atactggata actccggaaa agtggtagcc atagtcctag gaggagctaa tgaagtgcca    2100
ggaacggcac tttctgttgt cacctggaat aagaagggag ccgctattaa aaccacccac    2160
gaagatactg tagagtggtc gcgggctatt accgctatgt gcatcctgca gaacgtcaca    2220
ttcccatgtg accgaccgcc aacttgctat aatcgtaatc ctgacttgac cctaaccatg    2280
ttggaaacaa atgtcaatca cccttcgtac gacgttctgc tggacgctgc tctgaggtgc    2340
cccacgagac ggcacgtcag atcaacgccc accgatgact tcactctcac agcaccgtac    2400
ctcggcttgt gtcacagatg taagacgatg gaaccatgct acagccctat aaaaatcgaa    2460
aaagtgtggg atgatgccga tgacggagtt ctccgtatac aagtaagtgc ccagttaggg    2520
tacaacaggg cgggcactgc agctagcgcc cgactccggt tcatgggcgg aggagtgcct    2580
ccggaaatcc aggagggagc aattgcagat tttaaggtct tcacgtccaa accatgttta    2640
cacctatcac ataaaggata cttttgtcatt gtcaagtgcc ctcctggtga tagtattaca    2700
acatcattga aagtgcatgg ctcggatcaa acctgcacaa ttccaatgcg agtaggttac    2760
aagttcgtag gcagggaaaa atatactctg ccaccaatgc atgggacaca ataccttgc    2820 cttacctacg aaaggacacg agagaaaagt gcaggatacg tgaccatgca tcgtcccgga    2880
caacaatcca taaccatgct gatggaagag agcggagggg aggtgtacgt acaaccgacc    2940
agtgggcgaa acgtcaccta cgagtgtaaa tgcggagact ttaaaactgg gactgtcact    3000
gcgcgcacta aaatagacgg ctgtacagaa aggaaacaat gcattgcgat ttctgccgac    3060
cacgtcaaat gggtgtttaa ctcccctgac ttgatcaggc ataccgacca cacagcccaa    3120
gggaagttgc atataccatt cccgctacag caggctcaat gtacagtacc actggcgcac    3180
cttccaggcg ttaagcatgc ttatcgcagt atgtctctga cactgcacgc tgagcatcct    3240
acattgctta ctacccgcca tcttggagaa aatcctcagc ccactgcaga atggattgtc    3300
gggagtgtaa ctcgaaactt ctccataacc atacaagggt tcgagtatac ttggggaaat    3360
cagaaaccgg tccgagtgta cgcgcaggaa tcggcacctg gcaatcctca tggctggcca    3420
catgaaatcg tacgccatta ctaccacctc tatcccttct acaccgttac agtgctgagc    3480
ggcatgggac tggccatatg cgctggctta gtgatcagta ttttatgctg ctgcaaagca    3540
agaagggatt gcctaacacc ttaccaactg gccccgaacg ctaccgtacc atttctggta    3600
acattgtgtt gctgtttcca acggacttca gcggatgaat ttaccgatac catggggtac    3660
```

```
ctatggcaac acagtcaaac aatgttctgg atacaattgg tcataccttt agcagcagtg   3720
ataactttgg ttagatgttg ctcctgctgt ctaccttttt tattggttgc cagtcctcct   3780
aacaaagcgg acgcctacga acatacgatc actgtcccaa atgcgccgtt gaactcgtat   3840
aaagcactag tggaacggcc tgggtatgcc cccttgaatc ttgaagtcat ggtcatgaac   3900
acccagatca taccatcggt taaacgtgaa tacattacct gcaggtacca caccgttgtt   3960
ccttcaccgc agattaaatg ttgcggaact gtcgaatgcc cgaaaggtga aaaagcagac   4020
tatacctgca aggtgttcac tggtgtgtac ccatttctgt ggggaggagc acagtgtttt   4080
tgcgactccg aaaacagtca gcttagcgac aagtacgtcg aactgtcaac agattgcgcc   4140
acagaccatg ccgaggcggt cagagtacac acggcttcgg tgaaatcaca gctccgaata   4200
acctacggga actccacagc acaagtagac gtatttgtca acgtgtgac tccagccagg    4260
agcaaagaca tgaaattgat agccggccca ttatctacta cattttcccc gtttgataat   4320
aaggtcatta tatatcatgg gaaagtctat aactatgact tcccggaatt tggggccgga   4380
acacctggag ctttcggaga tgtccaagcg tcatccacca ccggatcaga tctattagca   4440
aacacagcaa ttcatttgca gaggccggaa gccagaaaca tacacgtccc gtacacccaa   4500
gctccaagcg ggttcgaatt ctggaagaat aacagcggtc agcctttatc tgacactgcc   4560
cctttcggat gcaaagtcaa tgtcaacccg ctacgtgcag acaagtgtgc cgtgggatca   4620
ctcccgatat ccgtggatat accggacgct gcatttacac gcgtatccga gccctgcca   4680
tcactgctta agtgcaccgt tactagttgc acatactcta cagactatgg cggagtgctc   4740
gtgttgacat acgagtcgga tcgcgcgggg caatgcgctg tacactcgca ttcatcaaca   4800
gcggtactgc gagacccatc ggtatacgtc gagcaaaaag gggagactac acttaaattt   4860
agtacgcgtt ccttgcaggc agacttcgag gtatcgatgt gcggaacgag aaccacttgc   4920
catgcccaat gtcaaccacc aacggaacac gtaatgaaca ccccagaa gtcgactcca    4980
gacttctcct cagcgatatc caaaacatca tggaactgga ttacagcgct tatggggga    5040
atttccagta tagctgctat agccgcaatt gtgctggtca tagcattagt atttacagca   5100
caacacagat gatctagacc aggccctgga tccagatctg ctgtgccttc tagttgccag   5160
ccatctgttg tttgccccct ccccgtgcct tccttgaccc tggaaggtgc cactcccact   5220
gtcctttcct aataaaatga ggaaattgca tcgcattgtc tgagtaggtg tcattctatt   5280
ctggggggtg gggtggggca ggacagcaag ggggaggatt gggaagacaa tagcaggcat   5340
gctgggggatg cggtgggctc tatgggtacc caggtgctga agaattgacc cggttcctcc   5400
tgggccagaa agaagcaggc acatcccctt ctctgtgaca caccctgtcc acgccctgg    5460
ttcttagttc cagccccact cataggacac tcatagctca ggagggctcc gccttcaatc   5520
ccacccgcta agtacttggg agcggtctct ccctccctca tcagcccacc aaaccaaacc   5580
tagcctccaa gagtgggaag aaattaaagc aagataggct attaagtgca gagggagaga   5640
aaatgcctcc aacatgtgag gaagtaatga gagaaatcat agaattttaa ggccatgatt   5700
taaggccatc atggccttaa tcttccgctt cctcgctcac tgactcgctg cgctcggtcg   5760
ttcggctgcg gcgagcggta tcagctcact caaaggcggt aatacggtta tccacagaat   5820
caggggataa cgcaggaaag aacatgtgag caaaaggcca gcaaaggcc aggaaccgta    5880
aaaaggccgc gttgctggcg ttttccata ggctccgccc ccctgacgag catcacaaaa    5940
atcgacgctc aagtcagagg tggcgaaacc cgacaggact ataaagatac caggcgtttc   6000
ccccctggaag ctccctcgtg cgctctcctg ttccgaccct gccgcttacc ggatacctgt   6060
```

```
ccgcctttct cccttcggga agcgtggcgc tttctcatag ctcacgctgt aggtatctca   6120
gttcggtgta ggtcgttcgc tccaagctgg gctgtgtgca cgaaccccccc gttcagcccg   6180 accgctgcgc cttatccggt aactatcgtc ttgagtccaa cccggtaaga cacgacttat   6240
cgccactggc agcagccact ggtaacagga ttagcagagc gaggtatgta ggcggtgcta   6300
cagagttctt gaagtggtgg cctaactacg gctacactag aagaacagta tttggtatct   6360
gcgctctgct gaagccagtt accttcggaa aaagagttgg tagctcttga tccggcaaac   6420
aaaccaccgc tggtagcggt ggtttttttg tttgcaagca gcagattacg cgcagaaaaa   6480
aaggatctca agaagatcct ttgatctttt ctacggggtc tgacgctcag tggaacgaaa   6540
actcacgtta agggattttg gtcatgagat tatcaaaaag gatcttcacc tagatccttt   6600
taaattaaaa atgaagtttt aaatcaatct aaagtatata tgagtaaact tggtctgaca   6660
gttaccaatg cttaatcagt gaggcaccta tctcagcgat ctgtctattt cgttcatcca   6720
tagttgcctg actcgggggg gggggcgct gaggtctgcc tcgtgaagaa ggtgttgctg   6780
actcatacca ggcctgaatc gccccatcat ccagccagaa agtgagggag ccacggttga   6840
tgagagcttt gttgtaggtg gaccagttgg tgattttgaa cttttgcttt gccacggaac   6900
ggtctgcgtt gtcgggaaga tgcgtgatct gatccttcaa ctcagcaaaa gttcgattta   6960
ttcaacaaag ccgccgtccc gtcaagtcag cgtaatgctc tgccagtgtt acaaccaatt   7020
aaccaattct gattagaaaa actcatcgag catcaaatga actgcaatt tattcatatc   7080 aggattatca ataccatatt tttgaaaaag ccgtttctgt aatgaaggag aaaactcacc   7140
gaggcagttc cataggatgg caagatcctg gtatcggtct gcgattccga ctcgtccaac   7200
atcaatacaa cctattaatt tcccctcgtc aaaaataagg ttatcaagtg agaaatcacc   7260
atgagtgacg actgaatccg gtgagaatgg caaaagctta tgcatttctt tccagacttg   7320
ttcaacaggc cagccattac gctcgtcatc aaaatcactc gcatcaacca accgttatt   7380 cattcgtgat tgcgcctgag cgagacgaaa tacgcgatcg ctgttaaaag gacaattaca   7440
aacaggaatc gaatgcaacc ggcgcaggaa cactgccagc gcatcaacaa tattttcacc   7500
tgaatcagga tattcttcta atacctggaa tgctgttttc ccggggatcg cagtggtgag   7560
taaccatgca tcatcaggag tacggataaa atgcttgatg gtcggaagag gcataaattc   7620
cgtcagccag tttagtctga ccatctcatc tgtaacatca ttggcaacgc tacctttgcc   7680
atgtttcaga aacaactctg gcgcatcggg cttcccatac aatcgataga ttgtcgcacc   7740
tgattgcccg acattatcgc gagcccattt atacccatat aaatcagcat ccatgttgga   7800
atttaatcgc ggcctcgagc aagacgtttc ccgttgaata tggctcataa cacccccttgt   7860 attactgttt atgtaagcag acagttttat tgttcatgat gatatatttt tatcttgtgc   7920
aatgtaacat cagagatttt gagacacaac gtggctttcc ccccccccc attattgaag   7980 catttatcag ggttattgtc tcatgagcgg atacatattt gaatgtattt agaaaaataa   8040
acaaataggg gttccgcgca catttccccg aaaagtgcca cctgacgtct aagaaaccat   8100
tattatcatg acattaacct ataaaaatag gcgtatcacg aggccctttc gtc          8153
```

<210> SEQ ID NO 19
<211> LENGTH: 2964
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
atgagcctcg ccctcccggt cttgtgcctg ttggcaaaca ctacattccc ctgctctcag      60
ccgccttgca cacctgctg ctacgaaaag gaaccggaaa gcaccttgcg catgcttgag     120
gacaacgtga tgagacccgg atactaccag ctactaaaag catcgctgac ttgctctccc    180
caccgccaaa gacgcagtac taaggacaat tttaatgtct ataaagccac aagaccatat   240
ctagctcatt gtcctgactg cggagaaggg cattcgtgcc acagccctat cgcattggag   300
cgcatcagaa atgaagcaac ggacggaacg ctgaaaatcc aggtctcttt gcagatcggg   360
ataaagacag atgacagcca cgattggacc aagctgcgct atatggatag ccatacgcca   420
gcggacgcgg agcgagccgg attgcttgta aggacttcag caccgtgcac gatcaccggg   480
accatgggac actttattct cgcccgatgc ccgaaaggag agacgctgac agtgggattt   540
acggacagca gaaagatcag ccacacatgc acacacccgt tccatcatga accacctgtg   600
ataggtagga gaggttcca ctctcgacca caacatggta aagagttacc ttgcagcacg    660
tacgtgcaga gcaccgctgc cactgctgag gagatagagg tgcatatgcc cccagatact   720
cctgaccgca cgctgatgac gcagcagtct ggcaacgtga agatcacagt taatgggcag   780
acggtgcggt acaagtgcaa ctgcggtggc tcaaacgagg gactgacaac cacagacaaa   840
gtgatcaata actgcaaaat tgatcagtgc catgctgcag tcactaatca aagaattgg    900
caatacaact cccctttagt cccgcgcaac gctgaactcg gggaccgtaa aggaaagatc   960
cacatcccat tcccattggc aaacgtgact tgcagagtgc aaaagcaag aaaccctaca   1020
gtaacttacg gaaaaaacca agtcaccatg ctgctgtatc ctgaccatcc gacactcttg  1080
tcttaccgta acatgggaca ggaaccaaat taccacgagg agtgggtgac acacaagaag  1140
gaggttacct tgaccgtgcc tactgagggt ctggaggtca cttggggcaa caacgaacca  1200
tacaagtact ggccgcagat gtctacgaac ggtactgctc atggtcaccc acatgagata  1260
atcttgtact attatgagct gtaccccact atgactgtag tcattgtgtc ggtggcctcg  1320
ttcgtgcttc tgtcgatggt gggcacagca gtgggaatgt gtgtgtgcgc acggcgcaga  1380
tgcattacac catatgaatt aacaccagga gccactgttc ccttcctgct cagcctgcta  1440
tgctgcgtca gaacgaccaa ggcggccaca tattacgagg ctgcggcata tctatggaac  1500
gaacagcagc cctgttctg gttgcaggct cttatcccgc tggccgcctt gatcgtcctg  1560
tgcaactgtc tgaaactctt gccatgctgc tgtaagaccc tggcttttt agccgtaatg  1620
agcatcggtg cccacactgt gagcgcgtac gaacacgtaa cagtgatccc gaacacggtg  1680
ggagtaccgt ataagactct tgtcaacaga ccgggttaca gcccatggt gttggagatg  1740
gagctacaat cagtcacctt ggaaccaaca ctgtcacttg actacatcac gtgcgagtac  1800
aaaactgtca tcccctcccc gtacgtgaag tgctgtggta cagcagagtg caaggacaag  1860
agcctaccag actacagctg caaggtctttt actggagtct acccatttat gtggggcggc  1920
gcctactgct tttgcgacgc cgaaaatacg caattgagcg aggcacatgt agagaaatct  1980
gaatcttgca aaacagagtt tgcatcggcc tacagagccc acaccgcatc ggcgtcggcg  2040
aagctccgcg tcctttacca aggaaacaac attaccgtag ctgcctacgc taacggtgac  2100
catgccgtca cagtaaagga cgccaagttt gtcgtgggcc caatgtcctc cgcctggaca  2160
ccttttgaca caaaaatcgt ggtgtacaaa ggcgacgtct acaacatgga ctacccacct  2220
tttggcgcag aagaccagg acaatttggt gacattcaaa gtcgtacacc ggaaagtaaa  2280
```

| | |
|---|---:|
| gacgtttatg ccaacactca gttggtacta cagaggccag cagcaggcac ggtacatgta | 2340 |
| ccatactctc aggcaccatc tggcttcaag tattggctga aggaacgagg agcatcgcta | 2400 |
| cagcacacgg caccgttcgg ttgccagatt gcgacaaacc cggtaagagc tgtaaattgc | 2460 |
| gctgtgggga acataccaat ttccatcgac ataccggatg cggcctttac tagggttgtc | 2520 |
| gatgcaccct ctgtaacgga catgtcatgc gaagtaccag cctgcactca ctcctccgac | 2580 |
| tttgggggcg tcgccatcat caaatacaca gctagcaaga aggtaaatg tgcagtacat | 2640 |
| tcgatgacca acgccgttac cattcgagaa gccgacgtag aagtagaggg gaactcccag | 2700 |
| ctgcaaatat ccttctcaac agccctggca agcgccgagt ttcgcgtgca agtgtgctcc | 2760 |
| acacaagtac actgcgcagc cgcatgccac cctccaaagg accacatagt caattaccca | 2820 |
| gcatcacaca ccaccttgg ggtccaggat atatccacaa cggcaatgtc ttgggtgcag | 2880 |
| aagattacgg gaggagtagg attaattgtt gctgttgctg ccttaattt aattgtggtg | 2940 |
| ctatgcgtgt cgtttagcag gcac | 2964 |

<210> SEQ ID NO 20
<211> LENGTH: 2964
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 20

| | |
|---|---:|
| atgagtcttg ccatcccagt tatgtgcctg ttggcaaaca ccacgttccc ctgctcccag | 60 |
| cccccttgca cgccctgctg ctacgaaaag gaaccggagg aaaccctacg catgcttgag | 120 |
| gacaacgtca tgagacctgg gtactatcag ctgctacaag catccttaac atgttctccc | 180 |
| caccgccagc gacgcagcac caaggacaac ttcaatgtct ataaagccac aagaccatac | 240 |
| ttagctcact gtcccgactg tggagaaggg cactcgtgcc atagtcccgt agcactagaa | 300 |
| cgcatcagaa atgaagcgac agacgggacg ctgaaaatcc aggtctcctt gcaaatcgga | 360 |
| ataaagacgg atgacagcca cgattggacc aagctgcgtt atatggacaa ccacatgcca | 420 |
| gcagacgcag agagggcggg gctatttgta agaacatcag caccgtgtac gattactgga | 480 |
| acaatgggac acttcatcct ggcccgatgt ccaaaggggg aaactctgac ggtgggattc | 540 |
| actgacagta ggaagattag tcactcatgt acgcacccat ttcaccacga ccctcctgtg | 600 |
| ataggtcggg aaaaattcca ttcccgaccg cagcacggta agagctacc ttgcagcacg | 660 |
| tacgtgcaga gcaccgccgc aactaccgag gagatagagg tacacatgcc cccagacacc | 720 |
| cctgatcgca cattaatgtc acaacagtcc ggcaacgtaa agatcacagt caatggccag | 780 |
| acggtgcggt acaagtgtaa ttgcggtggc tcaaatgaag gactaacaac tacagacaaa | 840 |
| gtgattaata actgcaaggt tgatcaatgt catgccgcgg tcaccaatca caaaaagtgg | 900 |
| cagtataact ccctctggt cccgcgtaat gctgaacttg ggaccgaaa aggaaaaatt | 960 |
| cacatcccgt ttccgctggc aaatgtaaca tgcagggtgc ctaaagcaag gaaccccacc | 1020 |
| gtgacgtacg ggaaaaacca agtcatcatg ctactgtatc ctgaccaccc aacactcctg | 1080 |
| tcctaccgga atatgggaga agaaccaaac tatcaagaag agtgggtgat gcataagaag | 1140 |
| gaagtcgtgc taaccgtgcc gactgaaggg ctcgaggtca cgtgggcaa caacgagccg | 1200 |
| tataagtatt ggccgcagtt atctacaaac ggtacagccc atggccaccc gcatgagata | 1260 |
| attctgtatt attatgagct gtaccccact atgactgtag tagttgtgtc agtggccacg | 1320 |

| | | | | |
|---|---|---|---|---|
| ttcatactcc | tgtcgatggt | gggtatggca | gcggggatgt | gcatgtgtgc acgacgcaga | 1380 |
| tgcatcacac | cgtatgaact | gacaccagga | gctaccgtcc | ctttcctgct tagcctaata | 1440 |
| tgctgcatca | gaacagctaa | agcggccaca | taccaagagg | ctgcgatata cctgtggaac | 1500 |
| gagcagcaac | ctttgttttg | gctacaagcc | cttattccgc | tggcagccct gattgttcta | 1560 |
| tgcaactgtc | tgagactctt | accatgctgc | tgtaaaacgt | tggctttttt agccgtaatg | 1620 |
| agcgtcggtg | cccacactgt | gagcgcgtac | gaacacgtaa | cagtgatccc gaacacggtg | 1680 |
| ggagtaccgt | ataagactct | agtcaataga | cctggctaca | gccccatggt attggagatg | 1740 |
| gaactactgt | cagtcacttt | ggagccaaca | ctatcgcttg | attacatcac gtgcgagtac | 1800 |
| aaaaccgtca | tcccgtctcc | gtacgtgaag | tgctgcggta | cagcagagtg caaggacaaa | 1860 |
| aacctacctg | actacagctg | taaggtcttc | accggcgtct | acccatttat gtggggcggc | 1920 |
| gcctactgct | tctgcgacgc | tgaaaacacg | cagttgagcg | aagcacacgt ggagaagtcc | 1980 |
| gaatcatgca | aaacagaatt | tgcatcagca | tacagggctc | ataccgcatc tgcatcagct | 2040 |
| aagctccgcg | tcctttacca | aggaaataac | atcactgtaa | ctgccatgc aaacggcgac | 2100 |
| catgccgtca | cagttaagga | cgccaaattc | attgtggggc | caatgtcttc agcctggaca | 2160 |
| cctttcgaca | caaaattgt | ggtgtacaaa | ggtgacgtct | ataacatgga ctacccgccc | 2220 |
| tttggcgcag | aagaccagg | acaatttggc | gatatccaaa | gtcgcacacc tgagagtaaa | 2280 |
| gacgtctatg | ctaatacaca | actggtactg | cagagaccgg | ctgtgggtac ggtacacgtg | 2340 |
| ccatactctc | aggcaccatc | tggctttaag | tattggctaa | agaacgcgg ggcgtcgctg | 2400 |
| cagcacacag | caccatttgg | ctgccaaata | gcaacaaacc | cggtaagagc ggtgaactgc | 2460 |
| gccgtaggga | acatgcccat | ctccatcgac | ataccggaag | cggccttcac tagggtcgtc | 2520 |
| gacgcgccct | ctttaacgga | catgtcgtgc | gaggtaccag | cctgcaccca ttcctcagac | 2580 |
| tttgggggcg | tcgccattat | taaatatgca | gccagcaaga | aaggcaagtg tgcggtgcat | 2640 |
| tcgatgacta | acgccgtcac | tattcgggaa | gctgagatag | aagttgaagg gaattctcag | 2700 |
| ctgcaaatct | ctttctcgac | ggccttagcc | agcgccgaat | ccgcgtaca agtctgttct | 2760 |
| acacaagtac | actgtgcagc | cgagtgccac | ccccgaagg | accacatagt caactacccg | 2820 |
| gcgtcacata | ccaccctcgg | ggtccaggac | atctccgcta | cggcgatgtc atgggtgcag | 2880 |
| aagatcacgg | gaggtgtggg | actggttgtt | gctgttgccg | cactgattct aatcgtggtg | 2940 |
| ctatgcgtgt | cgttcagcag | gcac | | | 2964 |

<210> SEQ ID NO 21
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

| | | | | |
|---|---|---|---|---|
| atggagttca | tcccgacgca | aactttctat | aacagaaggt | accaaccccg accctgggcc | 60 |
| ccacgcccta | caattcaagt | aattagacct | agaccacgtc | cacagaggca ggctgggcaa | 120 |
| ctcgcccagc | tgatctccgc | agtcaacaaa | ttgaccatgc | gcgcggtacc tcaacagaag | 180 |
| cctcgcagaa | atcggaaaaa | caagaagcaa | aggcagaaga | agcaggcgcc gcaaaacgac | 240 |
| ccaaagcaaa | agaagcaacc | accacaaaag | aagccggctc | aaaagaagaa gaaaccaggc | 300 |
| cgtagggaga | gaatgtgcat | gaaaattgaa | atgattgcat | tcttcgaagt caagcatgaa | 360 |

```
ggcaaagtga tgggctacgc atgcctggtg ggggataaag taatgaaacc agcacatgtg      420
aagggaacta tcgacaatgc cgatctggct aaactggcct ttaagcggtc gtctaaatac      480
gatcttgaat gtgcacagat accggtgcac atgaagtctg atgcctcgaa gtttacccac      540
gagaaacccg aggggtacta taactggcat cacggagcag tgcagtattc aggaggccgg      600
ttcactatcc cgacgggtgc aggcaagccg ggagacagcg gcagaccgat cttcgacaac      660
aaaggacggg tggtggccat cgtcctagga ggggccaacg aaggtgcccg cacggccctc      720
tccgtggtga cgtggaacaa agacatcgtc acaaaaatta ccctgaggg agccgaagag      780 tgg                                                                   783
```

<210> SEQ ID NO 22
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggagttca tcccaaccca aactttttac aataggaggt accagcctcg accctggact      60
ccgcgcccta ctatccaagt catcaggccc agaccgcgcc ctcagaggca agctgggcaa     120
cttgcccagc tgatctcagc agttaataaa ctgacaatgc gcgcggtacc acaacagaag     180
ccacgcagga atcggaagaa taagaagcaa aagcaaaaac aacaggcgcc acaaacaac     240 acaaatcaaa agaagcagcc acctaaaaag aaaccggctc aaaagaaaaa gaagccgggc     300
cgcagagaga ggatgtgcat gaaaatcgaa atgattgta ttttcgaagt caagcacgaa      360
ggtaaggtaa caggttacgc gtgcctggtg ggggacaaag taatgaaacc agcacacgta     420 aagggggacca tcgataacgc ggacctggcc aaactggcct ttaagcggtc atctaagtat     480
gaccttgaat gcgcgcagat acccgtgcac atgaagtccg acgcttcgaa gttcacccat     540
gagaaaccgg aggggtacta caactggcac cacggagcag tacagtactc aggaggccgg     600
ttcaccatcc ctacaggtgc tgcaaaacca gggacagcg gcagaccgat cttcgacaac      660
aagggacgcg tggtggccat agtcttagga ggagctaatg aaggagcccg tacagccctc     720
tcggtggtga cctggaataa agacattgtc actaaaatca ccccgaggg ggccgaagag     780 tgg                                                                   783
```

<210> SEQ ID NO 23
<211> LENGTH: 13756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggctgcgt gagacacacg tagcctacca gtttcttact gctctactct gcaaagcaag      60
agattaataa cccatcatgg atcctgtgta cgtggacata gacgctgaca gcgcctttt     120 gaaggccctg caacgtgcgt accccatgtt tgaggtggaa ccaaggcagg tcacaccgaa     180
tgaccatgct aatgctagag cgttctcgca tctagctata aaactaatag agcaggaaat     240
tgaccccgac tcaaccatcc tggatatcgg cagtgcgcca gcaaggagga tgatgtcgga     300
caggaagtac cactgcgtct gcccgatgcg cagtgcggaa gatcccgaga gactcgccaa     360
ttatgcgaga aagctagcat ctgccgcagg aaaagtcctg gacagaaaca tctctggaaa     420
```

```
gatcggggac ttacaagcag taatggccgt gccagacacg agacgccaa cattctgctt    480
acacacagac gtctcatgta gacagagagc agacgtcgct atataccaag acgtctatgc    540
tgtacacgca cccacgtcgc tataccacca ggcgattaaa ggggtccgag tggcgtactg    600
ggttgggttc gacacaaccc cgttcatgta caatgccatg gcgggtgcct acccctcata    660
ctcgacaaac tgggcagatg agcaggtact gaaggctaag aacataggat tatgttcaac    720
agacctgacg gaaggtagac gaggcaagtt gtctattatg agagggaaaa agctaaaacc    780
gtgcgaccgt gtgctgttct cagtagggtc aacgctctac ccggaaagcc gcaagctact    840
taagagctgg cacctgccat cggtgttcca tttaagggc aaactcagct tcacatgccg      900
ctgtgataca gtggtttcgt gtgagggcta cgtcgttaag agaataacga tgagcccagg    960
cctttatgga aaaccacag ggtatgcggt aacccaccac gcagacggat tcctgatgtg     1020
caagactacc gacacggttg acggcgaaag aatgtcattc tcggtgtgca catacgtgcc    1080
ggcgaccatt tgtgatcaaa tgaccggcat ccttgctaca gaagtcacgc cggaggatgc    1140
acagaagctg ttggtggggc tgaaccagag aatagtggtt aacggcagaa cgcaacggaa    1200
tacgaacacc atgaaaaatt atctgcttcc cgtggtcgcc caagccttca gtaagtgggc    1260
aaaggagtgc cggaaagaca tggaagatga aaaactcctg ggggtcagag aaagaacact    1320
gacctgctgc tgtctatggg cattcaagaa gcagaaaaca cacacggtct acaagaggcc    1380
tgatacccag tcaattcaga aggttcaggc cgagtttgac agctttgtgg taccgagtct    1440
gtggtcgtcc gggttgtcaa tcccttttgag gactagaatc aaatggttgt taagcaaggt   1500
gccaaaaacc gacctgatcc catacagcgg agacgcccga gaagcccggg acgcagaaaa    1560
agaagcagag gaagaacgag aagcagaact gactcgcgaa gccctaccac ctctacaggc    1620
agcacaggaa gatgttcagg tcgaaatcga cgtggaacag cttgaggaca gagcgggcgc    1680
aggaataata gagactccga gaggagctat caaagttact gcccaaccaa cagaccacgt    1740
cgtgggagag tacctggtac tctccccgca gaccgtacta cgtagccaga agctcagtct    1800
gattcacgct ttggcggagc aagtgaagac gtgcacgcac aacggacgag cagggaggta    1860
tgcggtcgaa gcgtacgacg gccgagtcct agtgccctca ggctatgcaa tctcgcctga    1920
agacttccag agtctaagcg aaagcgcaac gatggtgtat aacgaaagag agttcgtaaa    1980
cagaaagcta caccatattg cgatgcacgg accagccctg aacaccgacg aagagtcgta    2040
tgagctggtg agggcagaga ggacagaaca cgagtacgtc tacgacgtgg atcagagaag    2100
atgctgtaag aaggaagaag ccgcaggact ggtactggtg ggcgacttga ctaatccgcc    2160
ctaccacgaa ttcgcatatg aagggctaaa aatccgccct gcctgcccat acaaaattgc    2220
agtcatagga gtcttcggag taccgggatc tggcaagtca gctattatca agaacctagt    2280
taccaggcag gacctggtga ctagcggaaa gaaagaaaac tgccaagaaa tcaccaccga    2340
cgtgatgaga cagagaggtc tagagatatc tgcacgtacg gttgactcgc tgctcttgaa    2400
tggatgcaac agaccagtcg acgtgttgta cgtagacgag gcgtttgcgt gccactctgg    2460
aacgctactt gctttgatcg ccttggtgag accaaggcag aaagttgtac tttgtggtga    2520
cccgaagcag tgcggcttct tcaatatgat gcagatgaaa gtcaactata atcacaacat    2580
ctgcacccaa gtgtaccaca aaagtatctc caggcggtgt acactgcctg tgaccgccat    2640
tgtgtcatcg ttgcattacg aaggcaaaat gcgcactacg aatgagtaca acaagccgat    2700
tgtagtggac actacaggct caacaaaacc tgaccctgga gacctcgtgt taacgtgctt    2760
```

```
cagagggtgg gttaaacaac tgcaaattga ctatcgtgga tacgaggtca tgacagcagc    2820
cgcatcccaa gggttaacca gaaaaggagt ttacgcagtt agacaaaaag ttaatgaaaa    2880
cccgctctat gcatcaacgt cagagcacgt caacgtactc ctaacgcgta cggaaggtaa    2940
actggtatgg aagacacttt ccggcgaccc gtggataaag acgctgcaga acccaccgaa    3000
aggaaacttc aaagcaacta ttaaggagtg ggaggtggag catgcatcaa taatggcggg    3060
catctgcagt caccaaatga ccttcgatac attccaaaat aaagccaacg tttgttgggc    3120
taagagcttg gtccctatcc tcgaaacagc ggggataaaa ctaaatgata ggcagtggtc    3180
tcagataatt caagccttca aagaagacaa agcatactca cctgaagtag ccctgaatga    3240
aatatgtacg cgcatgtatg gggtggatct agacagcggg ctattttcta aaccgttggt    3300
gtctgtgtat tacgcggata accactggga taataggcct ggaggaaaaa tgttcggatt    3360
taaccccgag gcagcatcca ttctagaaag aaagtatcca ttcacaaaag ggaagtggaa    3420
catcaacaag cagatctgcg tgactaccag gaggatagaa gactttaacc ctaccaccaa    3480
catcataccg gccaacagga gactaccaca ctcattagtg gccgaacacc gcccagtaaa    3540
aggggaaaga atggaatggc tggttaacaa gataaacggc caccacgtgc tcctggtcag    3600
tggctataac cttgcactgc ctactaagag agtcacttgg gtagcgccgt taggtgtccg    3660
cggagcggac tacacataca acctagagtt gggtctgcca gcaacgcttg gtaggtatga    3720
cctagtggtc ataaacatcc acacaccttt tcgcatacac cattaccaac agtgcgtcga    3780
ccacgcaatg aaactgcaaa tgctcggggg tgactcattg agactgctca accgggcgg    3840 ctctctattg atcagagcat atggttacgc agatagaacc agtgaacgag tcatctgcgt    3900
attgggacgc aagtttagat cgtctagagc gttgaaacca ccatgtgtca ccagcaacac    3960
tgagatgttt ttcctattca gcaactttga caatggcaga aggaatttca caactcatgt    4020
catgaacaat caactgaatg cagccttcgt aggacaggtc acccgagcag gatgtgcacc    4080
gtcgtaccgg gtaaaacgca tggacatcgc gaagaacgat gaagagtgcg tagtcaacgc    4140
cgctaaccct cgcgggttac cgggtggcgg tgtttgcaag gcagtataca aaaaatggcc    4200
ggagtccttt aagaacagtg caacaccagt gggaaccgca aaaacagtta tgtgcggtac    4260
gtatccagta atccacgctg ttggaccaaa cttctctaat tattcggagt ctgaagggga    4320
ccgggaattg gcagctgcct atcgagaagt cgcaaaggaa gtaactaggc tgggagtaaa    4380
tagtgtagct ataccctctc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
agagctgctg gatgagcaca tctccataga ctgcgatatt gttcgcgtgc accctgacag    4620
cagcttggca ggcagaaaag gatacagcac cacggaaggc gcactgtact catatctaga    4680
agggacccgt tttcatcaga cggctgtgga tatggcggag atacatacta tgtgccaaa     4740 gcaaacagag gccaatgagc aagtctgcct atatgccctg ggggaaagta ttgaatcgat    4800
caggcagaaa tgcccggtgg atgatgcaga cgcatcatct ccccccaaaa ctgtcccgtg    4860
cctttgccgt tacgctatga ctccagaacg cgtcacccgg cttcgcatga accacgtcac    4920
aagcataatt gtgtgttctt cgtttcccct cccaaagtac aaaatagaag gagtgcaaaa    4980
agtcaaatgc tctaaggtaa tgctatttga ccacaacgtg ccatcgcgcg taagtccaag    5040
ggaatataga tcttcccagg agtctgcaca ggaggcgagt acaatcacgt cactgacgca    5100
tagtcaattc gacctaagcg ttgatggcga gatactgccc gtcccgtcag acctggatgc    5160
```

```
tgacgcccca gccctagaac cagcactaga cgacggggcg acacacacgc tgccatccac   5220
aaccggaaac cttgcggccg tgtctgattg ggtaatgagc accgtacctg tcgcgccgcc   5280
cagaagaagg cgagggagaa acctgactgt gacatgtgac gagagagaag ggaatataac   5340
acccatggct agcgtccgat tctttagggc agagctgtgt ccggtcgtac aagaaacagc   5400
ggagacgcgt gacacagcaa tgtctcttca ggcaccaccg agtaccgcca cggaaccgaa   5460
tcatccgccg atctccttcg gagcatcaag cgagacgttc cccattacat ttggggactt   5520
caacgaagga gaaatcgaaa gcttgtcttc tgagctacta actttcggag acttcttacc   5580
aggagaagtg gatgacttga cagacagcga ctggtccacg tgctcagaca cggacgacga   5640
gttaagacta gacagggcag gtgggtatat attctcgtcg gacaccggtc caggtcattt   5700
acaacagaag tcagtacgcc agtcagtgct gccggtgaac accctggagg aagtccacga   5760
ggagaagtgt tacccaccta agctggatga agcaaaggag caactattac ttaagaaact   5820
ccaggagagt gcatccatgg ccaacagaag caggtatcag tcgcgcaaag tagaaaacat   5880
gaaagcagca atcatccaga gactaaagag aggctgtaga ctatacttaa tgtcagagac   5940
cccaaaagtc cctacttacc ggactacata tccggcgcct gtgtactcgc tccgatcaa    6000 cgtccgattg tccaatcccg agtccgcagt ggcagcatgc aatgagttct tagctagaaa   6060
ctatccaact gtctcatcat accaaattac cgacgagtat gatgcatatc tagacatggt   6120
ggacgggtcg gagagttgcc tggaccgagc gacattcaat ccgtcaaaac tcaggagcta   6180
cccgaaacag cacgcttacc acgcgccctc catcagaagc gctgtaccgt ccccattcca   6240
gaacacacta cagaatgtac tggcagcagc cacgaaaaga aactgcaacg tcacacagat   6300
gagggaatta cccactttgg actcagcagt attcaacgtg gagtgtttca aaaaattcgc   6360
atgcaaccaa gaatactggg aagaatttgc tgccagccct attaggataa caactgagaa   6420
tttagcaacc tatgttacta aactaaaagg gccaaaagca gcagcgctat cgcaaaaaac   6480
ccataatcta ctgccactac aggaagtacc aatggatagg ttcacagtag atatgaaaag   6540
ggacgtaaag gtgactcctg gtacaaagca tacagaggaa agacctaagg tgcaggttat   6600
acaggcggct gaacccttgg cgacagcata cctatgtggg attcacagag agctggttag   6660
gaggctgaac gccgtcctcc tacccaatgt acatacacta tttgacatgt ctgccgagga   6720
tttcgatgcc atcatagccg cacactttaa gccaggagac actgttttgg aaacggacat   6780
agcctccttt gataagagcc aagatgattc acttgcgctt actgctttga tgctgttaga   6840
ggatttaggg gtggatcact ccctgctgga cttgatagag gctgctttcg agagagatttc  6900 cagctgtcac ctaccgacag gtacgcgctt caagttcggc gccatgatga atcaggtat    6960 gttcctaact ctgttcgtca acacattgtt aaacatcacc atcgccagcc gagtgctgga   7020
agatcgtctg acaaaatccg cgtgcgcggc cttcatcggc gacgacaaca taatacatgg   7080
agtcgtctcc gatgaattga tggcagccag atgtgccact tggatgaaca tggaagtgaa   7140
gatcatagat gcagttgtat ccttgaaagc cccttacttt tgtggagggt ttatactgca   7200
cgatactgtg acaggaacag cttgcagagt ggcagacccg ctaaaaaggc ttttttaaact  7260 gggcaaaccg ctagcggcag gtgacgaaca agatgaagat agaagacgag cgctggctga   7320
cgaagtgatc agatggcaac gaacagggct aattgatgag ctggagaaag cggtatactc   7380
taggtacgaa gtgcagggta tatcagttgt ggtaatgtcc atggccacct ttgcaagctc   7440
cagatccaac ttcgagaagc tcagaggacc cgtcataact ttgtacggcg gtcctaaata   7500
```

-continued

```
ggtacgcact acagctacct attttgcaga agccgacagc aagtatctaa acactaatca    7560
gctacaatgg agttcatccc aacccaaact ttttacaata ggaggtacca gcctcgaccc    7620
tggactccgc gccctactat ccaagtcatc aggcccagac cgcgccctca gaggcaagct    7680
gggcaacttg cccagctgat ctcagcagtt aataaactga caatgcgcgc ggtaccacaa    7740
cagaagccac gcaggaatcg aagaataag aagcaaaagc aaaacaaca ggcgccacaa      7800
aacaacacaa atcaaagaa gcagccacct aaaagaaac cggctcaaaa gaaaagaag       7860
ccgggccgca gagagaggat gtgcatgaaa atcgaaaatg attgtatttt cgaagtcaag    7920
cacgaaggta aggtaacagg ttacgcgtgc ctggtggggg acaaagtaat gaaaccagca    7980
cacgtaaagg ggaccatcga taacgcggac ctggccaaac tggccttta gcggtcatct     8040
aagtatgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgctggc aaaccagggg acagcggcag accgatcttc    8220
gacaacaagg gacgcgtggt ggccatagtc ttaggaggag ctaatgaagg agcccgtaca    8280
gccctctcgg tggtgacctg gaataaagac attgtcacta aaatcacccc cgagggggcc    8340
gaagagtgga gtcttgccat cccagttatg tgcctgttgg caaacaccac gttcccctgc    8400
tcccagcccc cttgcacgcc ctgctgctac gaaaaggaac cggaggaaac cctacgcatg    8460
cttgaggaca acgtcatgag acctgggtac tatcagctgc tacaagcatc cttaacatgt    8520
tctccccacc gccagcgacg cagcaccaag gacaacttca atgtctataa agccacaaga    8580
ccatacttag ctcactgtcc cgactgtgga aagggcact cgtgccatag tcccgtagca     8640
ctagaacgca tcagaaatga agcgacagac gggacgctga aaatccaggt ctccttgcaa    8700
atcggaataa agacggatga cagccacgat tggaccaagc tgcgttatat ggacaaccac    8760
atgccagcag acgcagagag ggcgggcta tttgtaagaa catcagcacc gtgtacgatt     8820
actgaacaa tgggacactt catcctggcc cgatgtccaa aggggaaac tctgacggtg      8880
ggattcactg acagtaggaa gattagtcac tcatgtacgc acccatttca ccacgaccct    8940
cctgtgatag gtcgggaaaa attccattcc gaccgcagc acggtaaaga gctaccttgc     9000
agcacgtacg tgcagagcac cgccgcaact accgaggaga tagaggtaca catgcccca     9060
gacacccctg atcgcacatt aatgtcacaa cagtccggca acgtaaagat cacagtcaat    9120
ggccagacgg tgcggtacaa gtgtaattgc ggtggctcaa atgaaggact aacaactaca    9180
gacaaagtga ttaataactg caaggttgat caatgtcatg ccgcggtcac caatcacaaa    9240
aagtggcagt ataactcccc tctggtcccg cgtaatgctg aacttgggga ccgaaaagga    9300
aaaattcaca tcccgttcc gctggcaaat gtaacatgca gggtgcctaa agcaaggaac    9360
cccaccgtga cgtacgggaa aaaccaagtc atcatgctac tgtatcctga ccacccaaca    9420
ctcctgtcct accggaatat gggagaagaa ccaaactatc aagaagagtg ggtgatgcat    9480
aagaaggaag tcgtgctaac cgtgccgact gaagggctcg aggtcacgtg ggcaacaac     9540
gagccgtata agtattggcc gcagttatct acaaacggta cagcccatgg ccacccgcat    9600
gagataattc tgtattatta tgagctgtac cccactatga ctgtagtagt tgtgtcagtg    9660
gccacgttca tactcctgtc gatggtgggt atggcagcgg ggatgtgcat gtgtgcacga    9720
cgcagatgca tcacaccgta tgaactgaca ccaggagcta ccgtcccttt cctgcttagc    9780
ctaatatgct gcatcagaac agctaaagcg gccacatacc aagaggctgc gatatacctg    9840
tggaacgagc agcaaccttt gttttggcta caagcccta ttccgctggc agccctgatt    9900
```

```
gttctatgca actgtctgag actcttacca tgctgctgta aaacgttggc ttttttagcc    9960
gtaatgagcg tcggtgccca cactgtgagc gcgtacgaac acgtaacagt gatcccgaac   10020
acggtgggag taccgtataa gactctagtc aatagacctg gctacagccc catggtattg   10080
gagatggaac tactgtcagt cactttggag ccaacactat cgcttgatta catcacgtgc   10140
gagtacaaaa ccgtcatccc gtctccgtac gtgaagtgct gcggtacagc agagtgcaag   10200
gacaaaaacc tacctgacta cagctgtaag gtcttcaccg gcgtctaccc atttatgtgg   10260
ggcggcgcct actgcttctg cgacgctgaa aacacgcagt tgagcgaagc acacgtggag   10320
aagtccgaat catgcaaaac agaatttgca tcagcataca gggctcatac cgcatctgca   10380
tcagctaagc tccgcgtcct ttaccaagga ataacatca ctgtaactgc ctatgcaaac    10440
ggcgaccatg ccgtcacagt taaggacgcc aaattcattg tggggccaat gtcttcagcc   10500
tggacacctt tcgacaacaa aattgtggtg tacaaaggtg acgtctataa catggactac   10560
ccgcccttg gcgcaggaag accaggacaa tttggcgata tccaaagtcg cacacctgag    10620
agtaaagacg tctatgctaa tacacaactg gtactgcaga gaccggctgt gggtacggta   10680
cacgtgccat actctcaggc accatctggc tttaagtatt ggctaaaaga acgcggggcg   10740
tcgctgcagc acacagcacc atttggctgc caaatagcaa caaacccggt aagagcggtg   10800
aactgcgccg tagggaacat gcccatctcc atcgacatac cggaagcggc cttcactagg   10860
gtcgtcgacg cgccctcttt aacggacatg tcgtgcgagg taccagcctg cacccattcc   10920
tcagactttg ggggcgtcgc cattattaaa tatgcagcca gcaagaaagg caagtgtgcg   10980
gtgcattcga tgactaacgc cgtcactatt cgggaagctg agatagaagt tgaagggaat   11040
tctcagctgc aaatctcttt ctcgacggcc ttagccagcg ccgaattccg cgtacaagtc   11100
tgttctacac aagtacactg tgcagccgag tgccaccccc cgaaggacca catagtcaac   11160
tacccggcgt cacataccac cctcgggtc caggacatct ccgctacggc gatgtcatgg    11220
gtgcagaaga tcacgggagg tgtgggactg gttgttgctg ttgccgcact gattctaatc   11280
gtggtgctat gcgtgtcgtt cagcaggcac taacttgaca attaagtatg aaggtatatg   11340
tgtcccctaa gagacacact gtacatagca aataatctat agatcaaagg gctacgcaac   11400
ccctgaatag taacaaaata caaaatcact aaaaattata aaaacagaaa aatacataaa   11460
taggtatacg tgtcccctaa gagacacatt gtatgtaggt gataagtata gatcaaaggg   11520
ccgaataacc cctgaatagt aacaaaatat gaaaatcaat aaaaatcata aatagaaaa    11580
accataaaca gaagtagttc aaagggctat aaaaccccctg aatagtaaca aacataaaa   11640
ttaataaaaa tcaaatgaat accataattg gcaaacggaa gagatgtagg tacttaagct   11700
tcctaaaagc agccgaactc actttgagaa gtaggcatag cataccgaac tcttccacga   11760
ttctccgaac ccacagggac gtaggagatg ttattttgtt tttaatattt caaaaaaaaa   11820
aaaaaaaaa aaaaaaaaa aaaaaaaaa agcggccgct taattaatcg agggggaatta    11880
attcttgaag acgaaagggc caggtggcac ttttcgggga aatgtgcgcg gaacccctat   11940
ttgtttattt ttctaaatac attcaaatat gtatccgctc atgagacaat aaccctgata   12000
aatgcttcaa taatattgaa aaaggaagag tatgagtatt caacatttcc gtgtcgccct   12060
tattcccttt tttgcggcat tttgccttcc tgttttgct cacccagaaa cgctggtgaa    12120
agtaaaagat gctgaagatc agttgggtgc acgagtgggt tacatcgaac tggatctcaa   12180
cagcggtaag atccttgaga gttttcgccc cgaagaacgt tttccaatga tgagcacttt   12240
```

```
taaagttctg ctatgtggcg cggtattatc ccgtgttgac gccgggcaag agcaactcgg   12300
tcgccgcata cactattctc agaatgactt ggttgagtac tcaccagtca cagaaaagca   12360
tcttacggat ggcatgacag taagagaatt atgcagtgct gccataacca tgagtgataa   12420
cactgcggcc aacttacttc tgacaacgat cggaggaccg aaggagctaa ccgcttttt    12480 gcacaacatg ggggatcatg taactcgcct tgatcgttgg gaaccggagc tgaatgaagc   12540
cataccaaac gacgagcgtg acaccacgat gcctgtagca atggcaacaa cgttgcgcaa   12600
actattaact ggcgaactac ttactctagc ttcccggcaa caattaatag actggatgga   12660
ggcggataaa gttgcaggac cacttctgcg ctcggccctt ccggctggct ggtttattgc   12720
tgataaatct ggagccggtg agcgtgggtc tcgcggtatc attgcagcac tggggccaga   12780
tggtaagccc tcccgtatcg tagttatcta cacgacgggg agtcaggcaa ctatggatga   12840
acgaaataga cagatcgctg agataggtgc ctcactgatt aagcattggt aactgtcaga   12900
ccaagtttac tcatatatac tttagattga tttaaaactt catttttaat ttaaaaggat   12960
ctaggtgaag atcctttttg ataatctcat gaccaaaatc ccttaacgtg agttttcgtt   13020
ccactgagcg tcagaccccg tagaaaagat caaaggatct tcttgagatc ctttttttct   13080
gcgcgtaatc tgctgcttgc aaacaaaaaa accaccgcta ccagcggtgg tttgtttgcc   13140
ggatcaagag ctaccaactc tttttccgaa ggtaactggc ttcagcagag cgcagatacc   13200
aaatactgtc cttctagtgt agccgtagtt aggccaccac ttcaagaact ctgtagcacc   13260
gcctacatac ctcgctctgc taatcctgtt accagtggct gctgccagtg gcgataagtc   13320
gtgtcttacc gggttggact caagacgata gttaccggat aaggcgcagc ggtcgggctg   13380
aacggggggt tcgtgcacac agcccagctt ggagcgaacg acctacaccg aactgagata   13440
cctacagcgt gagcattgag aaagcgccac gcttcccgaa gggagaaagg cggacaggta   13500
tccggtaagc ggcagggtcg aacaggaga gcgcacgagg gagcttccag ggggaaacgc   13560
ctggtatctt tatagtcctg tcgggtttcg ccacctctga cttgagcgtc gatttttgtg   13620
atgctcgtca ggggggcgga gcctatggaa aaacgccagc aacgcgagct cgtatggaca   13680
tattgtcgtt agaacgcggc tacaattaat acataacctt atgtatcata cacaatcgat   13740
ttaggtgaca ctatag                                                  13756
```

<210> SEQ ID NO 24
<211> LENGTH: 1248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Gln Ala Pro Gln Asn Asn
65                  70                  75                  80

Thr Asn Gln Lys Lys Gln Pro Pro Lys Lys Lys Pro Ala Gln Lys Lys

```
                 85                  90                  95
Lys Lys Pro Gly Arg Glu Arg Met Cys Met Lys Ile Glu Asn Asp
            100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
            210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
            245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
            275                 280                 285

Glu Lys Glu Pro Glu Glu Thr Leu Arg Met Leu Glu Asp Asn Val Met
            290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
            325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Lys Thr Asp
            370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
            405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Pro Val Ile Gly Arg Glu
            450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
            485                 490                 495

Pro Pro Asp Thr Pro Asp Arg Thr Leu Met Ser Gln Gln Ser Gly Asn
            500                 505                 510
```

```
Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
                580                 585                 590

Val Pro Lys Ala Arg Asn Pro Thr Val Thr Tyr Gly Lys Asn Gln Val
            595                 600                 605

Ile Met Leu Leu Tyr Pro Asp His Pro Thr Leu Leu Ser Tyr Arg Asn
            610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Thr Phe Ile Leu Leu
            690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
                740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
            915                 920                 925
```

```
Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Val Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Val Asn Cys Ala Val Gly
    1070                1075                1080

Asn Met Pro Ile Ser Ile Asp Ile Pro Glu Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Ala Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 25
<211> LENGTH: 1248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30
```

```
Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
 50                  55                  60

Arg Lys Asn Lys Lys Gln Arg Gln Lys Gln Ala Pro Gln Asn Asp
 65                  70                  75                  80

Pro Lys Gln Lys Gln Pro Pro Gln Lys Pro Ala Gln Lys Lys
                 85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
        210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
        290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
        370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445
```

```
Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Glu Leu Tyr
        675                 680                 685

Pro Thr Met Thr Val Val Ile Val Ser Val Ala Ser Phe Val Leu Leu
690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
```

```
                865                 870                 875                 880
Ser Leu Pro Asp Tyr Ser Cys Lys Val Phe Thr Gly Val Tyr Pro Phe
                    885                 890                 895

Met Trp Gly Gly Ala Tyr Cys Phe Cys Asp Ala Glu Asn Thr Gln Leu
                    900                 905                 910

Ser Glu Ala His Val Glu Lys Ser Glu Ser Cys Lys Thr Glu Phe Ala
                    915                 920                 925

Ser Ala Tyr Arg Ala His Thr Ala Ser Ala Ser Ala Lys Leu Arg Val
                    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                    965                 970                 975

Ser Ala Trp Thr Pro Phe Asp Asn Lys Ile Val Val Tyr Lys Gly Asp
                    980                 985                 990

Val Tyr Asn Met Asp Tyr Pro Pro Phe Gly Ala Gly Arg Pro Gly Gln
                    995                1000                1005

Phe Gly Asp Ile Gln Ser Arg Thr Pro Glu Ser Lys Asp Val Tyr
1010                1015                1020

Ala Asn Thr Gln Leu Val Leu Gln Arg Pro Ala Ala Gly Thr Val
1025                1030                1035

His Val Pro Tyr Ser Gln Ala Pro Ser Gly Phe Lys Tyr Trp Leu
1040                1045                1050

Lys Glu Arg Gly Ala Ser Leu Gln His Thr Ala Pro Phe Gly Cys
1055                1060                1065

Gln Ile Ala Thr Asn Pro Val Arg Ala Val Asn Cys Ala Val Gly
1070                1075                1080

Asn Ile Pro Ile Ser Ile Asp Ile Pro Asp Ala Ala Phe Thr Arg
1085                1090                1095

Val Val Asp Ala Pro Ser Val Thr Asp Met Ser Cys Glu Val Pro
1100                1105                1110

Ala Cys Thr His Ser Ser Asp Phe Gly Gly Val Ala Ile Ile Lys
1115                1120                1125

Tyr Thr Ala Ser Lys Lys Gly Lys Cys Ala Val His Ser Met Thr
1130                1135                1140

Asn Ala Val Thr Ile Arg Glu Ala Asp Val Glu Val Glu Gly Asn
1145                1150                1155

Ser Gln Leu Gln Ile Ser Phe Ser Thr Ala Leu Ala Ser Ala Glu
1160                1165                1170

Phe Arg Val Gln Val Cys Ser Thr Gln Val His Cys Ala Ala Ala
1175                1180                1185

Cys His Pro Pro Lys Asp His Ile Val Asn Tyr Pro Ala Ser His
1190                1195                1200

Thr Thr Leu Gly Val Gln Asp Ile Ser Thr Thr Ala Met Ser Trp
1205                1210                1215

Val Gln Lys Ile Thr Gly Gly Val Gly Leu Ile Val Ala Val Ala
1220                1225                1230

Ala Leu Ile Leu Ile Val Val Leu Cys Val Ser Phe Ser Arg His
1235                1240                1245

<210> SEQ ID NO 26
<211> LENGTH: 36
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 26
gctctagaca ccatgagcct cgccctcccg gtcttg                               36

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggatcctca ttagtgcctg ctaaacgaca                                      30

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctctagaca ccatgagtct tgccatccca gttatg                               36

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tggatcctca ttagtgcctg ctgaacgaca                                      30

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aagctccgcg tcctttacca ag                                              22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccaaattgtc ctggtcttcc t                                               21

<210> SEQ ID NO 32
<211> LENGTH: 26
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 32
ccaatgtctt cagcctggac accttt                                          26

<210> SEQ ID NO 33
<211> LENGTH: 13826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggctgcgt gagacacacg tagcctacca gtttcttact gctctactct gcttagcaag     60
agacttgaga acccatcatg gatcccgtgt acgtggacat agacgccgac agcgcctttt    120
taaaggccct gcagcgtgcg tacccccatgt ttgaggtgga accaaggcag gtcacaccga    180
atgaccatgc caatgctaga gcattctcgc atctagctat aaaactaata gagcaggaaa    240
ttgatcccga ctcaaccatc ctggacatag gcagcgcgcc agcaaggagg atgatgtcgg    300
ataggaagta ccactgcgtt tgccctatgc gcagcgcaga gaccctgag agactcgcca    360 actacgcgag aaaactagca tctgccgcag gaaaagtctt ggacagaaac atctccgaaa    420
aaattggaga tctacaagca gtaatggctg taccagacgc agaaacgccc acattctgct    480
tgcacactga cgtctcatgt agacaaaggg cggacgtcgc tatataccag gatgtctacg    540
ccgtgcatgc accaacatcg ctgtaccacc aggcgattaa aggagtccgt gtagcatact    600
ggatagggtt tgatacaacc ccgttcatgt ataatgccat ggcaggtgca taccccctcgt    660 actcgacaaa ctgggcagat gagcaggtgc tgaaggcaaa gaacatagga ttatgttcaa    720
cagacctgac ggaaggtaga cgaggtaaat tgtctatcat gagaggaaaa aagatgaagc    780
catgtgaccg cgtactgttc tcagtcgggt caacgctttta cccggagagc cgtaagcttc    840
ttaagagttg gcacttacct tcagtgttcc atctaaaagg gaagctcagc ttcacgtgcc    900
gctgtgatac agtggtttcg tgtgaaggct atgtcgttaa gagaataacg attagcccgg    960
gcctctacgg taaaaccaca gggtacgcag taacccacca tgcagacgga ttcctaatgt   1020
gcaaaacaac cgatacggta gatggcgaga gagtgtcatt ttcggtatgc acgtacgtac   1080
ccgcaaccat ttgtgatcaa atgacaggta ttcttgccac ggaggttaca ccggaggatg   1140
cacagaagct gctggtggga ctgaaccaga ggatagtggt caatggcaga acgcagagga   1200
acacgaacac aatgaagaat tacttgcttc ctgtagttgc ccaagccctc agtaagtggg   1260
caaaggaatg ccgagaagat atggaagatg aaaaactttt gggcatcaga gaaaggacac   1320
tgacatgctg ctgcctttgg gcgttcaaga agcagaagac acacggtc tacaagaggc    1380 ctgacactca gtcaattcag aaagtcccag ccgaatttga cagctttgtg gtaccaagtc   1440
tgtggtcatc tggactgtcg atcccgctac ggaccagaat caagtggctg ctaagcaaag   1500
tgccaaagac tgatttgatc ccttacagcg gtgacgccaa agaagcccgc gacgctgaaa   1560
aagaagcaga agaagaacga gaagcggagc taactcgcga ggcactacca ccactacagg   1620
cggcacagga cgacgtccag gtcgaaattg acgtggaaca gctcgaagac agagctgggg   1680
caggaataat tgaaactcca agaggagcta tcaaagtcac tgcccaacca acagaccacg   1740
tcgtgggaga gtacttggta ctttcccgc agaccgtgtt acgaagccag aagctcagcc   1800
tgatccacgc attggcggaa caagtgaaga catgcacaca cagcggacgg gcaggaaggt   1860
```

```
acgcggtcga agcatatgac ggcagaatcc ttgtgccctc aggctatgca atatcacctg    1920
aagacttcca gagcctgagc gaaagtgcga cgatggtgta caacgaaagg gagttcgtaa    1980
ataggaaatt acaccatatc gcgttgcacg gaccagccct gaacactgac gaggagtcgt    2040
acgagctggt aagggcagaa aggacagagc atgagtacgt ctatgatgtg gaccaaagaa    2100
ggtgctgcaa gaaagaggag gcagccgggc tggtactggt cggcgacttg accaacccgc    2160
cctaccatga gttcgcatat gaagggctga gaatccgccc cgcctgccca tacaagaccg    2220
cagtaatagg ggtctttgga gtgccaggat ccggcaaatc agcaatcatt aagaacctag    2280
ttaccaggca agacctagtg accagtgaaa gaaagaaaaa ctgccaagaa atctccaccg    2340
acgtgatgcg acagaggaac ctggagatat ctgcacgcac ggtcgactca ctgctcttga    2400
acggatgcaa tagaccagtc gacgtgttgt acgtcgacga agcttttgcg tgccattctg    2460
gcacgctact tgctctgata gccttggtga gaccgaggca gaaagtcgtg ctatgcggtg    2520 atcccgaaaca gtgcggcttc ttcaatatga tgcagatgaa agttaactac aaccataaca    2580
tctgcaccca gtgtaccat aaaagtattt ccaggcggtg tacactgcct gtgactgcca    2640
ttgtgtcctc gttgcattac gaaggcaaaa tgcgcacaac aaatgagtac aacaagccaa    2700
ttgtagtgga tactacaggc tcgacaaaac ccgaccccgg agaccttgtg ctaacatgtt    2760
tcagagggtg ggttaagcaa ctgcaaattg actatcgtgg acacgaggtc atgacagcag    2820
ctgcatctca ggggctaacc agaaaagggg tctatgccgt caggcaaaaa gttaatgaaa    2880
acccccttta cgcatcaaca tcagagcacg tgaacgtgct actgacgcgt acggaaggca    2940
aactagtatg gaagacactt tctggagacc catggataaa gacactgcag aacccgccga    3000
aaggaaattt taaagcaaca attaaggaat gggaagtgga acatgcttca ataatggcgg    3060
gtatctgtaa ccaccaagtg acctttgaca cgttccagaa taaagccaat gtctgctggg    3120
cgaagagctt agtccccatc ctagaaacag cagggataaa attaaacgac aggcagtggt    3180
cccagataat ccaggctttt aaagaagaca gagcatactc acccgaggtg gccctgaatg    3240
agatatgcac gcgcatgtac gggggtagacc tggacagcgg actgttctct aaaccactgg    3300
tgtccgtgca tcatgcggat aatcactggg acaacaggcc ggaggggaag atgttcggat    3360
tcaaccccga agcggcgtcc actggagga ggaaatacc gtttacaaaa gggaagtgga    3420
ataccaacaa gcaaatctgt gtgactacta ggaggattga agattttaac ccgaacacca    3480
acattatacc tgccaacagg agattaccgc attcattggt ggccgaacat cgcccggtaa    3540
aaggggagag gatggaatgg ttggtcaaca aaataaatgg ccaccatgtg ctcctggtca    3600
gcggctacaa cctcgttctg cccactaaga gagtcacctg ggtggcgccg ctgggcattc    3660
ggggagctga ctacacatac aacctagagt taggcctacc agcaacgctc ggtagatatg    3720
acctagtgat tataaacatc cacacaccct ttcgcataca tcattaccaa cagtgcgtgg    3780
atcacgcaat gaagctgcag atgctcggag gagactccct gagactgctc aagccgggtg    3840
gttcattact gatcagggca tacggctacg cagacagaac aagcgaacga gtagtctgcg    3900
tattgggacg caagtttcga tcatccagag cgttgaaacc gccgtgcgtc actagcaaca    3960
ccgagatgtt tttcttgttc agcaactttg ataacggcag aaggaacttt acgacgcacg    4020
taatgaacaa ccagctgaat gctgcttttg ttggtcaggc caccccgagca gggtgcgcac    4080 cgtcgtaccg ggtaaacgc atggacatcg caaagaacga tgaagagtgt gtagtcaacg    4140
ccgccaaccc tcgtgggcta ccaggcgatg gcgtctgtaa agcagtatac aaaaaatggc    4200
```

```
cggagtcctt caagaacagt gcaacaccag tgggaaccgc aaagacagtc atgtgcggta    4260
catacccggt aatccatgca gtaggaccta atttctcaaa ttactctgag tccgaaggag    4320
accgggaatt ggcagctgct taccgagaag tcgctaagga ggtgactaga ctaggagtaa    4380
acagcgtagc tataccgctc ctttccaccg gtgtgtactc tggagggaaa gacaggctga    4440
ctcagtcact aaaccacctt tttacagcat tagactcaac tgatgcagat gtggttatct    4500
actgccgcga caaggagtgg gagaagaaaa tagctgaggc catacaaatg aggacccaag    4560
tggaattact agacgaacac atctctgtag actgcgatat catccgagtg caccctgaca    4620
gcagtttggc aggtagaaaa gggtacagca ctacagaagg ttcactgtac tcctacttgg    4680
aagggacacg gttccatcag acggcagtgg acatggcaga agtatacacc atgtggccaa    4740
agcagacgga ggctaatgaa caagtttgct tgtacgcatt gggggaaagt atagaatcaa    4800
tcaggcaaaa gtgcccagtg gatgacgcag atgcatcgtc gcccccaaaa accgtcccgt    4860
gcctctgccg ttatgccatg acacccgaac gagtcaccag gcttcgtatg aaccatgtca    4920
caagcataat agtatgctca tcattccccc ttccaaagta taaaatagaa ggagtgcaga    4980
aagtcaagtg ttctaaagtg atgctgttcg accataacgt gccatcacgc gttagtccaa    5040
gggaatataa atcgcctcag gagaccgcac aagaagtaag ttcgaccacg tcactgacgc    5100
acagccaatt cgaccttagc gttgacggtg aggaactgcc cgctccgtct gacttggaag    5160
ctgacgctcc gattccggaa ccaacaccag acgacagagc ggtacttact ttgcctccca    5220
cgattgataa ttttttcggct gtgtcagact gggtaatgaa taccgcgcca gtcgcaccac    5280
ccagaagaag acgtgggaaa aacttgaatg tcacctgcga cgagagagaa gggaacgtac    5340
ttcccatggc tagcgttcgg ttcttcagag cggatctgca ctccatcgta caggaaacgg    5400
cagagatacg cgatacggcc gcgtccctcc aggcgcccct gagtgtcgct acagaaccga    5460
atcaactgcc gatctcattt ggagcaccaa acgagacttt ccccataacg ttcggggatt    5520
ttgatgaagg ggagattgaa agcttgtcct ctgagttact gaccttttggg gacttctcgc    5580
cgggcgaagt ggatgacctg acagacagcg actggtccac gtgttcagac acggacgacg    5640
aattatgact agatagggca ggtgggtaca tattctcatc tgacaccggc cccggccacc    5700
tgcaacagag gtctgtccgt cagacagtac tgccggtaaa taccttggag gaagttcagg    5760
aggagaaatg ttacccacct aagttggatg aagtgaaaga gcagttgtta cttaagaaac    5820
tccaggaaag tgcgtccatg gctaacagaa gcaggtacca atcccgcaaa gtagagaaca    5880
tgaaagcaac aatagtccaa ggctgaaggg gtggttgcaa actttattta atgtcggaga    5940
ccccgaaagt tcctacctac cgaactacat atccggcacc agtgtactca cccccaatca    6000
atatccgact gtccaacccc gagtctgctg tggcagcgtg caatgagttc ctagcaagga    6060
actatccgac agttgcgtcg taccaaatca ccgatgagta cgatgcatac ctagacatgg    6120
tggacgggtc ggaaagttgc cttgaccggg cgacgttcaa cccatcaaag cttagaagtt    6180
atccaaaaca gcactcctac catgcacccca caatcagaag tgccgtacct tccccgttcc    6240
agaacacgct gcagaacgta ctggctgctg ccacgaaaag aaattgcaac gtcacacaga    6300
tgagagaact gccctacttg gattcagcgg tatttaatgt tgagtgcttt aaaaaatttg    6360
cgtgcaatca agaatactgg aaggaatttg ccgccagccc tattaggata acgactgaga    6420
acttgacaac ttatgtcaca aaactaaaag gaccaaaagc agcagcactg tttgccaaga    6480
cacataacct gctaccactg caggaggtgc cgatggacag gtttactgta gacatgaaaa    6540
gggacgtgaa ggtgactccg gggacgaagc acactgagga aagacctaaa gtgcaggtca    6600
```

```
tacaggcagc cgaacctttg gcaacagcat atctgtgtgg gatccacaga gagttggtca    6660
gaaggctgaa tgcagtcctt ctacctaatg tacacacgct gtttgacatg tctgccgagg    6720
actttgacgc cattattgcc gcgcacttca agccggggga cgccgtattg gaaaccgata    6780
tagcctcctt tgacaagagc caagacgact cattggcgct cactgctcta atgttgctag    6840
aggatttggg ggtggatcat cccctgttgg acttgataga ggctgccttc ggggagatct    6900
ccagctgcca cctaccgacg ggcacccgtt ttaagttcgg cgccatgatg aagtctggta    6960
tgttcctaac cctgttcgtc aacacactgc taaacatcac catagccagc cgagtgctgg    7020
aggaccgctt gacaaggtct gcgtgcgcgg ccttcatcgg cgacgacaat ataatacatg    7080
gggttgtctc tgacgaactg atggcagcaa ggtgtgctac atggatgaac atggaagtga    7140
agatcataga tgcggtcgtg tctcagaaag ccccgtactt ctgcggaggg tttatactgt    7200
atgacacagt agcaggcacg gcctgcagag tggcagaccc gctaaagcgg ctgttcaagc    7260
tgggcaaacc gctggcagcg ggagatgaac aagacgacga cagaagacgt gcactggctg    7320
acgaagtggt tagatggcaa cgaacaggac taactgatga gctagaaaaa gcggtacact    7380
ccaggtatga agtgcagggc atatctgtcg tggtaatgtc tatggccacc tttgcaagct    7440
ctagatctaa ctttgagaag ctcagaggac ccgtcgtaac cctgtacggt ggtcctaaat    7500
aggtacgcac tacagctacc tatttcgtca gaaaccaatc gcagctactt gcataccctac   7560 cagctacaat ggagttcatc ccgacgcaaa cttctctataa cagaaggtac caaccccgac    7620
cctgggcccc acgccctaca attcaagtaa ttagacctag accacgtcca cagaggcagg    7680 ctggcaact cgcccagctg atctccgcag tcaacaaatt gaccatgcgc gcggtacctc    7740
aacagaagcc tcgcagaaat cggaaaaaca agaagcaaag gcagaagaag caggcgccgc    7800
aaaacgaccc aaagcaaaag aagcaaccac cacaaaagaa gccggctcaa agaagaaga    7860 aaccaggccg tagggagaga atgtgcatga aaattgaaaa tgattgcatc ttcgaagtca    7920
agcatgaagg caaagtgatg ggctacgcat gcctggtggg ggataaagta atgaaaccag    7980
cacatgtgaa gggaactatc gacaatgccg atctggctaa actggccttt aagcggtcgt    8040
ctaaatacga tcttgaatgt gcacagatac cggtgcacat gaagtctgat gcctcgaagt    8100
ttacccacga gaaacccgag gggtactata actggcatca cggagcagtg cagtattcag    8160
gaggccggtt cactatcccg acgggtgcag gcaagccggg agacagcggc agaccgatct    8220
tcgacaacaa aggacgggtg gtggccatcg tcctaggagg ggccaacgaa ggtgcccgca    8280
cggccctctc cgtggtgacg tggaacaaag acatcgtcac aaaaattacc cctgagggag    8340
ccgaagagtg gagcctcgcc ctcccggtct tgtgcctgtt ggcaaacact acattccct    8400 gctctcagcc gccttgcaca ccctgctgct acgaaaagga accggaaagc accttgcgca    8460
tgcttgagga caacgtgatg agacccggat actaccagct actaaaagca tcgctgactt    8520
gctctcccca ccgccaaaga cgcagtacta aggacaattt taatgtctat aaagccacaa    8580
gaccatatct agctcattgt cctgactgcg gagaagggca ttcgtgccac agccctatcg    8640
cattggagcg catcagaaat gaagcaacgg acggaacgct gaaaatccag gtctctttgc    8700
agatcgggat aaagacagat gacagccacg attggaccaa gctgcgctat atggatagcc    8760
atacgccagc ggacgcggag cgagccggat tgcttgtaag gacttcagca ccgtgcacga    8820
tcaccgggac catgggacac ttttattctg cccgatgccc gaaaggagag acgctgcacg    8880
tgggatttac ggacagcaga aagatcagcc acacatgcac acacccgttc catcatgaac    8940
```

```
cacctgtgat aggtagggag aggttccact ctcgaccaca acatggtaaa gagttacctt   9000
gcagcacgta cgtgcagagc accgctgcca ctgctgagga gatagaggtg catatgcccc   9060
cagatactcc tgaccgcacg ctgatgacgc agcagtctgg caacgtgaag atcacagtta   9120
atgggcagac ggtgcggtac aagtgcaact gcggtggctc aaacgaggga ctgacaacca   9180
cagacaaagt gatcaataac tgcaaaattg atcagtgcca tgctgcagtc actaatcaca   9240
agaattggca atacaactcc cctttagtcc cgcgcaacgc tgaactcggg gaccgtaaag   9300
gaaagatcca catcccattc ccattggcaa acgtgacttg cagagtgcca aaagcaagaa   9360
accctacagt aacttacgga aaaaaccaag tcaccatgct gctgtatcct gaccatccga   9420
cactcttgtc ttaccgtaac atgggacagg aaccaaatta ccacgaggag tgggtgacac   9480
acaagaagga ggttaccttg accgtgccta ctgagggtct ggaggtcact tggggcaaca   9540
acgaaccata caagtactgg ccgcagatgt ctacgaacgg tactgctcat ggtcacccac   9600
atgagataat cttgtactat tatgagctgt accccactat gactgtagtc attgtgtcgg   9660
tggcctcgtt cgtgcttctg tcgatggtgg gcacagcagt gggaatgtgt gtgtgcgcac   9720
ggcgcagatg cattacacca tatgaattaa caccaggagc cactgttccc ttcctgctca   9780
gcctgctatg ctgcgtcaga acgaccaagg cggcccacata ttacgaggct gcggcatatc   9840
tatggaacga acagcagccc ctgttctggt tgcaggctct tatcccgctg gccgccttga   9900
tcgtcctgtg caactgtctg aaactcttgc catgctgctg taagaccctg gcttttttag   9960
ccgtaatgag catcggtgcc cacactgtga gcgcgtacga acacgtaaca gtgatcccga  10020
acacggtggg agtaccgtat aagactcttg tcaacagacc gggttacagc cccatggtgt  10080
tggagatgga gctacaatca gtcaccttgg aaccaacact gtcacttgac tacatcacgt  10140
gcgagtacaa aactgtcatc ccctccccgt acgtgaagtg ctgtggtaca gcagagtgca  10200
aggacaagag cctaccagac tacagctgca aggtctttac tggagtctac ccatttatgt  10260
ggggcggcgc ctactgcttt tgcgacgccg aaaatacgca attgagcgag gcacatgtag  10320
agaaatctga atcttgcaaa acagagtttg catcggccta cagagcccac accgcatcgg  10380
cgtcggcgaa gctccgcgtc ctttaccaag gaaacaacat taccgtagct gcctacgcta  10440
acggtgacca tgccgtcaca gtaaaggacg ccaagtttgt cgtgggccca atgtcctccg  10500
cctggacacc ttttgacaac aaaatcgtgg tgtacaaagg cgacgtctac aacatggact  10560
acccaccttt tggcgcagga agaccaggac aatttggtga cattcaaagt cgtacaccgg  10620
aaagtaaaga cgtttatgcc aacactcagt tggtactaca gaggccagca gcaggcacgg  10680
tacatgtacc atactctcag gcaccatctg gcttcaagta ttggctgaag gaacgaggag  10740
catcgctaca gcacacggca ccgttcggtt gccagattgc gacaaacccg gtaagagctg  10800
taaattgcgc tgtggggaac ataccaattt ccatcgacat accggatgcg gcctttacta  10860
gggttgtcga tgcaccctct gtaacggaca tgtcatgcga agtaccagcc tgcactcact  10920
cctccgactt tggggggcgtc gccatcatca aatacacagc tagcaagaaa ggtaaatgtg  10980
cagtacattc gatgaccaac gccgttacca ttcgagaagc cgacgtagaa gtagagggga  11040
actcccagct gcaaatatcc ttctcaacag ccctggcaag cgccgagttt cgcgtgcaag  11100
tgtgctccac acaagtacac tgcgcagccg catgccaccc tccaaaggac cacatagtca  11160
attacccagc atcacacacc acccttgggg tccaggatat atccacaacg gcaatgtctt  11220
gggtgcagaa gattacggga ggagtaggat taattgttgc tgttgctgcc ttaattttaa  11280
ttgtggtgct atgcgtgtcg tttagcaggc actaaaccga tgataaggca cgaaataact  11340
```

-continued

```
aaatagcaaa agtagaaagt acataaccag gtatatgtgc cccttaagag gcacaatata   11400
tatagctaag cactattaga tcaaagggct atacaacccc tgaatagtaa caaaacacaa   11460
aaaccaataa aaatcataaa aagaaaaatc tcataaacag gtataagtgt cccctaagag   11520
acacattgta tgtaggtagt aagtatagat caaagggcta tattaacccc tgaatagtaa   11580
caaaacacaa aaacaataaa aactacaaaa tagaaaatct ataaacaaaa gtagttcaaa   11640
gggctacaaa acccctgaat agtaacaaaa cataaaatgt aataaaaatt aagtgtgtac   11700
ccaaaagagg tacagtaaga atcagtgaat atcacaattg gcaacgagaa gagacgtagg   11760
tatttaagct tcctaaaagc agccgaactc actttgagac gtaggcatag cataccgaac   11820
tcttccacta ttctccgaac ccacagggac gtaggagatg ttattttgtt tttaatattt   11880
caaaaaaaaa aaaaaaaaaa aaaaaaaaaa aaaaaaaaaa agcggccgct taattaatcg   11940
aggggaatta attcttgaag acgaaagggc caggtggcac ttttcgggga aatgtgcgcg   12000
gaacccctat ttgtttattt ttctaaatac attcaaatat gtatccgctc atgagacaat   12060
aaccctgata aatgcttcaa taatattgaa aaaggaagag tatgagtatt caacatttcc   12120
gtgtcgccct tattccctt tttgcggcat tttgccttcc tgtttttgct cacccagaaa   12180
cgctggtgaa agtaaaagat gctgaagatc agttgggtgc acgagtgggt tacatcgaac   12240
tggatctcaa cagcggtaag atccttgaga gttttcgccc cgaagaacgt tttccaatga   12300
tgagcacttt taaagttctg ctatgtggcg cggtattatc ccgtgttgac gccgggcaag   12360
agcaactcgg tcgccgcata cactattctc agaatgactt ggttgagtac tcaccagtca   12420
cagaaaagca tcttacggat ggcatgacag taagagaatt atgcagtgct gccataacca   12480
tgagtgataa cactgcggcc aacttacttc tgacaacgat cggaggaccg aaggagctaa   12540
ccgcttttt gcacaacatg ggggatcatg taactcgcct tgatcgttgg gaaccggagc   12600
tgaatgaagc cataccaaac gacgagcgtg acaccacgat gcctgtagca atggcaacaa   12660
cgttgcgcaa actattaact ggcgaactac ttactctagc ttcccggcaa caattaatag   12720
actggatgga ggcggataaa gttgcaggac cacttctgcg ctcggccctt ccggctggct   12780
ggtttattgc tgataaatct ggagccggtg agcgtgggtc tcgcggtatc attgcagcac   12840
tggggccaga tggtaagccc tcccgtatcg tagttatcta cacgacgggg agtcaggcaa   12900
ctatggatga acgaaataga cagatcgctg agataggtgc ctcactgatt aagcattggt   12960
aactgtcaga ccaagtttac tcatatatac tttagattga tttaaaactt catttttaat   13020
ttaaaggat ctaggtgaag atcctttttg ataatctcat gaccaaaatc ccttaacgtg   13080
agttttcgtt ccactgagcg tcagaccccg tagaaaagat caaaggatct tcttgagatc   13140
ctttttttct gcgcgtaatc tgctgcttgc aaacaaaaaa accaccgcta ccagcggtgg   13200
tttgtttgcc ggatcaagag ctaccaactc tttttccgaa ggtaactggc ttcagcagag   13260
cgcagatacc aaatactgtc cttctagtgt agccgtagtt aggccaccac ttcaagaact   13320
ctgtagcacc gcctacatac ctcgctctgc taatcctgtt accagtggct gctgccagtg   13380
gcgataagtc gtgtcttacc gggttggact caagacgata gttaccggat aaggcgcagc   13440
ggtcgggctg aacggggggt tcgtgcacac agcccagctt ggagcgaacg acctacaccg   13500
aactgagata cctacagcgt gagcattgag aaagcgccac gcttcccgaa gggagaaagg   13560
cggacaggta tccggtaagc ggcagggtcg gaacaggaga gcgcacgagg gagcttccag   13620
ggggaaacgc ctggtatctt tatagtcctg tcgggtttcg ccacctctga cttgagcgtc   13680
```

-continued

```
gatttttgtg atgctcgtca gggggggcgga gcctatggaa aaacgccagc aacgcgagct    13740
cgtatggaca tattgtcgtt agaacgcggc tacaattaat acataacctt atgtatcata    13800
cacaatcgat ttaggtgaca ctatag                                          13826
```

What is claimed is:

1. A method for producing a virus-like particle, comprising:
expressing in a cell one or more polynucleotides encoding Chikungunya virus (CHIKV) strain 37997 structural proteins under conditions for self-assembly of the CHIKV strain 37997 structural proteins to form a virus-like particle, wherein the CHIKV strain 37997 structural proteins comprise at least CHIKV capsid (C) protein, CHIKV E2 protein, and CHIKV E1 protein, and
wherein the cell does not express polynucleotides encoding CHIKV non-structural proteins.

2. The method of claim 1, wherein the CHIKV strain 37997 structural proteins comprise at least CHIKV capsid (C) protein, CHIKV E3 protein, CHIKV E2 protein, CHIKV 6K protein, and CHIKV E 1 protein.

3. The method of claim 1, wherein the one or more polynucleotides encode a polyprotein comprising the CHIKV capsid (C) protein, a CHIKV E3 protein, the CHIKV E2 protein, a CHIKV 6K protein, and the CHIKV E1 protein.

4. The method of claim 1, further comprising isolating the virus-like particle.

* * * * *

UNITED STATES PATENT AND TRADEMARK OFFICE
CERTIFICATE OF CORRECTION

| | | |
|---|---|---|
| PATENT NO. | : 11,992,523 B2 | Page 1 of 1 |
| APPLICATION NO. | : 17/850706 | |
| DATED | : May 28, 2024 | |
| INVENTOR(S) | : Nabel et al. | |

It is certified that error appears in the above-identified patent and that said Letters Patent is hereby corrected as shown below:

On the Title Page

Related U.S. Application Data (60), "Continuation of application No. 16/520,113" should read
-- Division of application No. 16/520,113 --

Signed and Sealed this
Seventh Day of January, 2025

Derrick Brent
*Acting Director of the United States Patent and Trademark Office*